(12) United States Patent
Tanaka et al.

(10) Patent No.: US 10,392,339 B2
(45) Date of Patent: *Aug. 27, 2019

(54) POLYMERIZABLE POLAR COMPOUND, LIQUID CRYSTAL COMPOSITION, AND LIQUID CRYSTAL DISPLAY ELEMENT

(71) Applicants: JNC CORPORATION, Tokyo (JP); JNC PETROCHEMICAL CORPORATION, Tokyo (JP)

(72) Inventors: Hiroyuki Tanaka, Chiba (JP); Masakazu Yano, Chiba (JP); Fumitaka Kondou, Chiba (JP); Kazuhiro Ogita, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 21 days.

This patent is subject to a terminal disclaimer.

(21) Appl. No.: 15/541,038

(22) PCT Filed: Feb. 4, 2016

(86) PCT No.: PCT/JP2016/053316
§ 371 (c)(1),
(2) Date: Jun. 30, 2017

(87) PCT Pub. No.: WO2016/129490
PCT Pub. Date: Aug. 18, 2016

(65) Prior Publication Data
US 2017/0369418 A1 Dec. 28, 2017

(30) Foreign Application Priority Data
Feb. 9, 2015 (JP) .................. 2015-023330

(51) Int. Cl.
*G02F 1/1333* (2006.01)
*C07C 69/732* (2006.01)
(Continued)

(52) U.S. Cl.
CPC .......... *C07C 69/732* (2013.01); *C07C 69/003* (2013.01); *C07C 69/013* (2013.01);
(Continued)

(58) Field of Classification Search
CPC .... C09K 19/04; C09K 19/062; C09K 19/063; C09K 19/12; C09K 19/126; C09K 19/18; C09K 19/3003; C09K 19/32; C09K 19/322; C09K 19/34; C09K 19/3402; C09K 19/3483; C09K 19/36; C09K 19/42; C09K 19/54; C09K 2019/0444; C07C 69/732; C07C 69/003; C07C 69/013;
(Continued)

(56) References Cited

U.S. PATENT DOCUMENTS

2015/0376504 A1  12/2015  Tanaka et al.
2016/0075950 A1   3/2016  Kobayashi et al.
(Continued)

FOREIGN PATENT DOCUMENTS

JP  50-35076      4/1975
JP  2005-128201   5/2005
(Continued)

OTHER PUBLICATIONS

International Search Report dated Apr. 12, 2016 in International Application No. PCT/JP2016/053316.
(Continued)

*Primary Examiner* — Geraldina Visconti
(74) *Attorney, Agent, or Firm* — Wenderoth, Lind & Ponack, L.L.P.

(57) ABSTRACT

Provided is a polar compound having high chemical stability, high capability of aligning liquid crystal molecules, high solubility in a liquid crystal composition, and a large voltage holding ratio when used in a liquid crystal display device. The compound is represented by formula (1):

$$R^1\text{—MES—Sp}^1\text{—O} \diagdown \diagup R^2 \atop O \diagup \diagdown M^2 \atop M^1 \quad (1)$$

in which, for example, $R^1$ is alkyl having 1 to 15 carbons; MES is a mesogen group having at least one ring; $Sp^1$ is a single bond or alkylene having 1 to 10 carbons; $M^1$ and $M^2$ are hydrogen; and $R^2$ is a group represented by formulas (1a) to (1c):

$$-\!\!\!\{\!\!-\text{Sp}^2\text{—X}^1 \quad (1a)$$

$$-\!\!\!\{\!\!-\text{Sp}^2\text{—S}^1\text{—Sp}^3\text{—X}^1 \atop \quad\ \ \text{Sp}^3\text{—X}^1 \quad (1b)$$

$$-\!\!\!\{\!\!-\text{Sp}^2\text{—S}^2\text{—Sp}^3\text{—X}^1 \atop \text{Sp}^3\text{—X}^1 \atop \text{Sp}^3\text{—X}^1 \quad (1c)$$

in which, $Sp^2$ and $Sp^3$ are a single bond or alkylene having 1 to 10 carbons; $S^1$ is >CH—; $S^2$ is >C<; and $X^1$ is —OH.

19 Claims, No Drawings

(51) Int. Cl.

| | |
|---|---|
| C07D 309/06 | (2006.01) |
| C07D 319/06 | (2006.01) |
| C07D 239/26 | (2006.01) |
| C07C 321/10 | (2006.01) |
| C07C 229/08 | (2006.01) |
| C07C 229/30 | (2006.01) |
| C07F 5/02 | (2006.01) |
| C07D 295/145 | (2006.01) |
| C07F 7/18 | (2006.01) |
| C07D 213/55 | (2006.01) |
| C09K 19/12 | (2006.01) |
| C09K 19/34 | (2006.01) |
| C09K 19/42 | (2006.01) |
| C09K 19/54 | (2006.01) |
| G02F 1/1337 | (2006.01) |
| C07C 69/003 | (2006.01) |
| C07C 69/013 | (2006.01) |
| C07C 69/017 | (2006.01) |
| C07C 229/12 | (2006.01) |
| C07J 9/00 | (2006.01) |
| C09K 19/06 | (2006.01) |
| C09K 19/30 | (2006.01) |
| C09K 19/36 | (2006.01) |
| C09K 19/04 | (2006.01) |
| C09K 19/18 | (2006.01) |
| C09K 19/32 | (2006.01) |
| G02F 1/1362 | (2006.01) |

(52) U.S. Cl.
CPC .......... *C07C 69/017* (2013.01); *C07C 229/08* (2013.01); *C07C 229/12* (2013.01); *C07C 229/30* (2013.01); *C07C 321/10* (2013.01); *C07D 213/55* (2013.01); *C07D 239/26* (2013.01); *C07D 295/145* (2013.01); *C07D 309/06* (2013.01); *C07D 319/06* (2013.01); *C07F 5/02* (2013.01); *C07F 7/18* (2013.01); *C07J 9/00* (2013.01); *C09K 19/04* (2013.01); *C09K 19/062* (2013.01); *C09K 19/063* (2013.01); *C09K 19/12* (2013.01); *C09K 19/126* (2013.01); *C09K 19/18* (2013.01); *C09K 19/3003* (2013.01); *C09K 19/32* (2013.01); *C09K 19/322* (2013.01); *C09K 19/34* (2013.01); *C09K 19/3402* (2013.01); *C09K 19/3483* (2013.01); *C09K 19/36* (2013.01); *C09K 19/42* (2013.01); *C09K 19/54* (2013.01); *G02F 1/1337* (2013.01); *G02F 1/133788* (2013.01); *C07C 2601/14* (2017.05); *C09K 2019/0444* (2013.01); *C09K 2019/0448* (2013.01); *C09K 2019/122* (2013.01); *C09K 2019/123* (2013.01); *C09K 2019/181* (2013.01); *C09K 2019/301* (2013.01); *C09K 2019/303* (2013.01); *C09K 2019/3004* (2013.01); *C09K 2019/3006* (2013.01); *C09K 2019/3009* (2013.01); *C09K 2019/3015* (2013.01); *C09K 2019/3016* (2013.01); *C09K 2019/3019* (2013.01); *C09K 2019/3025* (2013.01); *C09K 2019/3077* (2013.01); *C09K 2019/3422* (2013.01); *G02F 1/1362* (2013.01)

(58) Field of Classification Search
CPC . C07C 69/017; C07C 2601/14; C07C 321/10; C07C 229/08; C07C 229/12; C07C 229/30; G02F 1/1333; G02F 1/1337; G02F 1/133788; C07J 9/00; C07F 5/02; C07F 7/18; C07D 213/55; C07D 239/26; C07D 295/145; C07D 309/06; C07D 319/06
USPC ...................................... 252/299.63
See application file for complete search history.

(56) References Cited

U.S. PATENT DOCUMENTS

2018/0163138 A1* 6/2018 Saito ...................... C09K 19/30
2018/0327666 A1* 11/2018 Saito ...................... C09K 19/12

FOREIGN PATENT DOCUMENTS

| JP | 2012-255845 | 12/2012 |
| KR | 10-2013-0132032 | 12/2013 |
| WO | 2012/038026 | 3/2012 |
| WO | 2012/104008 | 8/2012 |
| WO | 2013/004372 | 1/2013 |
| WO | 2014/090362 | 6/2014 |
| WO | 2014/094959 | 6/2014 |
| WO | 2014/129268 | 8/2014 |
| WO | 2014/174929 | 10/2014 |

OTHER PUBLICATIONS

Extended European Search Report dated Jul. 4, 2018 in corresponding European patent application No. 16 74 9134.

* cited by examiner

POLYMERIZABLE POLAR COMPOUND, LIQUID CRYSTAL COMPOSITION, AND LIQUID CRYSTAL DISPLAY ELEMENT

TECHNICAL FIELD

The invention relates to a polymerizable polar compound, a liquid crystal composition and a liquid crystal display device. More specifically, the invention relates to a polymerizable polar compound having an acryloyloxy group in which replacement is made by a polar group such as a hydroxyalkyl group, a liquid crystal composition containing the compound and having positive or negative dielectric anisotropy, and a liquid crystal display device including the composition.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field-induced photo-reactive alignment (FPA) mode. A classification based on a driving mode in the device includes a passive matrix (PM) and an active matrix (AM). The PM is classified into static, multiplex and so forth, and the AM is classified into a thin film transistor (TFT), a metal insulator metal (MIM) and so forth. The TFT is further classified into amorphous silicon and polycrystal silicon. The latter is classified into a high temperature type and a low temperature type based on a production process. A classification based on a light source includes a reflective type utilizing natural light, a transmissive type utilizing backlight and a transflective type utilizing both the natural light and the backlight.

The liquid crystal display device includes a liquid crystal composition having a nematic phase. The composition has suitable characteristics. An AM device having good characteristics can be obtained by improving characteristics of the composition. Table 1 below summarizes a relationship in two characteristics therebetween. The characteristics of the composition will be further described based on a commercially available AM device. A temperature range of the nematic phase relates to a temperature range in which the device can be used. A preferred maximum temperature of the nematic phase is about 70° C. or higher, and a preferred minimum temperature of the nematic phase is about −10° C. or lower. Viscosity of the composition relates to a response time in the device. A short response time is preferred for displaying moving images on the device. A shorter response time even by one millisecond is desirable. Accordingly, a small viscosity in the composition is preferred. A small viscosity at low temperature is further preferred.

TABLE 1

Table 1. Characteristics of Composition and AM Device

| No. | Characteristics of Composition | Characteristics of AM Device |
| --- | --- | --- |
| 1 | Wide temperature range of a nematic phase | Wide usable temperature range |
| 2 | Small viscosity[1] | Short response time |
| 3 | Suitable optical anisotropy | Large contrast ratio |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |
| 7 | Large elastic constant | Large contrast ratio and short response time |

[1] A composition can be injected into a liquid crystal display device in a short time.

Optical anisotropy of the composition relates to a contrast ratio in the device. According to a mode of the device, large optical anisotropy or small optical anisotropy, more specifically, suitable optical anisotropy is required. A product (Δn×d) of the optical anisotropy (Δn) of the composition and a cell gap (d) in the device is designed so as to maximize the contrast ratio. A suitable value of the product depends on a type of the operating mode. In a device having a mode such as TN, the suitable value is about 0.45 micrometer. In a device having the VA mode, the suitable value is in the range of about 0.30 micrometer to about 0.40 micrometer, and in a device having the IPS mode or the FFS mode, the suitable value is in the range of about 0.20 micrometer to about 0.30 micrometer. In the above cases, a composition having the large optical anisotropy is preferred for a device having a small cell gap. Large dielectric anisotropy in the composition contributes to low threshold voltage, small electric power consumption and a large contrast ratio in the device. Accordingly, large positive or negative dielectric anisotropy is preferred. Large specific resistance in the composition contributes to a large voltage holding ratio and the large contrast ratio in the device. Accordingly, a composition having the large specific resistance at room temperature and also at a temperature close to the maximum temperature of the nematic phase in an initial stage is preferred. The composition having the large specific resistance at room temperature and also at a temperature close to the maximum temperature of the nematic phase even after the device has been used for a long period of time is preferred. Stability of the composition to ultraviolet light and heat relates to a service life of the device. In the case where the stability is high, the device has a long service life. Such characteristics are preferred for an AM device use in a liquid crystal projector, a liquid crystal television and so forth.

In a liquid crystal display device having a polymer sustained alignment (PSA) mode, a liquid crystal composition containing a polymer is used. First, a composition to which a small amount of a polymerizable compound is added is injected into the device. Next, the composition is irradiated with ultraviolet light while voltage is applied between substrates of the device. The polymerizable compound is polymerized to form a network structure of the polymer in the composition. In the composition, alignment of liquid crystal molecules can be controlled by the polymer, and therefore the response time in the device is shortened and also image persistence is improved. Such an effect of the polymer can be expected for a device having the mode such as the TN mode, the ECB mode, the OCB mode, the IPS mode, the VA mode, the FFS mode and the FPA mode.

In a general-purpose liquid crystal display device, vertical alignment of liquid crystal molecules is achieved by a polyimide alignment film. On the other hand, in a liquid crystal display device having no alignment film, a liquid crystal composition containing a polar compound and a polymer is used. First, a composition to which a small amount of the polar compound and a small amount of the polymerizable compound are added are injected into the device. Here, the liquid crystal molecules are aligned by action of the polar compound. Next, the composition is irradiated with ultraviolet light while voltage is applied between substrates of the device. Here, the polymerizable compound is polymerized to stabilize alignment of the liquid crystal molecules. In the composition, alignment of the liquid crystal molecules can be controlled by the polar compound and the polymer, and therefore the response time of the device is shortened, and image persistence is improved. Further, a step of forming an alignment film is unnecessary in the device having no alignment film. The device has no alignment film, and therefore reduction of electric resistance of the device by interaction between the alignment film and the composition is not caused. Such an effect by a combination of the polar compound and the polymer can be expected in a device having a mode such as TN, ECB, OCB, IPS, VA, FFS and FPA.

In the liquid crystal display device having no alignment film, various compounds each having a —OH group at a terminal have been so far synthesized as a compound that can cause vertical alignment of the liquid crystal molecules. Patent literature No. 1 describes biphenyl compound (S-1) having a —OH group at a terminal. However, in the compound, capability of vertically aligning liquid crystal molecules is high, but a voltage holding ratio is not sufficiently large when the compound is used in a liquid crystal display device.

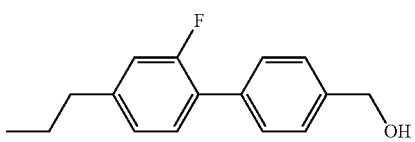

(S-1)

CITATION LIST

Patent Literature

Patent literature No. 1: WO 2014/090362 A.
Patent literature No. 2: WO 2014/094959 A.
Patent literature No. 3: WO 2013/004372 A.
Patent literature No. 4: WO 2012/104008 A.
Patent literature No. 5: WO 2012/038026 A.
Patent literature No. 6: JP S50-35076 A.

SUMMARY OF INVENTION

Technical Problem

A first object of the invention is to provide a polar compound having high chemical stability, high capability of aligning liquid crystal molecules, high solubility in a liquid crystal composition, and a large voltage holding ratio when used in a liquid crystal display device. A second object is to provide a liquid crystal composition containing the compound and satisfying at least one of characteristics such as high maximum temperature of a nematic phase, low minimum temperature of the nematic phase, small viscosity, suitable optical anisotropy, large positive or negative dielectric anisotropy, large specific resistance, high stability to ultraviolet light, high stability to heat and a large elastic constant. A third object is to provide a liquid crystal display device that includes the composition and has characteristics such as a wide temperature range in which the device can be used, a short response time, a high voltage holding ratio, low threshold voltage, a large contrast ratio and a long service life.

Solution to Problem

The invention concerns a compound represented by formula (1), a liquid crystal composition containing the compound, and a liquid crystal display device including the composition:

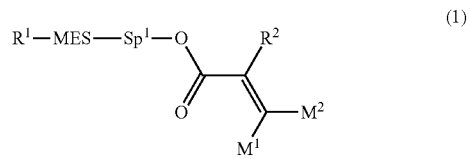

(1)

wherein, in formula (1), $R^1$ is alkyl having 1 to 15 carbons, and in the alkyl, at least one piece of —$CH_2$— may be replaced by —O— or —S—, and at least one piece of —$(CH_2)_2$— may be replaced by —CH=CH— or —C≡C—, and in the groups, at least one piece of hydrogen may be replaced by halogen;

MES is a mesogen group having at least one ring;

$Sp^1$ is a single bond or alkylene having 1 to 10 carbons, and in the alkylene, at least one piece of —$CH_2$— may be replaced by —O—, —CO—, —COO—, —OCO— or —OCOO—, and at least one piece of —$(CH_2)_2$— may be replaced by —CH=CH— or —C≡C—, and in the groups, at least one piece of hydrogen may be replaced by halogen;

$M^1$ and $M^2$ are independently hydrogen, halogen, alkyl having 1 to 5 carbons, or alkyl having 1 to 5 carbons in which at least one piece of hydrogen is replaced by halogen; and $R^2$ is a group represented by formula (1a), formula (1b) or formula (1c):

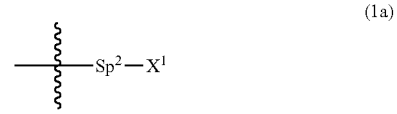

(1a)

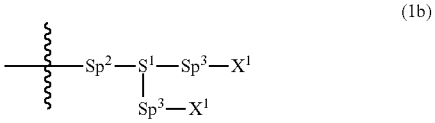

(1b)

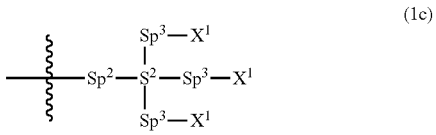

(1c)

wherein, in formula (1a), formula (1b) and formula (1c), $Sp^2$ and $Sp^3$ are independently a single bond or alkylene having 1 to 10 carbons, and in the alkylene, at least one piece of —$CH_2$— may be replaced by —O—, —NH—, —CO—, —COO—, —OCO— or —OCOO—, and at least one piece of —(CH$_2$)$_2$— may be replaced by —CH=CH— or —C≡C—, and in the groups, at least one piece of hydrogen may be replaced by halogen;

S$^1$ is >CH— or >N—;

S$^2$ is >C< or >Si<; and

X$^1$ is a group represented by —OH, —NH$_2$, —OR$^3$, —N(R$^3$)$_2$, formula (x1), —COOH, —SH, —B(OH)$_2$ or —Si(R$^3$)$_3$, in which R$^3$ is hydrogen or alkyl having 1 to 10 carbons, and in the alkyl, at least one piece of —CH$_2$— may be replaced by —O—, and at least one piece of —(CH$_2$)$_2$— may be replaced by —CH=CH—, and in the groups, at least one piece of hydrogen may be replaced by halogen, and w in formula (x1) is 1, 2, 3 or 4:

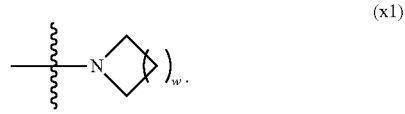

(x1)

Advantageous Effects of Invention

A first advantage of the invention is to provide a polar compound having high chemical stability, high capability of aligning liquid crystal molecules, high solubility in a liquid crystal composition, and a large voltage holding ratio when used in a liquid crystal display device. A second advantage is to provide a liquid crystal composition containing the compound and satisfying at least one of characteristics such as high maximum temperature of a nematic phase, low minimum temperature of the nematic phase, small viscosity, suitable optical anisotropy, large positive or negative dielectric anisotropy, large specific resistance, high stability to ultraviolet light, high stability to heat and a large elastic constant. A third advantage is to provide a liquid crystal display device that includes the composition and has characteristics such as a wide temperature range in which the device can be used, a short response time, a high voltage holding ratio, low threshold voltage, a large contrast ratio and a long service life.

DESCRIPTION OF EMBODIMENTS

Usage of terms herein is as described below. Terms "liquid crystal composition" and "liquid crystal display device" may be occasionally abbreviated as "composition" and "device," respectively. "Liquid crystal display device" is a generic term for a liquid crystal display panel and a liquid crystal display module. "Liquid crystal compound" is a generic term for a compound having a liquid crystal phase such as a nematic phase and a smectic phase, and a compound having no liquid crystal phase but to be mixed with a composition for the purpose of adjusting characteristics such as a temperature range of the nematic phase, viscosity and dielectric anisotropy. The compound has a six-membered ring such as 1,4-cyclohexylene and 1,4-phenylene, and has rod-like molecular structure. "Polymerizable compound" is a compound to be added for the purpose of forming a polymer in the composition. "Polar compound" helps alignment of liquid crystal molecules by interaction of a polar group with a substrate surface.

The liquid crystal composition is prepared by mixing a plurality of liquid crystal compounds. A proportion (content) of the liquid crystal compounds is expressed in terms of weight percent (% by weight) based on the weight of the liquid crystal composition. An additive such as an optically active compound, an antioxidant, an ultraviolet light absorber, a dye, an antifoaming agent, the polymerizable compound, a polymerization initiator, a polymerization inhibitor and a polar compound is added to the liquid crystal composition when necessary. A proportion (amount of addition) of the additive is expressed in terms of weight percent (% by weight) based on the weight of the liquid crystal composition in a manner similar to the proportion of the liquid crystal compound. Weight parts per million (ppm) may be occasionally used. A proportion of the polymerization initiator and the polymerization inhibitor is exceptionally expressed based on the weight of the polymerizable compound.

A compound represented by formula (1) may be occasionally abbreviated as "compound (1)." Compound (1) means one compound, a mixture of two compounds or a mixture of three or more compounds represented by formula (1). A same rule applies also to at least one compound selected from the group of compounds represented by formula (2), or the like. Symbol B$^1$, C$^1$, F or the like surrounded by a hexagonal shape corresponds to ring B$^1$, ring C$^1$ and ring F, respectively. The hexagonal shape represents a six-membered ring such as a cyclohexane ring and a benzene ring, or a condensed ring such as a naphthalene ring. An oblique line crossing the hexagonal shape represents that arbitrary hydrogen on the ring may be replaced by -Sp$^1$-P$^1$ group or the like. A subscript such as e represents the number of groups subjected to replacement. When the subscript is 0, no such replacement exists.

A symbol of terminal group R$^{11}$ is used in a plurality of component compounds. In the compounds, two groups represented by two pieces of arbitrary R$^{11}$ may be identical or different. For example, in one case, R$^{11}$ of compound (2) is ethyl and R$^{11}$ of compound (3) is ethyl. In another case, R$^{11}$ of compound (2) is ethyl and R$^{11}$ of compound (3) is propyl. A same rule applies also to a symbol of any other terminal group, a ring, a bonding group or the like. In formula (8), when i is 2, two of ring D$^1$ exists. In the compound, two groups represented by two of ring D$^1$ may be identical or different. A same rule applies also to two of arbitrary ring D$^1$ when i is larger than 2. A same rule applies also to a symbol of any other ring, a bonding group or the like.

An expression "at least one piece of 'A'" means that the number of 'A' is arbitrary. An expression "at least one piece of 'A' may be replaced by 'B'" means that, when the number of 'A' is 1, a position of 'A' is arbitrary, and also when the number of 'A' is 2 or more, positions thereof can be selected without restriction. A same rule applies also to an expression "at least one piece of 'A' is replaced by 'B'." An expression "at least one piece of A may be replaced by B, C or D" includes a case where at least one piece of A is replaced by B, a case where at least one piece of A is replaced by C, and a case where at least one piece of A is replaced by D, and also a case where a plurality of pieces of A are replaced by at least two pieces of B, C and D. For example, alkyl in which at least one piece of —CH$_2$— (or —(CH$_2$)$_2$—) may be replaced by —O— (or —CH=CH—) includes alkyl, alkenyl, alkoxy, alkoxyalkyl, alkoxyalkenyl and alkenyloxyalkyl. In addition, a case where two pieces of consecutive —CH$_2$— are replaced by —O— to form —O—O— is not preferred. In alkyl or the like, a case where —CH$_2$— of a methyl part (—CH$_2$—H) is replaced by —O— to form —O—H is not preferred, either.

Halogen means fluorine, chlorine, bromine or iodine. Preferred halogen is fluorine or chlorine. Further preferred halogen is fluorine. Alkyl is straight-chain alkyl or branched-chain alkyl, but includes no cyclic alkyl. In general, straight-chain alkyl is preferred to branched-chain alkyl. A same rule applies also to a terminal group such as alkoxy and alkenyl. With regard to a configuration of 1,4-cyclohexylene, trans is preferred to cis for increasing the maximum temperature of the nematic phase. Then, 2-fluoro-1,4-phenylene means two divalent groups described below. In a chemical formula, fluorine may be leftward (L) or rightward (R). A same rule applies also to an asymmetrical divalent group formed by removing two pieces of hydrogen from a ring, such as tetrahydropyran-2,5-diyl.

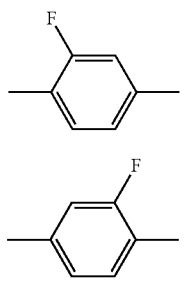
(L)
(R)

The invention includes items described below.

Item 1. A compound, represented by formula (1):

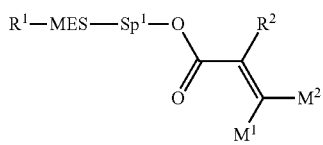
(1)

wherein, in formula (1), $R^1$ is alkyl having 1 to 15 carbons, and in the alkyl, at least one piece of —$CH_2$— may be replaced by —O— or —S—, and at least one piece of —$(CH_2)_2$— may be replaced by —CH=CH— or —C≡C—, and in the groups, at least one piece of hydrogen may be replaced by halogen;

MES is a mesogen group having at least one ring;

$Sp^1$ is a single bond or alkylene having 1 to 10 carbons, and in the alkylene, at least one piece of —$CH_2$— may be replaced by —O—, —CO—, —COO—, —OCO— or —OCOO—, and at least one piece of —$(CH_2)_2$— may be replaced by —CH=CH— or —C≡C—, and in the groups, at least one piece of hydrogen may be replaced by halogen;

$M^1$ and $M^2$ are independently hydrogen, halogen, alkyl having 1 to 5 carbons, or alkyl having 1 to 5 carbons in which at least one piece of hydrogen is replaced by halogen; and $R^2$ is a group represented by formula (1a), formula (1b) or formula (1c):

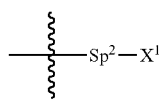
(1a)

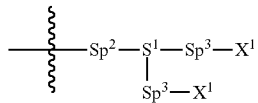
(1b)

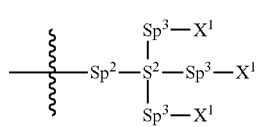
(1c)

wherein, in formula (1a), formula (1b) and formula (1c), $Sp^2$ and $Sp^3$ are independently a single bond or alkylene having 1 to 10 carbons, and in the alkylene, at least one piece of —$CH_2$— may be replaced by —O—, —NH—, —CO—, —COO—, —OCO— or —OCOO—, and at least one piece of —$(CH_2)_2$— may be replaced by —CH=CH— or —C≡C—, and in the groups, at least one piece of hydrogen may be replaced by halogen;

$S^1$ is >CH— or >N—;

$S^2$ is >C< or >Si<; and $X^1$ is a group represented —OH, —$NH_2$, —$OR^3$, —$N(R^3)_2$, formula (x1), —COOH, —SH, —$B(OH)_2$ or by —$Si(R^3)_3$, in which $R^3$ is hydrogen or alkyl having 1 to 10 carbons, and in the alkyl, at least one piece of —$CH_2$— may be replaced by —O—, and at least one piece of —$(CH_2)_2$— may be replaced by —CH=CH—, and in the groups, at least one piece of hydrogen may be replaced by halogen, and w in formula (x1) is 1, 2, 3 or 4:

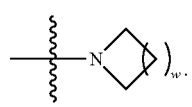
(x1)

Item 2. The compound according to item 1, represented by formula (1-1):

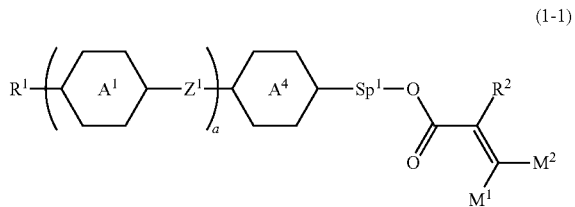
(1-1)

wherein, in formula (1-1), $R^1$ is alkyl having 1 to 15 carbons, and in the alkyl, at least one piece of —$CH_2$— may be replaced by —O— or —S—, and at least one piece of —$(CH_2)_2$— may be replaced by —CH=CH— or —C≡C—, and in the groups, at least one piece of hydrogen may be replaced by halogen;

ring $A^1$ and ring $A^4$ are independently 1,4-cyclohexylene, 1,4-cyclohexenylene, 1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5- diyl, pyrimidine-2,5-diyl, pyridine-2,5-diyl, fluorene-2,7-diyl, phenanthrene-2,7-diyl, anthracene-2,6-diyl, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one piece of hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one piece of hydrogen may be replaced by fluorine or chlorine;

$Z^1$ is a single bond or alkylene having 1 to 10 carbons, and in the alkylene, at least one piece of —$CH_2$— may be replaced by —O—, —CO—, —COO—, —OCO— or —OCOO—, and at least one piece of —$(CH_2)_2$— may be replaced by —CH=CH— or —C≡C—, and in the groups, at least one piece of hydrogen may be replaced by halogen;

$Sp^1$ is a single bond or alkylene having 1 to 10 carbons, and in the alkylene, at least one piece of —$CH_2$— may be replaced by —O—, —CO—, —COO—, —OCO— or —OCOO—, and at least one piece of —$(CH_2)_2$— may be replaced by —CH=CH— or —C≡C—, and in the groups, at least one piece of hydrogen may be replaced by halogen;

$M^1$ and $M^2$ are independently hydrogen, halogen, alkyl having 1 to 5 carbons, or alkyl having 1 to 5 carbons in which at least one piece of hydrogen is replaced by halogen;

a is 0, 1, 2, 3 or 4; and $R^2$ is a group represented by formula (1a) or formula (1b):

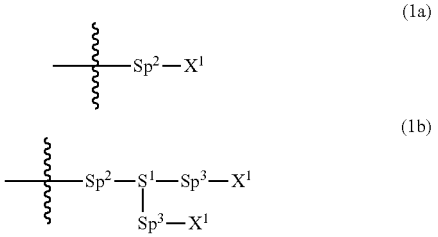

(1a)

(1b)

wherein, in formula (1a) and formula (1b), $Sp^2$ and $Sp^3$ are independently a single bond or alkylene having 1 to 10 carbons, and in the alkylene, at least one piece of —$CH_2$— may be replaced by —O—, —NH—, —CO—, —COO—, —OCO— or —OCOO—, and at least one piece of —$(CH_2)_2$— may be replaced by —CH=CH— or —C≡C—, and in the groups, at least one piece of hydrogen may be replaced by halogen;

$S^1$ is >CH— or >N—; and $X^1$ is a group represented by —OH, —$NH_2$, —$OR^3$, —$N(R^3)_2$, formula (x1), —COOH, —SH, —$B(OH)_2$ or —$Si(R^3)_3$, in which $R^3$ is hydrogen or alkyl having 1 to 10 carbons, and in the alkyl, at least one piece of —$CH_2$— may be replaced by —O—, and at least one piece of —$(CH_2)_2$— may be replaced by —CH=CH—, and in the groups, at least one piece of hydrogen may be replaced by halogen, and w in formula (x1) is 1, 2, 3 or 4:

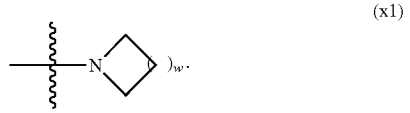

(x1)

Item 3. The compound according to item 1 or 2, represented by formula (1-2):

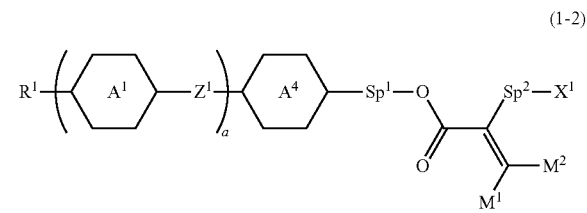

(1-2)

wherein, in formula (1-2), $R^1$ is alkyl having 1 to 15 carbons, alkenyl having 2 to 15 carbons, alkoxy having 1 to 14 carbons or alkenyloxy having 2 to 14 carbons, and in the groups, at least one piece of hydrogen may be replaced by fluorine or chlorine;

ring $A^1$ and ring $A^4$ are independently 1,4-cyclohexylene, 1,4-cyclohexenylene, 1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyridine-2,5-diyl, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one piece of hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one piece of hydrogen may be replaced by fluorine or chlorine;

$Z^1$ is a single bond, —$(CH_2)_2$—, —CH=CH—, —COO—, —OCO—, —$CF_2O$—, —$OCF_2$—, —$CH_2O$—, —$OCH_2$— or —CF=CF—;

$Sp^1$ and $Sp^2$ are independently a single bond or alkylene having 1 to 10 carbons, and in the alkylene, at least one piece of —$CH_2$— may be replaced by —O—, —COO— or —OCO—, and at least one piece of —$(CH_2)_2$— may be replaced by —CH=CH—, and in the groups, at least one piece of hydrogen may be replaced by fluorine or chlorine;

$M^1$ and $M^2$ are independently hydrogen, fluorine, alkyl having 1 to 5 carbons, or alkyl having 1 to 5 carbons in which at least one piece of hydrogen is replaced by fluorine;

$X^1$ is a group represented by —OH, —$NH_2$, —$OR^3$, —$N(R^3)_2$, formula (x1), —COOH, —SH, —$B(OH)_2$ or —$Si(R^3)_3$, in which $R^3$ is hydrogen or alkyl having 1 to 10 carbons, and in the alkyl, at least one piece of —$CH_2$— may be replaced by —O—, and at least one piece of —$(CH_2)_2$— may be replaced by —CH=CH—, and in the groups, at least one piece of hydrogen may be replaced by fluorine or chlorine, and w in formula (x1) is 1, 2, 3 or 4; and

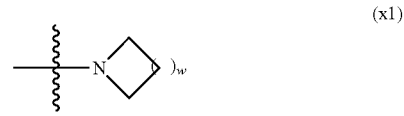

(x1)

wherein, a is 0, 1, 2, 3 or 4.

Item 4. The compound according to any one of items 1 to 3, represented by any one of formula (1-3) to formula (1-6):

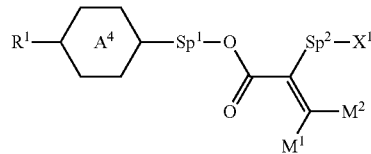 (1-3)

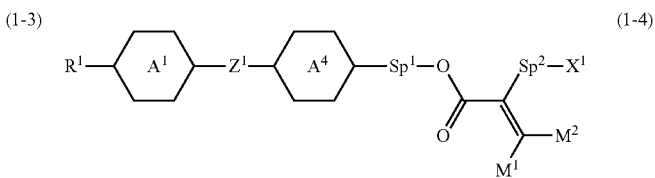 (1-4)

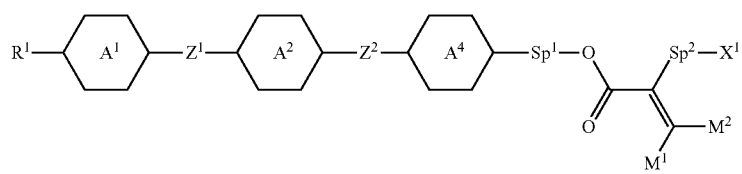 (1-5)

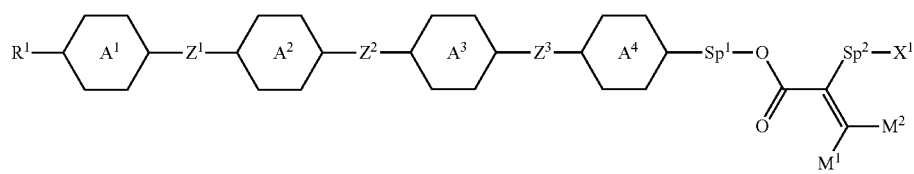 (1-6)

wherein, in formula (1-3) to formula (1-6), $R^1$ is alkyl having 1 to 15 carbons, alkenyl having 2 to 15 carbons, alkoxy having 1 to 14 carbons or alkenyloxy having 2 to 14 carbons, and in the groups, at least one piece of hydrogen may be replaced by fluorine;

ring $A^1$, ring $A^2$, ring $A^3$ and ring $A^4$ are independently 1,4-cyclohexylene, 1,4-cyclohexenylene, 1,4-phenylene, naphthalene-2,6-diyl, decahydronaphthalene-2,6-diyl, tetrahydropyran-2,5-diyl, 1,3-dioxane-2,5-diyl, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one piece of hydrogen may be replaced by fluorine, chlorine, alkyl having 1 to 7 carbons, alkenyl having 2 to 7 carbons or alkoxy having 1 to 6 carbons;

$Z^1$, $Z^2$ and $Z^3$ are independently a single bond, —(CH$_2$)$_2$—, —CH=CH—, —C≡C—, —COO—, —OCO—, —CF$_2$O—, —OCF$_2$—, —CH$_2$O—, —OCH$_2$— or —CF=CF—;

Sp$^1$ and Sp$^2$ are independently a single bond or alkylene having 1 to 7 carbons, and in the alkylene, at least one piece of —CH$_2$— may be replaced by —O—, —COO— or —OCO—, and at least one piece of —(CH$_2$)$_2$— may be replaced by —CH=CH—, and in the groups, at least one piece of hydrogen may be replaced by fluorine;

$M^1$ and $M^2$ are independently hydrogen, fluorine, methyl, ethyl or trifluoromethyl; and $X^1$ is a group represented by —OH, —NH$_2$, —OR$^3$, —N(R$^3$)$_2$, formula (x1) or —Si(R$^3$)$_3$, in which R$^3$ is hydrogen or alkyl having 1 to 5 carbons, and in the alkyl, at least one piece of —CH$_2$— may be replaced by —O—, and at least one piece of —(CH$_2$)$_2$— may be replaced by —CH=CH—, and in the groups, at least one piece of hydrogen may be replaced by fluorine, and w in formula (x1) is 1, 2, 3 or 4:

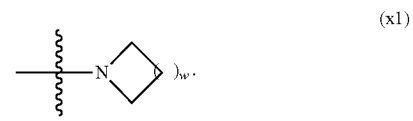 (x1)

Item 5. The compound according to any one of items 1 to 4, represented by any one of formula (1-7) to formula (1-10):

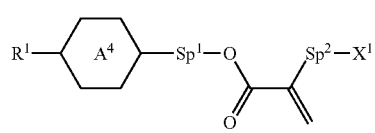 (1-7)

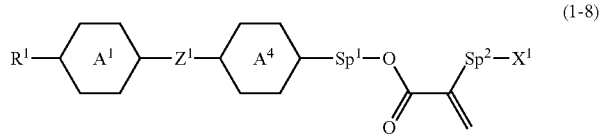 (1-8)

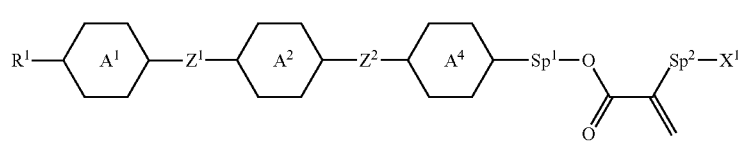 (1-9)

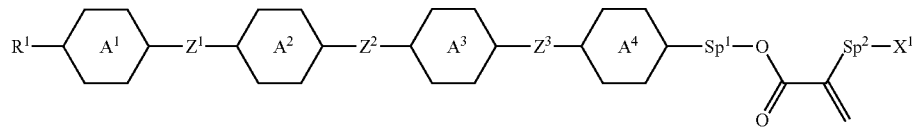
(1-10)

wherein, in formula (1-7) to formula (1-10), $R^1$ is alkyl having 1 to 10 carbons, alkenyl having 2 to 10 carbons or alkoxy having 1 to 9 carbons, and in the groups, at least one piece of hydrogen may be replaced by fluorine;

ring $A^1$, ring $A^2$, ring $A^3$ and ring $A^4$ are independently 1,4-cyclohexylene, 1,4-cyclohexenylene, 1,4-phenylene, tetrahydropyran-2,5-diyl, 1,3-dioxane-2,5-diyl, perhydrocyclopenta[a]phenanthrene-3,17-diyl or 2,3,4,7,8,9,10,11,12,13,14,15,16,17-tetradecahydrocyclopenta[a]phe nanthrene-3,17-diyl, and in the rings, at least one piece of hydrogen may be replaced by fluorine, chlorine, alkyl having 1 to 5 carbons, alkenyl having 2 to 5 carbons or alkoxy having 1 to 4 carbons;

$Z^1$, $Z^2$ and $Z^3$ are independently a single bond, —(CH$_2$)$_2$— or —CH=CH—;

Sp$^1$ is a single bond or alkylene having 1 to 7 carbons, and in the alkylene, at least one piece of —CH$_2$— may be replaced by —O—, and at least one piece of —(CH$_2$)$_2$— may be replaced by —CH=CH—;

Sp$^2$ is alkylene having 1 to 7 carbons, and in the alkylene, at least one piece of —CH$_2$— may be replaced by —O—; and $X^1$ is —OH, —NH$_2$ or —N(R$^3$)$_2$, in which R$^3$ is hydrogen or alkyl having 1 to 5 carbons, and in the alkyl, at least one piece of —CH$_2$— may be replaced by —O—, and at least one piece of —(CH$_2$)$_2$— may be replaced by —CH=CH—, and in the groups, at least one piece of hydrogen may be replaced by fluorine.

Item 6. The compound according to any one of items 1 to 5, represented by any one of formula (1-11) to formula (1-14):

wherein, in formula (1-11) to formula (1-14), $R^1$ is alkyl having 1 to 10 carbons, alkenyl having 2 to 10 carbons or alkoxy having 1 to 9 carbons, and in the groups, at least one piece of hydrogen may be replaced by fluorine;

ring $A^1$, ring $A^2$, ring $A^3$ and ring $A^4$ are independently 1,4-cyclohexylene, 1,4-phenylene, perhydrocyclopenta[a]phenanthrene-3,17-diyl or 2,3,4,7,8,9,10,11,12,13,14,15,16,17-tetradecahydrocyclopenta[a]phe nanthrene-3,17-diyl, and in the rings, at least one piece of hydrogen may be replaced by fluorine or alkyl having 1 to 5 carbons;

$Z^1$, $Z^2$ and $Z^3$ are independently a single bond or —(CH$_2$)$_2$—;

Sp$^1$ is a single bond or alkylene having 1 to 5 carbons, and in the alkylene, at least one piece of —CH$_2$— may be replaced by —O—;

Sp$^2$ is alkylene having 1 to 5 carbons, and in the alkylene, at least one piece of —CH$_2$— may be replaced by —O—; and $X^1$ is —OH, —NH$_2$ or —N(R$^3$)$_2$, in which R$^3$ is hydrogen or alkyl having 1 to 5 carbons, and in the alkyl, at least one piece of —CH$_2$— may be replaced by —O—, and at least one piece of —(CH$_2$)$_2$— may be replaced by —CH=CH—, and in the groups, at least one piece of hydrogen may be replaced by fluorine.

Item 7. The compound according to any one of items 1 to 6, represented by any one of formula (1-15) to formula (1-31):

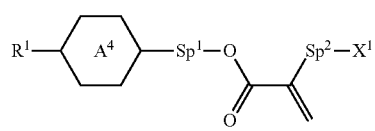
(1-11)

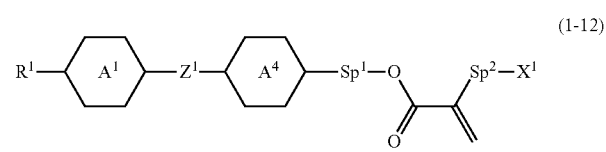
(1-12)

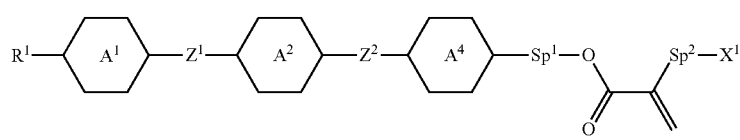
(1-13)

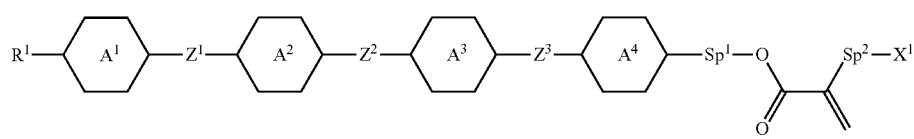
(1-14)

(1-15)
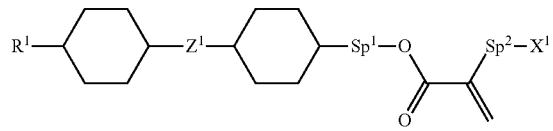
(1-16)
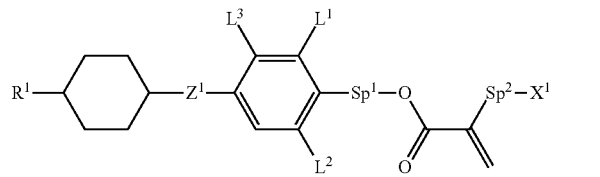
(1-17)
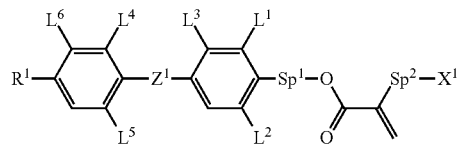
(1-18)
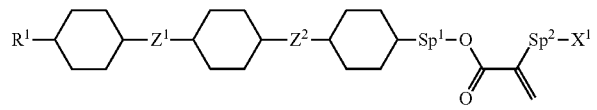
(1-19)
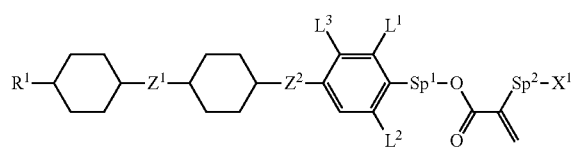
(1-20)
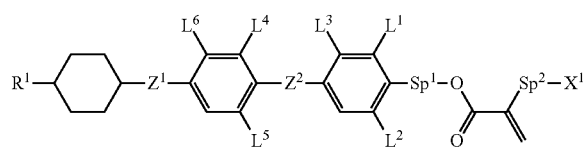
(1-21)
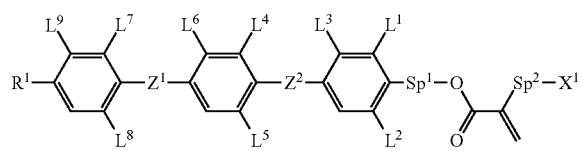
(1-22)
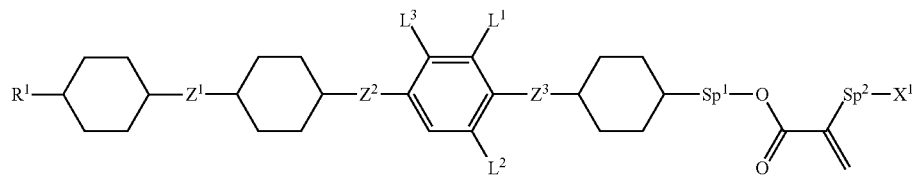
(1-23)
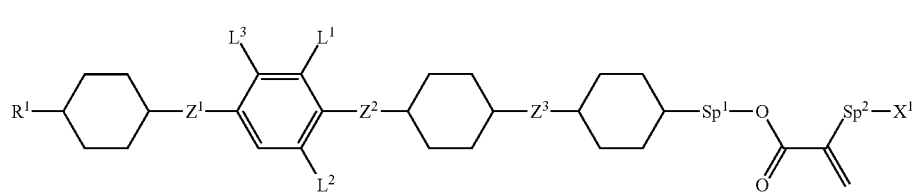
(1-24)
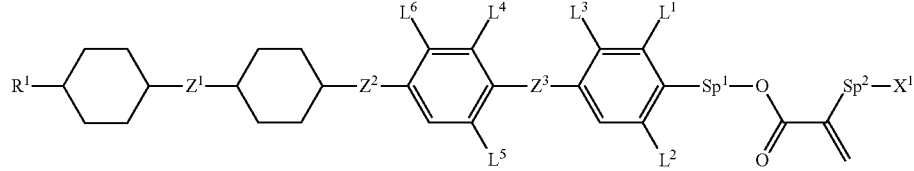
(1-25)
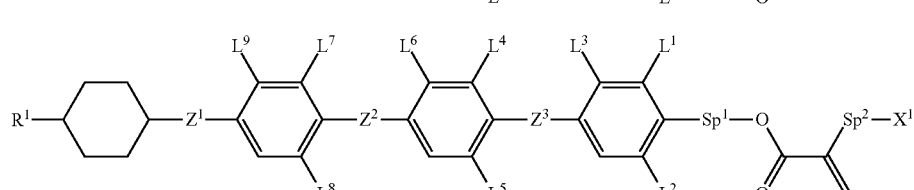
(1-26)
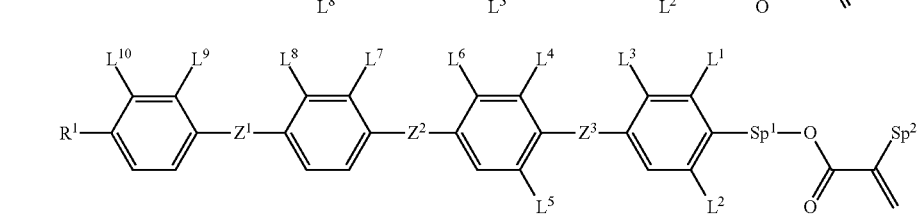

-continued

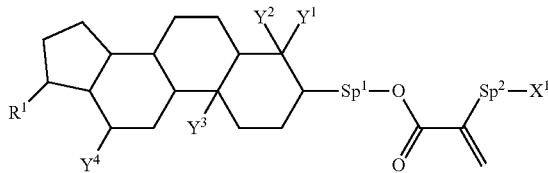
(1-27)

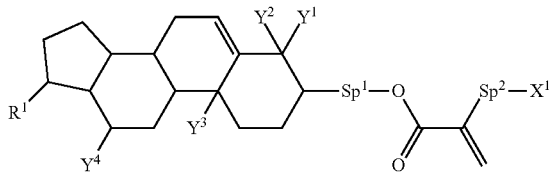
(1-28)

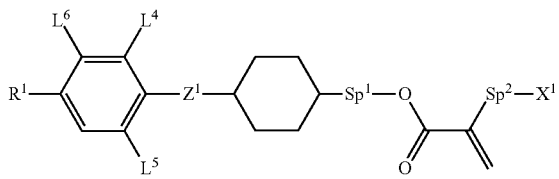
(1-29)

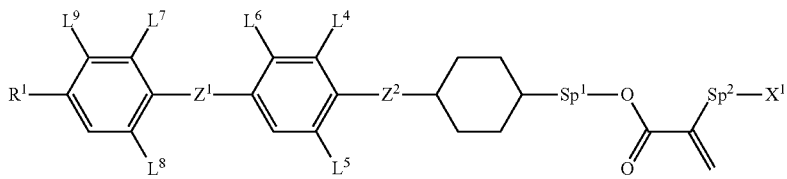
(1-30)

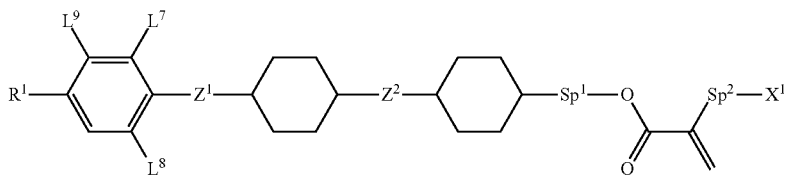
(1-31)

wherein, in formula (1-15) to formula (1-31), $R^1$ is alkyl having 1 to 10 carbons, alkenyl having 2 to 10 carbons or alkoxy having 1 to 9 carbons, and in the groups, at least one piece of hydrogen may be replaced by fluorine;

$Z^1$, $Z^2$ and $Z^3$ are independently a single bond or —(CH$_2$)$_2$—;

Sp$^1$ is a single bond or alkylene having 1 to 5 carbons, and in the alkylene, at least one piece of —CH$_2$— may be replaced by —O—;

Sp$^2$ is alkylene having 1 to 5 carbons, and in the alkylene, at least one piece of —CH$_2$— may be replaced by —O—;

$L^1$, $L^2$, $L^3$, $L^4$, $L^6$, $L^7$, $L^8$, $L^9$ and $L^{10}$ are independently hydrogen, fluorine, methyl or ethyl;

$Y^1$, $Y^2$, $Y^3$ and $Y^4$ are independently hydrogen or methyl; and $X^1$ is —OH, —NH$_2$ or —N(R$^3$)$_2$, in which R$^3$ is hydrogen or alkyl having 1 to 4 carbons, and in the alkyl, at least one piece of —CH$_2$— may be replaced by —O—, and in the groups, at least one piece of hydrogen may be replaced by fluorine.

Item 8. The compound according to any one of items 1 to 7, represented by any one of formula (1-32) to formula (1-43):

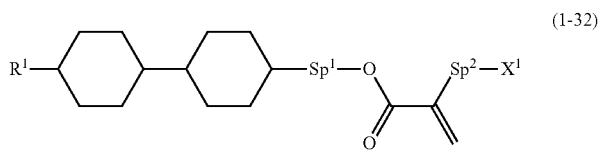
(1-32)

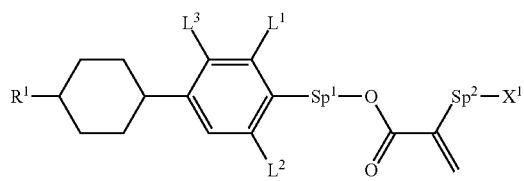
(1-33)

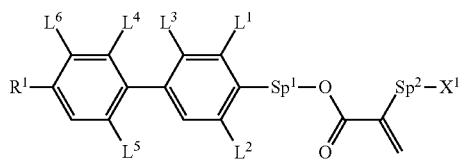
(1-34)

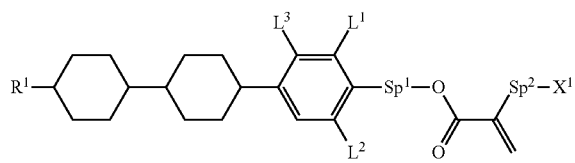
(1-35)

-continued (1-36)
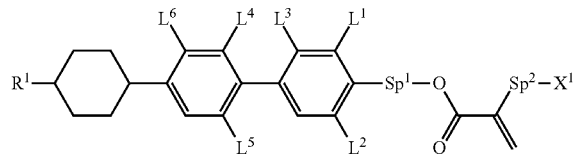

(1-37)
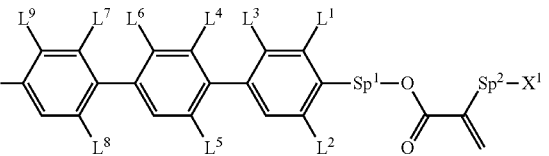

(1-38)
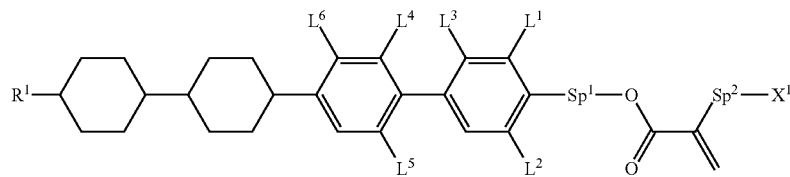

(1-39)
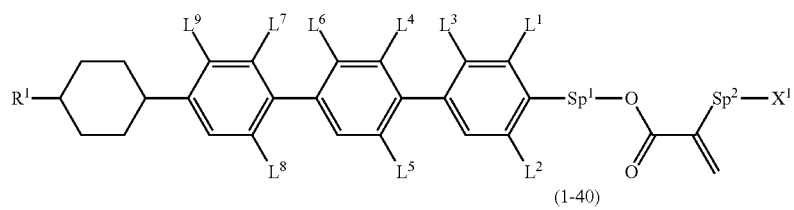

(1-40)
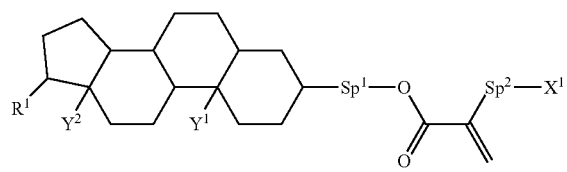

(1-41)
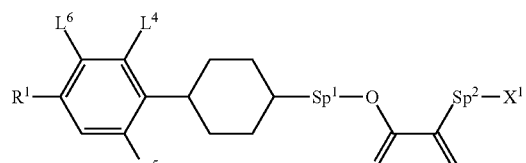

(1-42)
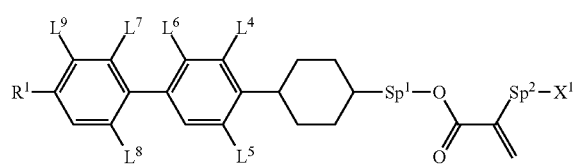

(1-43)
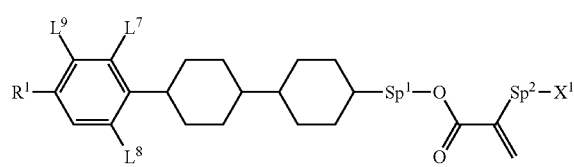

wherein, in formula (1-32) to formula (1-43), $R^1$ is alkyl having 1 to 10 carbons;

$Sp^1$ is a single bond or alkylene having 1 to 5 carbons, and in the alkylene, at least one piece of —$CH_2$— may be replaced by —O—, and in the groups, at least one piece of hydrogen may be replaced by fluorine;

$Sp^2$ is alkylene having 1 to 5 carbons, and in the alkylene, at least one piece of —$CH_2$— may be replaced by —O—;

$L^1$, $L^2$, $L^3$, $L^4$, $L^5$, $L^6$, $L^7$, $L^8$ and $L^9$ are independently hydrogen, fluorine, methyl or ethyl;

$Y^1$ and $Y^2$ are independently hydrogen or methyl; and $X^1$ is —OH, —$NH_2$ or —$N(R^3)_2$, in which $R^3$ is hydrogen or alkyl having 1 to 4 carbons, and in the alkyl, at least one piece of —$CH_2$— may be replaced by —O—.

Item 9. The compound according to any one of items 1 to 8, represented by any one of formula (1-44) to formula (1-63):

(1-44)
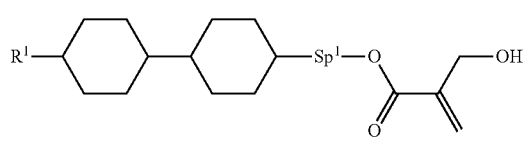

-continued (1-45)
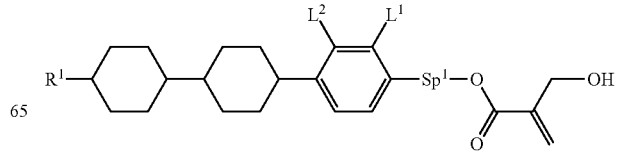

(1-46)

(1-47)

-continued
(1-48)
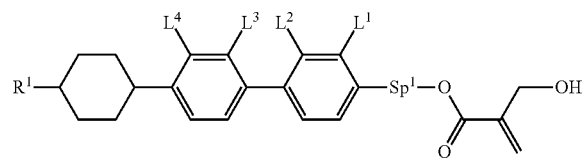
(1-49)
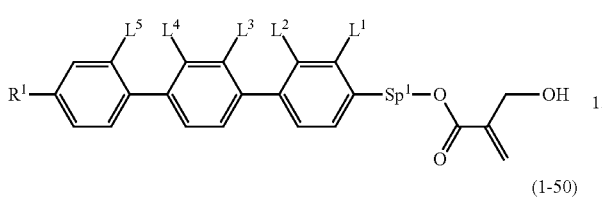
(1-50)
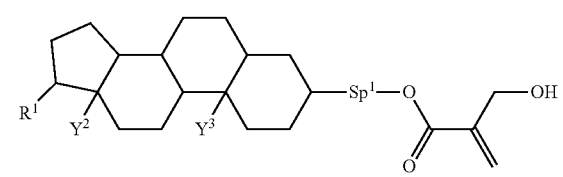
(1-51)
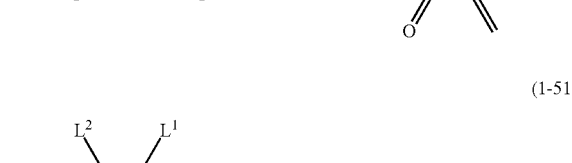
(1-52)
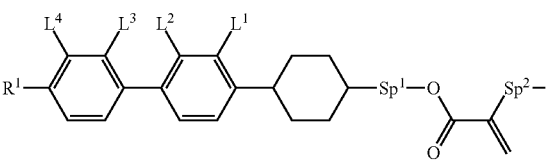
(1-53)
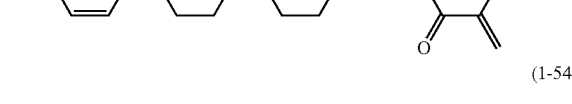
(1-54)
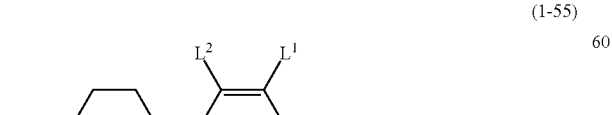
(1-55)
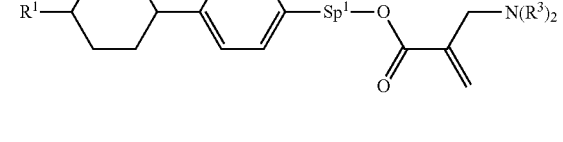
(1-56)
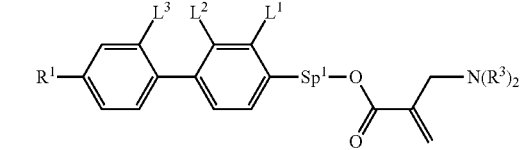
(1-57)
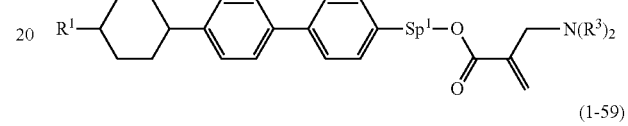
(1-58)
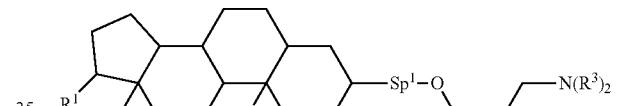
(1-59)
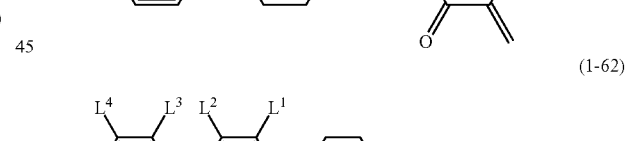
(1-60)
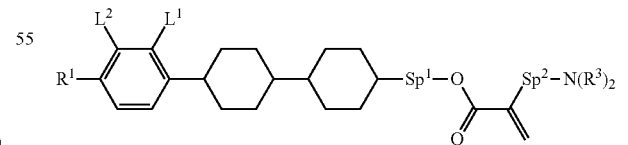
(1-61)
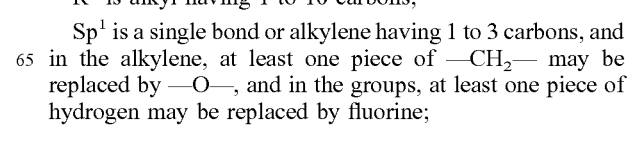
(1-62)
(1-63)
wherein, in formula (1-44) to formula (1-63),
$R^1$ is alkyl having 1 to 10 carbons;
$Sp^1$ is a single bond or alkylene having 1 to 3 carbons, and in the alkylene, at least one piece of —$CH_2$— may be replaced by —O—, and in the groups, at least one piece of hydrogen may be replaced by fluorine;

Sp$^2$ is alkylene having 1 to 5 carbons, and in the alkylene, at least one piece of —CH$_2$— may be replaced by —O—;

L$^1$, L$^2$, L$^3$, L$^4$, and L$^5$ are independently hydrogen, fluorine, methyl or ethyl;

Y$^1$ and Y$^2$ are independently hydrogen or methyl; and

R$^3$ is hydrogen, methyl or ethyl.

Item 10. A liquid crystal composition, containing at least one compound according to any one of items 1 to 9.

Item 11. The liquid crystal composition according to item 10, further containing at least one compound selected from the group of compounds represented by formula (2) to formula (4):

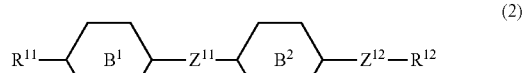
(2)

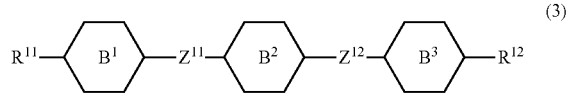
(3)

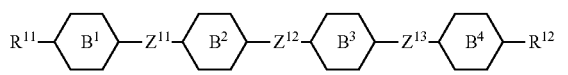
(4)

wherein, in formula (2) to formula (4),

R$^{11}$ and R$^{12}$ are independently alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

ring B$^1$, ring B$^2$, ring B$^3$ and ring B$^4$ are independently 1,4-cyclohexylene, 1,4-phenylene, 2-fluoro-1,4-phenylene, 2,5-difluoro-1,4-phenylene or pyrimidine-2,5-diyl; and Z$^{11}$, Z$^{12}$ and Z$^{13}$ are independently a single bond, —(CH$_2$)$_2$—, —CH═CH—, —C≡C— or —COO—.

Item 12. The liquid crystal composition according to item 10 or 11, further containing at least one compound selected from the group of compounds represented by formula (5) to formula (7):

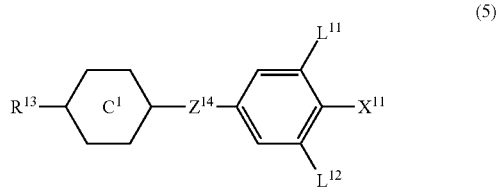
(5)

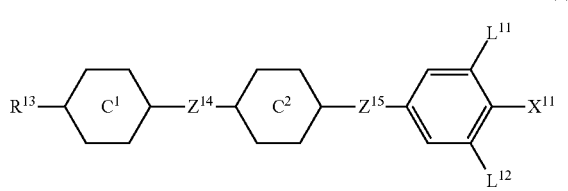
(6)

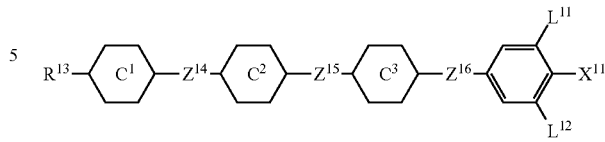
(7)

wherein, in formula (5) to formula (7),

R$^{13}$ is alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring C$^1$, ring C$^2$ and ring C$^3$ are independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

Z$^{14}$, Z$^{15}$ and Z$^{16}$ are independently a single bond, —(CH$_2$)$_2$—, —CH═CH—, —C≡C—, —COO—, —CF$_2$O—, —OCF$_2$—, —CH$_2$O— or —(CH$_2$)$_4$—; and L$^{11}$ and L$^{12}$ are independently hydrogen or fluorine.

Item 13. The liquid crystal composition according to item 10 or 11, further containing at least one compound selected from the group of compounds represented by formula (8):

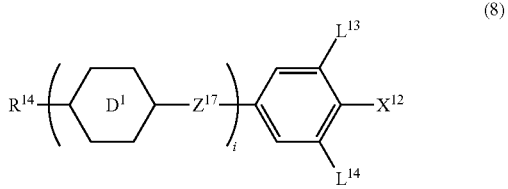
(8)

wherein, in formula (8),

R$^{14}$ is alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

X$^{12}$ is —C≡N or —C≡C—C≡N;

ring D$^1$ is 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

Z$^{17}$ is a single bond, —(CH$_2$)$_2$—, —C≡C—, —COO—, —CF$_2$O—, —OCF$_2$— or —CH$_2$O—;

L$^{13}$ and L$^{14}$ are independently hydrogen or fluorine; and i is 1, 2, 3 or 4.

Item 14. The liquid crystal composition according to item 10 or 11, further containing at least one compound selected from the group of compounds represented by formula (9) to formula (15):

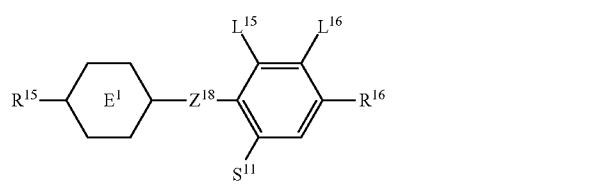
(9)

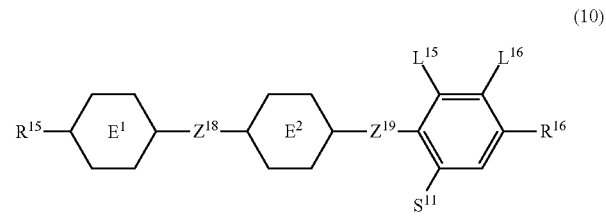
(10)

(11)
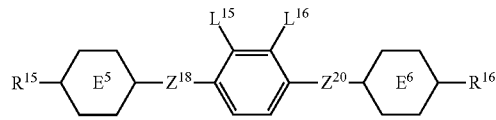

(12)
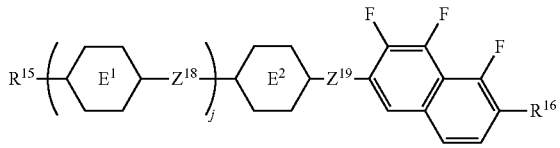

(13)
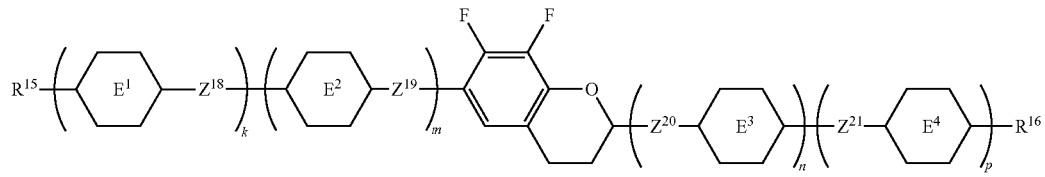

(14)
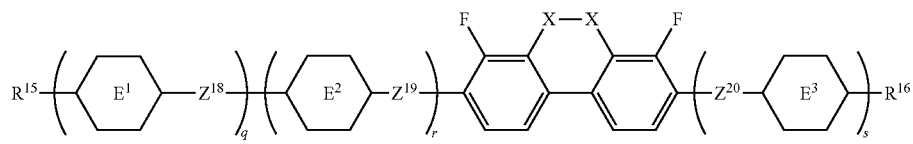

(15)
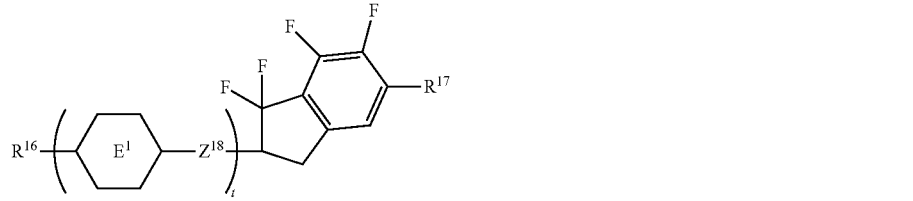

wherein, in formula (9) to formula (15), $R^{15}$ and $R^{16}$ are independently alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

$R^{17}$ is hydrogen, fluorine, alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one piece of hydrogen may be replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —(CH$_2$)$_2$—, —COO—, —CH$_2$O—, —OCF$_2$— or —OCF$_2$CH$_2$CH$_2$—;

$L^{15}$ and $L^{16}$ are independently fluorine or chlorine;

$S^{11}$ is hydrogen or methyl;

X is —CHF— or —CF$_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 15. The liquid crystal composition according to any one of items 10 to 14, containing at least one polymerizable compound selected from the group of compounds represented by formula (16):

(16)
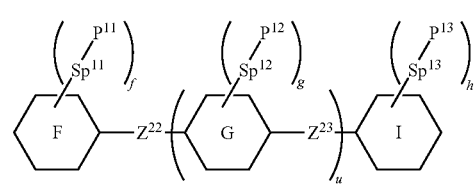

wherein, in formula (16), ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one piece of hydrogen may be replaced by halogen, alkyl having 1 to 12 carbons or alkyl having 1 to 12 carbons in which at least one piece of hydrogen is replaced by halogen;

ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen is replaced by halogen;

$Z^{22}$ and $Z^{23}$ are independently a single bond or alkylene having 1 to 10 carbons, and in the alkylene, at least one piece of —CH$_2$— may be replaced by —O—, —CO—, —COO— or —OCOO—, and at least one piece of —(CH$_2$)$_2$— may be replaced by —CH═CH—, —C(CH$_3$)═CH—, —CH═C (CH₃)— or —C(CH₃)=C(CH₃)—, and in the groups, at least one piece of hydrogen may be replaced by fluorine or chlorine;

$P^{11}$, $P^{12}$ and $P^{13}$ are independently a polymerizable group;

$Sp^{11}$, $Sp^{12}$ and $Sp^{13}$ are independently a single bond or alkylene having 1 to 10 carbons, and in the alkylene, at least one piece of —CH₂— may be replaced by —O—, —COO—, —OCO— or —OCOO—, and at least one piece of —(CH₂)₂— may be replaced by —CH=CH— or —C≡C—, and in the groups, at least one piece of hydrogen may be replaced by fluorine or chlorine;

u is 0, 1 or 2; and f, g and h are independently 0, 1, 2, 3 or 4, and a sum of f, g and h is 2 or more.

Item 16. The liquid crystal composition according to item 15, wherein, in formula (16) described in item 15, $P^{11}$, $P^{12}$ and $P^{13}$ are independently a polymerizable group selected from the group of groups represented by formula (P-1) to formula (P-5):

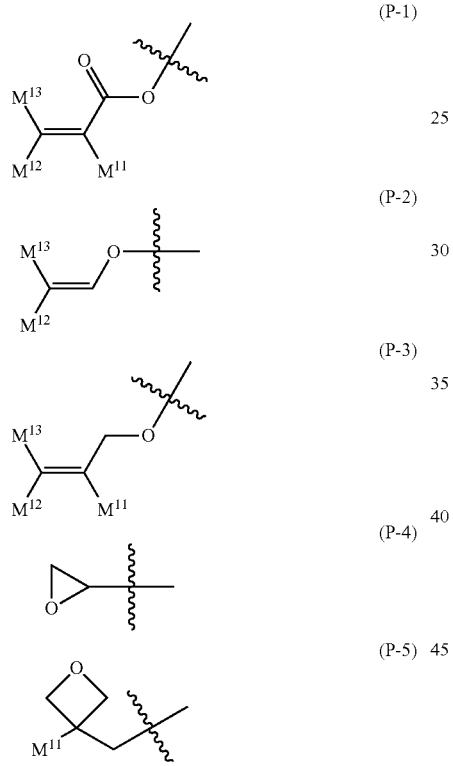

wherein, in formula (P-1) to formula (P-5), $M^{11}$, $M^{12}$ and $M^{13}$ are independently hydrogen, fluorine, alkyl having 1 to 5 carbons, or alkyl having 1 to 5 carbons in which at least one piece of hydrogen is replaced by halogen.

Item 17. The liquid crystal composition according to any one of items 10 to 16, containing at least one polymerizable compound selected from the group of compounds represented by formula (16-1) to formula (16-27):

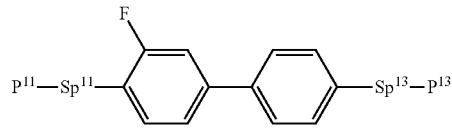

(16-1)

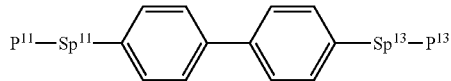

(16-2)

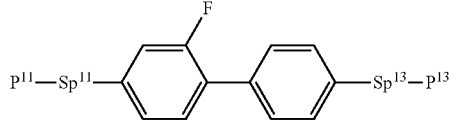

(16-3)

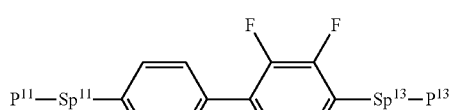

(16-4)

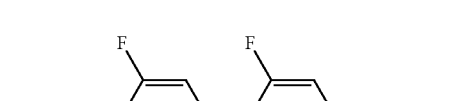

(16-5)

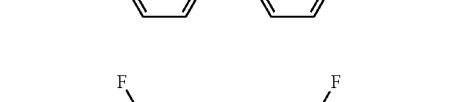

(16-6)

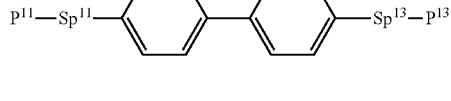

(16-7)

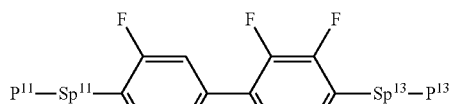

(16-8)

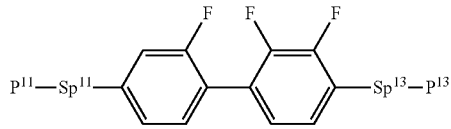

(16-9)

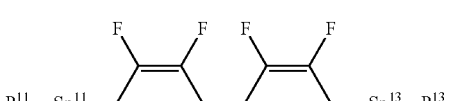

(16-10)

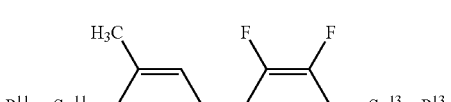

(16-11)

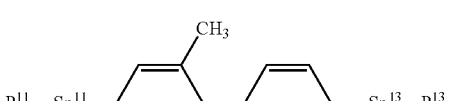

(16-12)

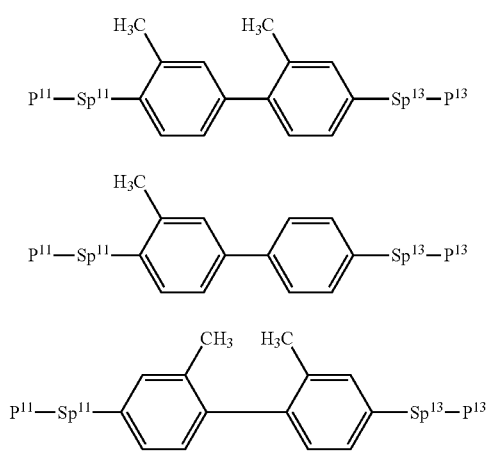
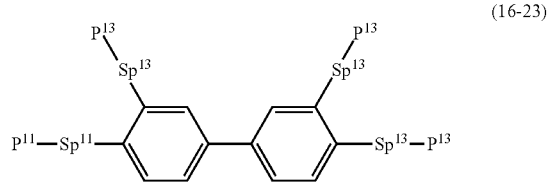
wherein, in formula (16-1) to formula (16-27),
$P^{11}$, $P^{12}$ and $P^{13}$ are independently a polymerizable group selected from the group of groups represented by formula (P-1) to formula (P-3), in which $M^{11}$, $M^{12}$ and $M^{13}$ are independently hydrogen, fluorine, alkyl having 1 to 5 carbons, or alkyl having 1 to 5 carbons in which at least one piece of hydrogen is replaced by halogen: and
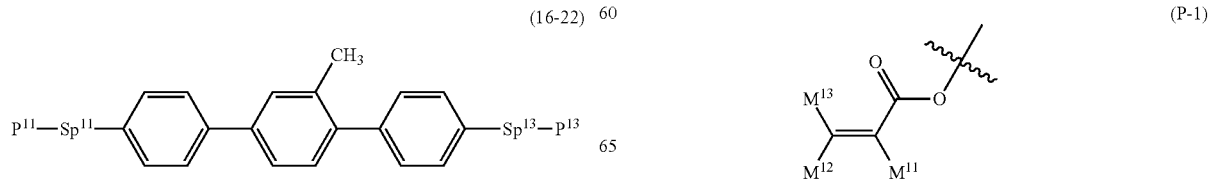

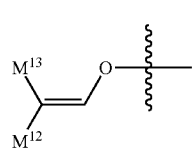
(P-2)

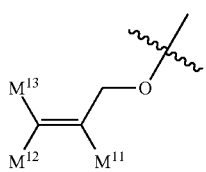
(P-3)

wherein, $p^{11}$, $Sp^{12}$ and $Sp^{13}$ are independently a single bond or alkylene having 1 to 10 carbons, and in the alkylene, at least one piece of —$CH_2$— may be replaced by —O—, —COO—, —OCO— or —OCOO—, and at least one piece of —$(CH_2)_2$— may be replaced by —CH=CH— or —C≡C—, and in the groups, at least one piece of hydrogen may be replaced by fluorine or chlorine.

Item 18. The liquid crystal composition according to any one of items 10 to 17, further containing at least one selected from a polymerizable compound other than formula (1) and formula (16), a polymerization initiator, a polymerization inhibitor, an optically active compound, an antioxidant, an ultraviolet light absorber, a light stabilizer, a heat stabilizer and an antifoaming agent.

Item 19. A liquid crystal display device, including at least one liquid crystal composition according to any one of items 10 to 18.

The invention further includes the following items: (a) the liquid crystal composition, further containing at least two of additives such as a polymerizable compound, a polymerization initiator, a polymerization inhibitor, an optically active compound, an antioxidant, an ultraviolet light absorber, a light stabilizer, a heat stabilizer and an antifoaming agent; (b) a polymerizable composition, prepared by adding a polymerizable compound different from compound (1) or compound (16) to the liquid crystal composition; (c) a polymerizable composition, prepared by adding compound (1) and compound (16) to the liquid crystal composition; (d) a liquid crystal composite, prepared by polymerizing a polymerizable composition; (e) a polymer sustained alignment mode device including the liquid crystal composite; and (f) a polymer sustained alignment mode device, prepared by using a polymerizable composition prepared by adding compound (1), compound (16) and a polymerizable compound different from compound (1) or compound (16) to the liquid crystal composition.

An aspect of compound (1), synthesis of compound (1), the liquid crystal composition and the liquid crystal display device will be described in the order.

1. Aspect of Compound (1)

Compound (1) of the invention has a feature of having a mesogen moiety constituted of at least one ring, and an acryloyloxy group in which replacement is made by a polar group such as a hydroxyalkyl group. The polar group noncovalently interacts with a substrate surface of glass (or metal oxide), and therefore compound (1) is useful. One of applications is an additive for the liquid crystal composition used in the liquid crystal display device. Compound (1) is added for the purpose of controlling alignment of liquid crystal molecules. Such an additive is preferably chemically stable under conditions that the additive is tighten sealed in the device, has high solubility in the liquid crystal composition, and a large voltage holding ratio when used in the liquid crystal display device. Compound (1) satisfies such characteristics to a significant extent.

Preferred examples of compound (1) will be described. Preferred examples of $R^1$, MES, $Sp^1$, $R^2$, $M^1$ or $M^2$ in compound (1) are also applied to a subordinate formula of formula (1) for compound (1). In compound (1), characteristics can be arbitrarily adjusted by suitably combining kinds of the groups. Compound (1) may contain a larger amount of isotope such as $^2H$ (deuterium) and $^{13}C$ than an amount of natural abundance because no significant difference exists in the characteristics of the compound.

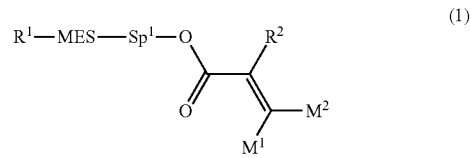
(1)

In formula (1), $R^1$ is alkyl having 1 to 15 carbons, and in the alkyl, at least one piece of —$CH_2$— may be replaced by —O— or —S—, and at least one piece of —$(CH_2)_2$— may be replaced by —CH=CH— or —C≡C—, and in the groups, at least one piece of hydrogen may be replaced by halogen.

Preferred $R^1$ is alkyl having 1 to 15 carbons, alkenyl having 2 to 15 carbons, alkoxy having 1 to 14 carbons or alkenyloxy having 2 to 14 carbons. Further preferred $R^1$ is alkyl having 1 to 10 carbons, alkenyl having 2 to 10 carbons or alkoxy having 1 to 9 carbons. Particularly preferred $R^1$ is alkyl having 1 to 10 carbons.

In formula (1), MES is a mesogen group having at least one ring. The mesogen group is well known by those skilled in the art. The mesogen group means a part that contributes to formation of a liquid crystal phase when the compound has the liquid crystal phase (intermediate phase). Specific examples of preferred compound (1) include compound (1-1).

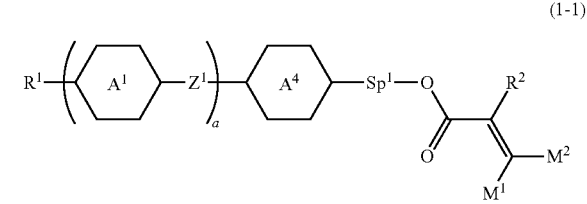
(1-1)

Preferred ring $A^1$ or ring $A^4$ is 1,4-cyclohexylene, 1,4-cyclohexenylene, 1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, perhydrocyclopenta[a]phenanthrene-3,17-diyl or 2,3,4,7,8,9,10,11,12,13,14,15,16,17-tetradecahydrocyclopenta[a]phe nanthrene-3,17-diyl, and in the rings, at least one piece of hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one piece of hydrogen may be replaced by fluorine or chlorine. Further preferred ring $A^1$ or ring $A^4$ is 1,4-cyclohexylene, 1,4-phenylene, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one piece of hydrogen may be replaced by fluorine or alkyl having 1 to 5 carbons. Particularly preferred ring $A^1$ or ring $A^4$ is 1,4-cyclohexylene, 1,4-phenylene or perhydrocyclopenta[a]phenanthrene-3,17-diyl, and in the rings, for example, as in 1-methyl-1,4-cyclohexylene, 2-ethyl-1,4-cyclohexylene and 2-fluoro-1,4-phenylene, at least one piece of hydrogen may be replaced by fluorine, methyl or ethyl.

In formula (1-1), $Z^1$ is a single bond or alkylene having 1 to 10 carbons, and in the alkylene, at least one piece of —$CH_2$— may be replaced by —O—, —CO—, —COO—, —OCO— or —OCOO—, and at least one piece of —$(CH_2)_2$— may be replaced by —CH=CH— or —C≡C—, and in the groups, at least one piece of hydrogen may be replaced by halogen.

Preferred $Z^1$ is a single bond, —$(CH_2)_2$—, —CH=CH—, —C≡C—, —COO—, —OCO—, —$CF_2O$—, —$OCF_2$—, —$CH_2O$—, —$OCH_2$— or —CF=CF—. Further preferred $Z^1$ is a single bond, —$(CH_2)_2$— or —CH=CH—. Particularly preferred $Z^1$ is a single bond.

In formula (1-1), a is 0, 1, 2, 3 or 4. Preferred a is 0, 1, 2 or 3. Further preferred a is 0, 1 or 2.

In formula (1), $Sp^1$ is a single bond or alkylene having 1 to 10 carbons, and in the alkylene, at least one piece of —$CH_2$— may be replaced by —O—, —CO—, —COO—, —OCO— or —OCOO—, and at least one piece of —$(CH_2)_2$— may be replaced by —CH=CH— or —C≡C—, and in the groups, at least one piece of hydrogen may be replaced by halogen.

Preferred $Sp^1$ is a single bond, alkylene having 1 to 5 carbons, or alkylene having 1 to 5 carbons in which one piece of —$CH_2$— is replaced by —O—. Further preferred $Sp^1$ is a single bond, alkylene having 1 to 3 carbons, or alkylene having 1 to 3 carbons in which one piece of —$CH_2$— is replaced by —O—.

In formula (1), $M^1$ and $M^2$ are independently hydrogen, halogen, alkyl having 1 to 5 carbons, or alkyl having 1 to 5 carbons in which at least one piece of hydrogen is replaced by halogen. Preferred $M^1$ or $M^2$ is hydrogen, fluorine, methyl, ethyl or trifluoromethyl. Further preferred $M^1$ or $M^2$ is hydrogen.

In formula (1), $R^2$ is a group represented by formula (1a), formula (1b) or formula (1c). Preferred $R^2$ is a group represented by formula (1a) or formula (1b). Further preferred $R^2$ is a group represented by formula (1a).

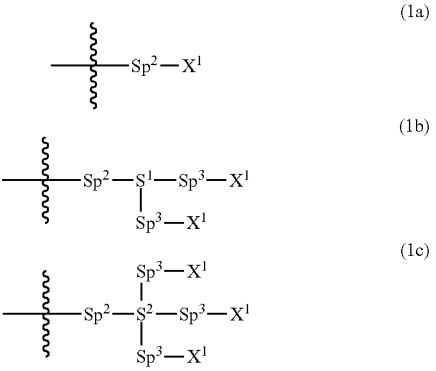

In formula (1a), formula (1b) and formula (1c), $Sp^2$ and $Sp^3$ are independently a single bond or alkylene having 1 to 10 carbons, and in the alkylene, at least one piece of —$CH_2$— may be replaced by —O—, —NH—, —CO—, —COO—, —OCO— or —OCOO—, and at least one piece of —$(CH_2)_2$— may be replaced by —CH=CH— or —C≡C—, and in the groups, at least one piece of hydrogen may be replaced by halogen.

Preferred $Sp^2$ or $Sp^3$ is alkylene having 1 to 7 carbons or alkylene having 1 to 5 carbons in which one piece of —$CH_2$— is replaced by —O—. Further preferred $Sp^2$ or $Sp^3$ is alkylene having 1 to 5 carbons or alkylene having 1 to 5 carbons in which one piece of —$CH_2$— is replaced by —O—. Particularly preferred $Sp^2$ or $Sp^3$ is —$CH_2$—.

In formulas (1a) to (1c), $S^1$ is >CH— or >N—; and $S^2$ is >C< or >Si<. Preferred $S^1$ is >CH— or >N—, and preferred $S^2$ is >C<. Formula (1b) is preferred to formula (1c).

In formulas (1a) to (1c), $X^1$ is a group represented by —OH, —$NH_2$, —$OR^3$, —$N(R^3)_2$, formula (x1), —COOH, —SH, —$B(OH)_2$ or —$Si(R^3)_3$, in which $R^3$ is hydrogen or alkyl having 1 to 10 carbons, and in the alkyl, at least one piece of —$CH_2$— may be replaced by —O—, and at least one piece of —$(CH_2)_2$— may be replaced by —CH=CH—, and in the groups, at least one piece of hydrogen may be replaced by halogen, and w in formula (x1) is 1, 2, 3 or 4.

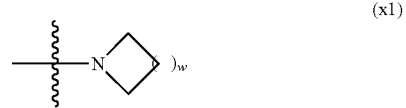

Preferred $X^1$ is a group represented by —OH, —$NH_2$, —$OR^3$, —$N(R^3)_2$, formula (x1) or —$Si(R^3)_3$, in which $R^3$ is hydrogen or alkyl having 1 to 5 carbons, and in the alkyl, at least one piece of —$CH_2$— may be replaced by —O—, and at least one piece of —$(CH_2)_2$— may be replaced by —CH=CH—, and in the groups, at least one piece of hydrogen may be replaced by fluorine, and w in formula (x1) is 1, 2, 3 or 4. Further preferred $X^1$ is —OH, —$NH_2$ or —$N(R^3)_2$. Particularly preferred $X^1$ is —OH.

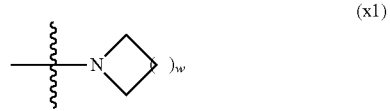

Formulas (2) to (15) show a component compound of the liquid crystal composition. Compounds (2) to (4) have small dielectric anisotropy. Compounds (5) to (7) have large positive dielectric anisotropy. Compound (8) has a cyano group, and therefore has larger positive dielectric anisotropy. Compounds (9) to (15) have large negative dielectric anisotropy. Specific examples of the compounds are described later.

In compound (16), $P^{11}$, $P^{12}$ and $P^{13}$ are independently a polymerizable group. Preferred $P^{11}$, $P^{12}$ or $P^{13}$ is a polymerizable group selected from the group of groups represented by formula (P-1) to formula (P-5). Further preferred $P^{11}$, $P^{12}$ or $P^{13}$ is group (P-1), group (P-2) or group (P-3). Particularly preferred group (P-1) is —OCO—CH=$CH_2$ or —OCO—C($CH_3$)=$CH_2$. A wavy line in group (P-1) to group (P-5) represents a site to form a bonding.

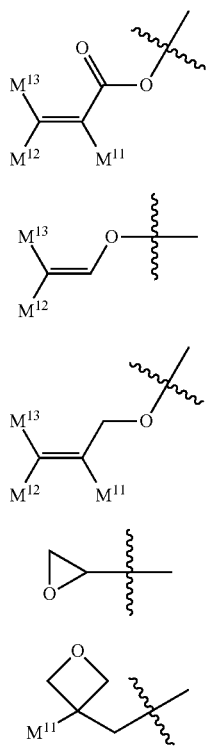

(P-1)

(P-2)

(P-3)

(P-4)

(P-5)

In group (P-1) to group (P-5), $M^{11}$, $M^{12}$ and $M^{13}$ are independently hydrogen, fluorine, alkyl having 1 to 5 carbons, or alkyl having 1 to 5 carbons in which at least one piece of hydrogen is replaced by halogen. Preferred $M^{11}$, $M^{12}$ or $M^{13}$ is hydrogen or methyl for increasing reactivity. Further preferred $M^{11}$ is methyl, and further preferred $M^{12}$ or $M^{13}$ is hydrogen.

$Sp^{11}$, $Sp^{12}$ and $Sp^{13}$ are independently a single bond or alkylene having 1 to 10 carbons, and in the alkylene, at least one piece of —$CH_2$— may be replaced by —O—, —COO—, —OCO— or —OCOO—, and at least one piece of —$(CH_2)_2$— may be replaced by —CH=CH— or —C≡C—, and in the groups, at least one piece of hydrogen may be replaced by fluorine or chlorine. Preferred $Sp^{11}$, $Sp^{12}$ or $Sp^{13}$ is a single bond.

Ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen is replaced by halogen. Preferred ring F or ring I is phenyl. Ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen is replaced by halogen. Particularly preferred ring G is 1,4-phenylene or 2-fluoro-1,4-phenylene.

$Z^{22}$ and $Z^{23}$ are independently a single bond or alkylene having 1 to 10 carbons, and in the alkylene, at least one piece of —$CH_2$— may be replaced by —O—, —CO—, —COO— or —OCO—, and at least one piece of —$(CH_2)_2$— may be replaced by —CH=CH—, —C($CH_3$)=CH—, —CH=C($CH_3$)— or —C($CH_3$)=C($CH_3$)—, and in the groups, at least one piece of hydrogen may be replaced by fluorine or chlorine. Preferred $Z^7$ or $Z^8$ is a single bond, —$(CH_2)_2$—, —$CH_2O$—, —$OCH_2$—, —COO— or —OCO—. Further preferred $Z^{22}$ or $Z^{23}$ is a single bond.

Then, u is 0, 1 or 2. Preferred u is 0 or 1. Then, f, g and h are independently 0, 1, 2, 3 or 4, and a sum of f, g and h is 1 or more. Preferred f, g or h is 1 or 2.

2. Synthesis of Compound (1)

A synthesis method of compound (1) will be described. Compound (1) can be prepared by suitably combining methods in synthetic organic chemistry. Any compounds whose synthetic methods are not described above are prepared according to methods described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course" (Shin Jikken Kagaku Koza in Japanese) (Maruzen Co., Ltd.).

2-1. Formation of a Bonding Group

An example of a method for forming a bonding group in compound (1) is as described in a scheme below. In the scheme, $MSG^1$ (or $MSG^2$) is a monovalent organic group having at least one ring. Monovalent organic groups represented by a plurality of $MSG^1$ (or $MSG^2$) may be identical or different. Compounds (1A) to (1G) correspond to compound (1) or an intermediate of compound (1).

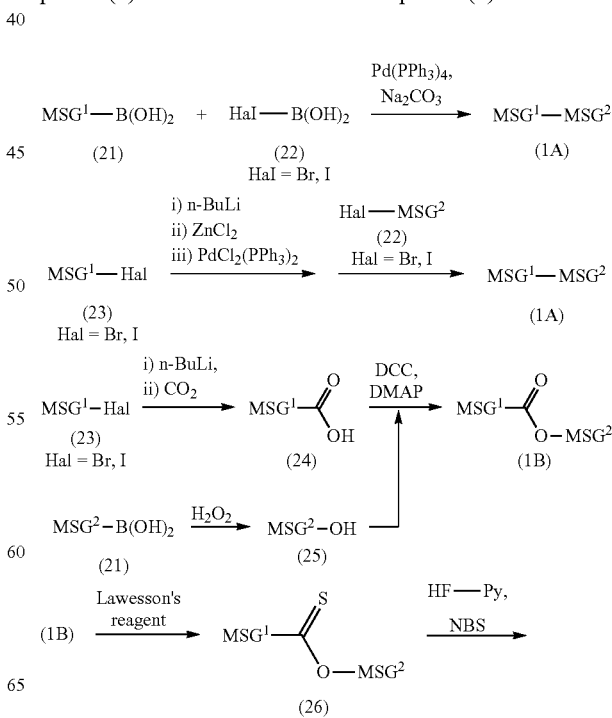

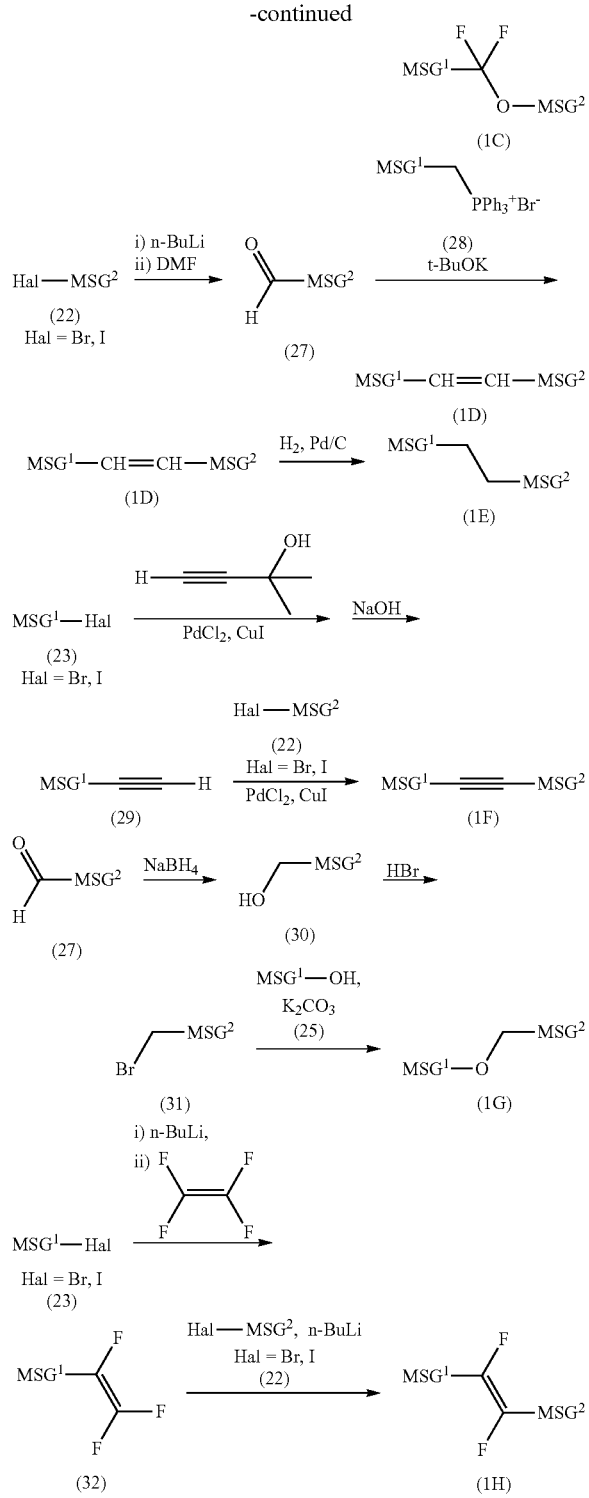

(I) Formation of a Single Bond

Compound (1A) is prepared by allowing arylboronic acid (21) to react with compound (22) in the presence of carbonate and a tetrakis(triphenylphosphine)palladium catalyst. Compound (1A) is also prepared by allowing compound (23) to react with n-butyllithium and subsequently with zinc chloride, and further with compound (22) in the presence of a dichlorobis(triphenylphosphine)palladium catalyst.

(II) Formation of —COO— and —OCO—

Carboxylic acid (24) is obtained by allowing compound (23) to react with n-butyllithium and subsequently with carbon dioxide. Compound (1B) having —COO— is prepared by dehydration of carboxylic acid (24) and phenol (25) derived from compound (21) in the presence of 1,3-dicyclohexylcarbodiimide (DCC) and 4-dimethylaminopyridine (DMAP). A compound having —OCO— is also prepared according to the method.

(III) Formation of —CF$_2$O— and —OCF$_2$—

Compound (26) is obtained by sulfurizing compound (1B) with a Lawesson's reagent. Compound (1C) having —CF$_2$O— is prepared by fluorinating compound (26) with a hydrogen fluoride-pyridine complex and N-bromosuccinimide (NBS). Refer to M. Kuroboshi et al., Chem. Lett., 1992, 827. Compound (1C) is also prepared by fluorinating compound (26) with (diethylamino) sulfur trifluoride (DAST). Refer to W. H. Bunnelle et al., J. Org. Chem. 1990, 55, 768. A compound having —OCF$_2$— is also prepared according to the method.

(IV) Formation of —CH═CH—

Aldehyde (27) is obtained by allowing compound (22) to react with n-butyllithium and subsequently with N,N-dimethylformamide (DMF). Compound (1D) is prepared by allowing phosphorus ylide generated by allowing phosphonium salt (28) to react with potassium t-butoxide to react with aldehyde (27). A cis isomer may be generated depending on reaction conditions, and therefore the cis isomer is isomerized into a trans isomer according to a publicly known method when necessary.

(V) Formation of —(CH$_2$)$_2$—

Compound (1E) is prepared by hydrogenating compound (1D) in the presence of a palladium on carbon catalyst.

(VI) Formation of —C≡C—

Compound (29) is obtained by allowing compound (23) to react with 2-methyl-3-butyn-2-ol in the presence of a catalyst of dichloropalladium and copper iodide, and then performing deprotection under basic conditions. Compound (1F) is prepared by allowing compound (29) to react with compound (22) in the presence of a catalyst of dichlorobis(triphenylphosphine)palladium and copper halide.

(VII) Formation of —CH$_2$O— and —OCH$_2$—

Compound (30) is obtained by reducing compound (27) with sodium borohydride. Compound (31) is obtained by brominating the obtained compound with hydrobromic acid. Compound (1G) is prepared by allowing compound (25) to react with compound (31) in the presence of potassium carbonate. A compound having —OCH$_2$— is also prepared according to the method.

(VIII) Formation of —CF═CF—

Compound (32) is obtained by treating compound (23) with n-butyllithium and then allowing the treated compound to react with tetrafluoroethylene. Compound (1H) is prepared by treating compound (22) with n-butyllithium and then allowing the treated compound to react with compound (32).

2-2. Formation of Ring A$^1$ and Ring A$^2$

A starting material is commercially available or a synthetic method is well known with regard to a ring such as 1,4-cyclohexylene, 1,4-cyclohexenylene, 1,4-phenylene, 2-fluoro-1,4-phenylene, 2-methyl-1,4-phenylene, 2-ethyl-1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, perhydrocyclopenta[a]phenanthrene-3, 17-diyl and 2,3,4,7,8,9,10,11,12,13,14,15,16,17-tetradecahydrocyclopenta[a]phenanthrene-3,17-diyl.

2-3. Synthesis Example

An example of a method for preparing compound (1) is as described below. In the compounds, definitions of $R^1$, MES, $M^1$ and $M^2$ are identical to definitions described above.

Compound (1-51) in which $R^2$ is a group represented by formula (1a), $Sp^2$ is —$CH_2$—, and $X^1$ is —OH can be prepared according to a method described below. Compound (53) is obtained by allowing compound (51) to react with compound (52) in the presence of DCC and DMAP. Compound (1-51) can be derived by allowing compound (53) to react with formaldehyde in the presence of 1,4-diazabicyclo[2.2.2]octane (DABCO). In addition, compound (53) can also be prepared by allowing compound (51) to react with compound (54) in the presence of a base such as triethylamine.

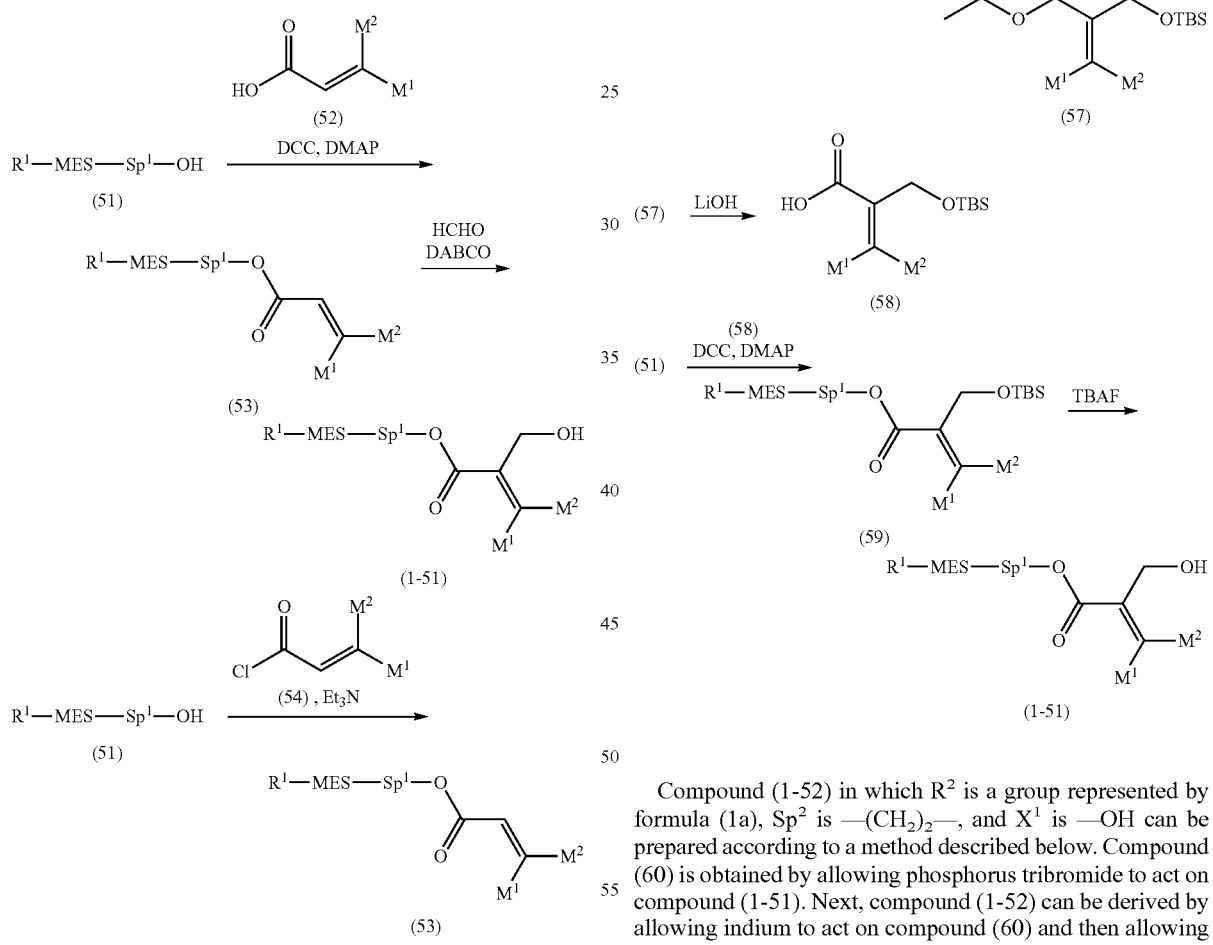

Compound (1-51) can also be prepared according to a method described below. Compound (56) is obtained by allowing compound (55) to react with formaldehyde in the presence of DABCO. Next, compound (57) is obtained by allowing t-butyldimethylsilyl chloride and imidazole to act on compound (56), and then compound (58) is obtained by allowing compound (57) to hydrolyze with a base such as lithium hydroxide. Compound (59) is obtained by allowing compound (51) to react with compound (58) in the presence of DCC and DMAP, and then compound (1-51) can be derived by performing deprotection of compound (59) by using tetrabutylammonium fluoride (TBAF).

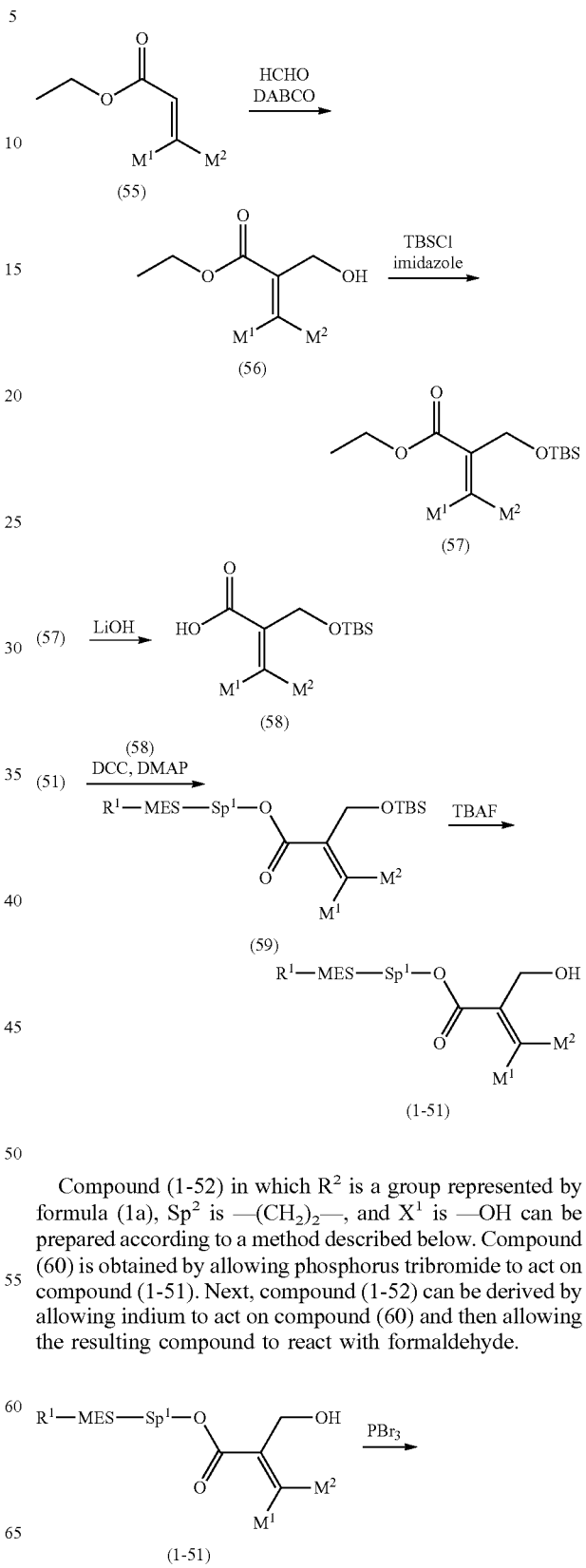

Compound (1-52) in which $R^2$ is a group represented by formula (1a), $Sp^2$ is —$(CH_2)_2$—, and $X^1$ is —OH can be prepared according to a method described below. Compound (60) is obtained by allowing phosphorus tribromide to act on compound (1-51). Next, compound (1-52) can be derived by allowing indium to act on compound (60) and then allowing the resulting compound to react with formaldehyde.

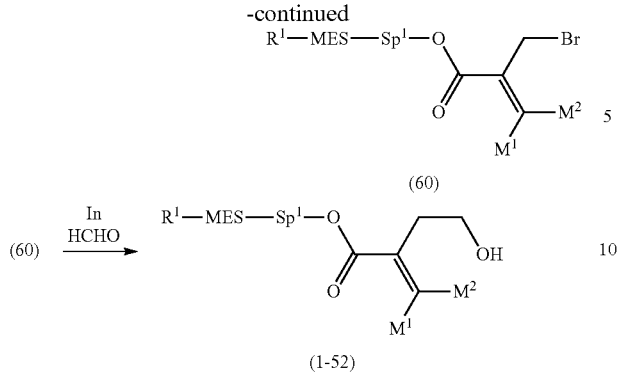

(1-52)

3. Liquid Crystal Composition

A liquid crystal composition of the invention contains compound (1) as component A. Compound (1) noncovalently interacts with a substrate of a device, and thus can control alignment of liquid crystal molecules. The composition contains compound (1) as component A, and preferably further contains a liquid crystal compound selected from components B, C, D and E described below. Component B includes compounds (2) to (4). Component C includes compounds (5) to (7). Component D includes compound (8). Component E includes compounds (9) to (15). The composition may contain any other liquid crystal compound different from compounds (2) to (15). When the composition is prepared, components B, C, D and E are preferably selected by taking into account magnitude of positive or negative dielectric anisotropy, or the like. A composition in which the components are suitably selected has high maximum temperature, low minimum temperature, small viscosity, suitable optical anisotropy (more specifically, large optical anisotropy or small optical anisotropy), large positive or negative dielectric anisotropy, large specific resistance, stability to heat or ultraviolet light and a suitable elastic constant (more specifically, a large elastic constant or a small elastic constant).

A preferred proportion of compound (1) is about 0.01%, by weight or more for maintaining high stability to ultraviolet light, and about 5% by weight or less for dissolution in the liquid crystal composition. A further preferred proportion is in the range of about 0.05% by weight to about 2% by weight. A most preferred proportion is in the range of about 0.05% by weight to about 1% by weight.

Component B includes a compound in which two terminal groups are alkyl or the like. Specific examples of preferred component B include compounds (2-1) to (2-11), compounds (3-1) to (3-19) and compounds (4-1) to (4-7). In a compound of component B, $R^{11}$ and $R^{12}$ are independently alkyl having 1 to 10 carbons or alkenyl having 2 to 10 carbons, and in the alkyl or the alkenyl, at least one piece of —$CH_2$— may be replaced by —O—, and at least one piece of hydrogen may be replaced by fluorine.

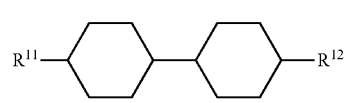
(2-1)

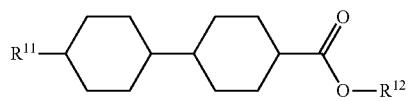
(2-2)

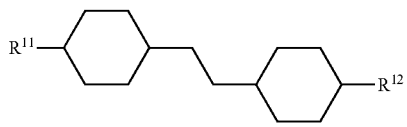
(2-3)

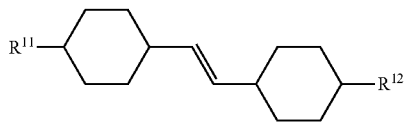
(2-4)

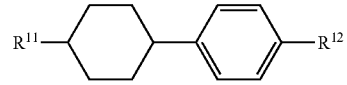
(2-5)

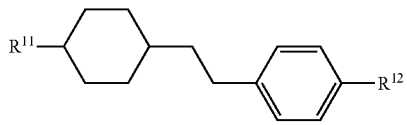
(2-6)

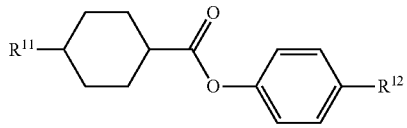
(2-7)

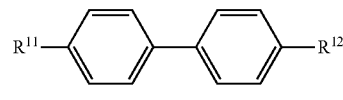
(2-8)

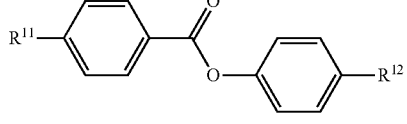
(2-9)

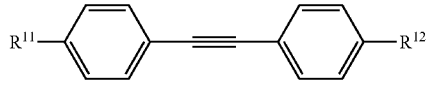
(2-10)

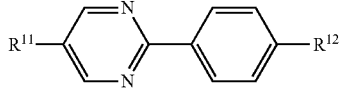
(2-11)

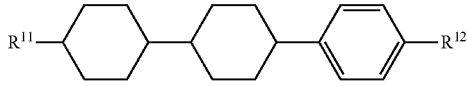
(3-1)

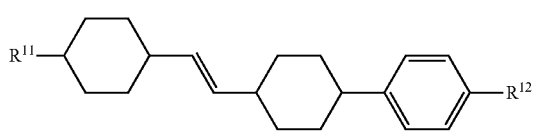
(3-2)

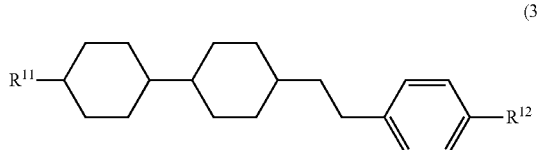
(3-3)

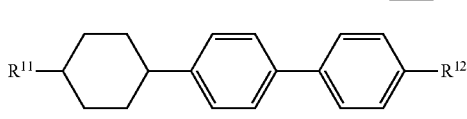
(3-4)

(3-5) 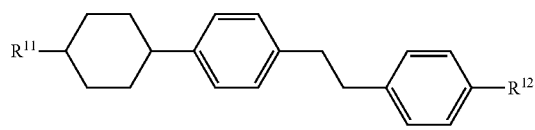
(3-6) 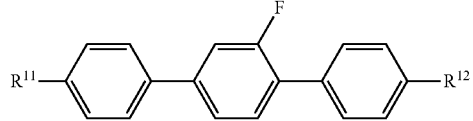
(3-7) 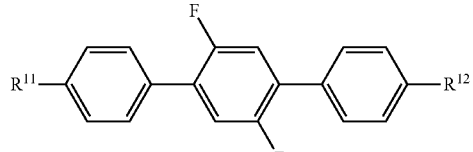
(3-8) 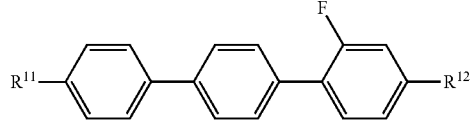
(3-9) 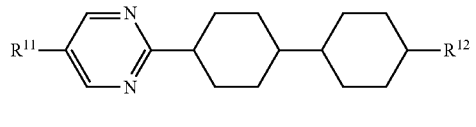
(3-10) 
(3-11) 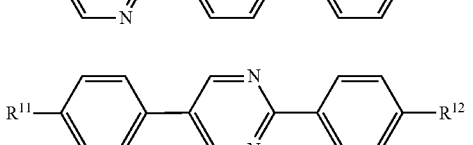
(3-12) 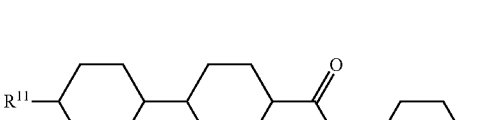
(3-13) 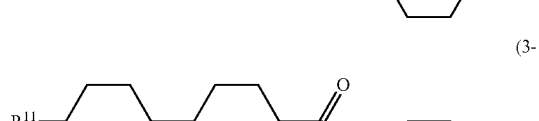
(3-14) 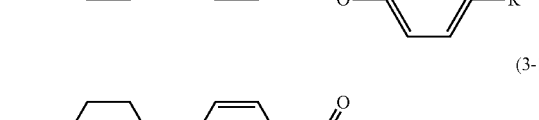
(3-15) 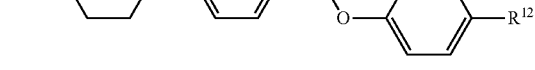
(3-16) 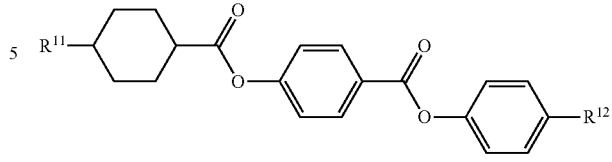
(3-17) 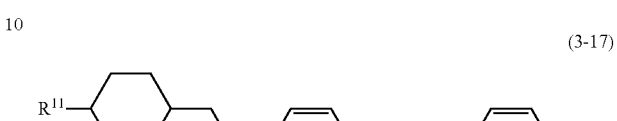
(3-18) 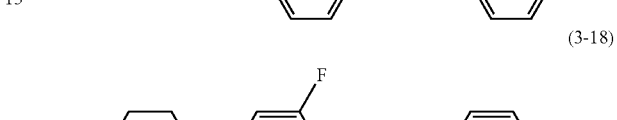
(3-19) 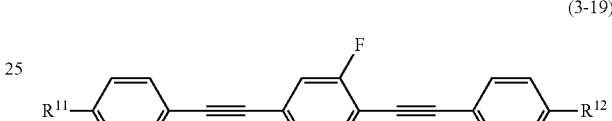
(4-1) 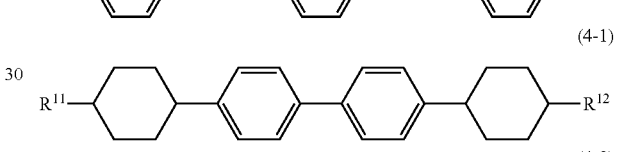
(4-2) 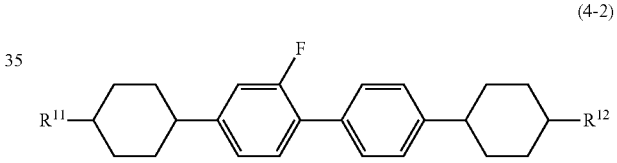
(4-3) 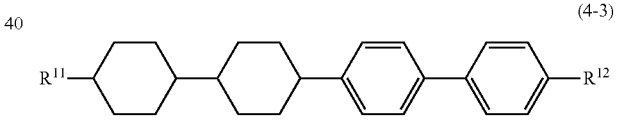
(4-4) 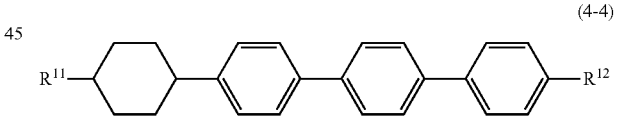
(4-5) 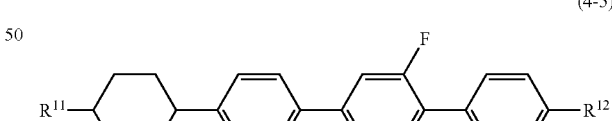
(4-6) 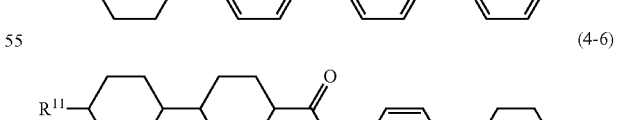
(4-7) 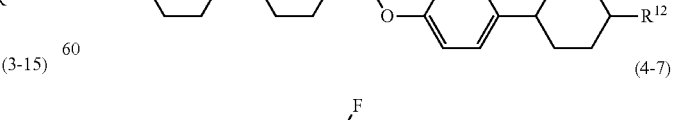

Component B has a small absolute value of dielectric anisotropy, and therefore is a compound close to neutrality. Compound (2) is mainly effective in decreasing the viscosity or adjusting the optical anisotropy. Compounds (3) and (4) are effective in extending a temperature range of the nematic phase by increasing the maximum temperature, or in adjusting the optical anisotropy.

As a content of component B is increased, the dielectric anisotropy of the composition is decreased, but the viscosity is decreased. Thus, as long as a desired value of a threshold voltage of the device is met, the content is preferably as large as possible. When a composition for the IPS mode, the VA mode or the like is prepared, the content of component B is preferably 30% by weight or more, and further preferably 40% by weight or more, based on the weight of the liquid crystal composition.

Component C is a compound having a halogen-containing group or a fluorine-containing group at a right terminal. Specific examples of preferred component C include compounds (5-1) to (5-16), compounds (6-1) to (6-113) and compounds (7-1) to (7-57). In a compound of component C, $R^{13}$ is alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine; and $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

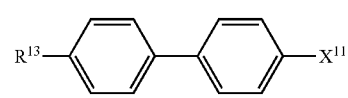
(5-1)

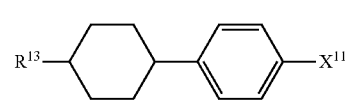
(5-2)

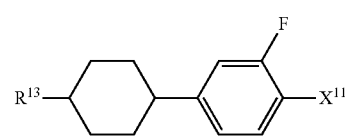
(5-3)

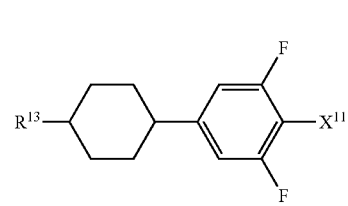
(5-4)

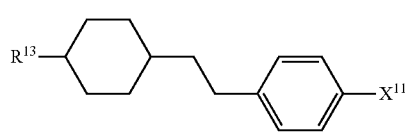
(5-5)

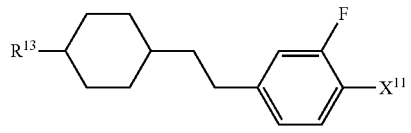
(5-6)

-continued

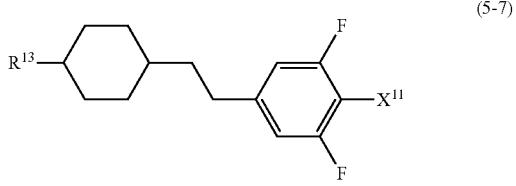
(5-7)

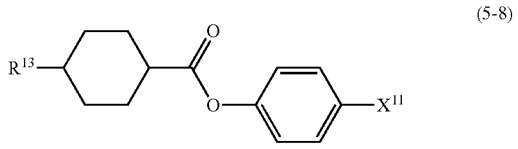
(5-8)

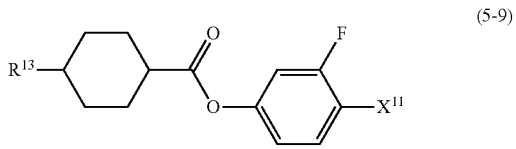
(5-9)

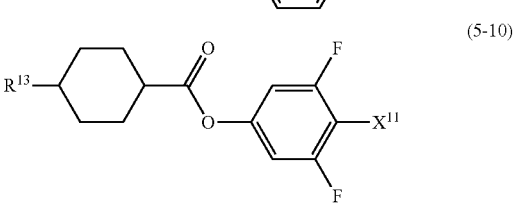
(5-10)

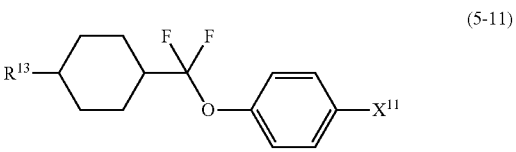
(5-11)

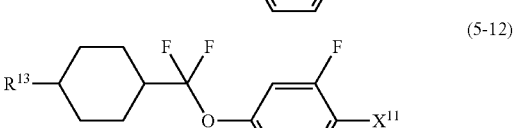
(5-12)

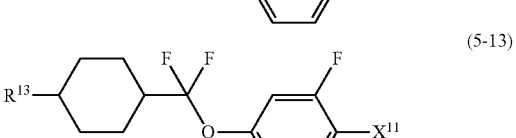
(5-13)

(5-14)

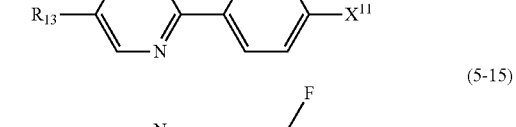
(5-15)

(5-16)

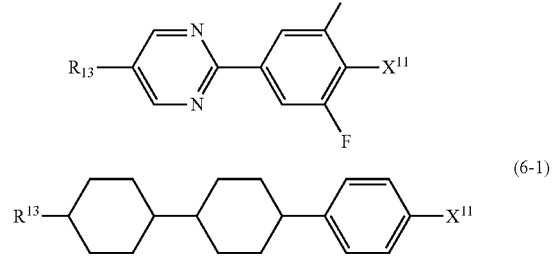
(6-1)

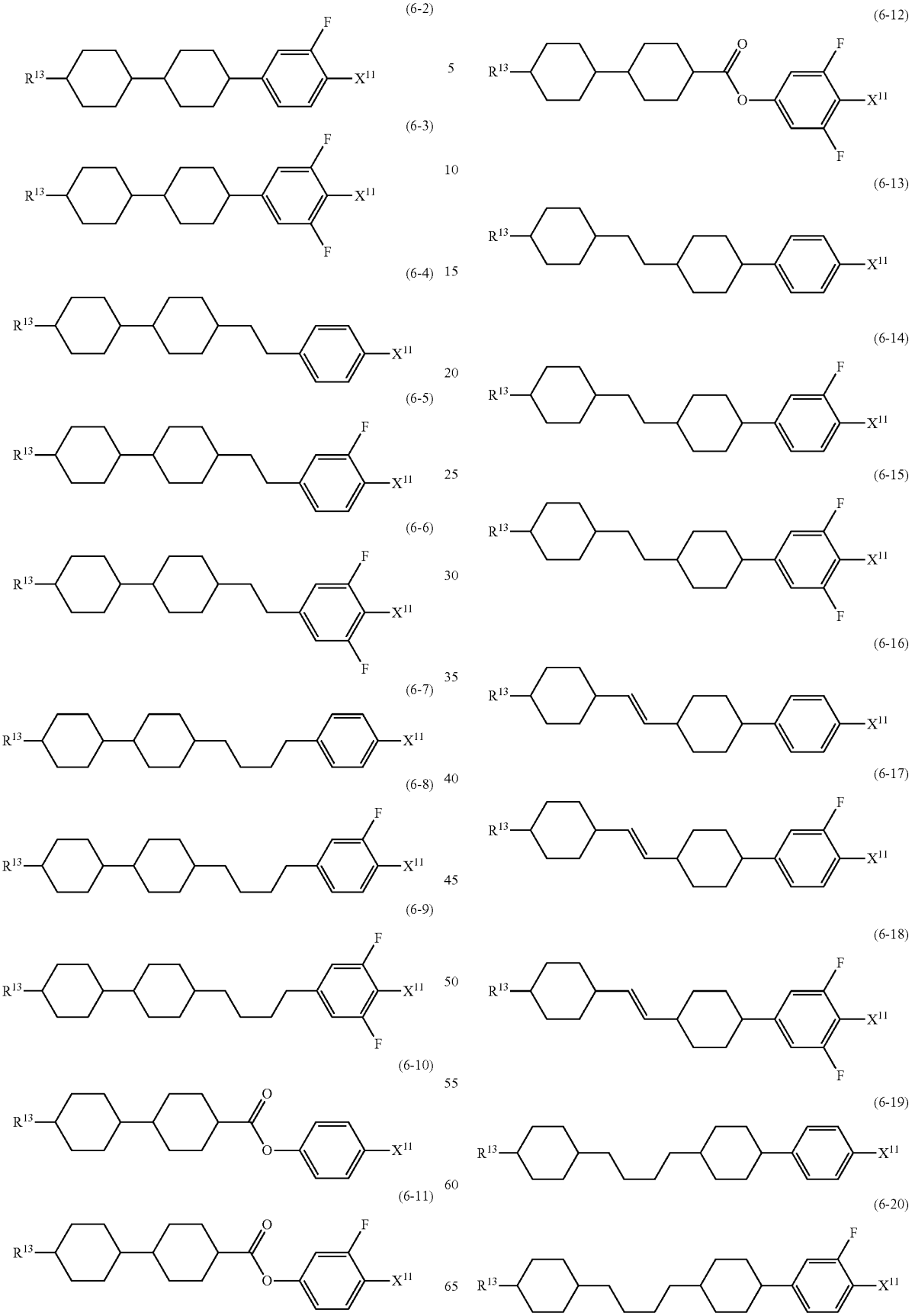

-continued
(6-21)
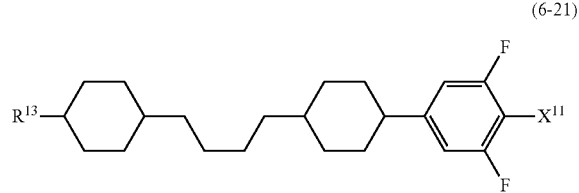
(6-22)
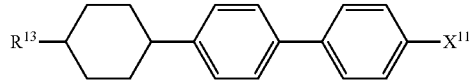
(6-23)
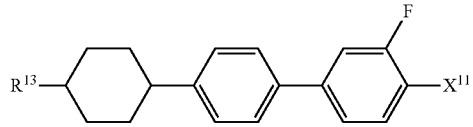
(6-24)
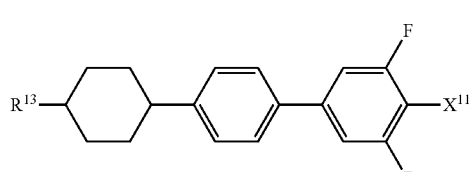
(6-25)
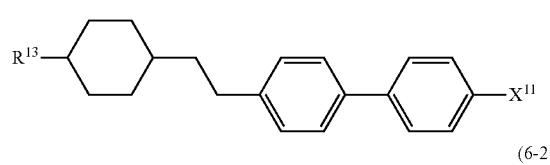
(6-26)

(6-27)

(6-28)
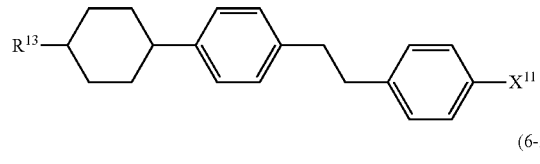
(6-29)
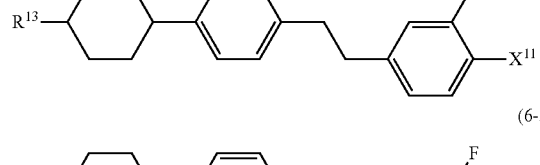
(6-30)
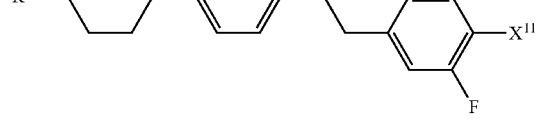
-continued
(6-31)
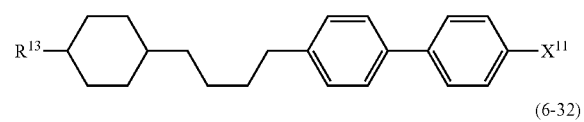
(6-32)
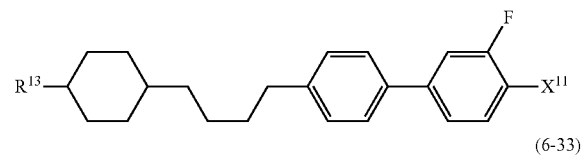
(6-33)
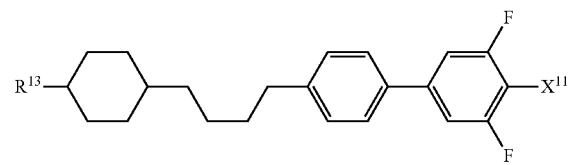
(6-34)
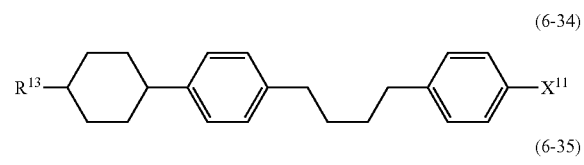
(6-35)
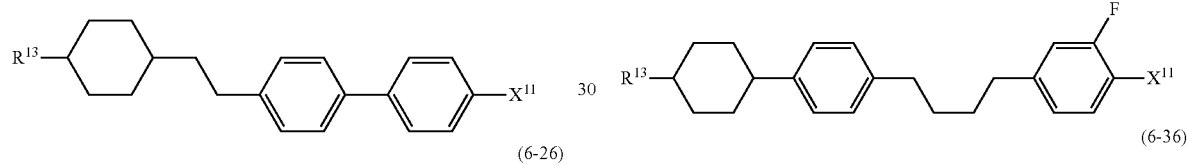
(6-36)
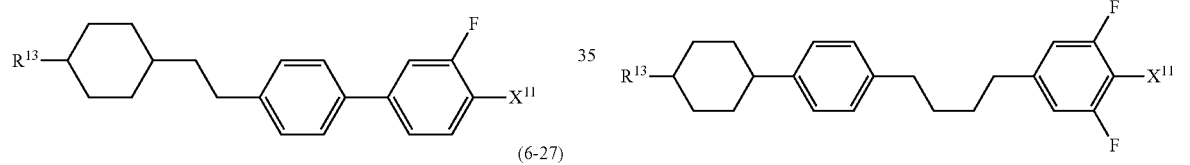
(6-37)
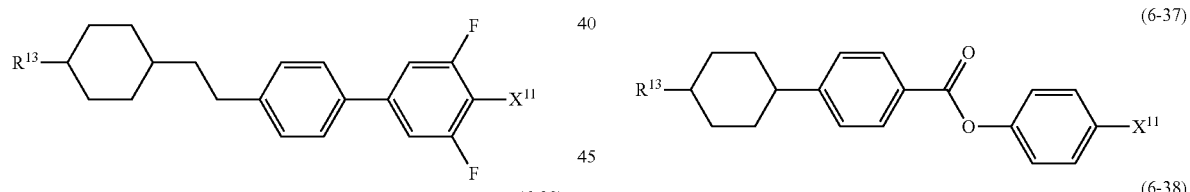
(6-38)
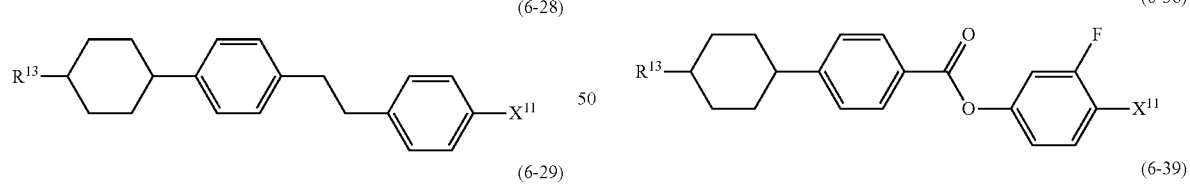
(6-39)
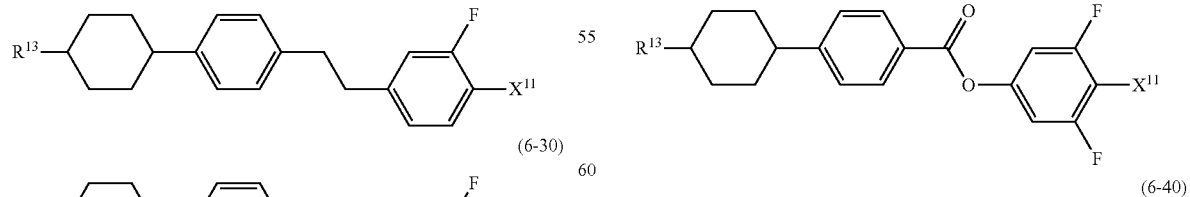
(6-40)
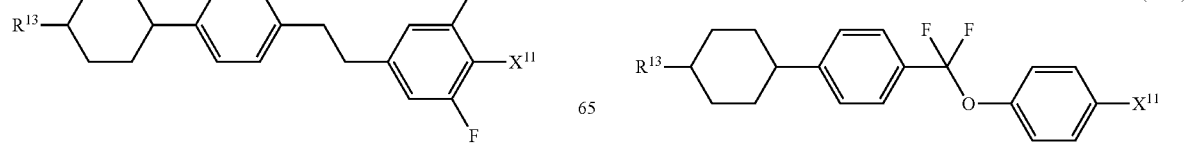

(6-41) 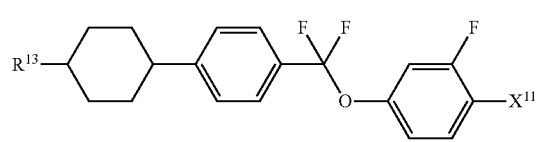
(6-42) 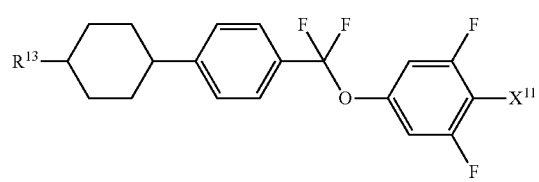
(6-43) 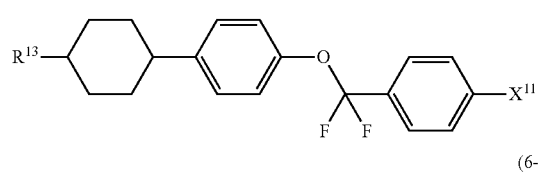
(6-44) 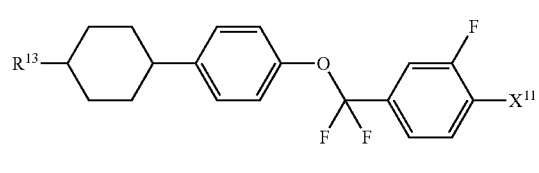
(6-45) 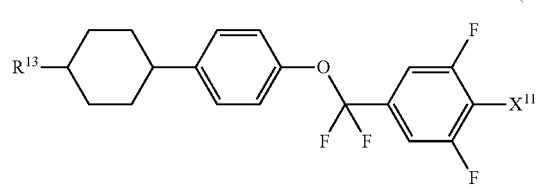
(6-46) 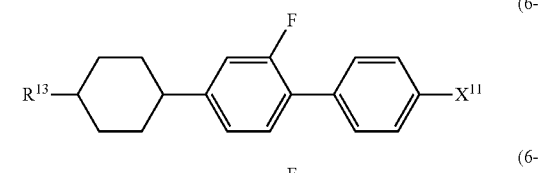
(6-47) 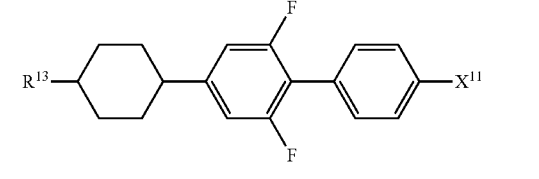
(6-48) 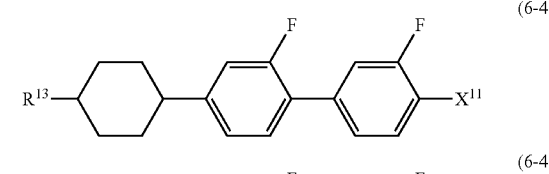
(6-49) 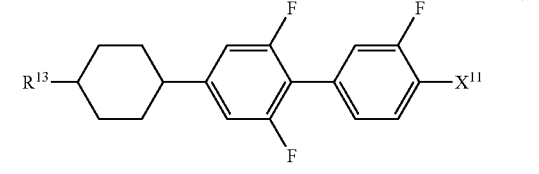
(6-50) 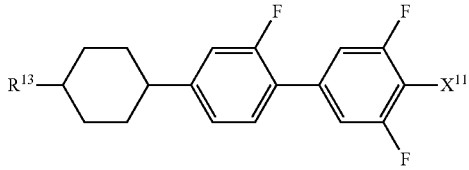
(6-51) 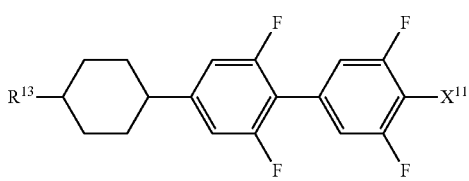
(6-52) 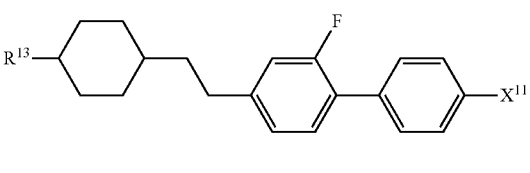
(6-53) 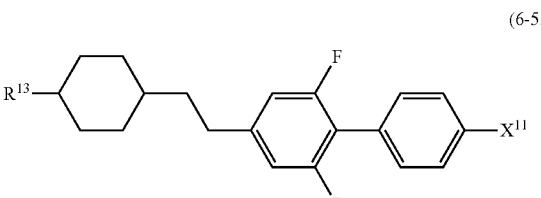
(6-54) 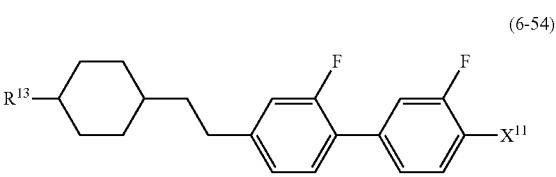
(6-55) 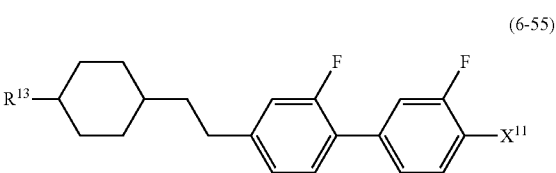
(6-56) 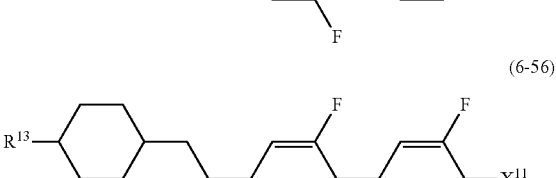
(6-57) 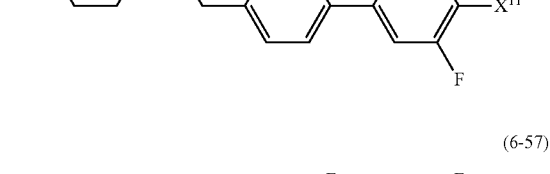

(6-58)
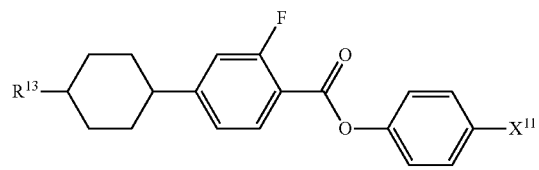
(6-59)
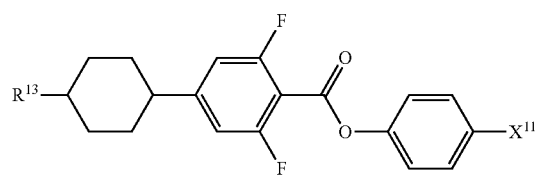
(6-60)
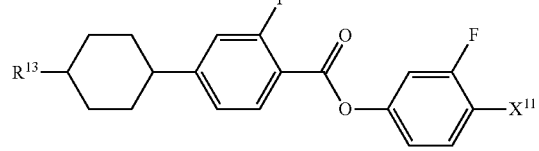
(6-61)
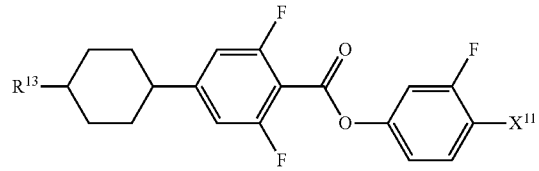
(6-62)
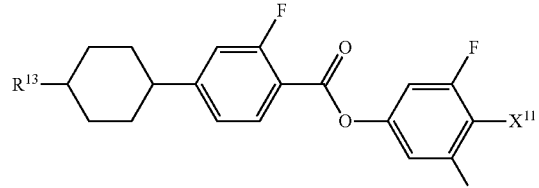
(6-63)
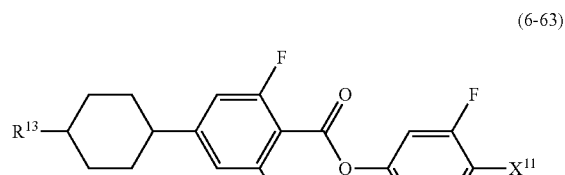
(6-64)
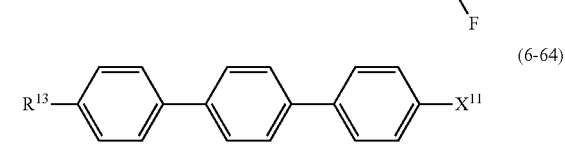
(6-65)
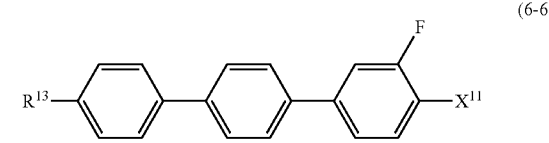
(6-66)
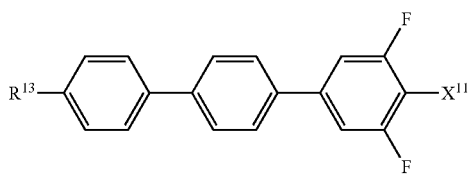
(6-67)
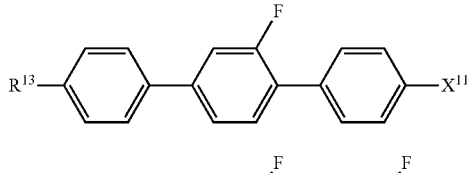
(6-68)
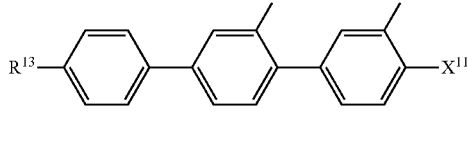
(6-69)
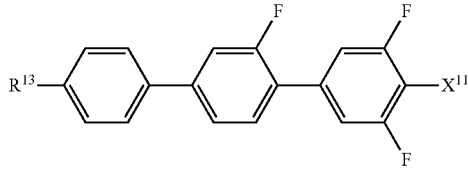
(6-70)
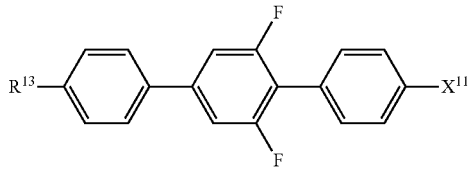
(6-71)
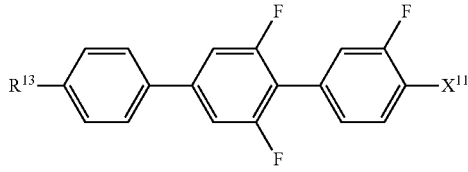
(6-72)
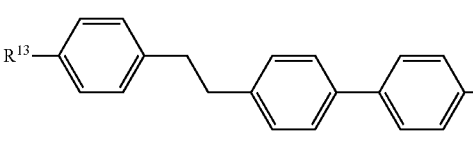
(6-73)
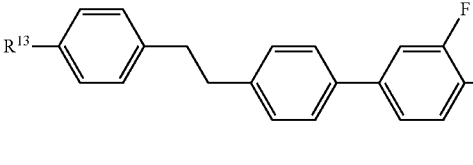
(6-74)
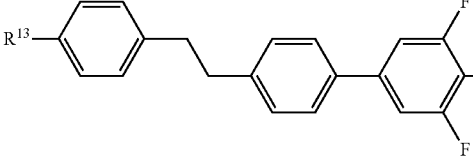

(6-75) 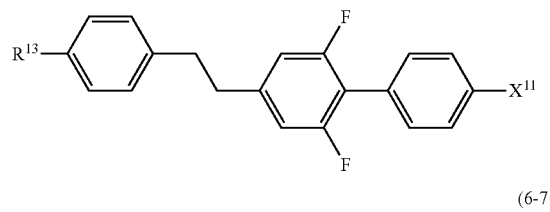
(6-76) 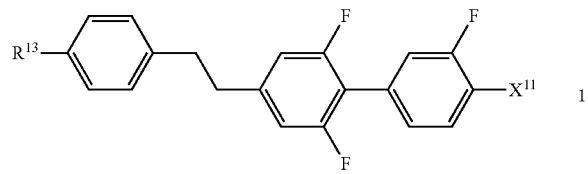
(6-77) 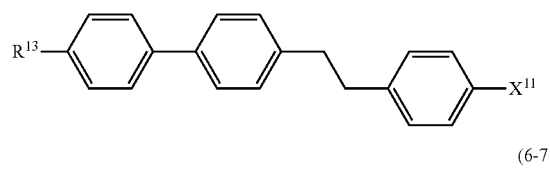
(6-78) 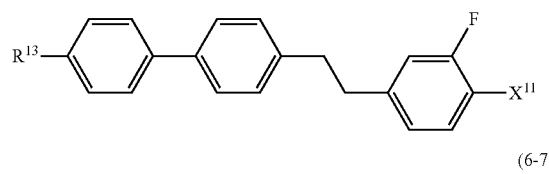
(6-79) 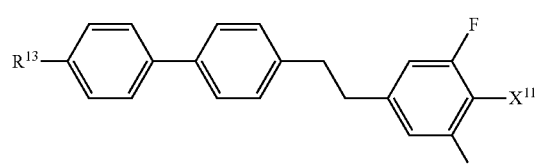
(6-80) 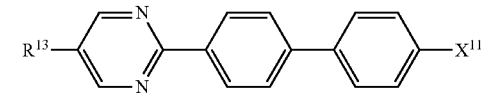
(6-81) 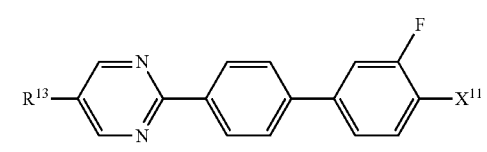
(6-82) 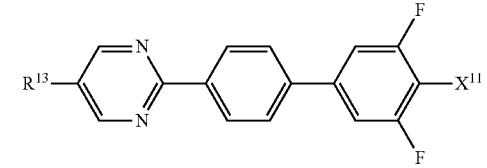
(6-83) 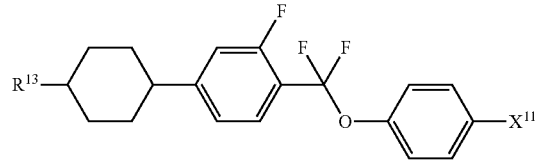
(6-84) 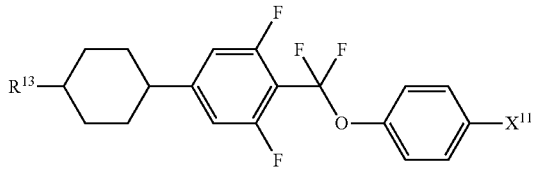
(6-85) 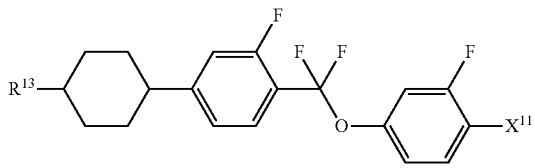
(6-86) 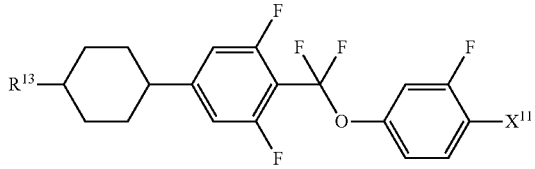
(6-87) 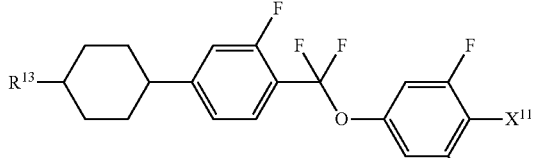
(6-88) 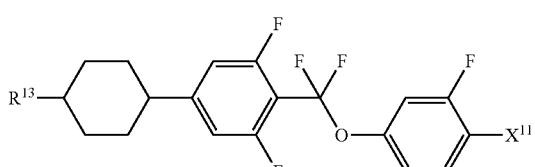
(6-89) 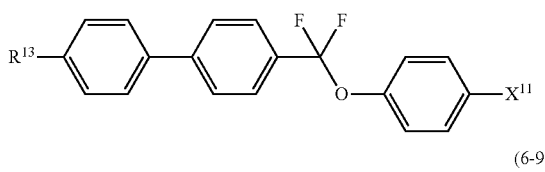
(6-90) 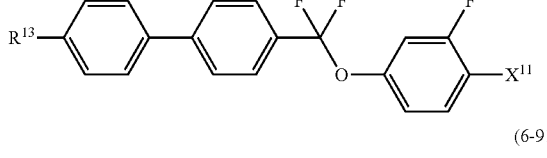
(6-91) 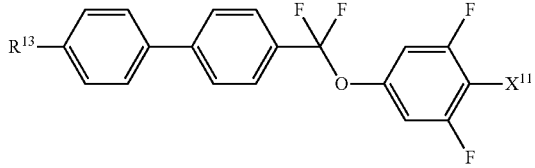

(6-92) 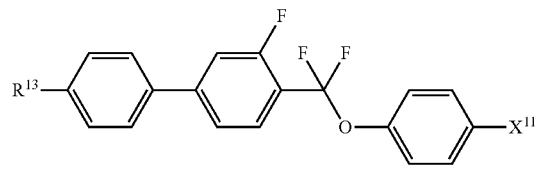
(6-93) 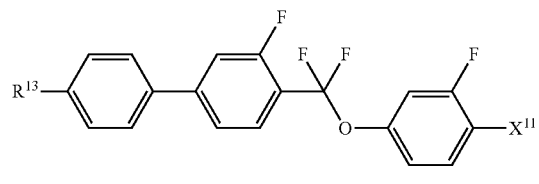
(6-94) 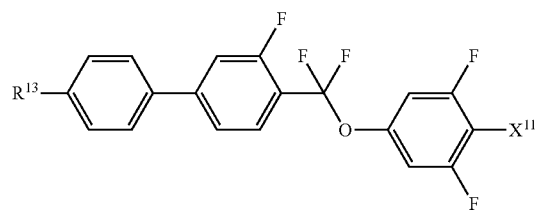
(6-95) 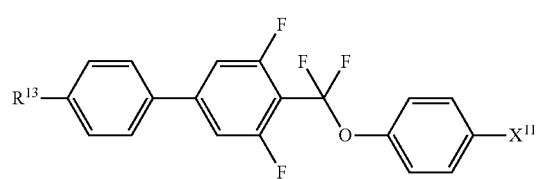
(6-96) 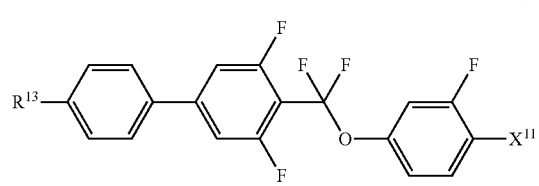
(6-97) 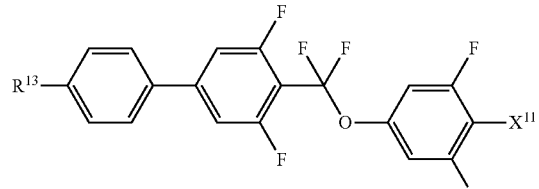
(6-98) 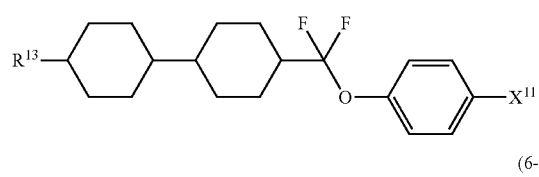
(6-99) 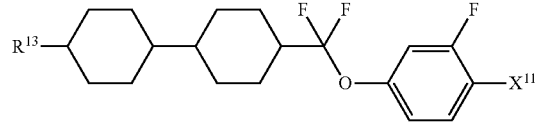
(6-100) 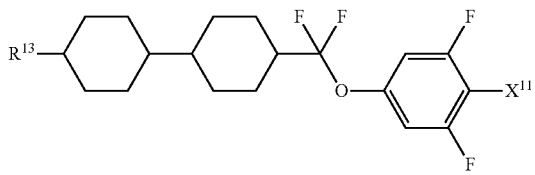
(6-101) 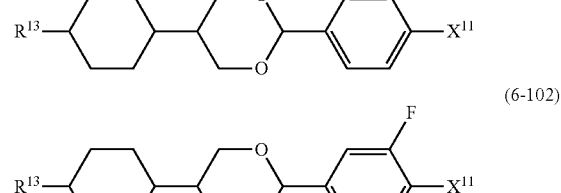
(6-102) 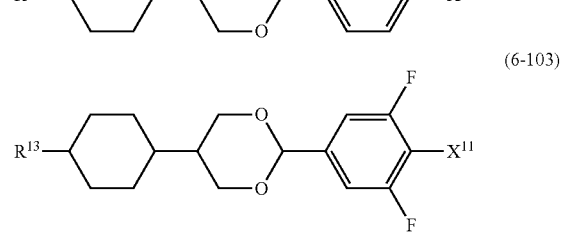
(6-103) 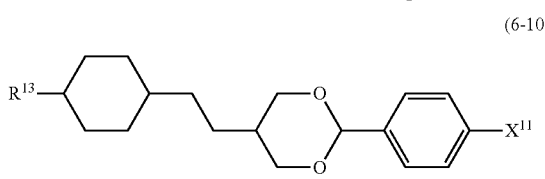
(6-104) 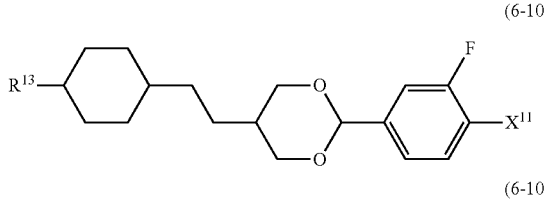
(6-105) 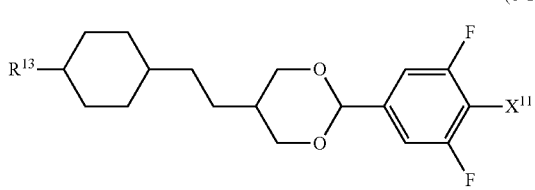
(6-106) 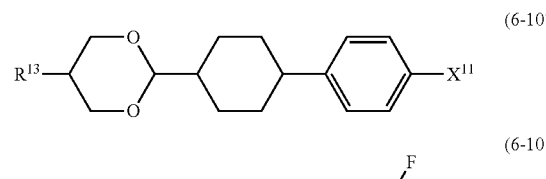
(6-107) 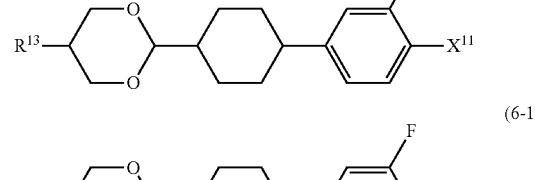
(6-108) 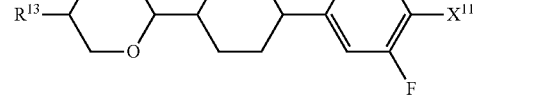
(6-109)

(6-110) 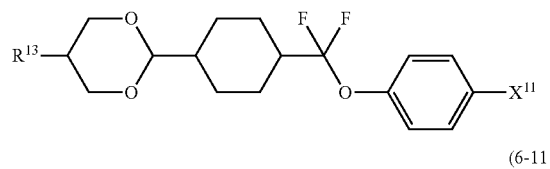
(6-111) 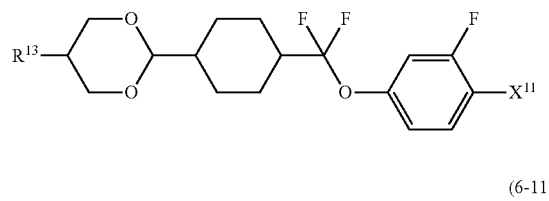
(6-112) 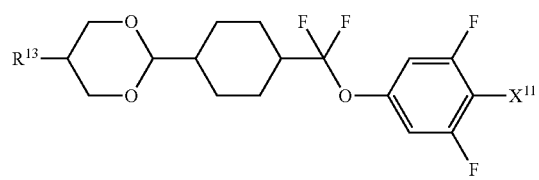
(6-113)
(7-1)
(7-2)
(7-3)
(7-4)
(7-5)
(7-6) 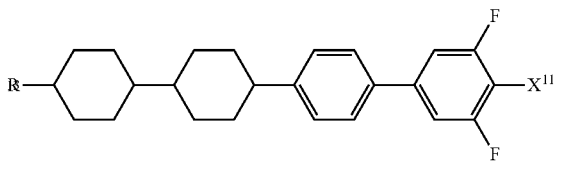
(7-7) 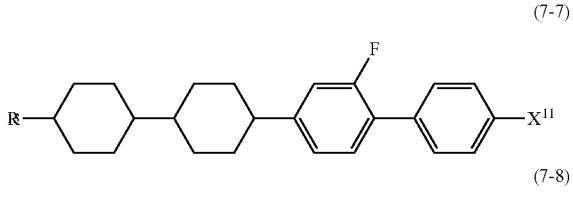
(7-8) 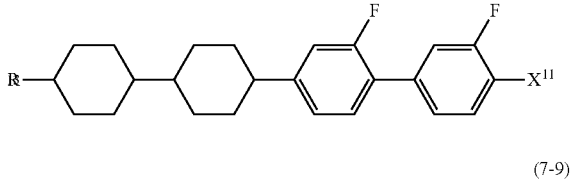
(7-9) 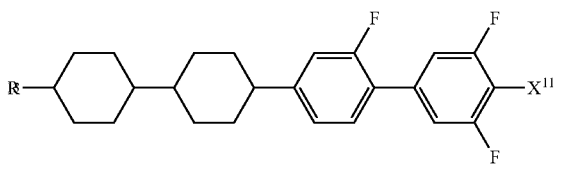
(7-10) 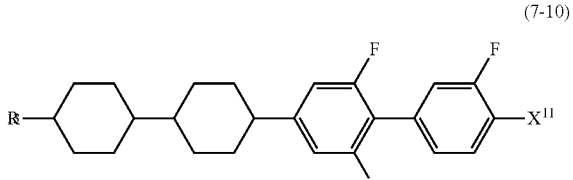
(7-11) 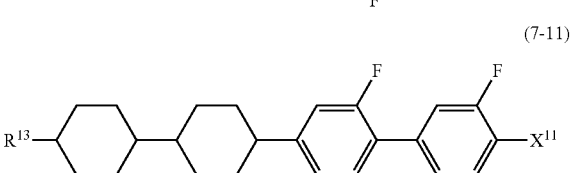
(7-12) 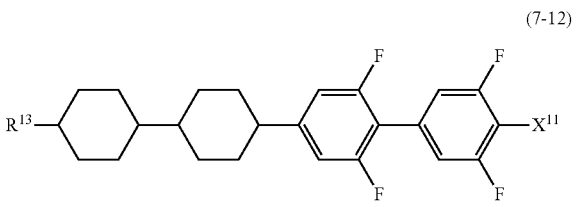
(7-13) 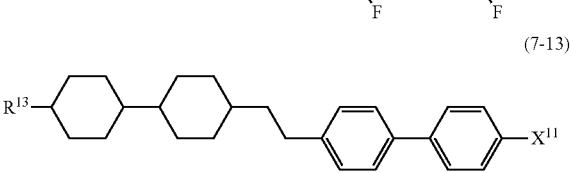
(7-14) 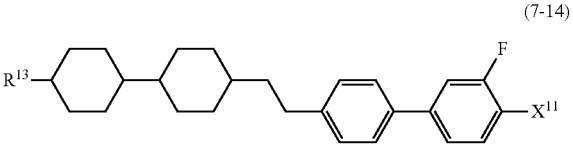

(7-15) 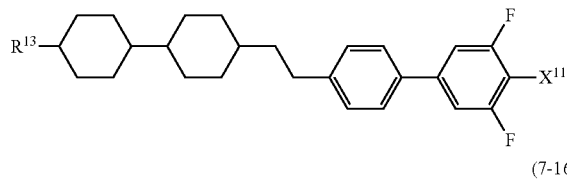
(7-16) 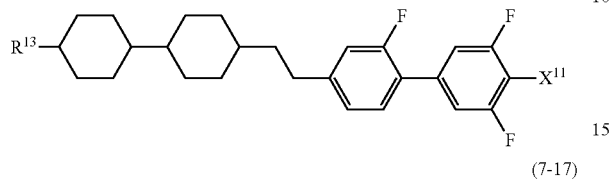
(7-17) 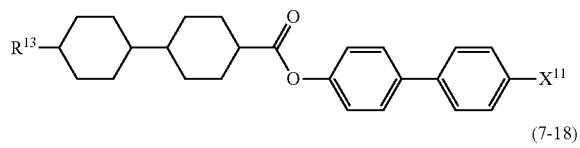
(7-18) 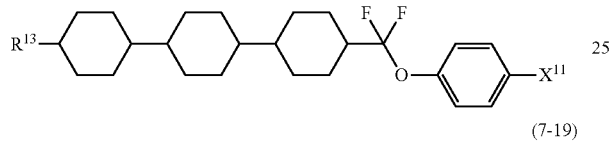
(7-19) 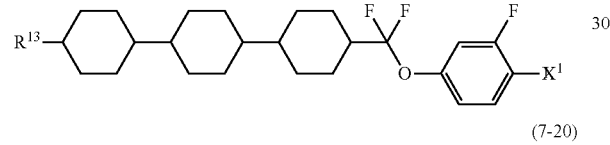
(7-20) 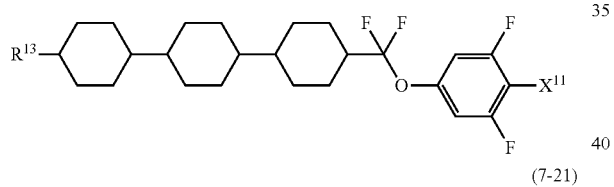
(7-21) 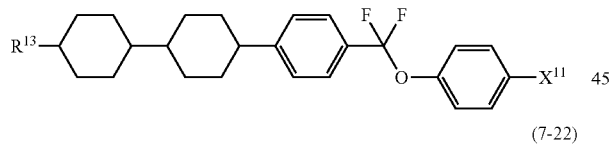
(7-22) 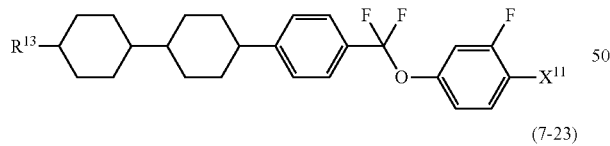
(7-23) 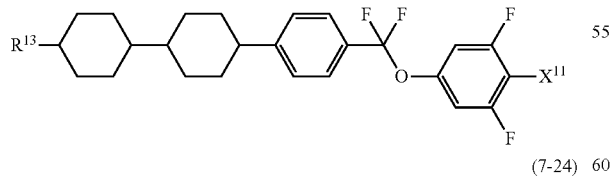
(7-24) 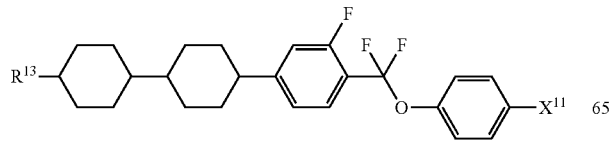
(7-25) 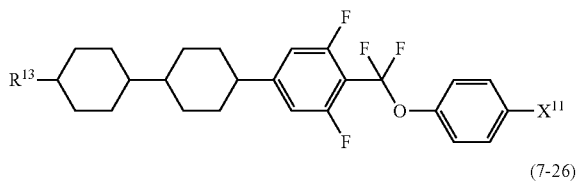
(7-26) 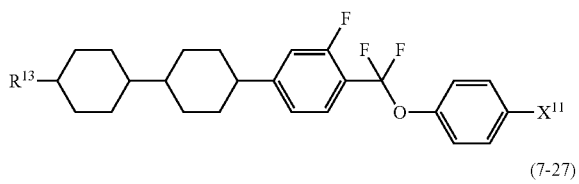
(7-27) 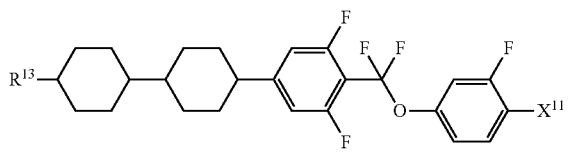
(7-28) 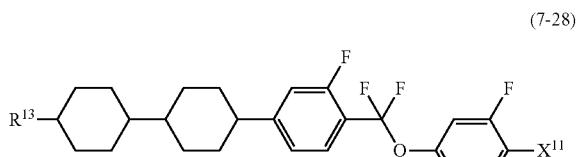
(7-29) 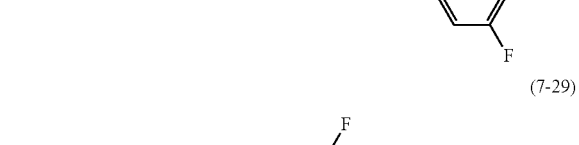
(7-30) 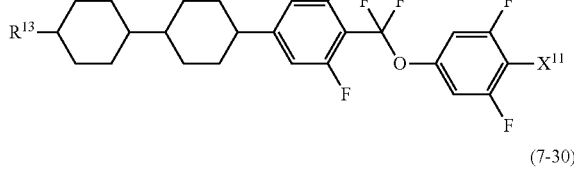
(7-31) 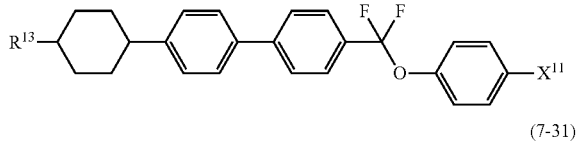
(7-32) 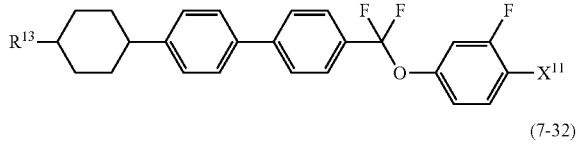
(7-33) 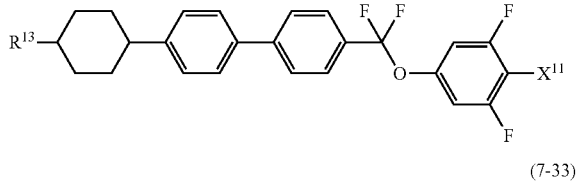
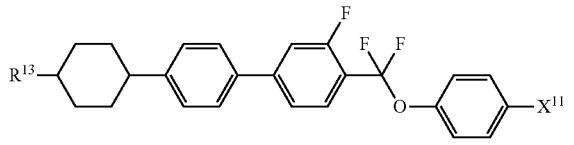

(7-34) 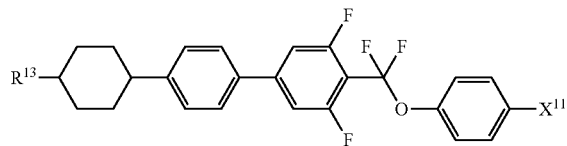
(7-35) 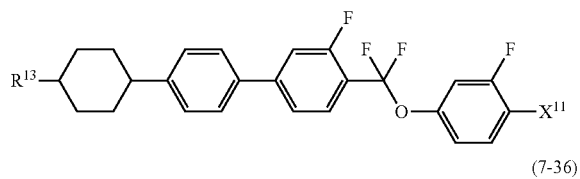
(7-36) 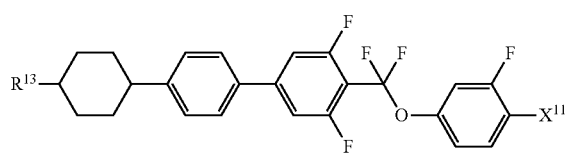
(7-37) 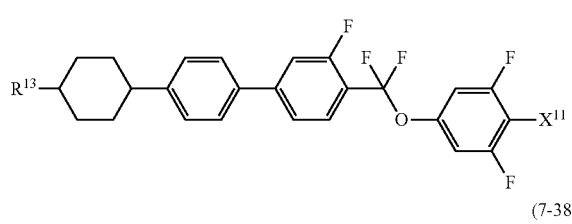
(7-38) 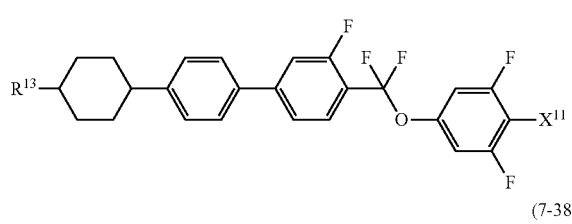
(7-39) 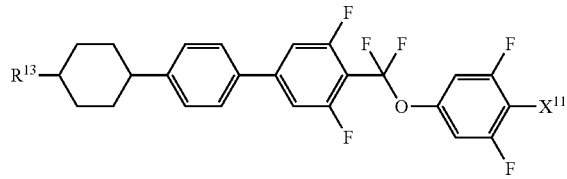
(7-40) 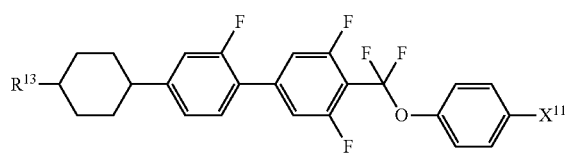
(7-41) 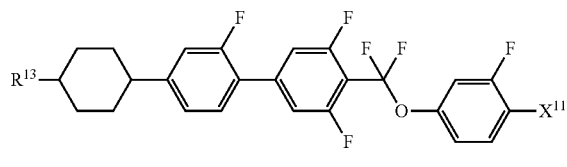
(7-42) 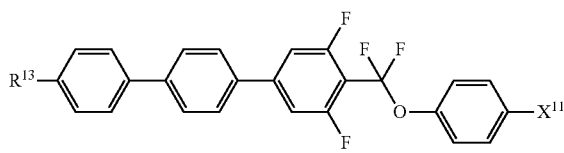
(7-43) 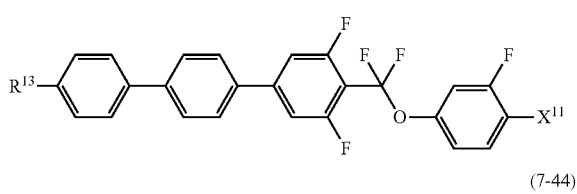
(7-44) 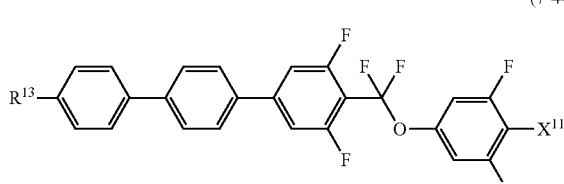
(7-45) 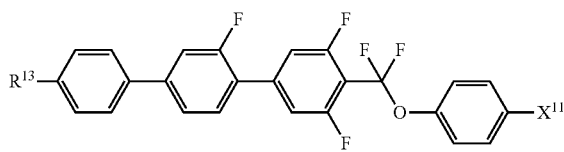
(7-46) 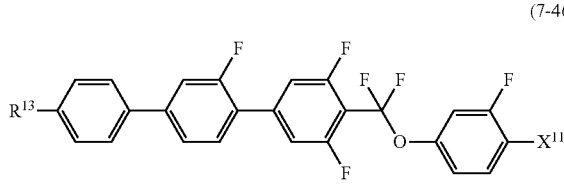
(7-47) 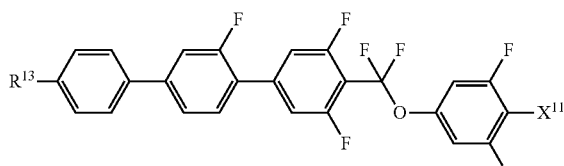
(7-48) 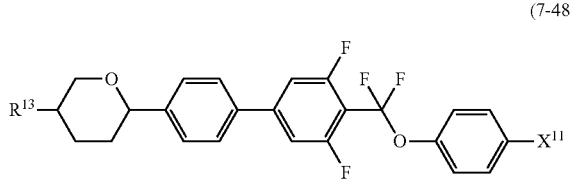
(7-49) 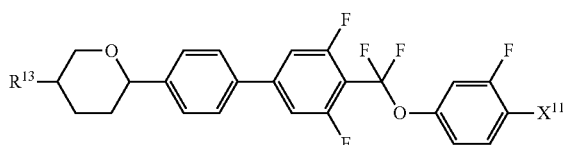

-continued (7-50)
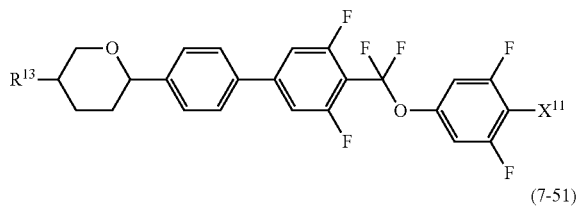

(7-51)
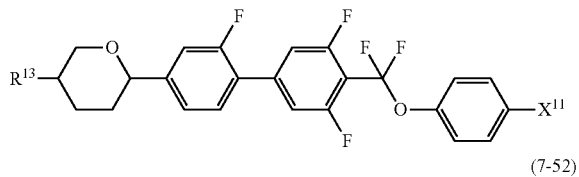

(7-52)
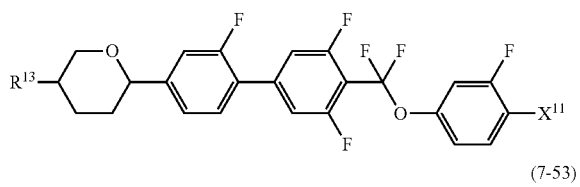

(7-53)
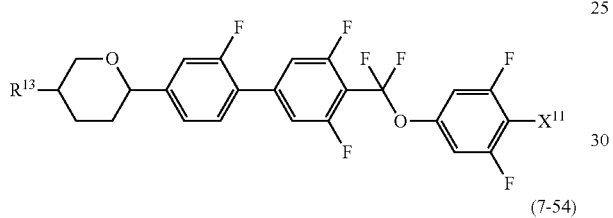

(7-54)
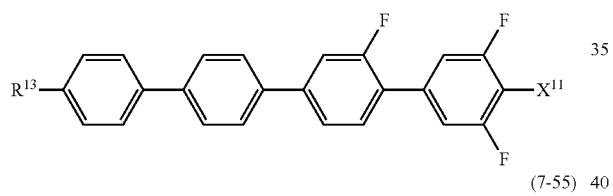

(7-55)
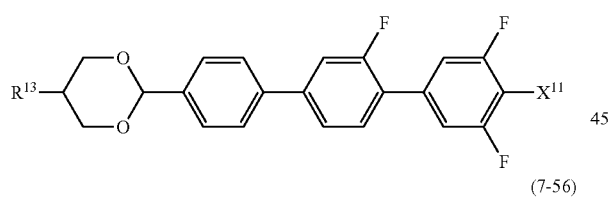

(7-56)
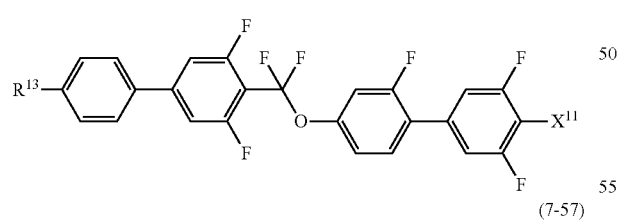

(7-57)
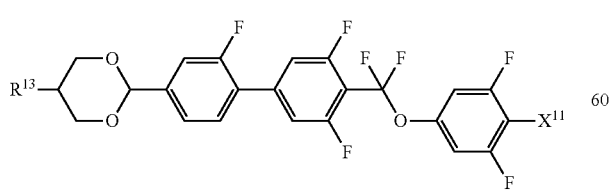

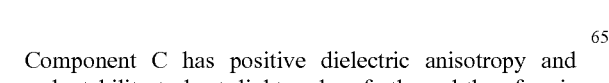

Component C has positive dielectric anisotropy and superb stability to heat, light and so forth, and therefore is used when a composition for the IPS mode, the FFS mode, the OCB mode or the like is prepared. A content of component C is suitably in the range of 1% by weight to 99% by weight, preferably in the range of 10% by weight to 97% by weight, and further preferably in the range of 40% by weight to 95% by weight, based on the weight of the liquid crystal composition. When component C is added to a composition having negative dielectric anisotropy, the content of component C is preferably 30% by weight or less based on the weight of the liquid crystal composition. Addition of component C allows adjustment of the elastic constant of the composition and adjustment of a voltage-transmittance curve of the device.

Component D is compound (8) in which a right-terminal group is —C≡N or —C≡C—C≡N. Specific examples of preferred component D include compounds (8-1) to (8-64). In a compound of component D, $R^{14}$ is alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine; and —$X^{12}$ is —C≡N or —C≡C—C≡N.

(8-1)
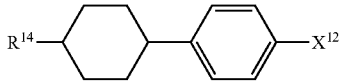

(8-2)

(8-3)
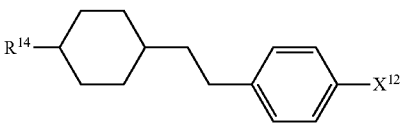

(8-4)
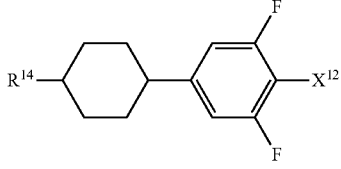

(8-5)
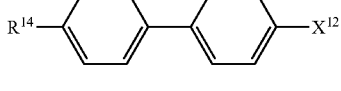

(8-6)
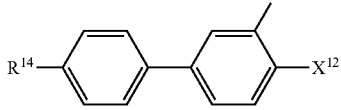

(8-7)
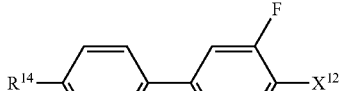

(8-8)
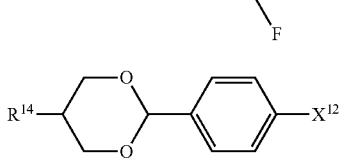

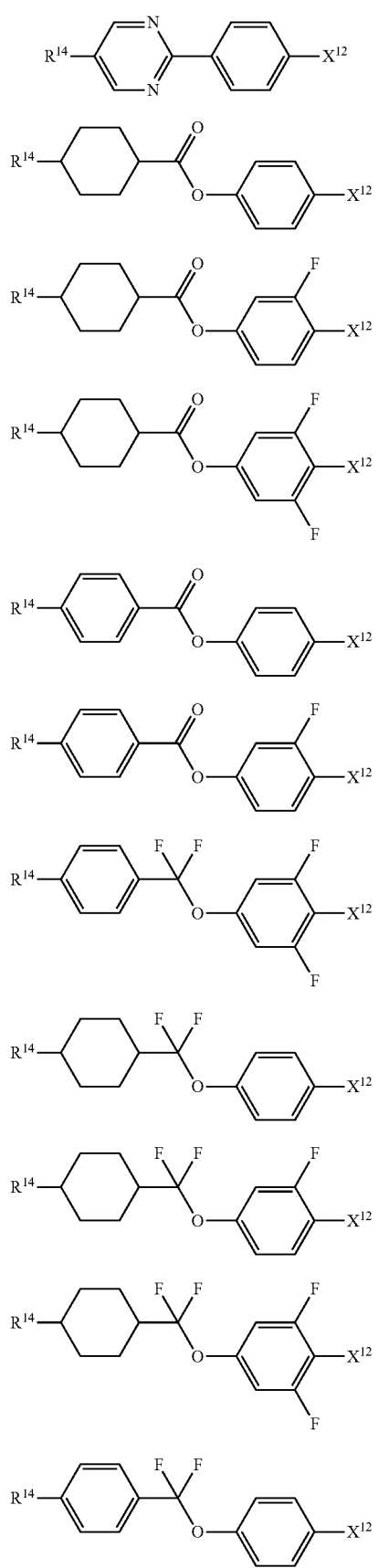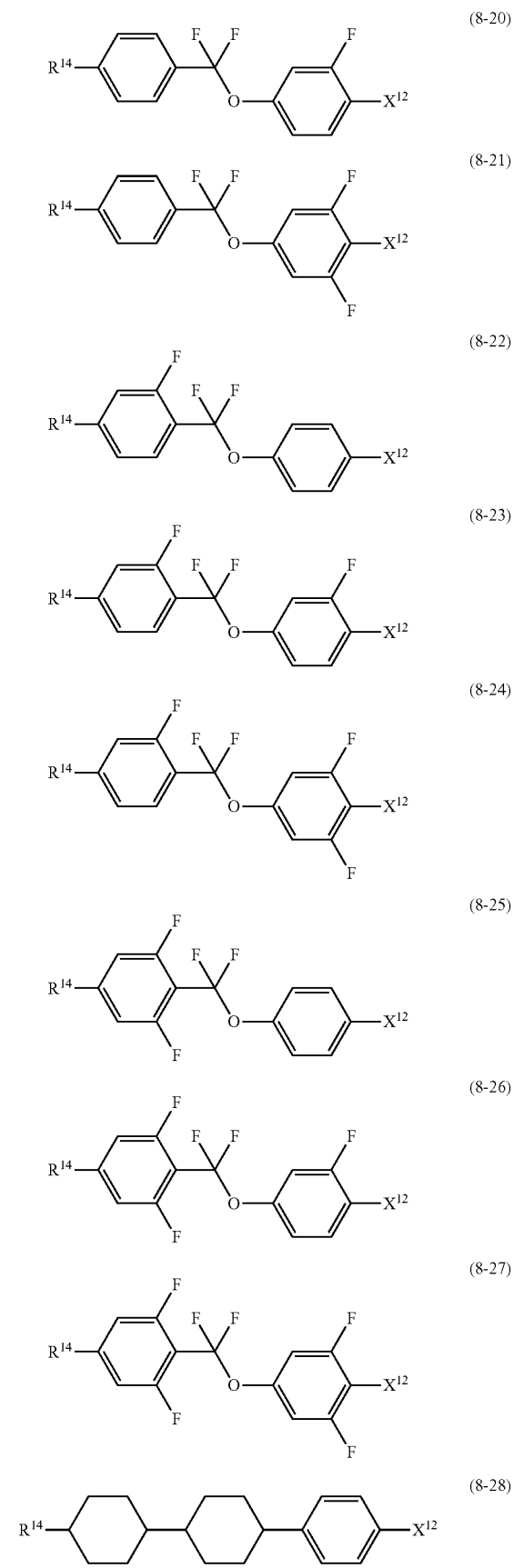

(8-29) 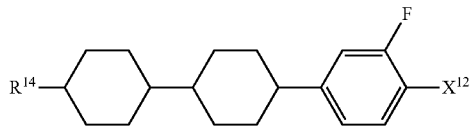
(8-30) 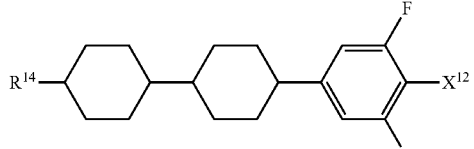
(8-31) 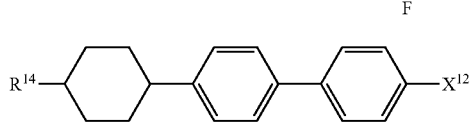
(8-32) 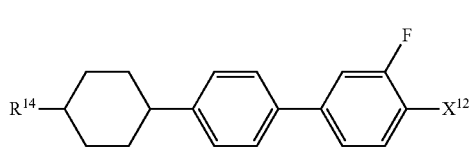
(8-33) 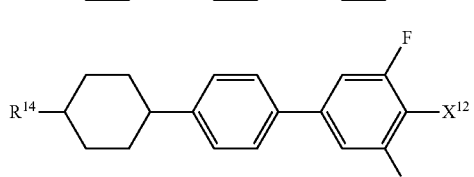
(8-34) 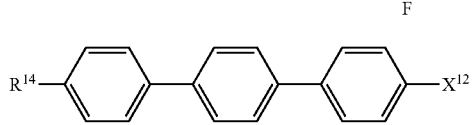
(8-35) 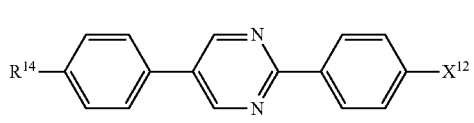
(8-36) 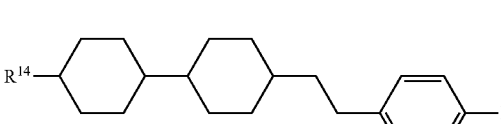
(8-37) 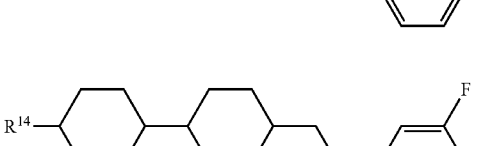
(8-38) 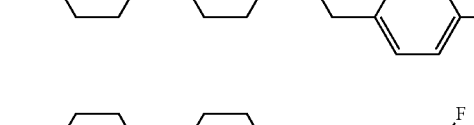
(8-39) 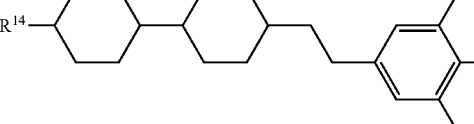
(8-40) 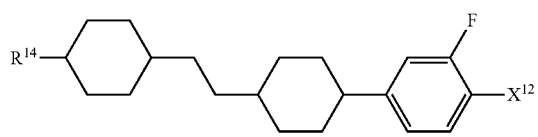
(8-41) 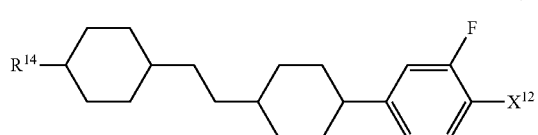
(8-42) 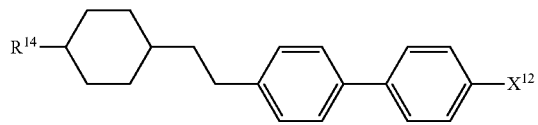
(8-43) 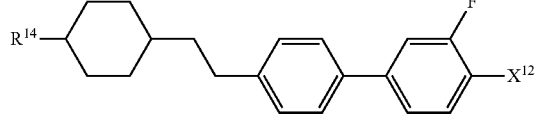
(8-44) 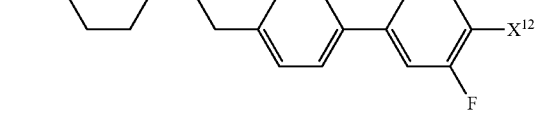
(8-45) 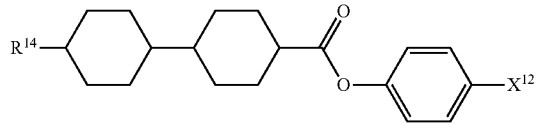
(8-46) 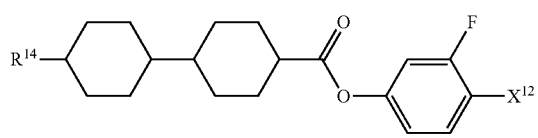
(8-47) 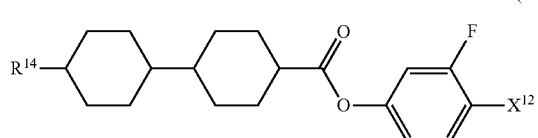
(8-48) 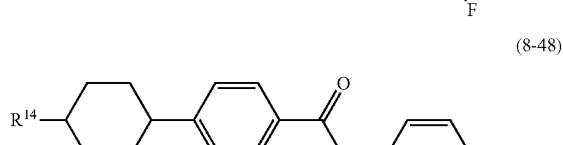

(8-49)
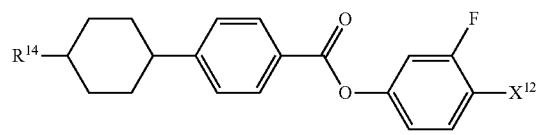

(8-50)
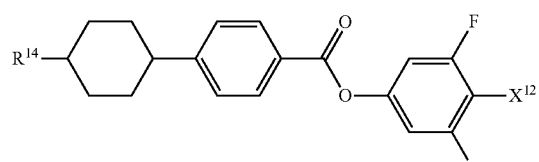

(8-51)
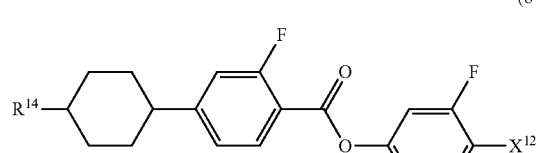

(8-52)
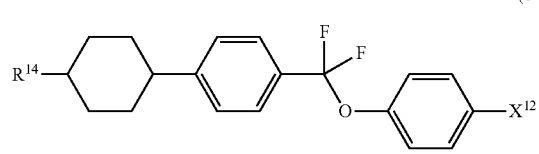

(8-53)
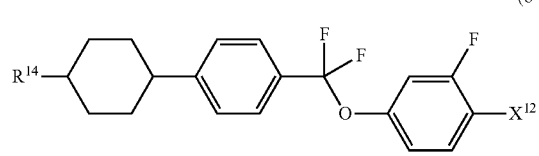

(8-54)
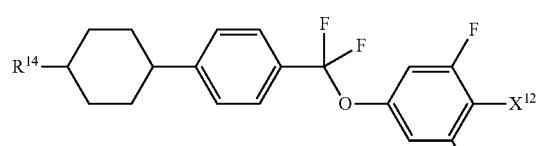

(8-55)
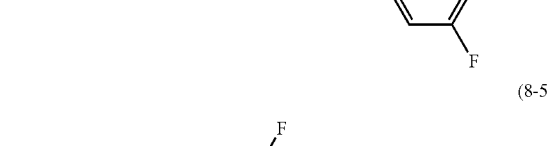

(8-56)
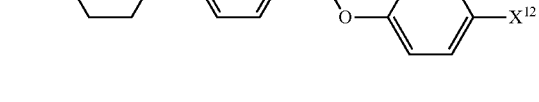

(8-57)
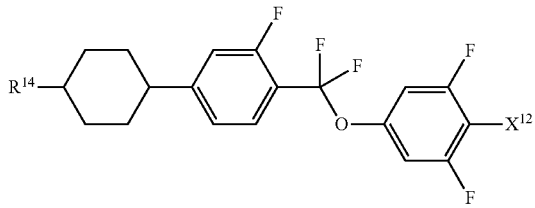

(8-58)
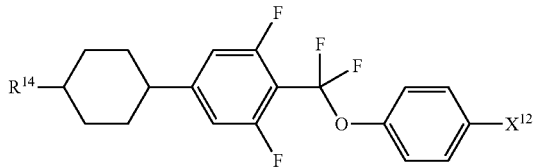

(8-59)
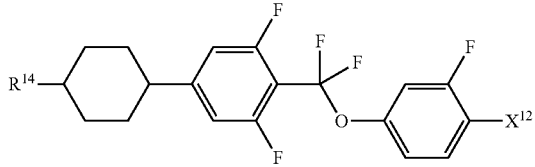

(8-60)
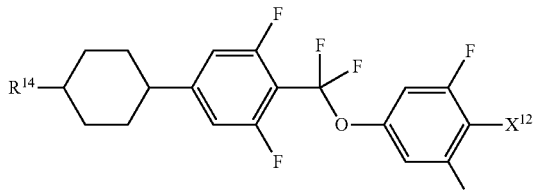

(8-61)
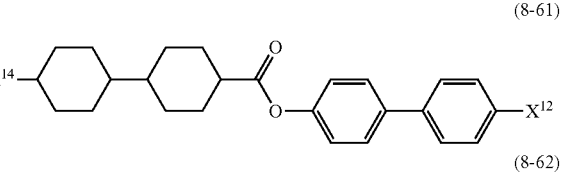

(8-62)
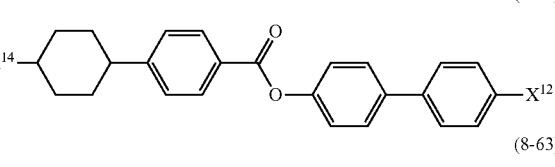

(8-63)
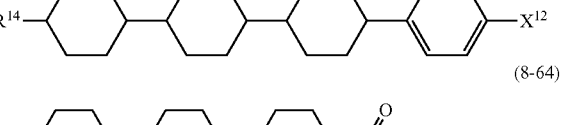

(8-64)
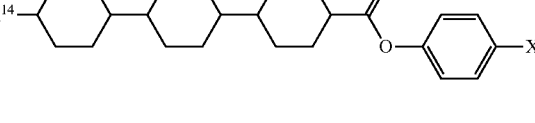

Component D has positive dielectric anisotropy and a value thereof is large, and therefore is mainly used when a composition for the TN mode or the like is prepared. Addition of component D can increase the dielectric anisotropy of the composition. Component D is effective in extending the temperature range of the liquid crystal phase, adjusting the viscosity or adjusting the optical anisotropy. Component D is also useful for adjustment of the voltage-transmittance curve of the device.

When the composition for the TN mode or the like is prepared, a content of component D is suitably in the range of 1% by weight to 99% by weight, preferably in the range of 10% by weight to 97% by weight, and further preferably in the range of 40% by weight to 95% by weight, based on the weight of the liquid crystal composition. When component D is added to a composition having negative dielectric anisotropy, the content of component D is preferably 30% by weight or less based on the weight of the liquid crystal composition. Addition of component D allows adjustment of the elastic constant of the composition and adjustment of the voltage-transmittance curve of the device.

Component E includes compounds (9) to (15). The compounds have phenylene in which hydrogen in lateral positions are replaced by two pieces of halogen, such as 2,3-difluoro-1,4-phenylene. Specific examples of preferred component E include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In a compound of component E, $R^{15}$ and $R^{16}$ are independently alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine; and $R^1$ is hydrogen, fluorine, alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine.

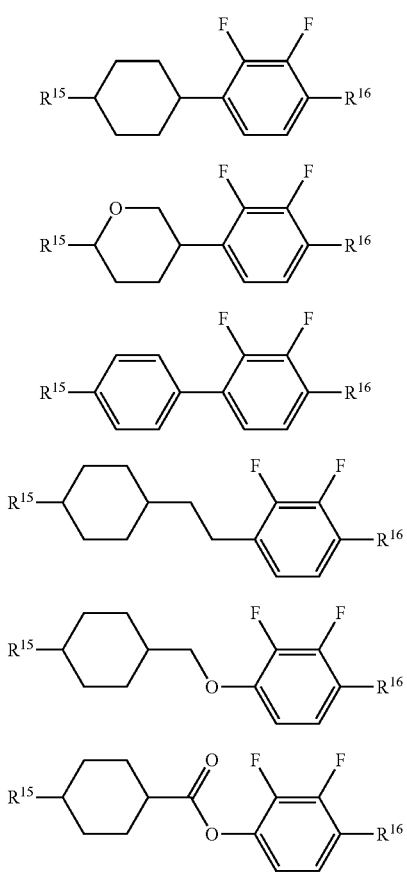

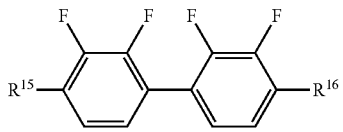

(9-7)

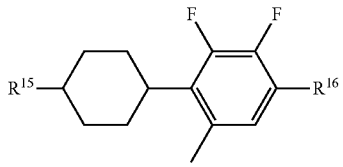

(9-8)

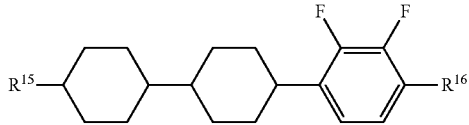

(10-1)

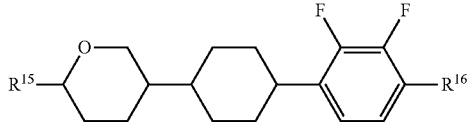

(10-2)

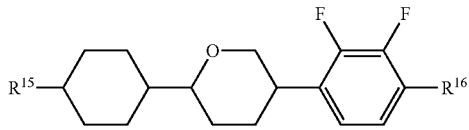

(10-3)

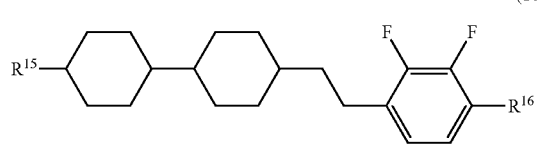

(10-4)

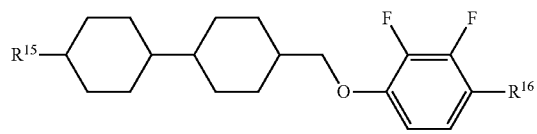

(10-5)

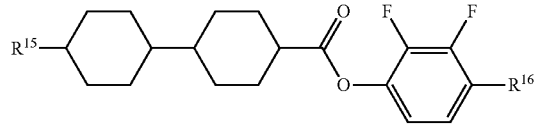

(10-6)

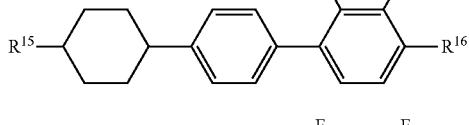

(10-7)

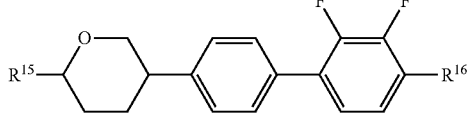

(10-8)

(10-9) 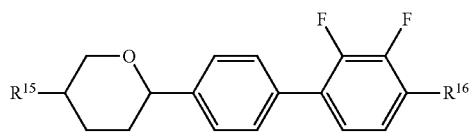
(10-10) 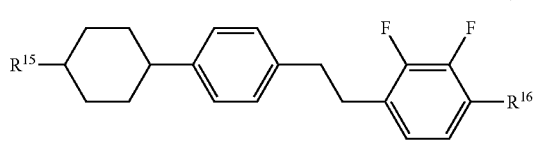
(10-11) 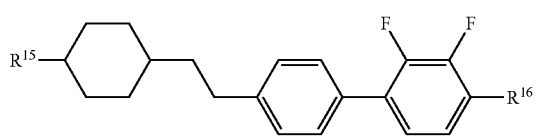
(10-12) 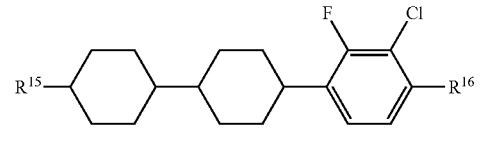
(10-13) 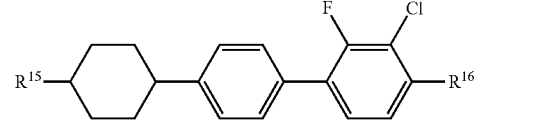
(10-14) 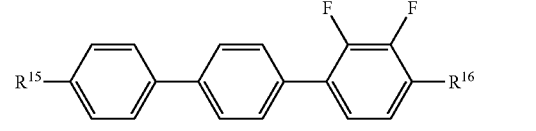
(10-15) 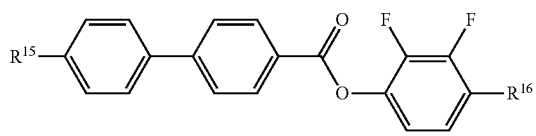
(10-16) 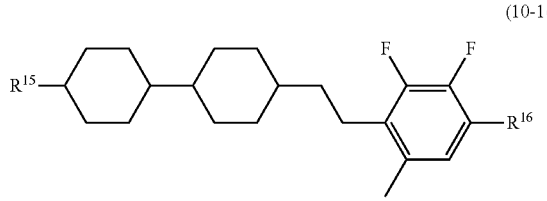
(10-17) 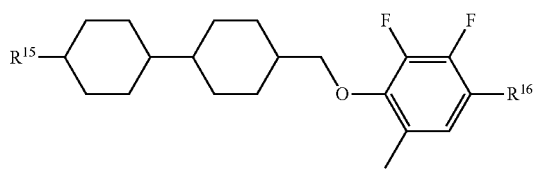
(11-1) 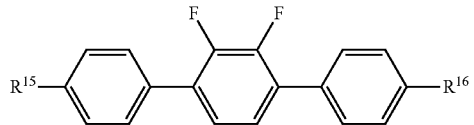
(12-1) 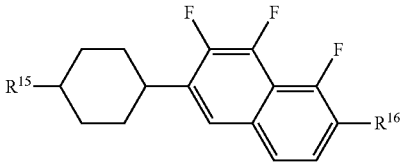
(12-2) 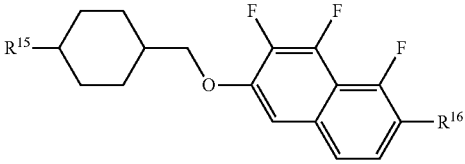
(12-3) 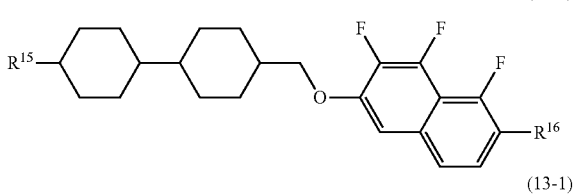
(13-1) 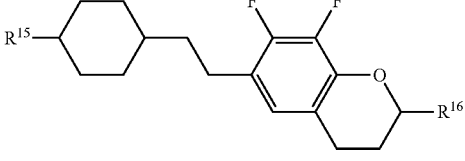
(13-2) 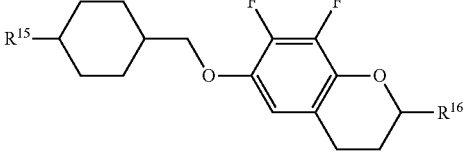
(13-3) 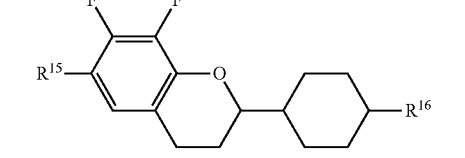
(13-4) 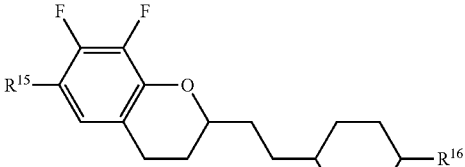
(13-5) 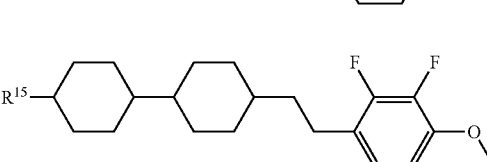
(13-6) 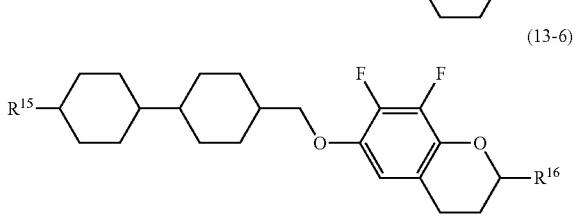

(13-7)
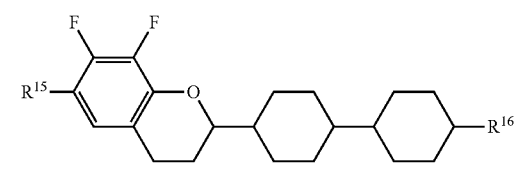

(13-8)
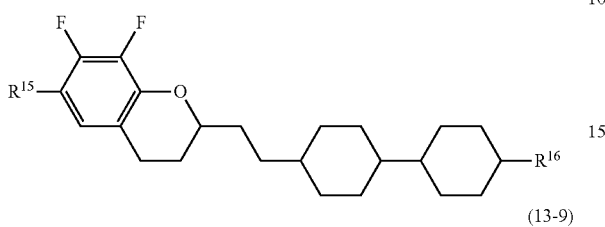

(13-9)
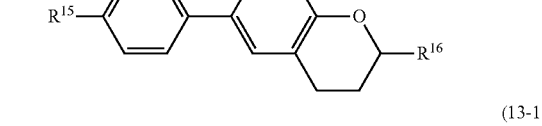

(13-10)
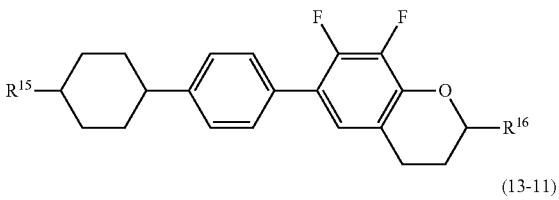

(13-11)
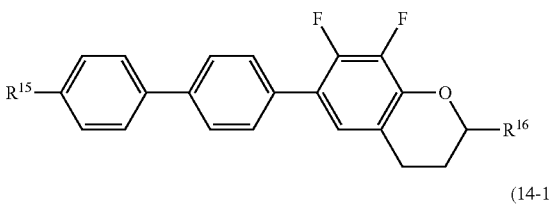

(14-1)
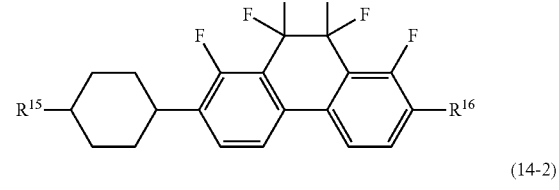

(14-2)
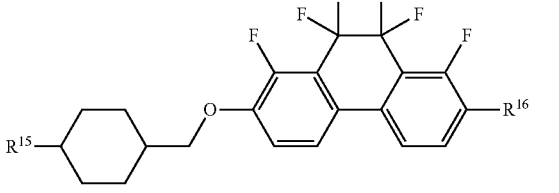

(14-3)
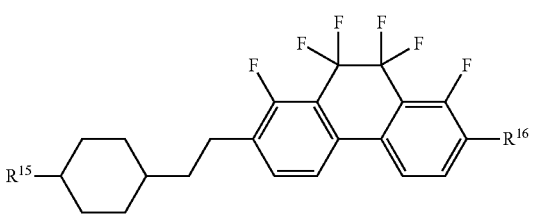

(15-1)
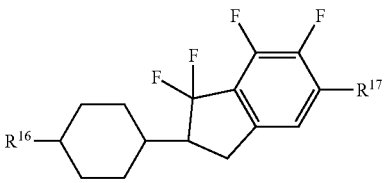

(15-2)
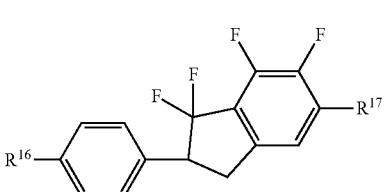

(15-3)
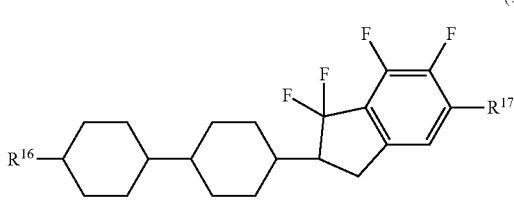

Component E has large negative dielectric anisotropy. Component E is used when a composition for the IPS mode, the VA mode, the PSA mode or the like is prepared. As a content of component E is increased, the dielectric anisotropy of the composition is negatively increased, but the viscosity is increased. Thus, as long as a desired value of a threshold voltage of the device is met, the content is preferably as small as possible. When the dielectric anisotropy at a degree of −5 is taken into account, the content is preferably 40% by weight or more in order to allow a sufficient voltage driving.

Among types of component E, compound (9) is a bicyclic compound, and therefore is mainly effective in decreasing the viscosity, adjusting the optical anisotropy or increasing the dielectric anisotropy. Compounds (10) and (11) are a tricyclic compound, and therefore are effective in increasing the maximum temperature, the optical anisotropy or the dielectric anisotropy. Compounds (12) to (15) are effective in increasing the dielectric anisotropy.

When a composition for the IPS mode, the VA mode, the PSA mode or the like is prepared, the content of component E is preferably 40% by weight or more, and further preferably in the range of 50% by weight to 95% by weight, based on the weight of the liquid crystal composition. When component E is added to a composition having positive dielectric anisotropy, the content of component E is preferably 30% by weight or less based on the weight of the liquid crystal composition. Addition of component E allows adjustment of the elastic constant of the composition and adjustment of the voltage-transmittance curve of the device.

A liquid crystal composition satisfying at least one of characteristics such as high maximum temperature, low minimum temperature, small viscosity, suitable optical anisotropy, large positive or negative dielectric anisotropy, large specific resistance, high stability to ultraviolet light, high stability to heat and a large elastic constant can be prepared by suitably combining components B, C, D and E described above. A liquid crystal compound different from components B, C, D and E may be added when necessary.

A liquid crystal composition is prepared according to a publicly known method. For example, the component compounds are mixed and dissolved in each other by heating. According to an application, an additive may be added to the composition. Specific examples of the additives include the polymerizable compound other than formula (1) and formula (16), the polymerization initiator, the polymerization inhibitor, the optically active compound, the antioxidant, the ultraviolet light absorber, the light stabilizer, the heat stabilizer and the antifoaming. Such additives are well known to those skilled in the art, and described in literature.

The polymerizable compound is added for the purpose of forming the polymer in the liquid crystal composition. The polymerizable compound and compound (1) are copolymerized by irradiation with ultraviolet light while voltage is applied between electrodes, and thus the polymer is formed in the liquid crystal composition. On the occasion, compound (1) is immobilized in a state in which the polar group noncovalently interacts with a substrate surface of glass (or metal oxide). Thus, capability of controlling alignment of liquid crystal molecules is further improved, and simultaneously the polar compound no longer leaks into the liquid crystal composition. Moreover, suitable pretilt can be obtained even in the substrate surface of glass (or metal oxide), and therefore a liquid crystal display device in which a response time is shortened and the voltage holding ratio is large can be obtained. Preferred examples of the polymerizable compounds include acrylate, methacrylate, a vinyl compound, a vinyloxy compound, propenyl ether, an epoxy compound (oxirane, oxetane) and vinyl ketone. Further preferred examples include a compound having at least one piece of acryloyloxy, and a compound having at least one piece of methacryloyloxy. Still further preferred examples also include a compound having both acryloyloxy and methacryloyloxy.

Further preferred examples include compounds (M-1) to (M-17). In compounds (M-1) to (M-17), $R^{25}$ to $R^{31}$ are independently hydrogen or methyl; s, v and x are independently 0 or 1; t and u are independently an integer from 1 to 10; and $L^{21}$ to $L^{26}$ are independently hydrogen or fluorine, and $L^{27}$ and $L^{28}$ are independently hydrogen, fluorine or methyl.

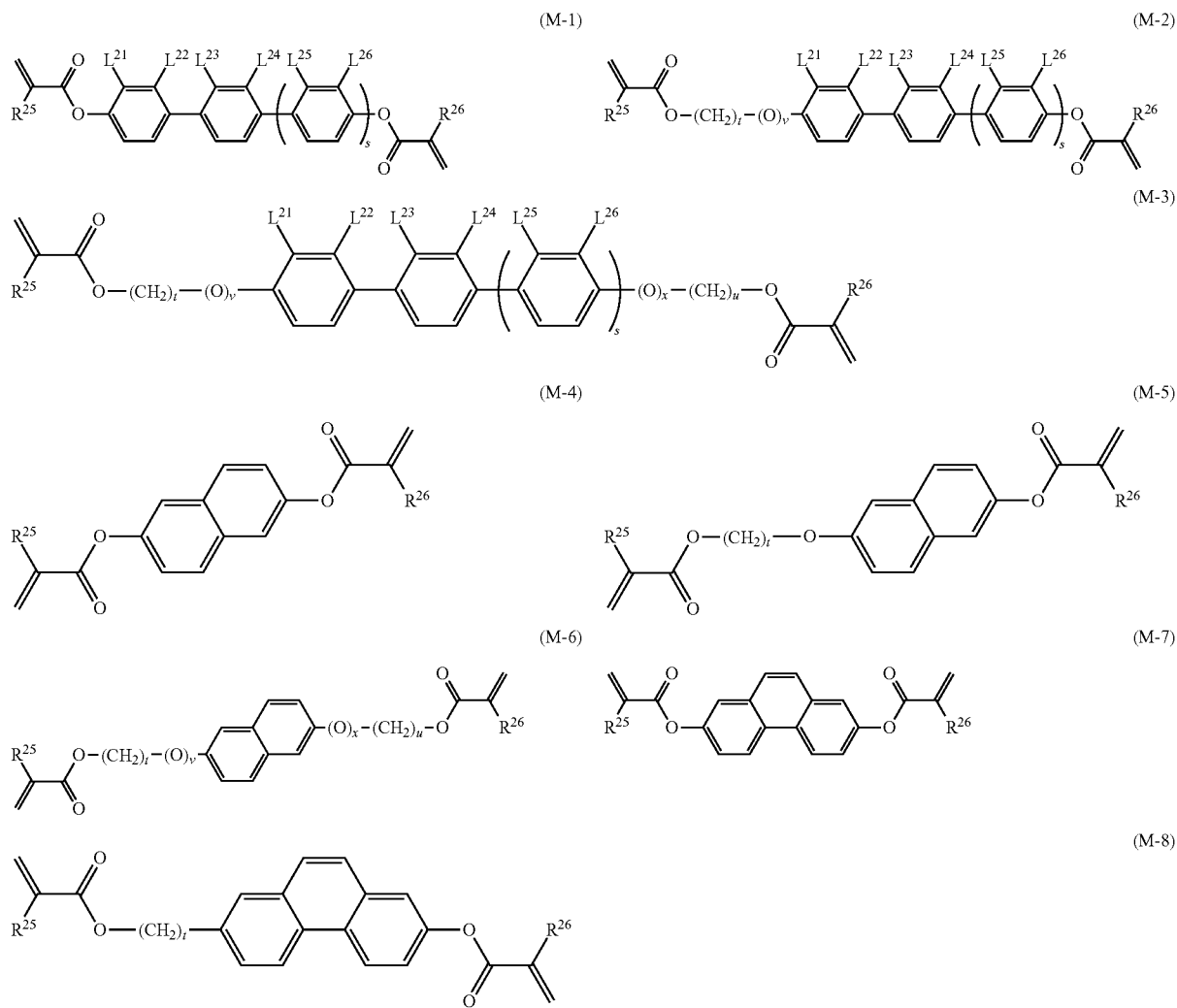

(M-9)
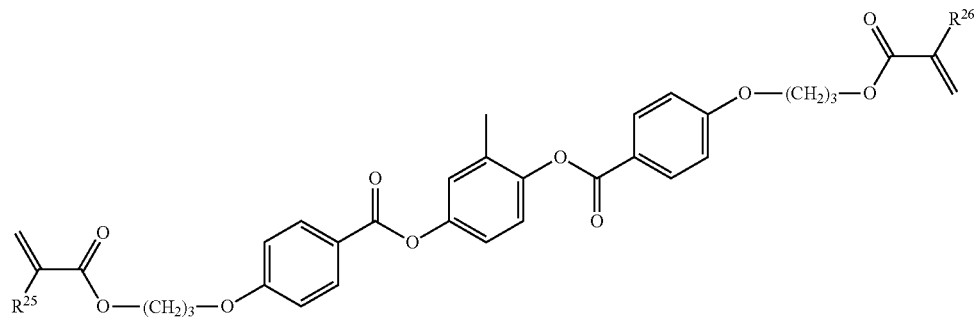
(M-10)
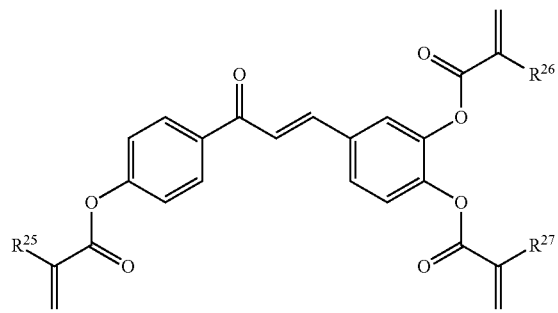
(M-11)
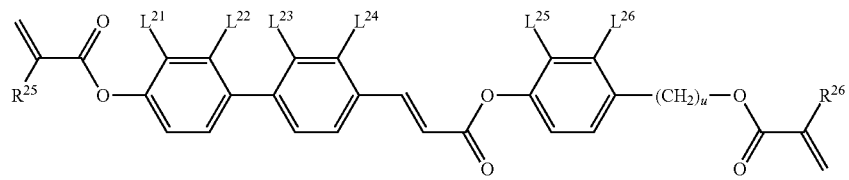
(M-12)
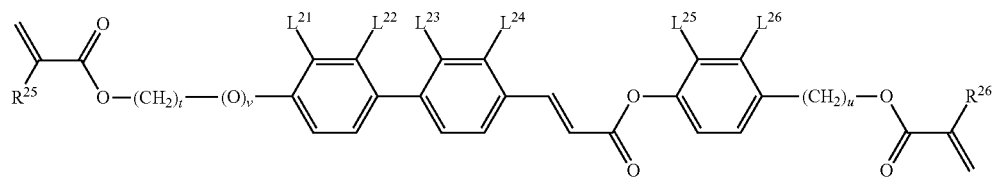
(M-13)
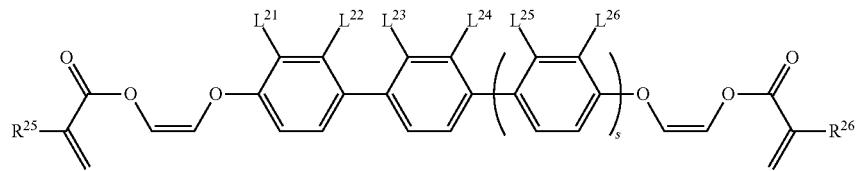
(M-14)
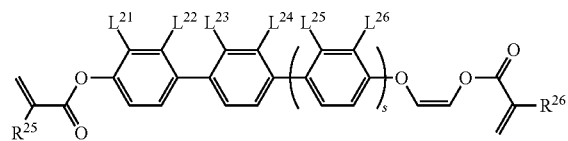
(M-15)
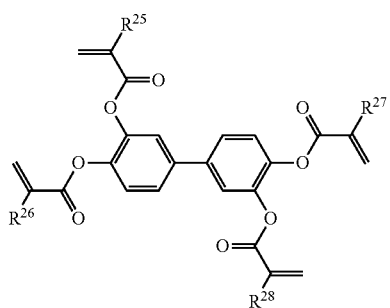

-continued

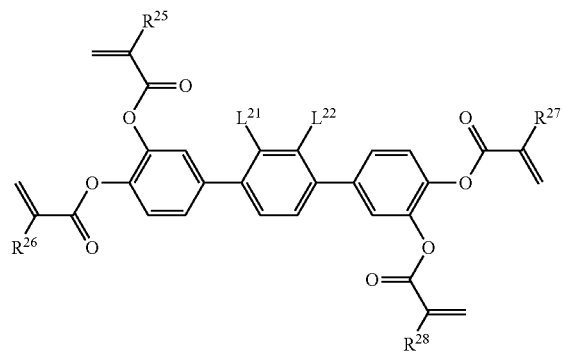

(M-16)

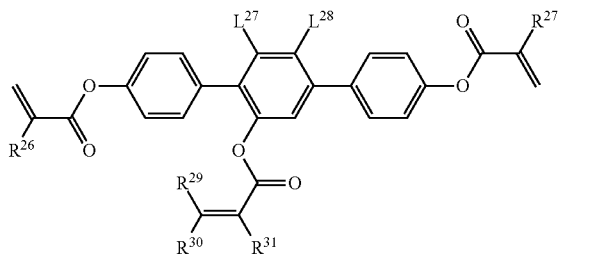

(M-17)

The polymerizable compound can be rapidly polymerized by adding the polymerization initiator. An amount of a remaining polymerizable compound can be decreased by optimizing a reaction temperature. Specific examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a mixture of 2,4-diethylxanthone and methyl p-dimethylaminobenzoate, and a mixture of benzophenone and methyltriethanolamine.

After the photoradical polymerization initiator is added to the liquid crystal composition, polymerization can be performed by irradiation with ultraviolet light while an electric field is applied. However, an unreacted polymerization initiator or a decomposition product of the polymerization initiator may cause a poor display such as the image persistence in the device. In order to prevent such an event, photopolymerization may be performed with no addition of the polymerization initiator. A preferred wavelength of irradiation light is in the range of 150 nanometers to 500 nanometers. A further preferred wavelength is in the range of 250 nanometers to 450 nanometers, and a most preferred wavelength is in the range of 300 nanometers to 400 nanometers.

Upon storing the polymerizable compound, the polymerization inhibitor may be added thereto for preventing polymerization. The polymerizable compound is ordinarily added to the composition without removing the polymerization inhibitor. Specific examples of the polymerization inhibitor include hydroquinone, a hydroquinone derivative such as methylhydroquinone, 4-t-butylcatechol, 4-methoxyphenol and phenothiazine.

The optically active compound is effective in inducing a helical structure in liquid crystal molecules to give a required twist angle, and thereby preventing a reverse twist. A helical pitch can be adjusted by adding the optically active compound thereto. Two or more optically active compounds may be added for the purpose of adjusting temperature dependence of the helical pitch. Specific examples of a preferred optically active compound include compounds (Op-1) to (Op-18) described below. In compound (Op-18), ring J is 1,4-cyclohexylene or 1,4-phenylene, and $R^{28}$ is alkyl having 1 to 10 carbons.

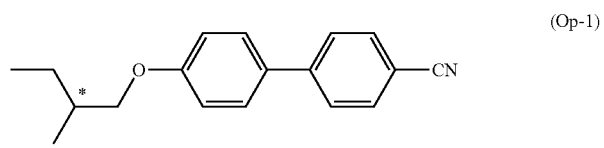

(Op-1)

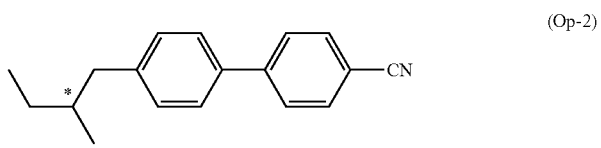

(Op-2)

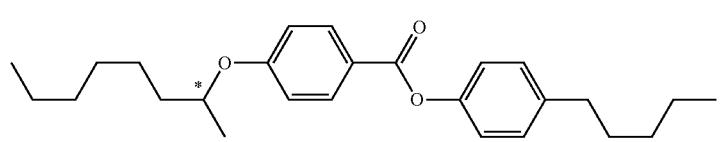

(Op-3)

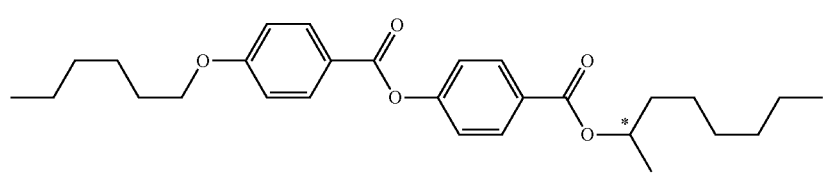

(Op-4)

(Op-5)
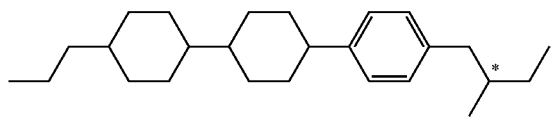
(Op-6)
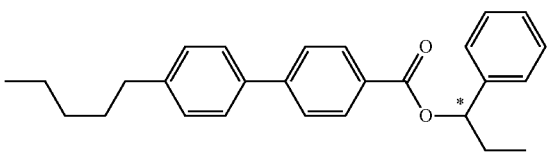
(Op-7)
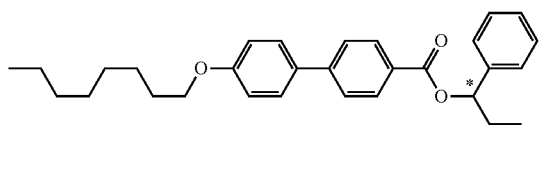
(Op-8)
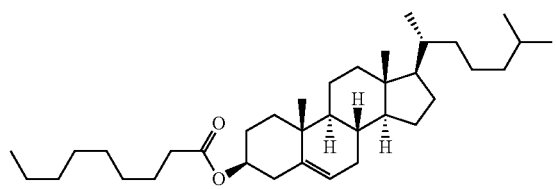
(Op-9)
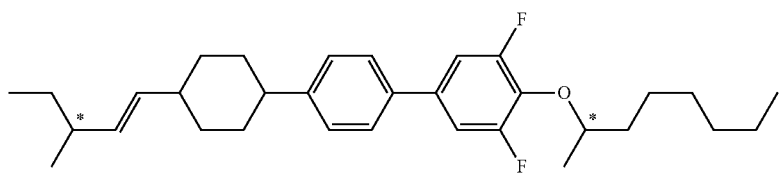
(Op-10)
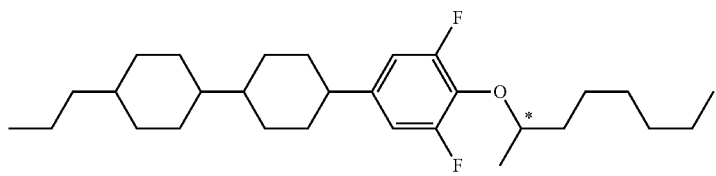
(Op-11)
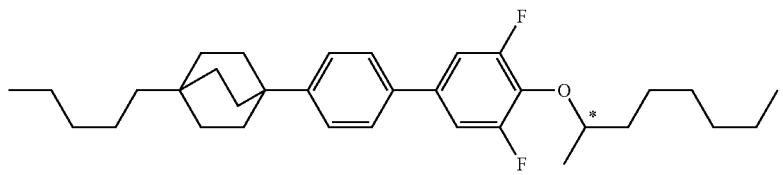
(Op-12)
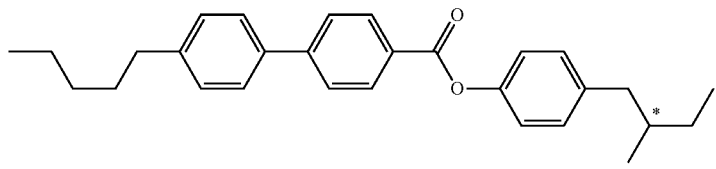
(Op-13)
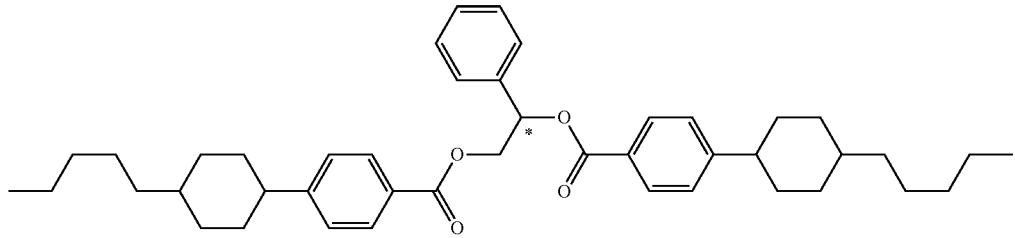
(Op-14)
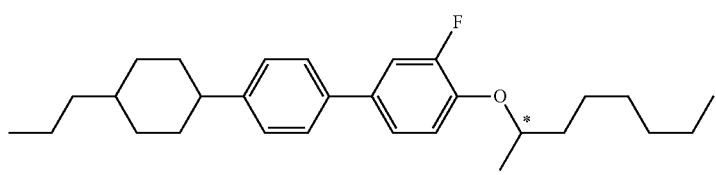

(Op-15)

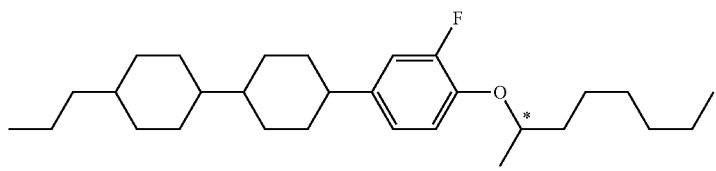

(Op-16)

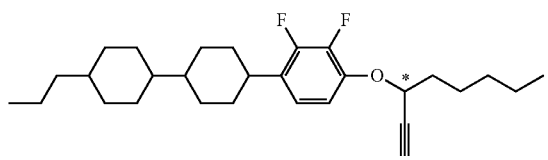

(Op-17)

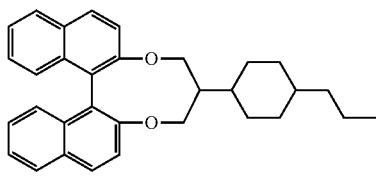

(Op-18)

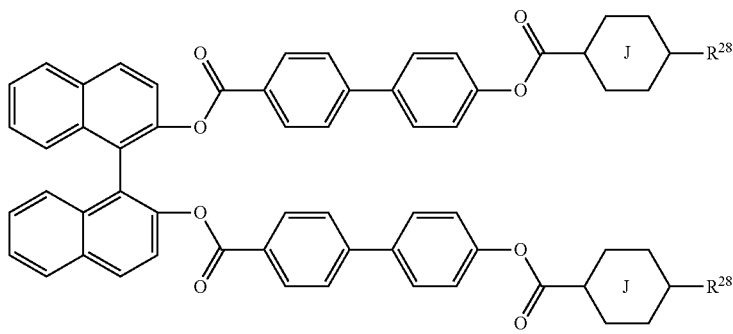

The antioxidant is effective for maintaining a large voltage holding ratio. Specific examples of a preferred antioxidant include compounds (AO-1) and (AO-2) described below; and IRGANOX 415, IRGANOX 565, IRGANOX 1010, IRGANOX 1035, IRGANOX 3114 and IRGANOX 1098 (trade names: BASF SE). The ultraviolet light absorber is effective for preventing a decrease of the maximum temperature. Specific examples of a preferred ultraviolet light absorber include a benzophenone derivative, a benzoate derivative and a triazole derivative. Specific examples include compounds (AO-3) and (AO-4) described below; TINUVIN 329, TINUVIN P, TINUVIN 326, TINUVIN 234, TINUVIN 213, TINUVIN 400, TINUVIN 328 and TINUVIN 99-2 (trade names: BASF SE); and 1,4-diazabicyclo[2.2.2]octane (DABCO).

The light stabilizer such as an amine having steric hindrance is preferred for maintaining the large voltage holding ratio. Specific examples of a preferred light stabilizer include compounds (AO-5) and (AO-6) described below; and TINUVIN 144, TINUVIN 765 and TINUVIN 770DF (trade names: BASF SE). The heat stabilizer is also effective for maintaining the large voltage holding ratio, and preferred examples include IRGAFOS 168 (trade name: BASF SE). The antifoaming agent is effective for preventing foam formation. Specific examples of a preferred antifoaming agent include dimethyl silicone oil and methylphenyl silicone oil.

(AO-1)

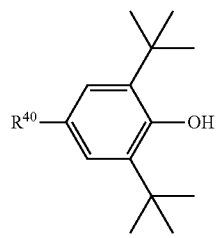

(AO-2)

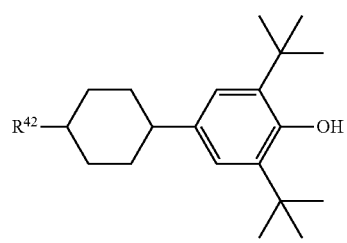

(AO-3)

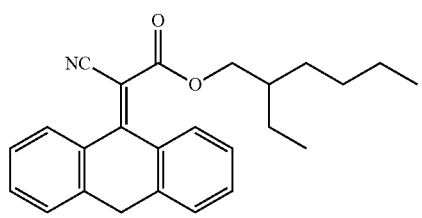

(AO-4)

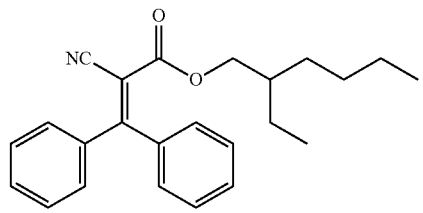

(AO-5)

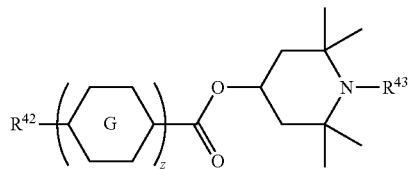

(AO-6)

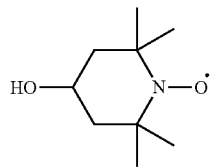

In compound (AO-1), $R^{40}$ is alkyl having 1 to 20 carbons, alkoxy having 1 to 20 carbons, —$COOR^{41}$ or —$CH_2CH_2COOR^{41}$, in which $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O (oxygen radical), ring G is 1,4-cyclohexylene or 1,4-phenylene, and Z is 1, 2 or 3.

4. Liquid Crystal Display Device

The liquid crystal composition can be used in the liquid crystal display device having an operating mode such as the PC mode, the TN mode, the STN mode, the OCB mode and the PSA mode, and driven by an active matrix mode. The composition can also be used in the liquid crystal display device having the operating mode such as the PC mode, the TN mode, the STN mode, the OCB mode, the VA mode and the IPS mode, and driven by a passive matrix mode. The devices can be applied to any of a reflective type, a transmissive type and a transflective type.

The composition can also be used in a nematic curvilinear aligned phase (NCAP) device prepared by microencapsulating a nematic liquid crystal, a polymer dispersed liquid crystal display device (PDLCD) and a polymer network liquid crystal display device (PNLCD) in which a three-dimensional network-polymer is formed in the liquid crystal. When an amount of adding the polymerizable compound is about 10% by weight or less based on the weight of the liquid crystal composition, the liquid crystal display device having the PSA mode can be prepared. A preferred proportion is in the range of about 0.1% by weight to about 2% by weight. A further preferred proportion is in the range of about 0.2% by weight to about 1.0% by weight. The device having the PSA mode can be driven by the driving mode such as the active matrix mode and the passive matrix mode. Such devices can be applied to any of the reflective type, the transmissive type and the transflective type. A device having a polymer dispersed mode can also be prepared by increasing the amount of adding the polymerizable compound.

In a device having a polymer sustained alignment mode, a polymer contained in a composition aligns the liquid crystal molecules. A polar compound assists alignment of the liquid crystal molecules. More specifically, the polar compound can be used in place of an alignment film. One example of the method for manufacturing such a device is as described below. A device having two substrates referred to as an array substrate and a color filter substrate is arranged. The substrate has no the alignment film. At least one of the substrates has an electrode layer. The liquid crystal composition is prepared by mixing the liquid crystal compounds. The polymerizable compound and the polar compound are added to the composition. The additive may be further added thereto when necessary. The composition is injected into the device. The device is irradiated with light in a state in which voltage is applied thereto. Ultraviolet light is preferred. The polymerizable compound is polymerized by irradiation with light. The composition containing the polymer is formed by the polymerization, and a device having the PSA mode can be manufactured.

In the procedure, the polar compound is arranged on the substrate because the polar group interacts with the surface of the substrate. The polar compound aligns the liquid crystal molecules. When voltage is applied thereto, alignment of the liquid crystal molecules is further promoted by action of an electric field. The polymerizable compound is also aligned according to the alignment. The polymerizable compound is polymerized by ultraviolet light in the above state, and therefore a polymer maintaining the alignment is formed. The alignment of the liquid crystal molecules is additionally stable by an effect of the polymer, and therefore the response time of the device is shortened. The image persistence is caused due to poor operation in the liquid crystal molecules, and therefore the persistence is also simultaneously improved by the effect of the polymer. In particular, compound (1) of the invention is a polymerizable polar compound, and therefore aligns liquid crystal molecules, and simultaneously is copolymerized with any other polymerizable compound. Thus, the polar compound no longer leaks into the liquid crystal composition, and therefore the liquid crystal display device having large voltage holding ratio can be obtained.

EXAMPLES

The invention will be described in greater detail by way of Examples (including Synthesis Examples and Use Examples). However, the invention is not limited by the Examples. The invention includes a mixture of a composition in Use Example 1 and a composition in Use Example 2. The invention also includes a mixture prepared by mixing at least two of the compositions in the Use Examples.

1. Example of Compound (1)

Compound (1) was prepared according to procedures shown in Examples. Unless otherwise described, a reaction was performed under a nitrogen atmosphere. Compound (1) was prepared according to procedures shown in Example 1 or the like. The thus prepared compound was identified by a method such as an NMR analysis. Characteristics of compound (1), the liquid crystal compound, the composition and the device were measured by methods described below.

NMR analysis: For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, CFCl$_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Gas chromatographic analysis: For measurement, GC-2010 Gas Chromatograph made by Shimadzu Corporation was used. As a column, a capillary column DB-1 (length 60 m, bore 0.25 mm, film thickness 0.25 μm) made by Agilent Technologies, Inc. was used. As a carrier gas, helium (1 mL/minute) was used. A temperature of a sample vaporizing chamber and a temperature of a detector (FID) part were set to 300° C. and 300° C., respectively. A sample was dissolved in acetone and prepared to be a 1 weight % solution, and then 1 microliter of the solution obtained was injected into the sample vaporizing chamber. As a recorder, GC Solution System made by Shimadzu Corporation or the like was used.

HPLC Analysis: For measurement, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector, a CORONA detector or the like was appropriately used. When the UV detector was used, a detection wavelength was set at 254 nanometers. A sample was dissolved in acetonitrile and prepared to be a 0.1 weight % solution, and then 1 microliter of the solution was injected into a sample chamber. As a recorder, C-R7Aplus made by Shimadzu Corporation was used.

Ultraviolet-Visible Spectrophotometry: For measurement, PharmaSpec UV-1700 made by Shimadzu Corporation was used. A detection wavelength was adjusted in the range of 190 nanometers to 700 nanometers. A sample was dissolved in acetonitrile and prepared to be a 0.01 mmol/L solution, and measurement was carried out by putting the solution in a quartz cell (optical path length: 1 cm).

Sample for measurement: Upon measuring phase structure and a transition temperature (a clearing point, a melting point, a polymerization starting temperature or the like), a compound itself was used as a sample.

Measuring method: Characteristics were measured according to the methods described below. Most of the measuring methods are applied as described in the Standard of Japan Electronics and Information Technology Industries Association (hereinafter abbreviated as JEITA) (JEITA ED-2521B) discussed and established by JEITA, or modified thereon. No thin film transistor (TFT) was attached to a TN device used for measurement.

(1) Phase Structure

A sample was placed on a hot plate in a melting point apparatus (FP-52 Hot Stage made by Mettler-Toledo International Inc.) equipped with a polarizing microscope. A state of phase and a change thereof were observed with the polarizing microscope while the sample was heated at a rate of 3° C. per minute, and a kind of the phase was specified.

(2) Transition Temperature (° C.)

For measurement, a differential scanning calorimeter, Diamond DSC System, made by PerkinElmer, Inc., or a high sensitivity differential scanning calorimeter, X-DSC7000, made by SSI NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. A melting point and a polymerization starting temperature of a compound were also measured using the apparatus. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to liquid may be occasionally abbreviated as "clearing point."

A crystal was expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Maximum Temperature of Nematic Phase ($T_{NI}$ or NI; ° C.)

A sample was placed on a hot plate in a melting point apparatus equipped with a polarizing microscope, and heated at a rate of 1° C. per minute. Temperature when part of the sample began to change from a nematic phase to an isotropic liquid was measured. A maximum temperature of the nematic phase may be occasionally abbreviated as "maximum temperature." When the sample was a mixture of compound (1) and the base liquid crystal, the maximum temperature was expressed in terms of a symbol $T_{NI}$. When the sample was a mixture of compound (1) and a compound such as components B, C and D, the maximum temperature was expressed as a symbol NI.

(4) Minimum Temperature of Nematic Phase ($T_C$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., Tc was expressed as $T_C \leq -20°$ C. A minimum temperature of the nematic phase may be occasionally abbreviated as "minimum temperature."

(5) Viscosity (Bulk Viscosity; η; Measured at 20° C.; mPa·s)

For measurement, a cone-plate (E type) rotational viscometer made by Tokyo Keiki Inc. was used.

(6) Optical Anisotropy (Refractive Index Anisotropy; Measured at 25° C.; Δn)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when the direction of polarized light was perpendicular to the direction of rubbing. A value of optical anisotropy (Δn) was calculated from an equation: Δn=n∥−n⊥.

(7) Specific Resistance (ρ; Measured at 25° C.; Ωcm)

Into a vessel equipped with electrodes, 1.0 milliliter of sample was injected. A direct current voltage (10 V) was applied to the vessel, and a direct current after 10 seconds was measured. Specific resistance was calculated from the following equation: (specific resistance)={(voltage)×(electric capacity of a vessel)}/{(direct current)×(dielectric constant of vacuum)}.

The measuring method of the characteristics may be occasionally different between a sample having positive dielectric anisotropy and a sample having negative dielectric anisotropy. The measuring methods when the dielectric anisotropy is positive were described in sections (8a) to (12a). The methods when the dielectric anisotropy is negative were described in sections (8b) to (12b).

(8a) Viscosity (Rotational Viscosity; $\gamma1$; Measured at 25° C.; mPa·s)

Positive dielectric anisotropy: Measurement was carried out according to a method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and calculation equation (8) described on page 40 of the paper presented by M. Imai et al. A value of dielectric anisotropy required for the calculation was determined using the device by which the rotational viscosity was measured and by a method described below.

(8b) Viscosity (Rotational Viscosity; $\gamma1$; Measured at 25° C.; mPa·s)

Negative dielectric anisotropy: Measurement was carried out according to a method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device in the range of 39 V to 50 V at an increment of 1 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and calculation equation (8) described on page 40 of the paper presented by M. Imai et al. In dielectric anisotropy required for the calculation, a value measured according to items of dielectric anisotropy described below was used.

(9a) Dielectric Anisotropy ($\Delta\varepsilon$; Measured at 25° C.)

Positive dielectric anisotropy: A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant ($\varepsilon\|$) of liquid crystal molecules in a major axis direction was measured. Sine waves (0.5 V, 1 kHz) were applied to the device, and after 2 seconds, a dielectric constant ($\varepsilon\perp$) of liquid crystal molecules in a minor axis direction was measured. A value of dielectric anisotropy was calculated from an equation: $\Delta\varepsilon=\varepsilon\|-\varepsilon\perp$.

(9b) Dielectric Anisotropy ($\Delta\varepsilon$; measured at 25° C.)

Negative dielectric anisotropy: A value of dielectric anisotropy was calculated from an equation: $\Delta\varepsilon=\varepsilon\|-\varepsilon\perp$. A dielectric constant ($\varepsilon\|$ and $\varepsilon\perp$) was measured as described below.

(1) Measurement of dielectric constant ($\varepsilon\|$): An ethanol (20 mL) solution of octadecyltriethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant ($\varepsilon\|$) of liquid crystal molecules in a major axis direction was measured.

(2) Measurement of dielectric constant ($\varepsilon\perp$): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant ($\varepsilon\perp$) of liquid crystal molecules in a minor axis direction was measured.

(10a) Elastic Constant (K; Measured at 25° C.; pN)

Positive dielectric anisotropy: For measurement, HP4284A LCR Meter made by Yokogawa-Hewlett-Packard Co. was used. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; Nikkan Kogyo Shimbun, Ltd.), and values of $K_{11}$ and $K_{33}$ were obtained from equation (2.99). Next, $K_{22}$ was calculated using the previously determined values of $K_{11}$ and $K_{33}$ in equation (3.18) on page 171. Elastic constant K was expressed in terms of a mean value of the thus determined $K_{11}$, $K_{22}$ and $K_{33}$.

(10b) Elastic Constant ($K_{11}$ and $K_{33}$; Measured at 25° C.; pN)

Negative dielectric anisotropy: For measurement, Elastic Constant Measurement System Model EC-1 made by TOYO Corporation was used. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of "Liquid Crystal Device Handbook" (Ekisho Debaisu Handobukku in Japanese; Nikkan Kogyo Shimbun, Ltd.) and a value of elastic constant was obtained from equation (2.100).

(11a) Threshold Voltage (Vth; Measured at 25° C.; V)

Positive dielectric anisotropy: For measurement, an LCD-5100 luminance meter made by Otsuka Electronics Co., Ltd. was used. A light source was a halogen lamp. A sample was put in a normally white mode TN device in which a distance (cell gap) between two glass substrates was 0.45/$\Delta$n (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 90% transmittance.

(11b) Threshold Voltage (Vth; Measured at 25° C.; V)

Negative dielectric anisotropy: For measurement, an LCD-5100 luminance meter made by Otsuka Electronics Co., Ltd. was used. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 10% transmittance.

(12a) Response Time (τ; Measured at 25° C.; ms)

Positive dielectric anisotropy: For measurement, an LCD-5100 luminance meter made by Otsuka Electronics Co., Ltd. was used. A light source was a halogen lamp. A low-pass filter was set to 5 kHz. A sample was put in a normally white mode TN device in which a distance (cell gap) between two glass substrates was 5.0 micrometers and a twist angle was 80 degrees. A voltage (rectangular waves; 60 Hz, 5 V, 0.5 second) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A rise time (τr; millisecond) is expressed in terms of time required for a change from 90% transmittance to 10% transmittance. A fall time (τf; millisecond) is expressed in terms of time required for a change from 10% transmittance to 90% transmittance. A response time is expressed by a sum of the rise time and the fall time thus obtained.

(12b) Response Time (τ; Measured at 25° C.; ms)

Negative dielectric anisotropy: For measurement, an LCD-5100 luminance meter made by Otsuka Electronics Co., Ltd. was used. A light source was a halogen lamp. A low-pass filter was set to 5 kHz. A sample was put in a normally black mode PVA device in which a distance (cell gap) between two glass substrates was 3.2 micrometers and a rubbing direction was anti-parallel. The device was sealed with an ultraviolet-curable adhesive. The device was applied with a voltage of a little exceeding a threshold voltage for 1 minute, and then was irradiated with ultraviolet light of 23.5 mW/cm² for 8 minutes, while applying a voltage of 5.6 V. A voltage (rectangular waves; 60 Hz, 10 V, 0.5 second) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A response time is expressed in terms of time required for a change from 90% transmittance to 10% transmittance (fall time; millisecond).

Raw Material

Solmix (registered trade name) A-11 is a mixture of ethanol (85.5%), methanol (13.4%) and isopropanol (1.1%), and was purchased from Japan Alcohol Trading Co., Ltd.

Synthesis Example 1

Synthesis of Compound (1-4-2)

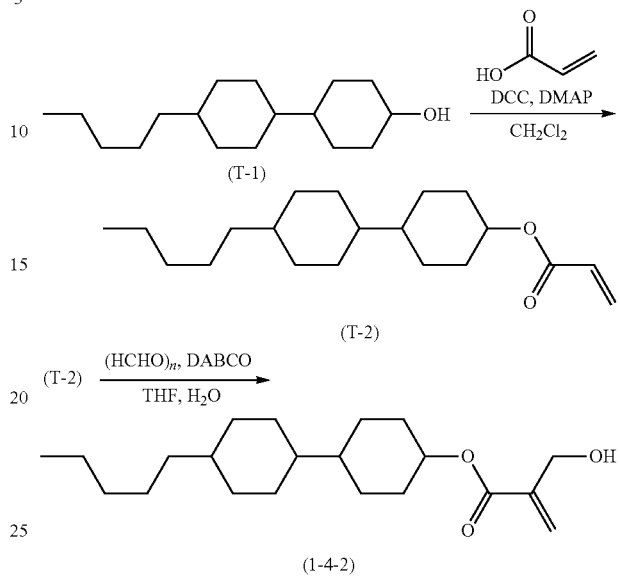

First Step

Compound (T-1) (25.0 g), acrylic acid (7.14 g), DMAP (1.21 g) and dichloromethane (300 mL) were put in a reaction vessel, and the resulting mixture was cooled down to 0° C. Thereto, a dichloromethane (125 mL) solution of DCC (24.5 g) was slowly added dropwise, and the resulting mixture was stirred for 12 hours while returning to room temperature. An insoluble matter was filtered off, and then the resulting reaction mixture was poured into water, and an aqueous layer was subjected to extraction with dichloromethane. A combined organic layer was washed with water, and dried over anhydrous magnesium sulfate. The resulting solution was concentrated under reduced pressure, and the residue was purified by silica gel chromatography (heptane:toluene=2:1 in a volume ratio). The residue was further purified by recrystallization from Solmix (registered trade name) A-11 to obtain compound (T-2) (11.6 g; 380).

Second Step

Paraformaldehyde (2.75 g), DABCO (4.62 g) and water (40 mL) were put in a reaction vessel, and the resulting mixture was stirred at room temperature for 15 minutes. Thereto, a THF (90 mL) solution of compound (T-2) (6.31 g) was added dropwise, and stirred at room temperature for 72 hours. The resulting reaction mixture was poured into water, and an aqueous layer was subjected to extraction with ethyl acetate. A combined organic layer was washed with water, and dried over anhydrous magnesium sulfate. The resulting solution was concentrated under reduced pressure, and the residue was purified by silica gel chromatography (toluene:ethyl acetate=5:1 in a volume ratio). The residue was further purified by recrystallization from a mixed solvent of heptane and toluene (1:1 in a volume ratio) to obtain compound (1-4-2) (1.97 g; 29%).

An NMR analysis value of the resulting compound (1-4-2) was as described below.

$^{1}$H-NMR: Chemical shift δ (ppm; CDCl$_3$): 6.23 (s, 1H), 5.79 (d, J=1.2 Hz, 1H), 4.79-4.70 (m, 1H), 4.32 (d, J=6.7 Hz, 2H), 2.29 (t, J=6.7 Hz, 1H), 2.07-2.00 (m, 2H), 1.83-1.67 (m, 6H), 1.42-1.18 (m, 8H), 1.18-0.91 (m, 9H), 0.91-0.79 (m, 5H).

Physical properties of compound (1-4-2) were as described below.

Transition temperature: C 40.8 S$_A$ 109 I.

Synthesis Example 2

Synthesis of Compound (1-4-22)

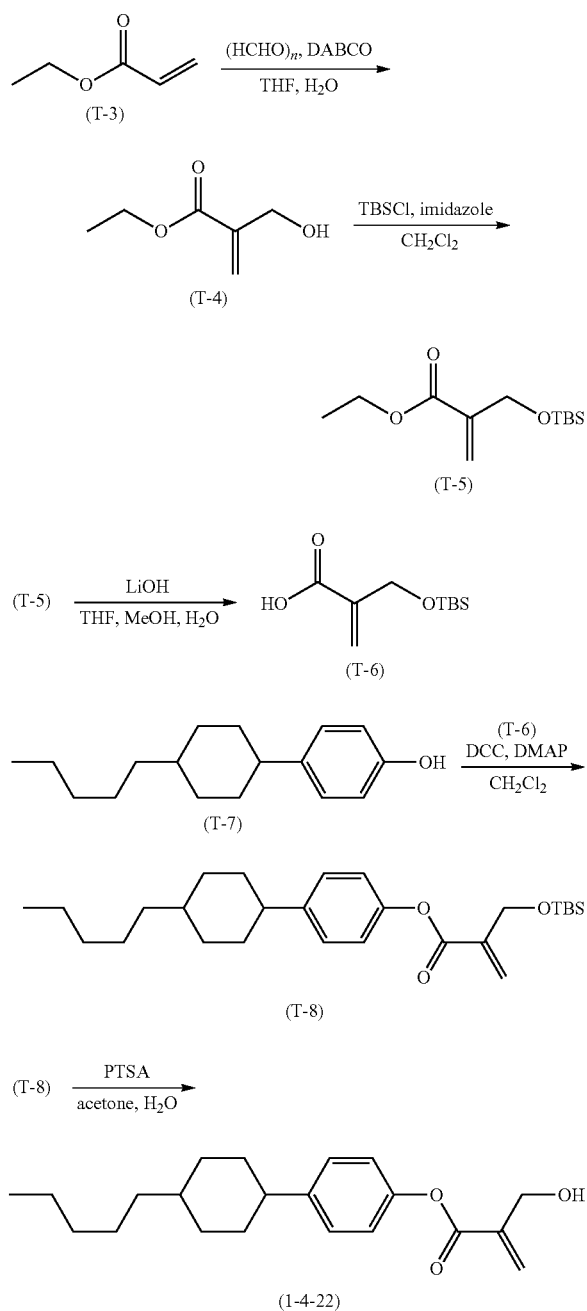

First Step

Compound (T-4) (42.5 g; 65%) was obtained by using compound (T-3) (50.0 g) as a raw material in a manner similar to the procedures in the second step in Synthesis Example 1.

Second Step

Compound (T-4) (42.5 g), imidazole (24.5 g) and dichloromethane (740 mL) were put in a reaction vessel, and the resulting mixture was cooled down to 0° C. Thereto, a dichloromethane (110 mL) solution of t-butyldimethylsilyl chloride (54.1 g) was slowly added dropwise, and stirred for 12 hours while returning to room temperature. The resulting reaction mixture was poured into water, and an aqueous layer was subjected to extraction with dichloromethane. A combined organic layer was washed with water, and dried over anhydrous magnesium sulfate. The resulting solution was concentrated under reduced pressure, and the residue was purified by silica gel chromatography (heptane:ethyl acetate=10:1 in a volume ratio) to obtain compound (T-5) (79.8 g; 100%).

Third Step

Compound (T-5) (79.8 g), THF (640 mL), methanol (160 mL) and water (80 mL) were put in a reaction vessel, and the resulting mixture was cooled down to 0° C. Thereto, lithium hydroxide monohydrate (27.4 g) was added, and stirred for 12 hours while returning to room temperature. The resulting reaction mixture was poured into water, and 6 N hydrochloric acid (15 mL) was slowly added to make the resulting mixture acidic, and then an aqueous layer was subjected to extraction with ethyl acetate. A combined organic layer was washed with water, and dried over anhydrous magnesium sulfate. The resulting solution was concentrated under reduced pressure to obtain compound (T-6) (60.6 g; 86%).

Fourth Step

Compound (T-7) (2.83 g), compound (T-6) (2.98 g), DMAP (0.140 g) and dichloromethane (80 mL) were put in a reaction vessel, and the resulting mixture was cooled down to 0° C. Thereto, a dichloromethane (40 mL) solution of DCC (2.84 g) was slowly added dropwise, and stirred for 12 hours while returning to room temperature. An insoluble matter was filtered off, and then the resulting reaction mixture was poured into water, and an aqueous layer was subjected to extraction with dichloromethane. A combined organic layer was washed with water, and dried over anhydrous magnesium sulfate. The resulting solution was concentrated under reduced pressure, and the residue was purified by silica gel chromatography (heptane:toluene=2:1 in a volume ratio) to obtain compound (T-8) (3.22 g; 63%).

Fifth Step

Compound (T-8) (3.22 g), p-toluenesulfonic acid monohydrate (PTSA, 0.551 g), acetone (50 mL) and water (3.5 mL) were put in a reaction vessel, and the resulting mixture was stirred at room temperature for 1 hour. Next, pyridine (0.30 mL) was added, and then the resulting reaction mixture was poured into water, and an aqueous layer was subjected to extraction with ethyl acetate. A combined organic layer was washed with water, and dried over anhydrous magnesium sulfate. The resulting solution was concentrated under reduced pressure, and the residue was purified by silica gel chromatography (heptane:ethyl acetate=2:1 in a volume ratio). The residue was further purified by recrystallization from a mixed solvent of heptane and toluene (1:1 in a volume ratio) to obtain compound (1-4-22) (2.05 g; 86%).

An NMR analysis value of the resulting compound (1-4-22) was as described below.

$^1$H-NMR: Chemical shift δ (ppm; CDCl$_3$): 7.23 (d, J=8.6 Hz, 2H), 7.03 (d, J=8.6 Hz, 2H), 6.50 (s, 1H), 6.03 (d, J=1.0 Hz, 1H), 4.44 (d, J=6.7 Hz, 2H), 2.47 (tt, J=12.2 Hz, J=3.3 Hz, 1H), 2.24 (t, J=6.6 Hz, 1H), 1.93-1.83 (m, 4H), 1.48-1.37 (m, 2H), 1.37-1.18 (m, 9H), 1.10-0.98 (m, 2H), 0.90 (t, J=7.2 Hz, 3H).

Physical properties of compound (1-4-22) were as described below.

Transition temperature: C 67.6 S$_C$ 84.4 S$_A$ 87.7 N 89.8 I.

Synthesis Example 3

Synthesis of Compound (1-4-27)

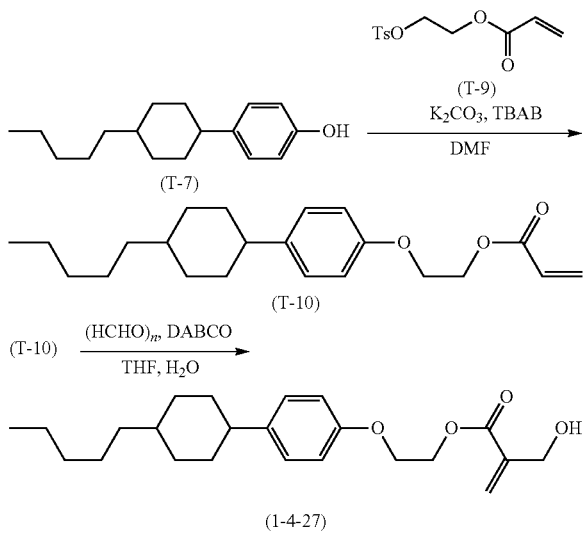

First Step

Compound (T-7) (4.00 g), potassium carbonate (4.49 g), tetrabutylammonium bromide (TBAB) (1.05 g) and DMF (60 mL) were put in a reaction vessel, and the resulting mixture was stirred at 80° C. for 1 hour. Thereto, a DMF (20 mL) solution of compound (T-9) (5.27 g) prepared according to a technique described in JP 2011-21118 A was slowly added dropwise, and further stirred at 80° C. for 2 hours. The resulting reaction mixture was poured into water, and an aqueous layer was subjected to extraction with ethyl acetate. A combined organic layer was washed with water, and dried over anhydrous magnesium sulfate. The resulting solution was concentrated under reduced pressure, and the residue was purified by silica gel chromatography (heptane:toluene=2:1 in a volume ratio) to obtain compound (T-10) (4.00 g; 72%).

Second Step

Compound (1-4-27) (1.81 g; 42%) was obtained by using compound (T-10) (4.00 g) as a raw material in a manner similar to the procedures in the second step in Synthesis Example 1.

An NMR analysis value of the resulting compound (1-4-27) was as described below.

$^1$H-NMR: Chemical shift δ (ppm; CDCl$_3$): 7.13 (d, J=8.6 Hz, 2H), 6.84 (d, J=8.7 Hz, 2H), 6.29 (s, 1H), 5.85 (d, J=1.2 Hz, 1H), 4.52 (t, J=4.8 Hz, 2H), 4.33 (d, J=6.7 Hz, 2H), 4.21 (t, J=4.8 Hz, 2H), 2.41 (tt, J=12.3 Hz, J=3.0 Hz, 1H), 2.26 (t, J=6.6 Hz, 1H), 1.90-1.81 (m, 4H), 1.46-1.17 (m, 11H), 1.09-0.98 (m, 2H), 0.89 (t, J=7.3 Hz, 3H).

Physical properties of compound (1-4-27) were as described below.

Transition temperature: C 40.4 S$_A$ 69.9 I.

Synthesis Example 4

Synthesis of Compound (1-5-31)

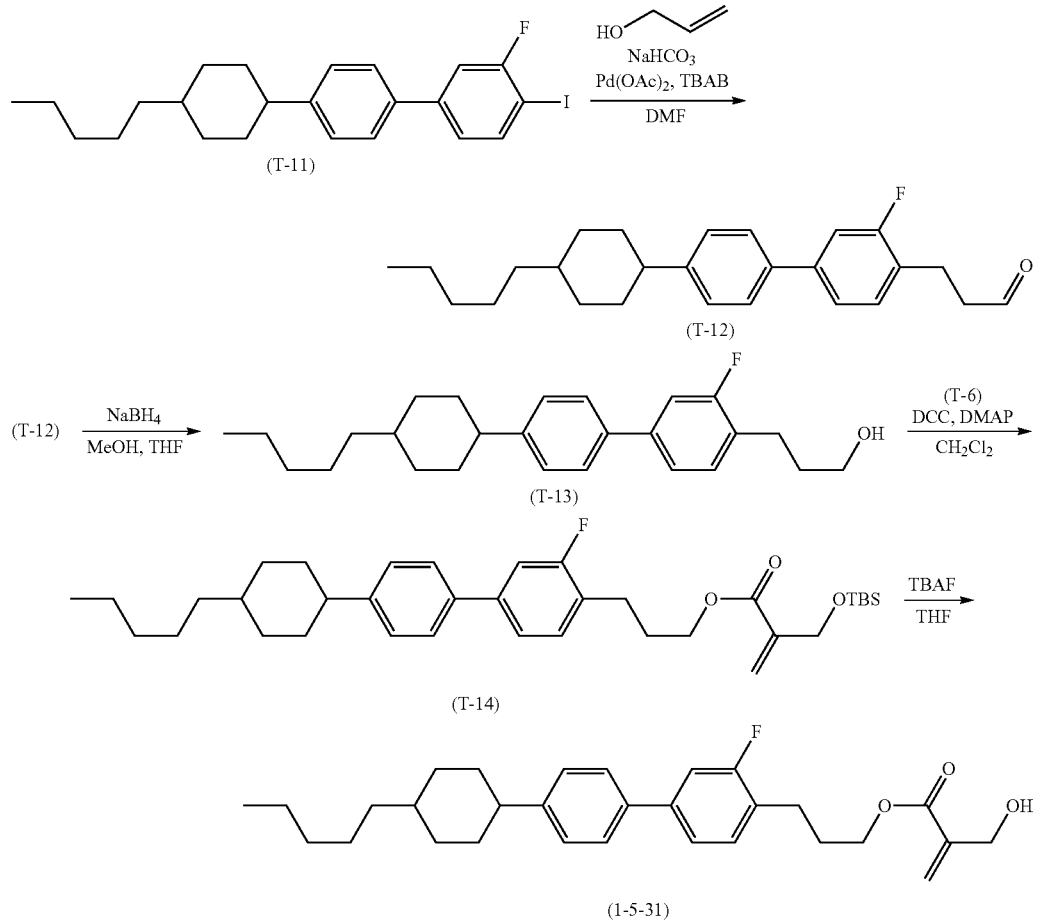

First Step

Compound (T-11) (10.7 g) prepared according to a technique described in WO 2008/105286 A, allyl alcohol (3.3 mL), palladium acetate (0.107 g), sodium hydrogencarbonate (5.99 g), TBAB (8.42 g) and DMF (110 mL) were put in a reaction vessel, and the resulting mixture was stirred at 40° C. for 8 hours. The resulting reaction mixture was poured into water, and an aqueous layer was subjected to extraction with ethyl acetate. A combined organic layer was washed with brine, and dried over anhydrous magnesium sulfate. The resulting solution was concentrated under reduced pressure, and the residue was purified by silica gel chromatography (toluene). The residue was further purified by recrystallization from a mixed solvent of heptane and toluene (1:1 in a volume ratio) to obtain compound (T-12) (6.93 g; 77%).

Second Step

Sodium borohydride (0.723 g) and methanol (110 mL) were put in a reaction vessel, and the resulting mixture was cooled down to 0° C. Thereto, a THF (30 mL) solution of compound (T-12) (6.93 g) was slowly added, and stirred for 2 hours while returning to room temperature. The resulting reaction mixture was poured into water, and an aqueous layer was subjected to extraction with ethyl acetate. A combined organic layer was washed with brine, and dried over anhydrous magnesium sulfate. The resulting solution was concentrated under reduced pressure, and the residue was purified by silica gel chromatography (toluene:ethyl acetate=5:1 in a volume ratio). The residue was further purified by recrystallization from a mixed solvent of heptane and toluene (1:1 in a volume ratio) to obtain compound (T-13) (5.73 g; 82%).

Third Step

Compound (T-14) (3.36 g; 47%) was obtained by using compound (T-13) (4.73 g) as a raw material in a manner similar to the procedures in the fourth step in Synthesis Example 2.

Fourth Step

Compound (T-14) (2.36 g) and THF (50 mL) were put in a reaction vessel, and the resulting mixture was cooled down to 0° C. Thereto, a TBAF (1.00 M; THF solution; 4.5 mL) was slowly added, and stirred for 1 hour while returning to room temperature. The resulting reaction mixture was poured into water, and an aqueous layer was subjected to extraction with ethyl acetate. A combined organic layer was washed with brine, and dried over anhydrous magnesium sulfate. The resulting solution was concentrated under reduced pressure, and the residue was purified by silica gel chromatography (toluene:ethyl acetate=5:1 in a volume ratio). The residue was further purified by recrystallization from a mixed solvent of heptane and toluene (1:1 in a volume ratio) to obtain compound (1-5-31) (1.47 g; 77%).

An NMR analysis value of the resulting compound (1-5-31) was as described below.

$^1$H-NMR: Chemical shift δ (ppm; CDCl$_3$): 7.48 (d, J=8.2 Hz, 2H), 7.31-7.14 (m, 5H), 6.25 (s, 1H), 5.84 (d, J=1.2 Hz, 1H), 4.34 (d, J=6.4 Hz, 2H), 4.24 (t, J=6.4 Hz, 2H), 2.78 (t, J=7.5 Hz, 2H), 2.51 (tt, J=12.1 Hz, J=3.2 Hz, 1H), 2.20 (t, J=6.5 Hz, 1H), 2.10-2.20 (m, 2H), 1.96-1.84 (m, 4H), 1.54-1.42 (m, 2H), 1.38-1.20 (m, 9H), 1.13-1.01 (m, 2H), 0.90 (t, J=7.2 Hz, 3H).

Physical properties of compound (1-5-31) were as described below.

Transition temperature: S$_A$ 115 I.

Synthesis Example 5

Synthesis of Compound (1-3-1)

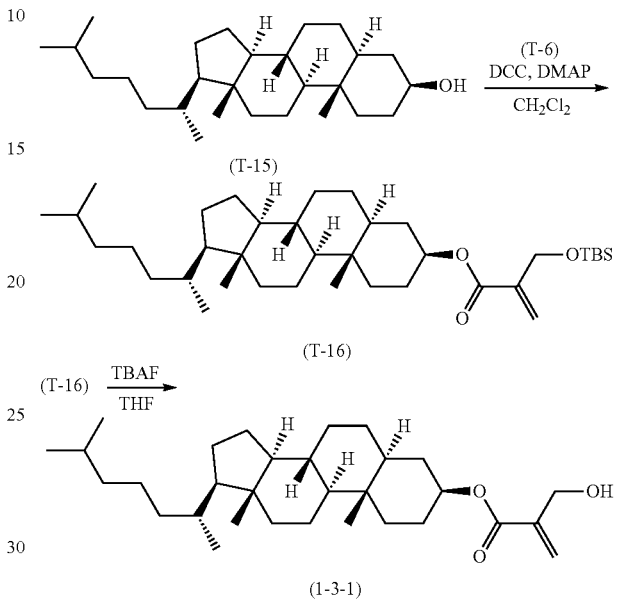

First Step

Compound (T-16) (3.56 g; 24%) was obtained by using compound (T-15) (10.0 g) as a raw material in a manner similar to the procedures in the fourth step in Synthesis Example 2.

Second Step

Compound (1-3-1) (2.34 g; 82%) was obtained by using compound (T-16) (3.56 g) as a raw material in a manner similar to the procedures in the fourth step in Synthesis Example 4.

An NMR analysis value of the resulting compound (1-3-1) was as described below.

$^1$H-NMR: Chemical shift δ (ppm; CDCl$_3$): 6.23 (s, 1H), 5.79 (d, J=1.1 Hz, 1H), 4.87-4.76 (m, 1H), 4.32 (d, J=6.6 Hz, 2H), 2.26 (t, J=6.5 Hz, 1H), 1.97 (dt, J=12.6 Hz, J=3.2 Hz, 1H), 1.90-1.72 (m, 3H), 1.69-0.81 (m, 38H), 0.70-0.61 (m, 4H).

Physical properties of compound (1-3-1) were as described below.

Transition temperature: C 122 I.

Synthesis Example 6

Synthesis of Compound (1-4-82)

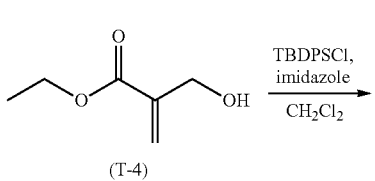

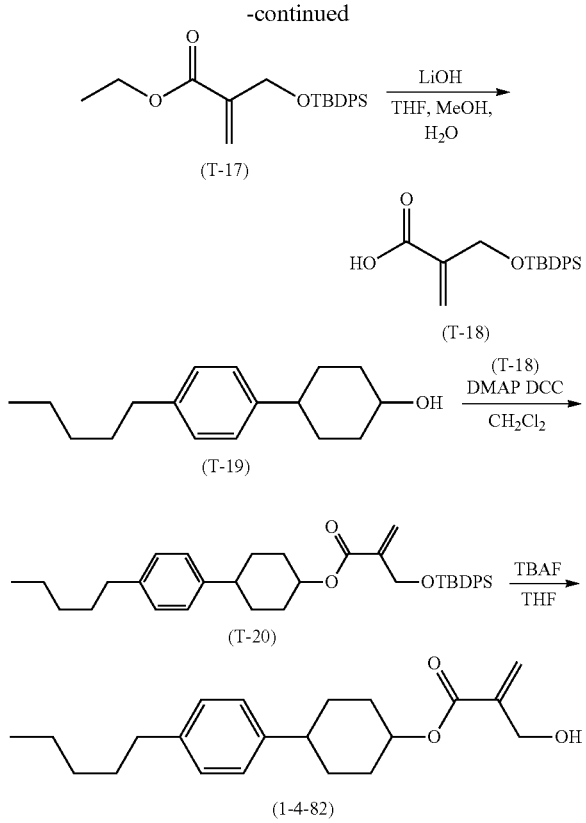

First Step

Compound (T-4) (50.0 g) was used as a raw material, imidazole (28.7 g) and dichloromethane (800 mL) were put in a reaction vessel, and the resulting mixture was cooled down to 0° C. Thereto, a dichloromethane (110 mL) solution of t-butyl diphenylchlorosilane (116.1 g) was slowly added dropwise, and stirred for 12 hours while returning to room temperature. The resulting reaction mixture was poured into water, and an aqueous layer was subjected to extraction with dichloromethane. A combined organic layer was washed with water, and dried over anhydrous magnesium sulfate. The resulting solution was concentrated under reduced pressure, and the residue was purified by silica gel chromatography (heptane:ethyl acetate=10:1 in a volume ratio) to obtain compound (T-17) (127.4 g; 900).

Second Step

Compound (T-18) (63.6 g; 54%) was obtained by using compound (T-17) (127.4 g) as a raw material in a manner similar to the procedures in the third step in Synthesis Example 2.

Third Step

Compound (T-19) (5.00 g), compound (T-18) (8.29 g), DMAP (1.0 g) and dichloromethane (80 mL) were put in a reaction vessel, and the resulting mixture was cooled down to 0° C. Thereto, a dichloromethane (40 mL) solution of DCC (5.00 g) was slowly added dropwise, and stirred for 12 hours while returning to room temperature. An insoluble matter was filtered off, and then the resulting reaction mixture was poured into water, and an aqueous layer was subjected to extraction with dichloromethane. A combined organic layer was washed with water, and dried over anhydrous magnesium sulfate. The resulting solution was concentrated under reduced pressure, and the residue was purified by silica gel chromatography (heptane:toluene=1:1 in a volume ratio) to obtain compound (T-20) (8.66 g; 750).

Fourth Step

Compound (T-20) (8.66 g) and THF (50 mL) were put in a reaction vessel, and the resulting mixture was cooled down to 0° C. Thereto, a TBAF (1.00 M; THF solution; 18 mL) was slowly added, and stirred for 1 hour while returning to room temperature. The resulting reaction mixture was poured into water, and an aqueous layer was subjected to extraction with ethyl acetate. A combined organic layer was washed with brine, and dried over anhydrous magnesium sulfate. The resulting solution was concentrated under reduced pressure, and the residue was purified by silica gel chromatography (toluene:ethyl acetate=9:1 in a volume ratio). The residue was further purified by recrystallization from heptane to obtain compound (1-4-82) (4.43 g; 88%).

An NMR analysis value of the resulting compound (1-4-82) was as described below.

$^{1}$H-NMR: Chemical shift δ (ppm; CDCl$_3$): 7.11 (s, 4H), 6.26 (s, 1H), 5.82 (d, J=1.1 Hz, 1H), 4.92-4.87 (m, 1H), 4.34 (d, J=6.4 Hz, 2H), 2.58-2.48 (m, 3H), 2.34-2.33 (m, 1H), 2.15-2.13 (m, 2H), 1.98-1.93 (m, 2H), 1.65-1.52 (m, 6H), 1.37-1.25 (m, 4H), 0.89 (t, J=6.8 Hz, 3H).

Physical properties of compound (1-4-82) were as described below.

Transition temperature: C 44.0 (S$_A$ 40.0) I

Synthesis Example 7

Synthesis of Compound (1-4-41)

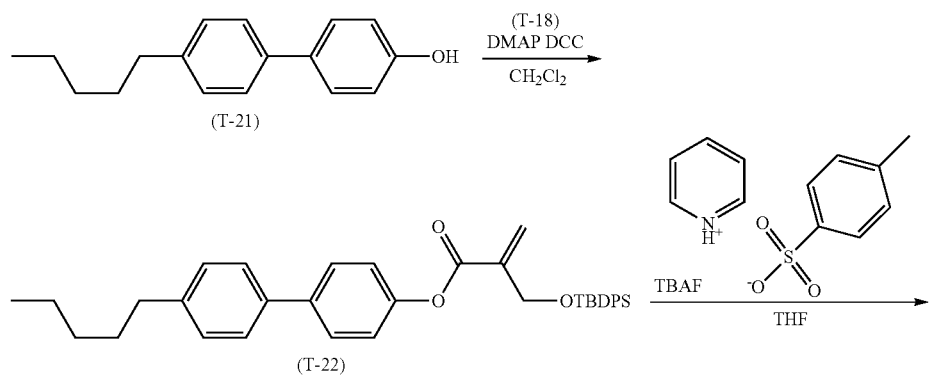

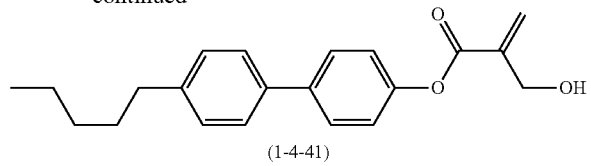

(1-4-41)

First Step

Compound (T-22) (9.13 g; 78%) was obtained by using compound (T-21) (5.00 g) as a raw material in a manner similar to the procedures in the third step in Synthesis Example 6.

Second Step

Compound (T-22) (9.13 g) and THF (50 mL) were put in a reaction vessel, and the resulting mixture was cooled down to 0° C. Thereto, pyridinium p-toluenesulfonate (4.89 g) and TBAF (1.00 M; THF solution; 19 mL) were slowly added, and stirred for 1 hour while returning to room temperature. The resulting reaction mixture was poured into water, and an aqueous layer was subjected to extraction with ethyl acetate. A combined organic layer was washed with brine, and dried over anhydrous magnesium sulfate. The resulting solution was concentrated under reduced pressure, and the residue was purified by silica gel chromatography (toluene:ethyl acetate=9:1 in a volume ratio). The residue was further purified by recrystallization from a mixed solvent of heptane and toluene (1:1 in a volume ratio) to obtain compound (1-4-41) (4.53 g; 86%).

An NMR analysis value of the resulting compound (1-4-41) was as described below.

$^1$H-NMR: Chemical shift δ (ppm; CDCl$_3$): 7.60 (d, J=8.7 Hz, 2H), 7.48 (d, J=8.1 Hz, 2H), 7.25 (d, J=8.1 Hz, 2H), 7.18 (d, J=8.7 Hz, 2H), 6.54 (s, 1H), 6.06 (d, J=0.8 Hz, 1H), 4.46 (d, J=6.5 Hz, 2H), 2.64 (t, J=7.6 Hz, 2H), 2.28-2.26 (m, 1H), 1.66-1.63 (m, 2H), 1.36-1.33 (m, 4H), 0.90 (t, J=6.8 Hz, 3H).

Physical properties of compound (1-4-41) were as described below.

Transition temperature: C 66.7 S$_A$ 135.1 I.

Synthesis Example 8

Synthesis of Compound (1-6-121)

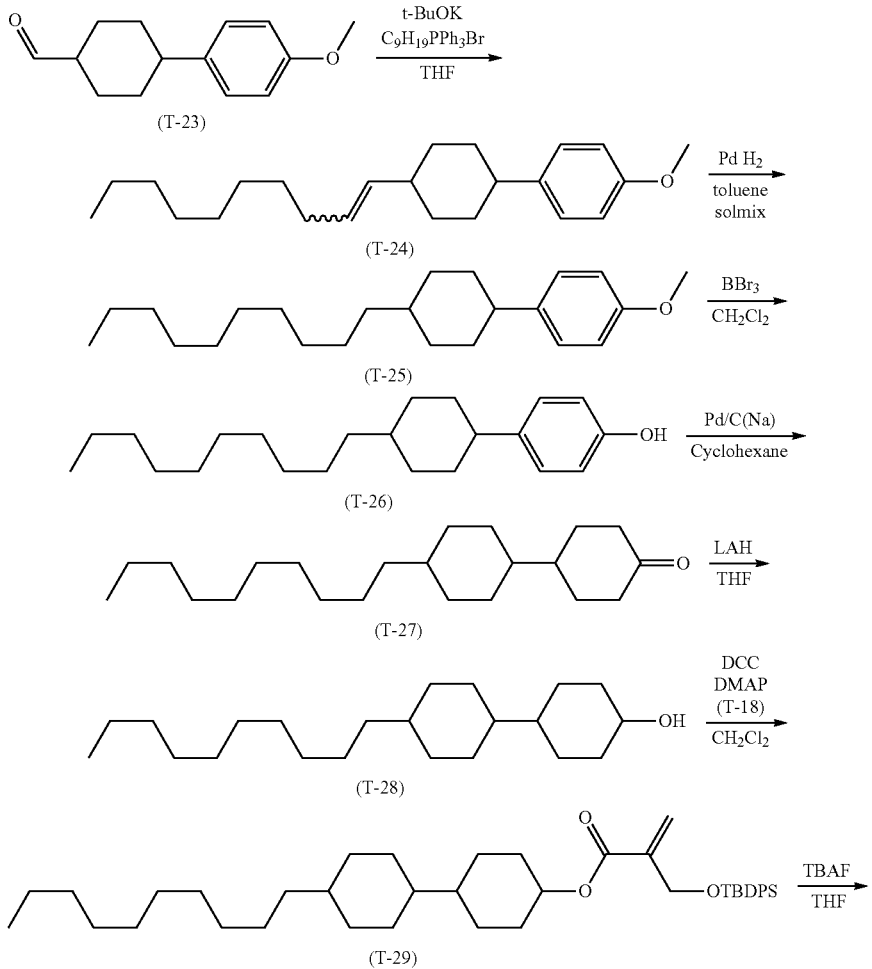

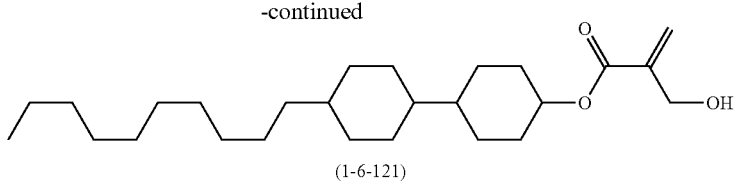

(1-6-121)

First Step

Decyltriphenylphosphonium bromide (50.0 g) and THF (200 mL) were put in a reaction vessel, and the resulting mixture was cooled down to −30° C. Potassium t-butoxide (11.9 g) was slowly added, and stirred at −30° C. for 1 hour. A THF (50 mL) solution of compound (T-23) (19.3 g) prepared according to a technique described in WO 2012/058187 A was added. The resulting mixture was stirred for 5 hours while returning to room temperature. The resulting reaction mixture was poured into water, and an aqueous layer was subjected to extraction with toluene. A combined organic layer was washed with brine, and dried over anhydrous magnesium sulfate. The resulting solution was concentrated under reduced pressure, and the residue was purified by silica gel chromatography (heptane:toluene=4:1 in a volume ratio) to obtain compound (T-24) (23.9 g; 82%).

Second Step

Compound (T-24) (23.9 g), toluene (400 mL) and IPA (400 mL) were put in a reaction vessel, Pd/C (0.38 g) was added, and the resulting mixture was stirred at room temperature for 12 hours under a hydrogen atmosphere. The resulting reaction mixture was poured into water, and an aqueous layer was subjected to extraction with toluene. A combined organic layer was washed with brine, and dried over anhydrous magnesium sulfate. The resulting solution was concentrated under reduced pressure, and the residue was purified by silica gel chromatography (heptane:toluene=4:1 in a volume ratio) to obtain compound (T-25) (22.8 g; 95%).

Third Step

Compound (T-25) (22.8 g) and dichloromethane (300 mL) were put in a reaction vessel, and the resulting mixture was cooled with ice. Thereto, boron tribromide (1.00M; dichloromethane solution; 76 mL) was added, and stirred for 5 hours while returning to room temperature. The resulting reaction mixture was poured into water, and an aqueous layer was subjected to extraction with dichloromethane. A combined organic layer was washed with brine, and dried over anhydrous magnesium sulfate. The resulting solution was concentrated under reduced pressure, and the residue was purified by silica gel chromatography with toluene. The residue was further purified by recrystallization from heptane to obtain compound (T-26) (18.8 g; 860).

Fourth Step

Compound (T-26) (18.8 g) and cyclohexane (400 mL) were put in an autoclave, and the resulting mixture was stirred at 70° C. for 6 hours. The resulting reaction mixture was poured into water, and an aqueous layer was subjected to extraction with toluene. A combined organic layer was washed with brine, and dried over anhydrous magnesium sulfate. The resulting solution was concentrated under reduced pressure, and the residue was purified by silica gel chromatography with toluene to obtain compound (T-27) (17.1 g; 900).

Fifth Step

Lithium aluminum hydride (1.21 g) and THF (200 mL) were put in a reaction vessel, and the resulting mixture was cooled with ice. A THF (200 mL) solution of compound (T-27) (17.1 g) was slowly added, and stirred for 2 hours while returning to room temperature. The resulting reaction mixture was poured into water, and an aqueous layer was subjected to extraction with ethyl acetate. A combined organic layer was washed with brine, and dried over anhydrous magnesium sulfate. The resulting solution was concentrated under reduced pressure, and the residue was purified by silica gel chromatography (toluene:ethyl acetate=9:1 in a volume ratio). The residue was further purified by recrystallization from heptane to obtain compound (T-28) (14.2 g; 83%).

Sixth Step

Compound (T-29) (10.1 g; 84%) was obtained by using compound (T-28) (6.0 g) as a raw material in a manner similar to the procedures in the third step in Synthesis Example 6.

Seventh Step

Compound (1-6-121) (5.48 g; 86%) was obtained by using compound (T-29) (10.1 g) as a raw material in a manner similar to the procedures in the fourth step in Synthesis Example 6.

An NMR analysis value of the resulting compound (1-6-121) was as described below.

$^1$H-NMR: Chemical shift δ (ppm; CDCl$_3$): 6.23 (s, 1H), 5.79 (d, J=0.8 Hz, 1H), 4.77-4.71 (m, 1H), 4.32 (d, J=6.5 Hz, 2H), 2.31 (t, J=6.6 Hz, 1H), 2.04-2.02 (m, 2H), 1.80-1.68 (m, 6H), 1.39-1.25 (m, 18H), 1.13-0.80 (m, 14H).

Physical properties of compound (1-6-121) were as described below.

Transition temperature: C 79.8 S$_A$ 122.0 I.

Synthesis Example 9

Synthesis of Compound (1-4-4)

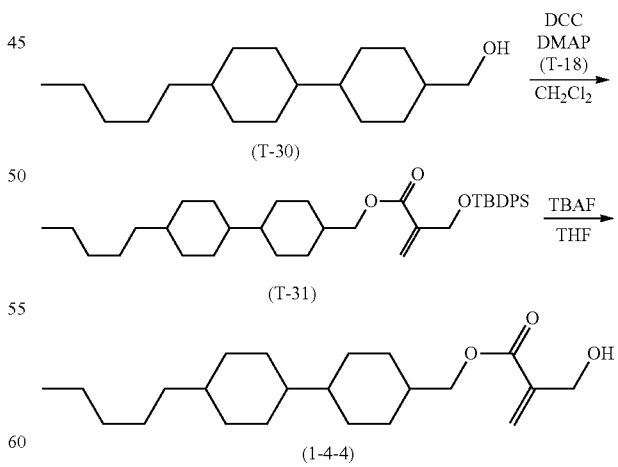

First Step

Compound (T-31) (8.84 g; 80%) was obtained by using compound (T-30) (5.00 g) as a raw material in a manner similar to the procedures in the third step in Synthesis Example 6.

Second Step

Compound (1-4-4) (4.26 g; 81%) was obtained by using compound (T-31) (8.84 g) as a raw material in a manner similar to the procedures in the fourth step in Synthesis Example 6.

An NMR analysis value of the resulting compound (1-4-4) was as described below.

$^1$H-NMR: Chemical shift δ (ppm; CDCl$_3$): 6.25 (s, 1H), 5.82 (d, J=1.1 Hz, 1H), 4.33 (d, J=6.6 Hz, 2H), 3.99 (d, J=6.5 Hz, 2H), 2.33 (t, J=6.7 Hz, 1H), 1.80-1.62 (m, 9H), 1.32-0.80 (m, 22H).

Physical properties of compound (1-4-4) were as described below.

Transition temperature: C 51.9 S$_A$ 72.5 I.

Synthesis Example 10

Synthesis of Compound (1-4-108)

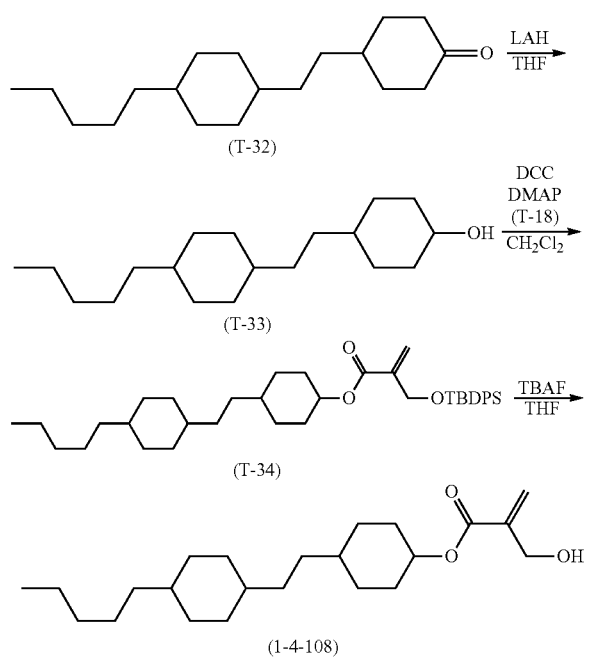

First Step

Compound (T-33) (4.13 g; 82%) was obtained by using compound (T-32) (5.00 g) as a raw material in a manner similar to the procedures in the fifth step in Synthesis Example 8.

Second Step

Compound (T-34) (7.10 g; 80%) was obtained by using compound (T-33) (4.13 g) as a raw material in a manner similar to the procedures in the third step in Synthesis Example 6.

Third Step

Compound (1-4-108) (3.65 g; 85%) was obtained by using compound (T-34) (7.10 g) as a raw material in a manner similar to the procedures in the fourth step in Synthesis Example 6.

An NMR analysis value of the resulting compound (1-4-108) was as described below.

$^1$H-NMR: Chemical shift δ (ppm; CDCl$_3$): 6.22 (s, 1H), 5.79 (d, J=1.1 Hz, 1H), 4.79-4.73 (m, 1H), 4.31 (d, J=6.7 Hz, 2H), 2.32 (t, J=6.5 Hz, 1H), 2.02-1.99 (m, 2H), 1.82-1.79 (m, 2H), 1.72-1.70 (m, 4H), 1.42-0.98 (m, 19H), 0.89-0.80 (m, 7H).

Physical properties of compound (1-4-108) were as described below.

Transition temperature: C 46.1 S$_A$ 122 I.

Synthesis Example 11

Synthesis of Compound (1-4-5)

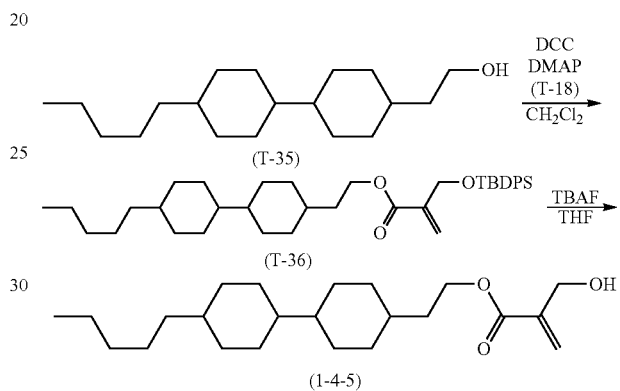

First Step

Compound (T-36) (8.60 g; 80%) was obtained by using compound (T-35) (5.00 g) as a raw material in a manner similar to the procedures in the third step in Synthesis Example 6.

Second Step

Compound (1-4-5) (4.21 g; 81%) was obtained by using compound (T-36) (8.60 g) as a raw material in a manner similar to the procedures in the fourth step in Synthesis Example 6.

An NMR analysis value of the resulting compound (1-4-5) was as described below.

$^1$H-NMR: Chemical shift δ (ppm; CDCl$_3$): 6.24 (s, 1H), 5.82 (d, J=1.1 Hz, 1H), 4.33 (d, J=6.6 Hz, 2H), 4.21 (t, J=6.8 Hz, 2H), 2.29-2.26 (m, 1H), 1.78-1.67 (m, 8H), 1.60-1.55 (m, 2H), 1.31-1.07 (m, 10H), 1.00-0.79 (m, 13H).

Physical properties of compound (1-4-5) were as described below.

Transition temperature: C 69.4 S$_A$ 124.6 I.

Synthesis Example 12

Synthesis of Compound (1-4-6)

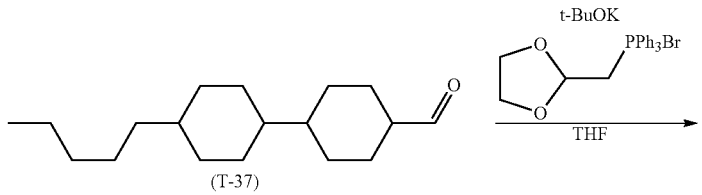

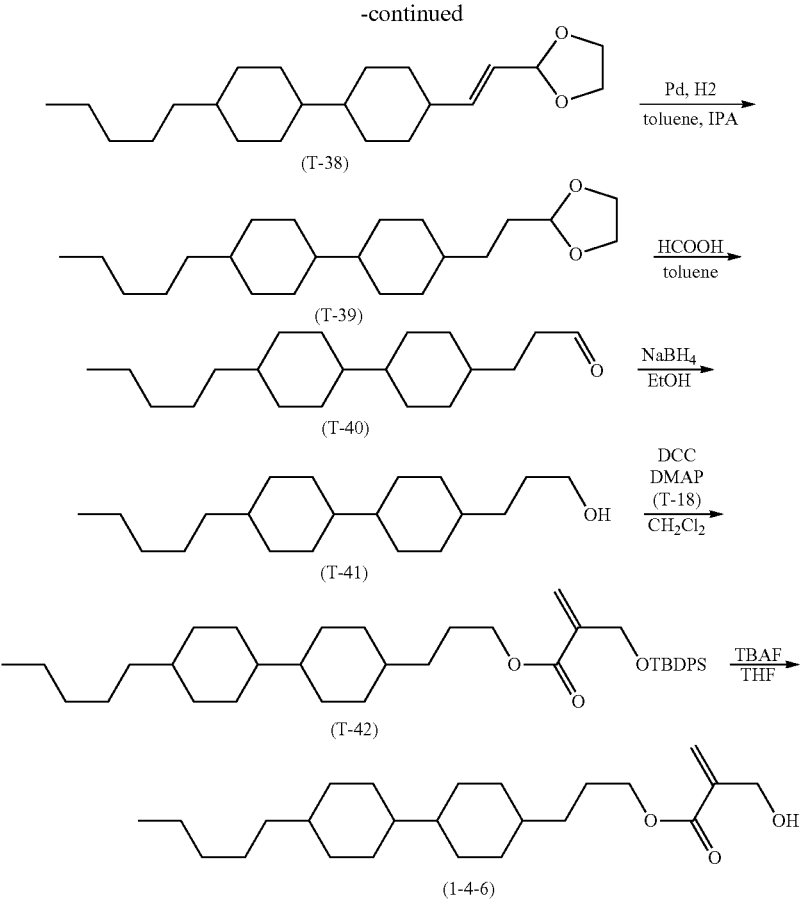

First Step (1,3-dioxolan-2-yl)methyltriphenylphosphonium bromide (19.5 g) and THF (200 mL) were put in a reaction vessel, and the resulting mixture was cooled down to −30° C. Potassium t-butoxide (5.09 g) was added, and stirred at −30° C. for 1 hour. Compound (T-37) (10.0 g) was added, and stirred for 5 hours while returning to room temperature. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-38) (11.4 g; 90%).

Second Step

Compound (T-38) (11.4 g), Pd/C (0.18 g), IPA (200 mL) and toluene (200 mL) were put in a reaction vessel, and the resulting mixture was stirred at room temperature for 12 hours under a hydrogen atmosphere. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-39) (10.6 g; 920).

Third Step

Compound (T-39) (10.6 g), formic acid (14.5 g) and toluene (200 mL) were put in a reaction vessel, and the resulting mixture was stirred at 100° C. for 4 hours. An insoluble matter was filtered off, and then the resulting material was neutralized with a sodium hydrogencarbonate aqueous solution, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-40) (8.11 g; 88%).

Fourth Step

Sodium borohydride (0.62 g) and ethanol (100 mL) were put in a reaction vessel, and the resulting mixture was cooled down to 0° C. Thereto, an ethanol (100 mL) solution of compound (T-40) (8.11 g) was added dropwise. The resulting mixture was stirred for 4 hours while returning to room temperature. An insoluble matter was filtered off, and then the resulting reaction mixture was poured into water, and an aqueous layer was subjected to extraction with ethyl acetate. A combined organic layer was washed with water, and dried over anhydrous magnesium sulfate. The resulting solution was concentrated under reduced pressure, and the residue was purified by silica gel chromatography (toluene:ethyl acetate=9:1 in a volume ratio). The residue was further purified by recrystallization from heptane to obtain compound (T-41) (6.37 g; 78%).

Fifth Step

Compound (T-42) (8.67 g; 65%) was obtained by using compound (T-41) (6.37 g) as a raw material in a manner similar to the procedures in the third step in Synthesis Example 6.

Sixth Step

Compound (1-4-6) (4.52 g; 85%) was obtained by using compound (T-42) (8.67 g) as a raw material in a manner similar to the procedures in the fourth step in Synthesis Example 6.

An NMR analysis value of the resulting compound (1-4-6) was as described below.

$^1$H-NMR: Chemical shift δ (ppm; CDCl$_3$): 6.25 (s, 1H), 5.82 (d, J=0.9 Hz, 1H), 4.33 (d, J=6.7 Hz, 2H), 4.15 (t, J=6.7 Hz, 2H), 2.27 (t, J=6.5 Hz, 1H), 1.76-1.62 (m, 10H), 1.32-1.06 (m, 12H), 1.02-0.79 (m, 13H).

Physical properties of compound (1-4-6) were as described below.

Transition temperature: C 53.6 S$_A$ 113 I.

Synthesis Example 13

Synthesis of Compound (1-4-26)

First Step

Compound (T-44) (11.2 g; 88%) was obtained by using compound (T-43) (10.0 g) as a raw material in a manner similar to the procedures in the first step in Synthesis Example 12.

Second Step

Compound (T-45) (10.1 g; 90%) was obtained by using compound (T-44) (11.2 g) as a raw material in a manner similar to the procedures in the second step in Synthesis Example 12.

Third Step

Compound (T-46) (7.44 g; 85%) was obtained by using compound (T-45) (10.1 g) as a raw material in a manner similar to the procedures in the third step in Synthesis Example 12.

Fourth Step

Compound (T-47) (6.07 g; 81%) was obtained by using compound (T-46) (7.44 g) as a raw material in a manner similar to the procedures in the fourth step in Synthesis Example 12.

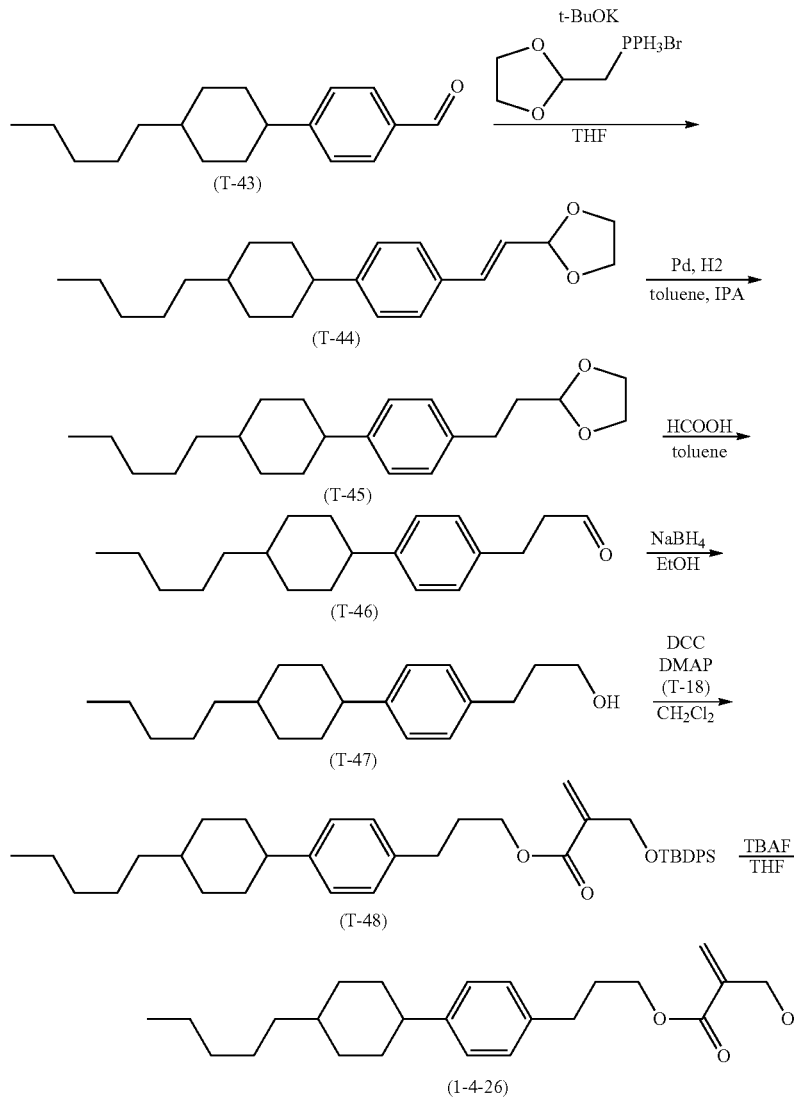

Fifth Step

Compound (T-48) (9.38 g; 73%) was obtained by using compound (T-47) (6.07 g) as a raw material in a manner similar to the procedures in the third step in Synthesis Example 6.

Sixth Step

Compound (1-4-26) (3.32 g; 58%) was obtained by using compound (T-48) (9.38 g) as a raw material in a manner similar to the procedures in the fourth step in Synthesis Example 6.

An NMR analysis value of the resulting compound (1-4-26) was as described below.

$^1$H-NMR: Chemical shift δ (ppm; CDCl$_3$): 7.13 (d, J=8.2 Hz, 2H), 7.10 (d, J=8.2 Hz, 2H), 6.23 (s, 1H), 5.82 (d, J=1.1 Hz, 1H), 4.32 (d, J=6.7 Hz, 2H), 4.20 (t, J=6.4 Hz, 2H), 2.68 (t, J=7.3 Hz, 2H), 2.43 (tt, J=12.2 Hz, J=3.2 Hz, 1H), 2.21 (t, J=6.8 Hz, 1H), 2.04-1.98 (m, 2H), 1.88-1.84 (m, 4H), 1.46-1.38 (m, 2H), 1.35-1.19 (m, 9H), 1.07-0.99 (m, 2H), 0.89 (t, J=7.2 Hz, 3H).

Physical properties of compound (1-4-26) were as described below.

Transition temperature: C 41.4 I.

Synthesis Example 14

Synthesis of Compound (1-6-122)

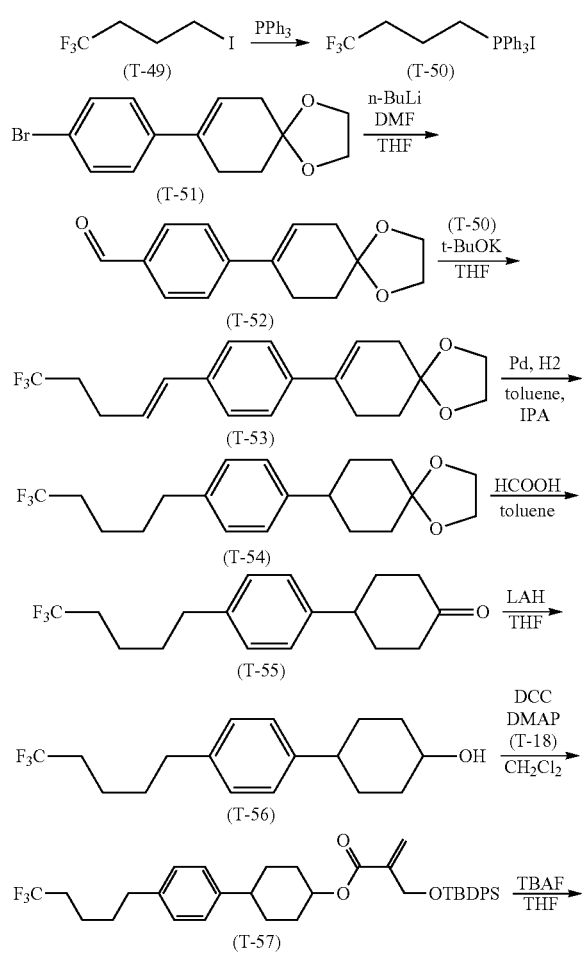

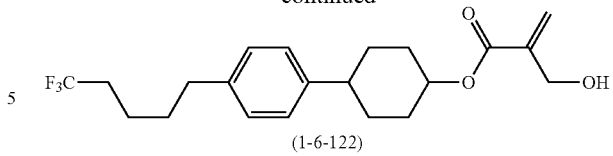

(1-6-122)

First Step

Compound (T-49) (15.0 g) and triphenylphosphine (24.8 g) were put in a reaction vessel, and the resulting mixture was stirred at 100° C. for 6 hours. The resulting material was filtrated and washed with heptane cooled with ice to obtain compound (T-50) (16.4 g; 52%).

Second Step

Compound (T-51) (10.0 g) and THF (200 mL) were put in a reaction vessel, and the resulting mixture was cooled down to −70° C. N-butyllithium (1.63M; hexane solution; 25 mL) was slowly added, and stirred for 1 hour. DMF (4.0 mL) was slowly added, and stirred for 12 hours while returning to room temperature. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography (toluene: ethyl acetate=9:1 in a volume ratio) to obtain compound (T-52) (6.37 g; 77%).

Third Step

Compound (T-50) (14.3 g) and THF (200 mL) were put in a reaction vessel, and the resulting mixture was cooled down to −30° C. Thereto, potassium t-butoxide (3.21 g) was slowly added, and stirred at −30° C. for 1 hour. A THF (100 mL) solution of compound (T-52) (6.37 g) was slowly added, and stirred for 4 hours while returning to room temperature. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-53) (7.50 g; 85%).

Fourth Step

Compound (T-53) (7.50 g), Pd/C (0.11 g), IPA (200 mL) and toluene (200 mL) were put in a reaction vessel, and the resulting mixture was stirred at room temperature for 12 hours under a hydrogen atmosphere. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-54) (7.21 g; 95%).

Fifth Step

Compound (T-54) (7.21 g), formic acid (9.70 g) and toluene (200 mL) were put in a reaction vessel, and the resulting mixture was stirred at 100° C. for 4 hours. An insoluble matter was filtered off, and then the resulting material was neutralized with a sodium hydrogencarbonate aqueous solution, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-55) (5.65 g; 90%).

Sixth Step

Lithium aluminum hydride (0.43 g) and THF (100 mL) were put in a reaction vessel, and the resulting mixture was cooled with ice. A THF (100 mL) solution of compound (T-55) (5.65 g) was slowly added, and stirred for 2 hours while returning to room temperature. The resulting reaction mixture was poured into water, and an aqueous layer was subjected to extraction with ethyl acetate. A combined organic layer was washed with brine, and dried over anhydrous magnesium sulfate. The resulting solution was concentrated under reduced pressure, and the residue was purified by silica gel chromatography (toluene:ethyl acetate=9:1 in a volume ratio). The residue was further purified by recrystallization from heptane to obtain compound (T-56) (4.83 g; 85%).

Seventh Step

Compound (T-57) (8.41 g; 84%) was obtained by using compound (T-56) (4.83 g) as a raw material in a manner similar to the procedures in the third step in Synthesis Example 6.

Eighth Step

Compound (1-6-122) (3.22 g; 62%) was obtained by using compound (T-57) (8.41 g) as a raw material in a manner similar to the procedures in the fourth step in Synthesis Example 6.

An NMR analysis value of the resulting compound (1-6-122) was as described below.

$^1$H-NMR: Chemical shift δ (ppm; CDCl$_3$): 7.13 (d, J=8.2 Hz, 2H), 7.10 (d, J=8.2 Hz, 2H), 6.26 (s, 1H), 5.82 (d, J=1.1 Hz, 1H), 4.92-4.87 (m, 1H), 4.34 (d, J=6.7 Hz, 2H), 2.60 (t, J=7.3 Hz, 2H), 2.54-2.49 (m, 1H), 2.31 (t, J=6.5 Hz, 1H), 2.15-2.04 (m, 4H), 1.98-1.96 (m, 2H), 1.66-1.52 (m, 8H).

Physical properties of compound (1-6-122) were as described below.

Transition temperature: C 62.0 I.

Synthesis Example 15

Synthesis of Compound (1-6-123)

First Step

Compound (T-59) (7.74 g; 70%) was obtained by using compound (T-58) (5.00 g) as a raw material in a manner similar to the procedures in the third step in Synthesis Example 6.

Second Step

Compound (1-6-123) (3.82 g; 83%) was obtained by using compound (T-59) (7.74 g) as a raw material in a manner similar to the procedures in the fourth step in Synthesis Example 6.

An NMR analysis value of the resulting compound (1-6-123) was as described below.

$^1$H-NMR: Chemical shift δ (ppm; CDCl$_3$): 6.22 (s, 1H), 5.79 (s, 1H), 4.77-4.71 (m, 1H), 4.31 (d, J=6.5 Hz, 2H), 2.29-2.26 (m, 1H), 2.04-2.01 (m, 2H), 1.80-1.68 (m, 6H), 1.39-1.24 (m, 10H), 1.13-0.80 (m, 14H).

Physical properties of compound (1-6-123) were as described below.

Transition temperature: C59.1 S$_A$ 114 I.

Synthesis Example 16

Synthesis of Compound (1-4-3)

First Step

Compound (T-61) (8.49 g; 79%) was obtained by using compound (T-60) (5.00 g) as a raw material in a manner similar to the procedures in the third step in Synthesis Example 6.

Second Step

Compound (1-4-3) (3.54 g; 69%) was obtained by using compound (T-61) (8.49 g) as a raw material in a manner similar to the procedures in the fourth step in Synthesis Example 6.

An NMR analysis value of the resulting compound (1-4-3) was as described below.

$^1$H-NMR: Chemical shift δ (ppm; CDCl$_3$): 6.22 (s, 1H), 5.79 (d, J=1.1 Hz, 1H), 4.76-4.72 (m, 1H), 4.31 (d, J=6.8 Hz, 2H), 2.29-2.26 (m, 1H), 2.04-2.01 (m, 2H), 1.80-1.68 (m, 6H), 1.40-1.25 (m, 12H), 1.16-0.80 (m, 14H).

Physical properties of compound (1-4-3) were as described below.

Transition temperature: C60.9 S$_A$ 109 I.

Synthesis Example 17

Synthesis of Compound (1-6-124)

-continued

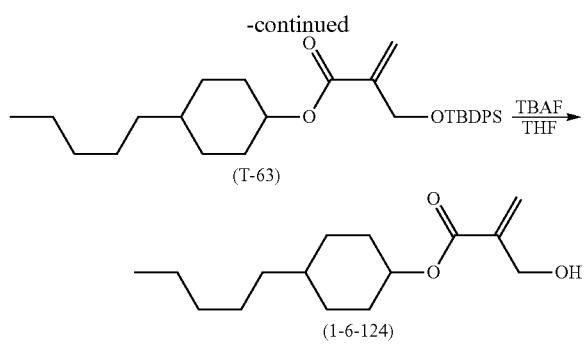

First Step

Compound (T-63) (8.39 g; 58%) was obtained by using compound (T-62) (5.00 g) as a raw material in a manner similar to the procedures in the third step in Synthesis Example 6.

Second Step

Compound (1-6-124) (3.85 g; 89%) was obtained by using compound (T-63) (8.39 g) as a raw material in a manner similar to the procedures in the fourth step in Synthesis Example 6.

An NMR analysis value of the resulting compound (1-6-124) was as described below.

$^1$H-NMR: Chemical shift δ (ppm; CDCl$_3$): 6.22 (s, 1H), 5.80 (d, J=1.1 Hz, 1H), 4.78-4.72 (m, 1H), 4.31 (s, 2H), 2.74 (s, 1H), 2.02-1.98 (m, 2H), 1.82-1.79 (m, 2H), 1.42-1.16 (m, 11H), 1.07-0.97 (m, 2H), 0.88 (t, J=6.8 Hz, 3H).

Physical properties of compound (1-6-124) were as described below.

Transition temperature: <−50.0 I.

Synthesis Example 18

Synthesis of Compound (1-6-125)

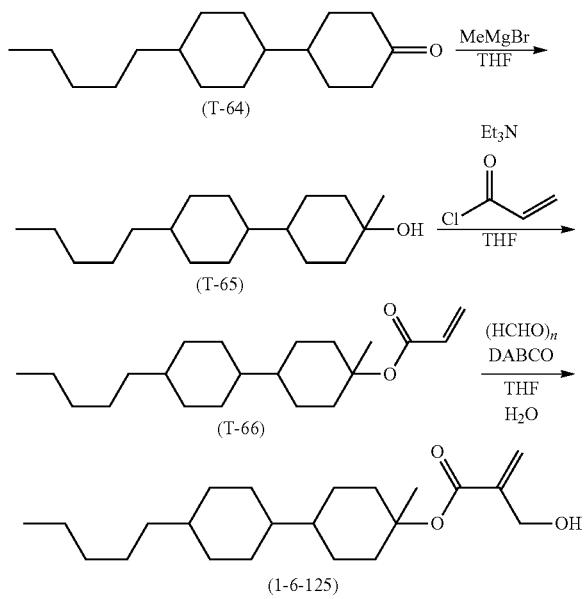

First Step

Compound (T-64) (10.0 g) and THF (200 mL) were put in a reaction vessel, and the resulting mixture was cooled down to 0° C. Methylmagnesium bromide (1.00 M; THF solution; 48 mL) was slowly added, and stirred for 6 hours while returning to room temperature. An insoluble matter was filtered off, and then the resulting reaction mixture was poured into water, and an aqueous layer was subjected to extraction with ethyl acetate. A combined organic layer was washed with water, and dried over anhydrous magnesium sulfate. The resulting solution was concentrated under reduced pressure, and the residue was purified by silica gel chromatography (toluene:ethyl acetate=9:1 in a volume ratio) to obtain compound (T-65) (4.58 g; 43%).

Second Step

Compound (T-65) (4.58 g), triethylamine (2.87 mL) and THF (200 mL) were put in a reaction vessel, and the resulting mixture was cooled down to 0° C. Acryloyl chloride (1.68 mL) was slowly added, and stirred for 5 hours while returning to room temperature. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography (toluene:heptane=3:2 in a volume ratio) to obtain compound (T-66) (3.20 g; 580).

Third Step

Compound (1-6-125) (1.12 g; 32%) was obtained by using compound (T-66) (3.20 g) as a raw material in a manner similar to the procedures in the second step in Synthesis Example 1.

An NMR analysis value of the resulting compound (1-6-125) was as described below.

$^1$H-NMR: Chemical shift δ (ppm; CDCl$_3$): 6.15 (5, 1H), 5.73 (d, J=1.2 Hz, 1H), 4.28 (d, J=6.6 Hz, 2H), 2.34-2.32 (m, 1H), 2.13-2.11 (m, 2H), 1.76-1.67 (m, 8H), 1.54 (s, 3H), 1.32-1.03 (m, 13H), 0.97-0.80 (m, 7H).

Physical properties of compound (1-6-125) were as described below.

Transition temperature: C 66.5 S$_A$ 81.1 I.

Synthesis Example 19

Synthesis of Compound (1-6-126)

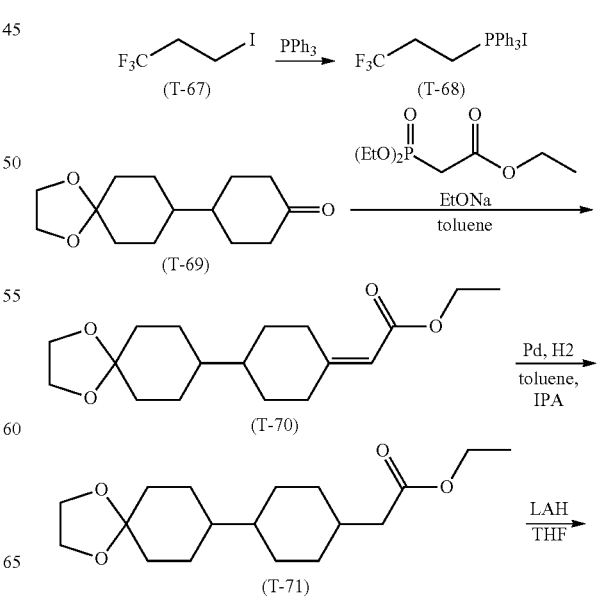

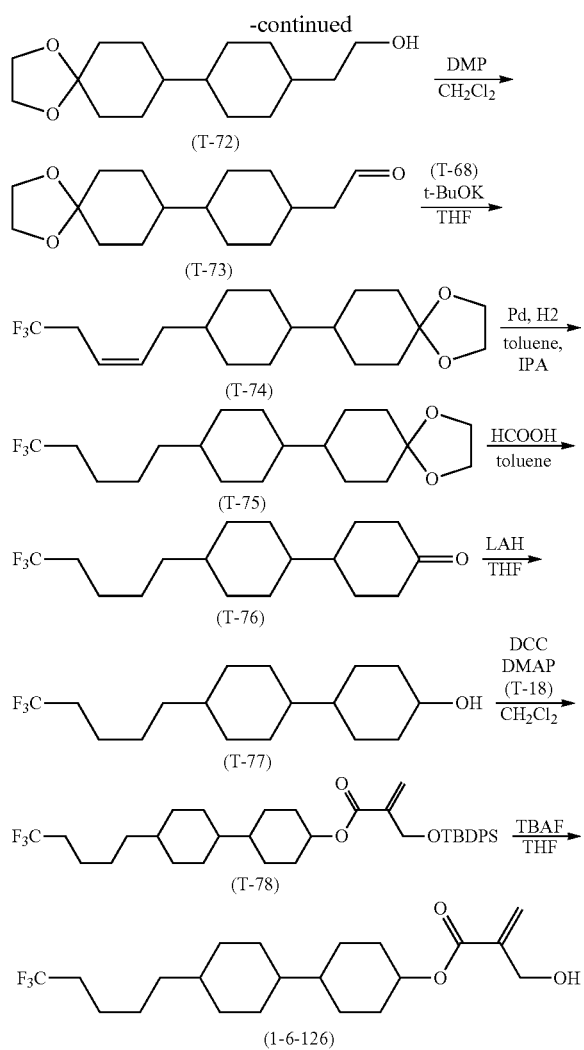

First Step

Compound (T-67) (25.0 g) and triphenylphosphine (43.9 g) were put in a reaction vessel, and the resulting mixture was stirred at 90° C. for 6 hours. The resulting material was filtrated and washed with heptane to obtain compound (T-68) (22.8 g; 42%).

Second Step

Compound (T-69) (20.0 g), triethyl phosphonoacetate (22.5 g) and toluene (300 mL) were put in a reaction vessel, and the resulting mixture was cooled down to 0° C. Thereto, sodium ethoxide (20% ethanol solution) (34.2 g) was slowly added, and stirred for 6 hours while returning to room temperature. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-70) (23.3 g; 90%).

Third Step

Compound (T-70) (23.3 g), toluene (400 mL) and IPA (400 mL) were put in a reaction vessel, Pd/C (0.40 g) was added, and the resulting mixture was stirred at room temperature for 12 hours under a hydrogen atmosphere. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-71) (21.5 g; 92%).

Fourth Step

Lithium aluminum hydride (1.57 g) and THF (200 mL) were put in a reaction vessel, and the resulting mixture was cooled with ice. A THF (200 mL) solution of compound (T-71) (21.5 g) was slowly added, and stirred for 5 hours while returning to room temperature. An insoluble matter was filtered off, and then the resulting reaction mixture was poured into water, and an aqueous layer was subjected to extraction with ethyl acetate. A combined organic layer was washed with brine, and dried over anhydrous magnesium sulfate. The resulting solution was concentrated under reduced pressure, and the residue was purified by silica gel chromatography (toluene:ethyl acetate=4:1 in a volume ratio) to obtain compound (T-72) (14.3 g; 77%).

Fifth Step

Compound (T-72) (14.3 g) and dichloromethane (300 mL) were put in a reaction vessel, and the resulting mixture was cooled with ice. Dess-Martin Periodinane (27.1 g) was slowly added, and stirred for 5 hours while returning to room temperature. An insoluble matter was filtered off, and then the resulting reaction mixture was poured into water, and an aqueous layer was subjected to extraction with dichloromethane. A combined organic layer was washed with brine, and dried over anhydrous magnesium sulfate. The resulting solution was concentrated under reduced pressure, and the residue was purified by silica gel chromatography (toluene:ethyl acetate=9:1 in a volume ratio) to obtain compound (T-73) (9.93 g; 700).

Sixth Step

Compound (T-68) (21.7 g) and THF (200 mL) were put in a reaction vessel, and the resulting mixture was cooled down to −30° C. Potassium t-butoxide (5.01 g) was slowly added thereto, and stirred at −30° C. for 1 hour. A THF (100 mL) solution of compound (T-73) (9.93 g) was slowly added, and stirred for 5 hours while returning to room temperature. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-74) (6.97 g; 54%).

Seventh Step

Compound (T-74) (6.97 g), Pd/C (0.10 g), IPA (100 mL) and toluene (100 mL) were put in a reaction vessel, and the resulting mixture was stirred at room temperature for 12 hours under a hydrogen atmosphere. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-54) (6.31 g; 90%).

Eighth Step

Compound (T-76) (4.96 g; 90%) was obtained by using compound (T-75) (6.31 g) as a raw material in a manner similar to the procedures in the fifth step in Synthesis Example 14.

Ninth Step

Compound (T-77) (4.24 g; 85%) was obtained by using compound (T-76) (4.96 g) as a raw material in a manner similar to the procedures in the sixth step in Synthesis Example 14.

Tenth Step

Compound (T-78) (5.40 g; 62%) was obtained by using compound (T-77) (4.24 g) as a raw material in a manner similar to the procedures in the third step in Synthesis Example 6.

Eleventh Step

Compound (1-6-126) (2.37 g; 90%) was obtained by using compound (T-78) (4.24 g) as a raw material in a manner similar to the procedures in the fourth step in Synthesis Example 6.

An NMR analysis value of the resulting compound (1-6-126) was as described below.

$^1$H-NMR: Chemical shift δ (ppm; CDCl$_3$): 6.25 (5, 1H), 5.81 (d, J=0.8 Hz, 1H), 4.79-4.73 (m, 1H), 4.34 (d, J=6.7 Hz, 2H), 2.32-2.29 (m, 1H), 2.12-2.03 (m, 4H), 1.82-1.72 (m, 6H), 1.57-1.49 (m, 2H), 1.44-1.35 (m, 4H), 1.22-0.84 (m, 11H).

Physical properties of compound (1-6-126) were as described below.

Transition temperature: C 72.0 S$_A$ 81.1 I.

Synthesis Example 20

Synthesis of Compound (1-6-127)

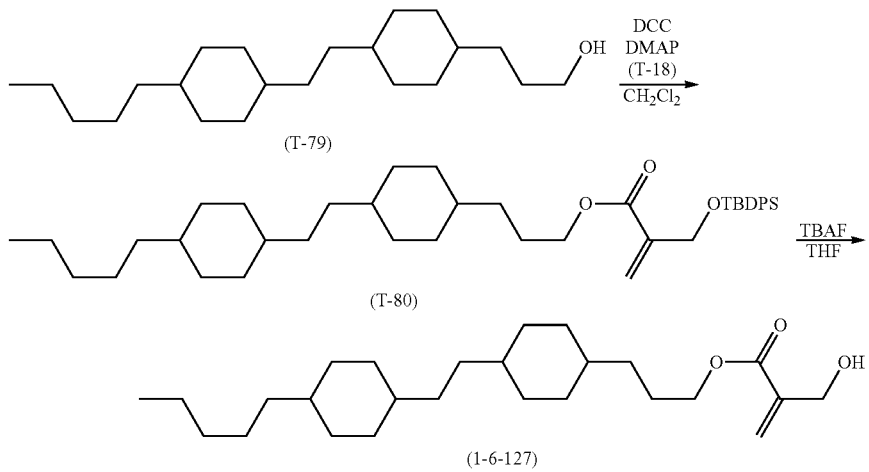

First Step

Compound (T-80) (6.40 g; 64%) was obtained by using compound (T-79) (5.00 g) as a raw material in a manner similar to the procedures in the third step in Synthesis Example 6.

Second Step

Compound (1-6-127) (2.02 g; 50%) was obtained by using compound (T-80) (6.40 g) as a raw material in a manner similar to the procedures in the fourth step in Synthesis Example 6.

An NMR analysis value of the resulting compound (1-6-127) was as described below.

$^1$H-NMR: Chemical shift δ (ppm; CDCl$_3$): 6.24 (s, 1H), 5.82 (d, J=1.3 Hz, 1H), 4.33 (d, J=5.5 Hz, 2H), 4.15 (t, J=6.8 Hz, 2H), 2.39-2.37 (m, 1H), 1.73-1.66 (m, 10H), 1.32-1.09 (m, 18H), 0.91-0.80 (m, 11H).

Physical properties of compound (1-6-127) were as described below.

Transition temperature: C 110 I.

Synthesis Example 21

Synthesis of Compound (1-6-128)

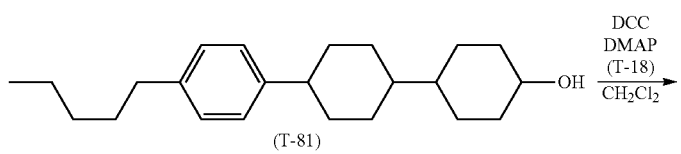

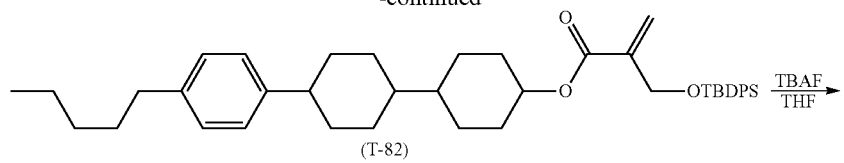

First Step

Compound (T-82) (5.94 g; 60%) was obtained by using compound (T-81) (5.00 g) as a raw material in a manner similar to the procedures in the third step in Synthesis Example 6.

Second Step

Compound (1-6-128) (2.64 g; 70%) was obtained by using compound (T-82) (5.94 g) as a raw material in a manner similar to the procedures in the fourth step in Synthesis Example 6.

An NMR analysis value of the resulting compound (1-6-128) was as described below.

$^1$H-NMR: Chemical shift δ (ppm; CDCl$_3$): 7.12-7.08 (m, 4H), 6.23 (s, 1H), 5.80 (d, J=1.0 Hz, 1H), 4.78-4.74 (m, 1H), 4.32 (d, J=6.6 Hz, 2H), 2.55 (t, J=7.6 Hz, 2H), 2.41 (tt, J=12.1 Hz, J=3.3 Hz, 1H), 2.28 (t, J=6.5 Hz, 1H), 2.07-2.04 (m, 2H), 1.93-1.90 (m, 2H), 1.85-1.82 (m, 4H), 1.61-1.57 (m, 2H), 1.44-1.30 (m, 8H), 1.20-1.13 (m, 6H), 0.88 (t, J=6.8 Hz, 3H).

Physical properties of compound (1-6-128) were as described below.

Transition temperature: C 85.0 I.

Synthesis Example 22

Synthesis of Compound (1-6-129)

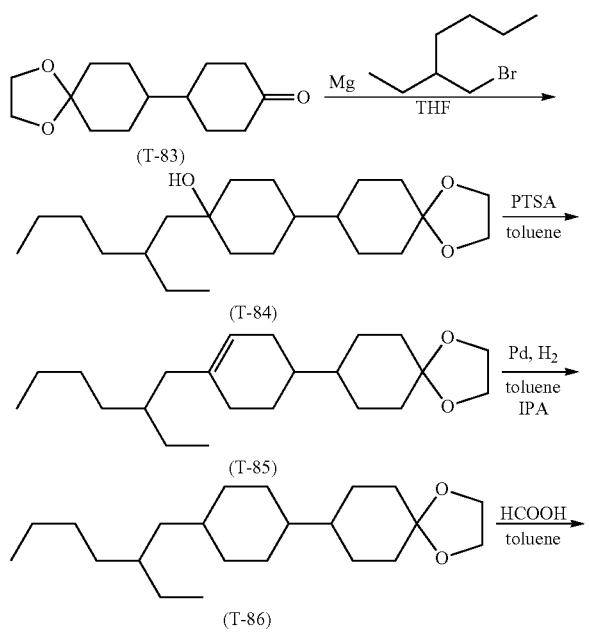

First Step

Magnesium (turnings) (3.67 g) and THF (50 mL) were put in a reaction vessel, a THF (50 mL) solution of 1-bromo-2-hexaethylene (29.1 g) was slowly added dropwise, and the resulting mixture was stirred at 30° C. for 1 hour. Thereto, a THF (100 mL) solution of compound (T-83) (30.0 g) was slowly added dropwise, and stirred at room temperature for 6 hours. The resulting reaction mixture was poured into water, and an aqueous layer was subjected to extraction with ethyl acetate. A combined organic layer was washed with water, and dried over anhydrous magnesium sulfate. The resulting solution was concentrated under reduced pressure, and the residue was purified by silica gel chromatography (toluene:ethyl acetate=4:1 in a volume ratio) to obtain compound (T-84) (8.88 g; 206).

Second Step

Compound (T-84) (8.88 g), p-toluenesulfonic acid monohydrate (0.47 g), ethylene glycol (1.87 g) and toluene (200 mL) were put in a reaction vessel, and the resulting mixture was stirred at 90° C. for 5 hours. The resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-85) (8.00 g; 956).
Third Step
Compound (T-85) (8.00 g), Pd/C (0.12 g), IPA (200 mL) and toluene (200 mL) were put in a reaction vessel, and the resulting mixture was stirred at room temperature for 14 hours under a hydrogen atmosphere. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-86) (7.48 g; 93%).
Fourth Step
Compound (T-87) (5.72 g; 88%) was obtained by using compound (T-86) (7.48 g) as a raw material in a manner similar to the procedures in the fifth step in Synthesis Example 14.
Fifth Step
Sodium borohydride (0.45 g) and ethanol (50 mL) were put in a reaction vessel, and the resulting mixture was cooled down to 0° C. Thereto, an ethanol (50 mL) solution of compound (T-87) (5.72 g) was slowly added dropwise, and stirred for 6 hours while returning to room temperature. An insoluble matter was filtered off, and then the resulting reaction mixture was poured into water, and an aqueous layer was subjected to extraction with ethyl acetate. A combined organic layer was washed with water, and dried over anhydrous magnesium sulfate. The resulting solution was concentrated under reduced pressure, and the residue was purified by silica gel chromatography (toluene:ethyl acetate=9:1 in a volume ratio) to obtain compound (T-88) (2.65 g; 46%).
Sixth Step
Compound (T-82) (3.72 g; 67%) was obtained by using compound (T-88) (2.65 g) as a raw material in a manner similar to the procedures in the third step in Synthesis Example 6.
Second Step
Compound (1-6-129) (1.60 g; 70%) was obtained by using compound (T-82) (3.72 g) as a raw material in a manner similar to the procedures in the fourth step in Synthesis Example 6.
An NMR analysis value of the resulting compound (1-6-129) was as described below.
$^1$H-NMR: Chemical shift δ (ppm; CDCl$_3$): 6.22 (s, 1H), 5.79 (d, J=1.0 Hz, 1H), 4.77-4.71 (m, 1H), 4.31 (d, J=6.5 Hz, 2H), 2.31 (d, J=6.7 Hz, 1H), 2.04-2.01 (m, 2H), 1.80-1.68 (m, 6H), 1.39-0.92 (m, 20H), 0.90-0.80 (m, 8H).
Physical properties of compound (1-6-129) were as described below.
Transition temperature: C<−50.0 I.

Synthesis Example 23

Synthesis of Compound (1-6-130)

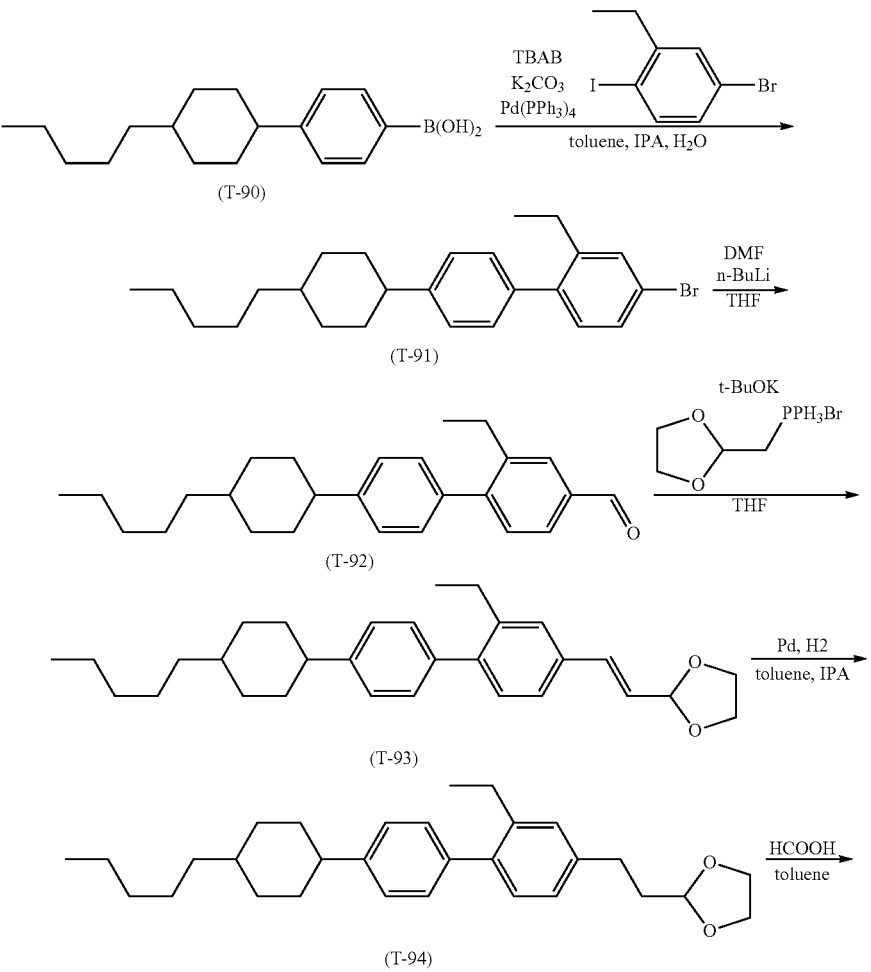

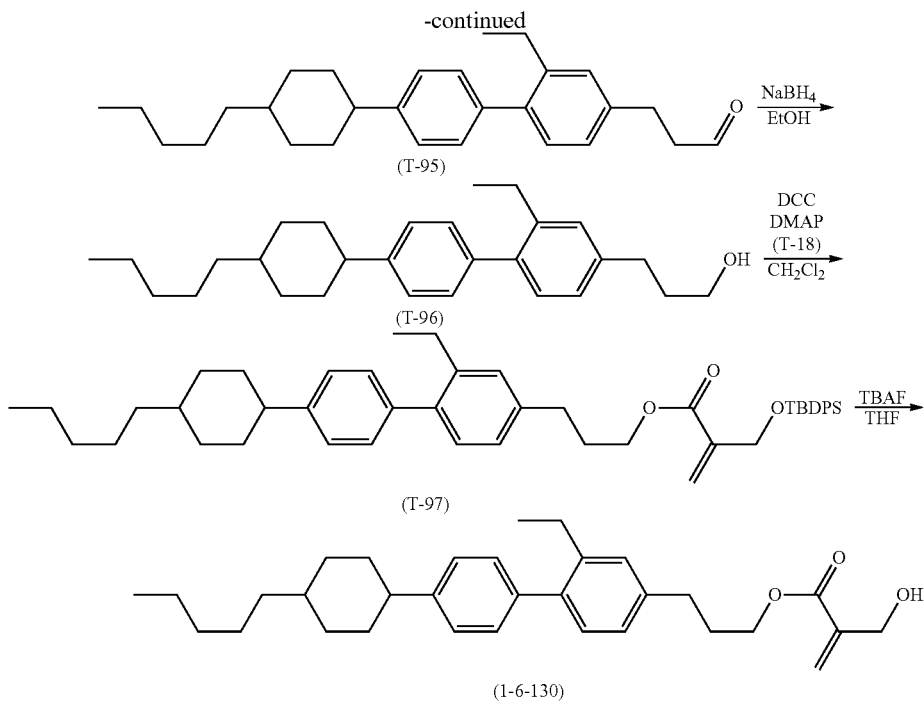

First Step

Compound (T-90) (21.1 g), tetrakis(triphenylphosphine) palladium (0.74 g), potassium carbonate (17.7 g), tetrabutylammonium bromide (8.3 g), 4-bromo-2-ethyl-1-iodobenzene (20.0 g), toluene (200 mL), IPA (150 mL) and $H_2O$ (50 mL) were put in a reaction vessel, and the resulting mixture was stirred at 80° C. for 6 hours. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography (heptane:toluene=4:1 in a volume ratio) to obtain compound (T-91) (22.6 g; 85%).

Second Step

Compound (T-91) (22.6 g) and THF (200 mL) were put in a reaction vessel, the resulting mixture was cooled down to −70° C., and butyllithium (1.60 M; hexane solution; 41 mL) was slowly added dropwise, and stirred at −70° C. for 1 hour. Thereto, a DMF (6.35 mL) was slowly added dropwise, and stirred for 12 hours while returning to room temperature. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-92) (16.1 g; 81%).

Third Step (1,3-dioxolan-2-yl)methyltriphenylphosphonium bromide (22.8 g) and THF (200 mL) were put in a reaction vessel, and the resulting mixture was cooled down to −30° C. Potassium t-butoxide (5.90 g) was added, and stirred at −30° C. for 1 hour. Compound (T-92) (16.1 g) was added, and stirred for 6 hours while returning to room temperature. An insoluble matter was filtered off, and then the resulting reaction mixture was poured into water, and an aqueous layer was subjected to extraction with toluene. A combined organic layer was washed with water, and dried over anhydrous magnesium sulfate. The resulting solution was concentrated under reduced pressure, and the residue was purified by silica gel chromatography with toluene to obtain compound (T-93) (16.5 g; 86%).

Fourth Step

Compound (T-94) (14.9 g; 90%) was obtained by using compound (T-93) (16.5 g) as a raw material in a manner similar to the procedures in the second step in Synthesis Example 12.

Fifth Step

Compound (T-95) (11.7 g; 88%) was obtained by using compound (T-94) (14.9 g) as a raw material in a manner similar to the procedures in the third step in Synthesis Example 12.

Sixth Step

Compound (T-96) (9.41 g; 80%) was obtained by using compound (T-95) (11.7 g) as a raw material in a manner similar to the procedures in the fourth step in Synthesis Example 12.

Seventh Step

Compound (T-97) (6.37 g; 70%) was obtained by using compound (T-96) (5.00 g) as a raw material in a manner similar to the procedures in the third step in Synthesis Example 6.

Seventh Step

Compound (1-6-130) (3.40 g; 80%) was obtained by using compound (T-97) (6.37 g) as a raw material in a manner similar to the procedures in the fourth step in Synthesis Example 6.

An NMR analysis value of the resulting compound (1-6-130) was as described below.

$^1$H-NMR: Chemical shift δ (ppm; $CDCl_3$): 7.23-7.19 (m, 4H), 7.13-7.10 (m, 2H), 7.05-7.03 (m, 1H), 6.25 (s, 1H), 5.84 (d, J=1.1 Hz, 1H), 4.33 (d, J=6.7 Hz, 2H), 4.25 (t, J=6.6 Hz, 2H), 2.74 (t, J=7.3 Hz, 2H), 2.58 (q, J=7.5 Hz, 2H), 2.50 (tt, J=12.1 Hz, J=3.3 Hz, 1H), 2.22 (t, J=6.7 Hz, 1H), 2.10-2.04 (m, 2H), 1.96-1.87 (m, 4H), 1.52-1.44 (m, 2H), 1.33-1.21 (m, 9H), 1.11-1.02 (m, 5H), 0.90 (t, J=6.9 Hz, 3H).

Physical properties of compound (1-6-130) were as described below.

Transition temperature: C 40.0 I.

Synthesis Example 24

Synthesis of Compound (1-6-131)

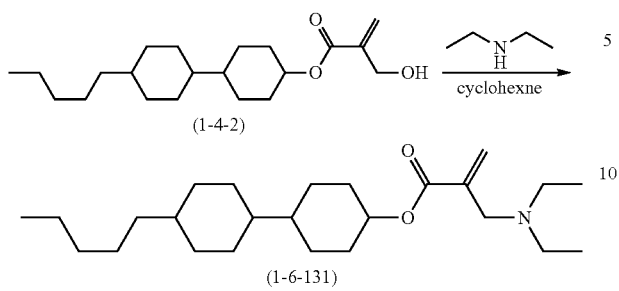

Compound (1-4-2) (3.00 g), diethylamine (1.30 g) and cyclohexane (100 mL) were put in a reaction vessel, and the resulting mixture was stirred at 75° C. for 12 hours. An insoluble matter was filtered off, and then the resulting reaction mixture was poured into water, and an aqueous layer was subjected to extraction with ethyl acetate. A combined organic layer was washed with water, and dried over anhydrous magnesium sulfate. The resulting solution was concentrated under reduced pressure, and the residue was purified by silica gel chromatography (toluene:ethyl acetate=1:1 in a volume ratio) to obtain compound (1-6-131) (0.52 g; 15%).

An NMR analysis value of the resulting compound (1-6-131) was as described below.

$^1$H-NMR: Chemical shift δ (ppm; CDCl$_3$): 6.18 (s, 1H), 5.74 (s, 1H), 4.74-4.67 (m, 1H), 3.23 (s, 2H), 2.50 (q, J=7.1 Hz, 4H), 2.03-2.01 (m, 2H), 1.78-1.68 (m, 6H), 1.37-0.80 (m, 28H).

Physical properties of compound (1-6-131) were as described below.

Transition temperature: C 14.1 S$_A$ 58.9 I.

Comparative Example 1

Compound (S-1) was prepared as a comparative compound, and characteristics thereof were measured. The reason is that the compound is described in WO 2014/090362 A, and similar to the compound of the invention.

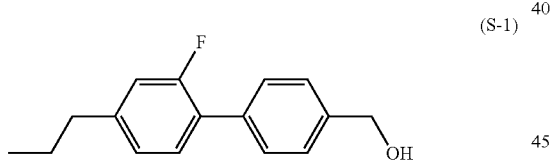

An NMR analysis value of the resulting comparative compound (S-1) was as described below.

$^1$H-NMR: Chemical shift δ (ppm; CDCl$_3$): 7.57-7.52 (m, 2H), 7.45-7.42 (m, 2H), 7.36-7.30 (m, 1H), 7.04-6.95 (m, 2H), 4.75 (d, 6.0 Hz, 2H), 2.62 (t, J=7.8 Hz, 2H), 1.75-1.64 (m, 3H), 0.98 (t, J=7.4 Hz, 3H).

Comparison was made on vertical alignment properties and a voltage holding ratio (VHR) between compound (1-4-22) and comparative compound (S-1). In addition, composition (1) and polymerizable compound (M-1-1) were used for evaluation.

A proportion of a component of composition (i) is expressed in terms of % by weight.

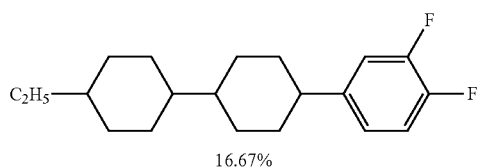

16.67%

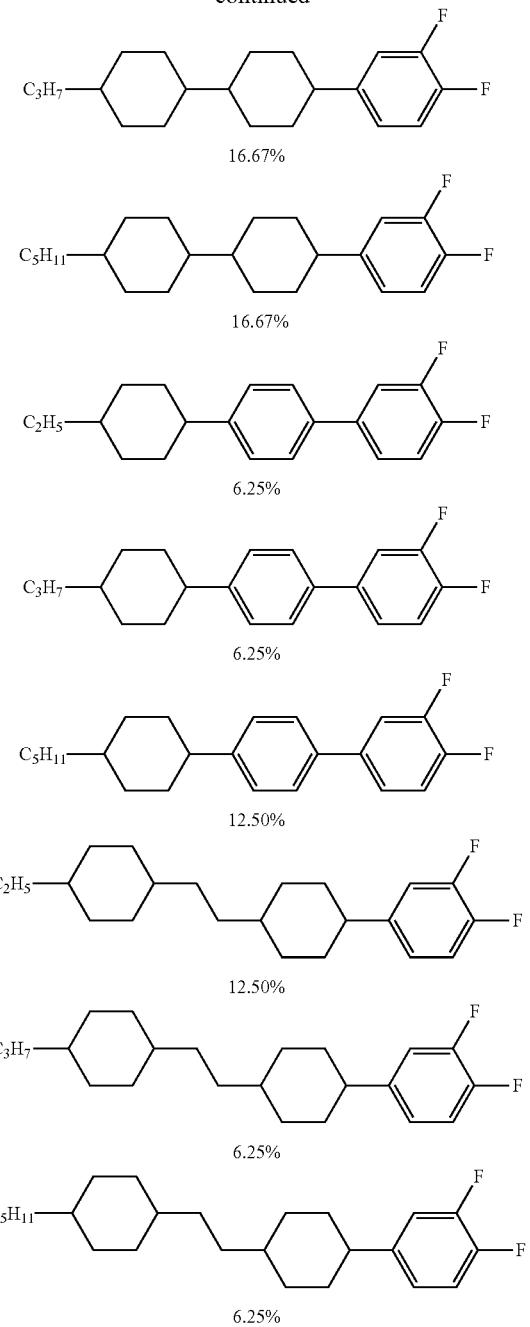

Polymerizable compound (M-1-1) is as described below.

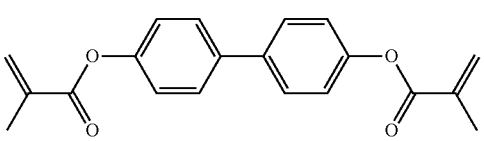

Vertical Alignment Properties

Polymerizable compound (M-1-1) was added to composition (i) in a proportion of 0.4% by weight. Compound (1-4-22) or comparative compound (S-1) was added thereto in a proportion of 3.5% by weight. The resulting mixture was injected into a device having no alignment film in which a distance (cell gap) between two glass substrates was 3.5 micrometers. The device was set to a polarizing microscope, and irradiated with light from below, and presence or absence of light leakage was observed. When liquid crystal molecules were sufficiently aligned and no light passed through the device, the vertical alignment properties were judged to be "Good." When light passing through the device was observed, the vertical alignment properties were represented as "Poor."

Voltage Holding Ratio (VHR)

The polymerizable compound was polymerized by irradiating the device prepared as described above with ultra violet light (30 J) using a black light, F40T10/BL (peak wavelength of 369 nm) made by Eye Graphics Co., Ltd. The device was charged by applying a pulse voltage (60 microseconds at 1 V) at 60° C. A decaying voltage was measured for 1.67 seconds with a high-speed voltmeter, and area A between a voltage curve and a horizontal axis in a unit cycle was determined. Area B is an area without decay. A voltage holding ratio is expressed in terms of a percentage of area A to area B.

TABLE 2

Table 2. Physical properties of compound (1-4-22) and comparative compound (S-1)

| | Compound (1-4-22) | Comparative compound (S-1) |
|---|---|---|
| Vertical alignment properties | Good | Good |
| Voltage holding ratio (VHR) | 80.30% | 23.79% |

Physical properties of compound (1-4-22) in Synthesis Example 2 and comparative compound (S-1) are summarized in Table 2. Both compounds exhibited good vertical alignment properties in the device having no alignment film. On the other hand, when compound (1-4-22) is used, a voltage holding ratio is higher in comparison with comparative compound (S-1). The reason is that a polar compound having a —OH group as in comparative compound (S-1) significantly reduces a voltage holding ratio of the device, but reduction of the voltage holding ratio was suppressed by causing incorporation of the polar compound into the polymer produced by the polymerizable compound by providing polymerizability for the compound as in compound (1-4-22). Accordingly, compound (1-4-22) is reasonably a superior compound exhibiting the good vertical alignment properties without decreasing the voltage holding ratio of the device.

In accordance with the synthesis method described in Example 1, compounds (1-3-1) to (1-3-40), compounds (1-4-1) to (1-4-120), compounds (1-5-1) to (1-5-140), compounds (1-6-1) to (1-6-120), compounds (1-6-121) to (1-6-240) and compounds (1-4-241) to (1-4-260) described below can be prepared.

| No. | |
|---|---|
| 1-3-1 | 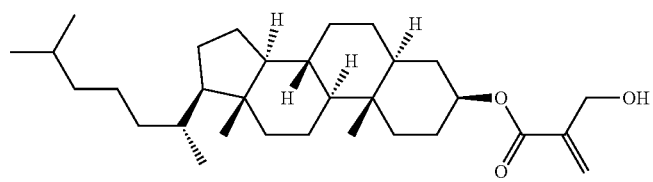 |
| 1-3-2 | 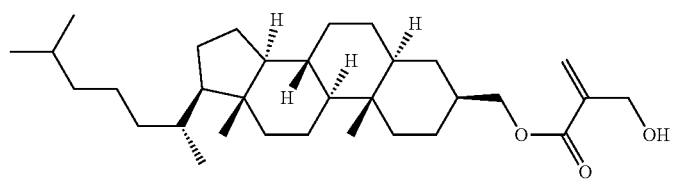 |

| No. | |
|---|---|
| 1-3-3 | 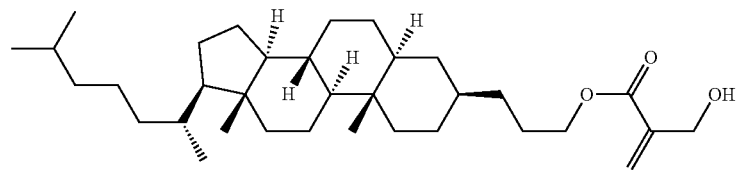 |
| 1-3-4 | 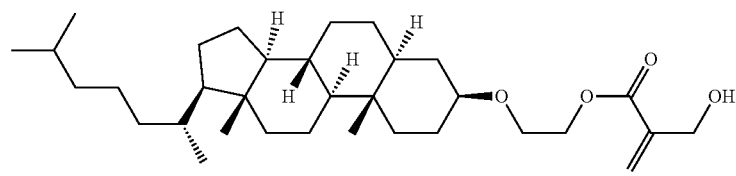 |
| 1-3-5 | 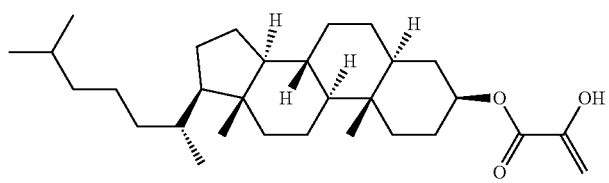 |
| 1-3-6 | 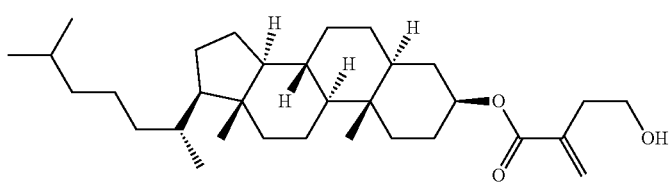 |
| 1-3-7 | 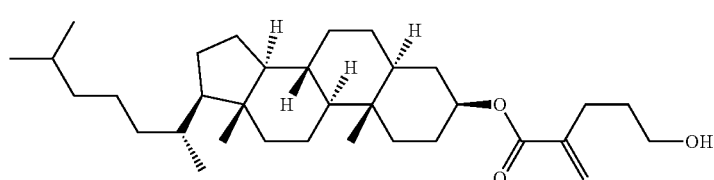 |
| 1-3-8 | 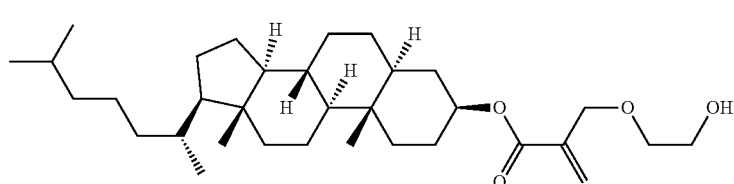 |
| 1-3-9 | 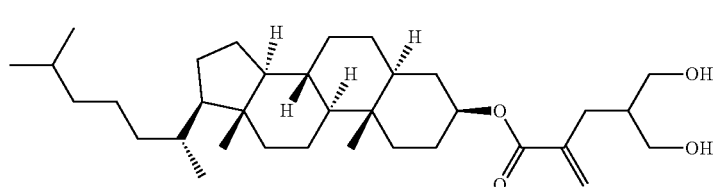 |
| 1-3-10 | 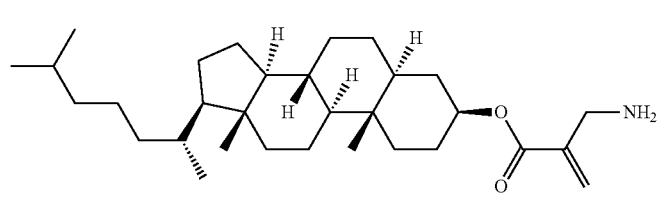 |

-continued
| No. | |
|---|---|
| 1-3-11 | 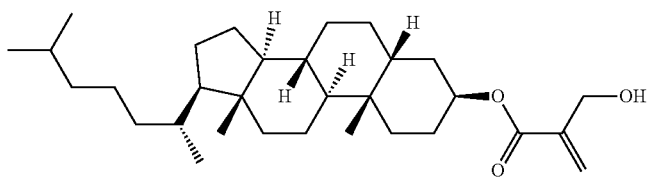 |
| 1-3-12 | 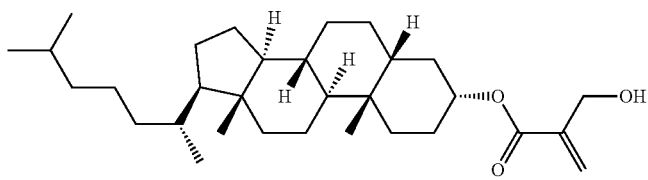 |
| 1-3-13 | 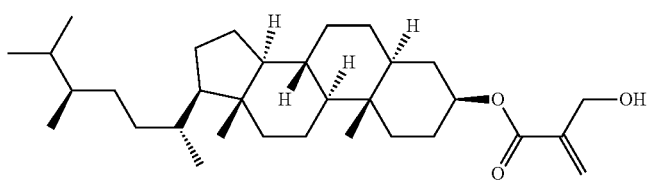 |
| 1-3-14 | 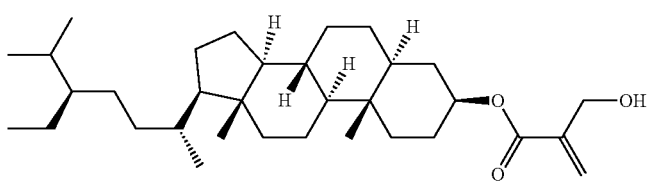 |
| 1-3-15 | 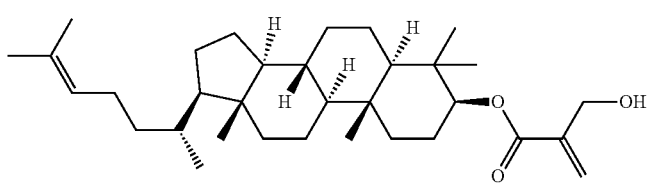 |
| 1-3-16 | 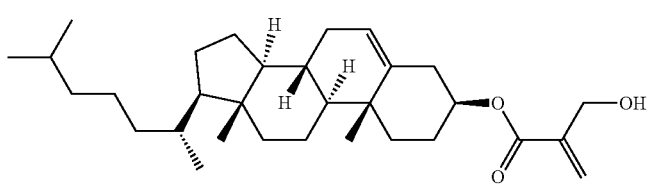 |
| 1-3-17 | 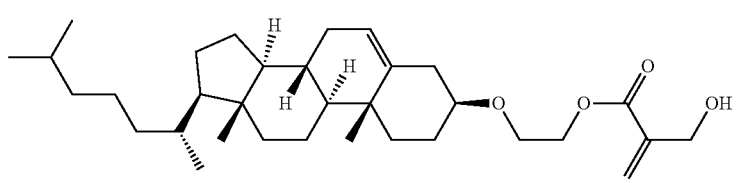 |
| 1-3-18 | 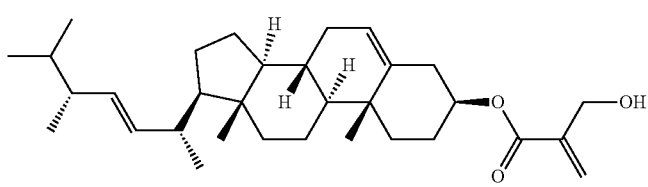 |

-continued
| No. | |
|---|---|
| 1-3-19 | 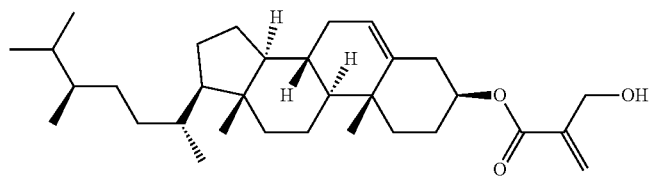 |
| 1-3-20 | 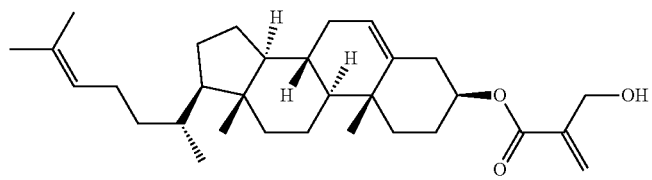 |
| 1-3-21 | 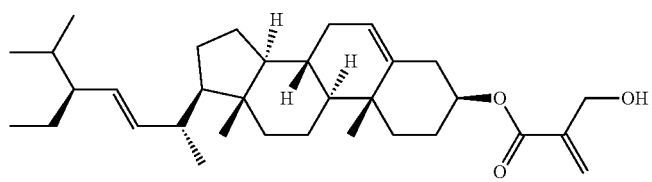 |
| 1-3-22 | 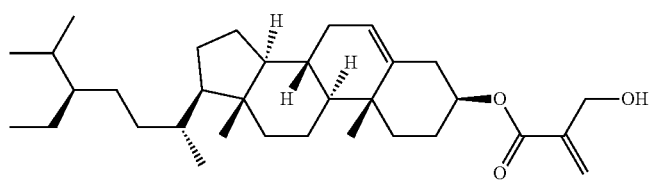 |
| 1-3-23 | 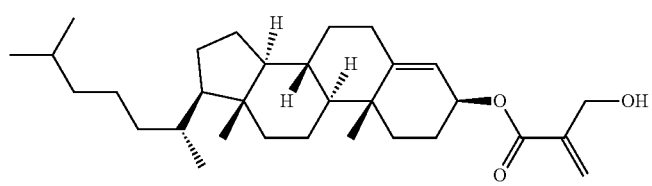 |
| 1-3-24 | 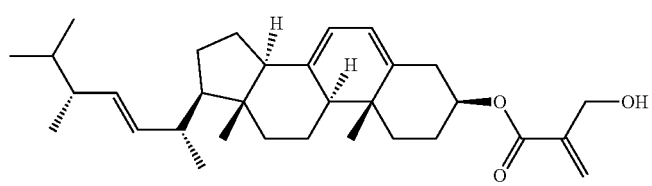 |
| 1-3-25 | 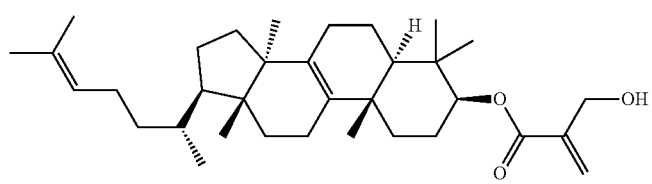 [SMILES: C=C(CO)C(=O)O[C@H]1CC[C@]2(C)C3=C(CC[C@H]2C1(C)C)[C@]1(C)CC[C@H]([C@H](C)CCC=C(C)C)[C@@]1(C)CC3] |
| 1-3-26 | 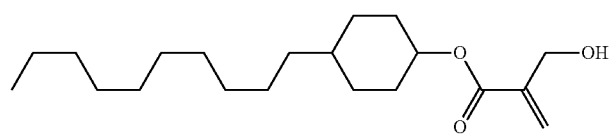 [SMILES: C=C(CO)C(=O)OC1CCC(CCCCCCCCCC)CC1] |
| 1-3-27 | 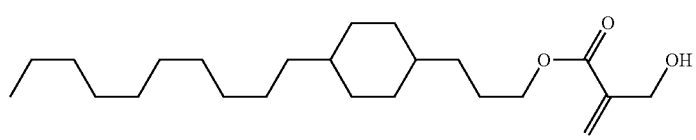 |

| No. | |
|---|---|
| 1-3-28 | 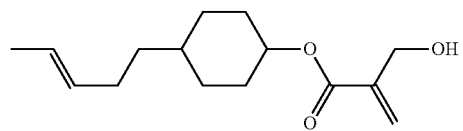 [SMILES: C=C(CO)C(=O)OC1CCC(CC/C=C/C)CC1] |
| 1-3-29 | 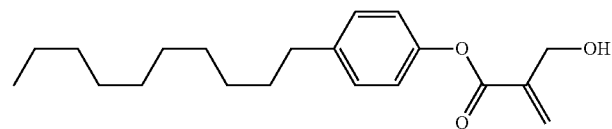 |
| 1-3-30 | 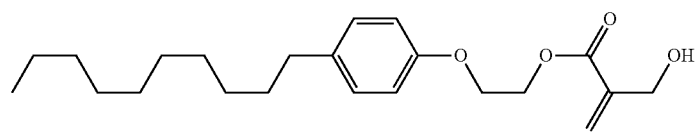 [SMILES: C=C(CO)C(=O)OCCOc1ccc(CCCCCCCCCC)cc1] |
| 1-3-31 | 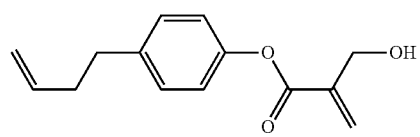 |
| 1-3-32 | 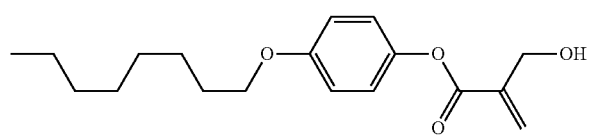 [SMILES: C=C(CO)C(=O)Oc1ccc(OCCCCCCCC)cc1] |
| 1-3-33 | 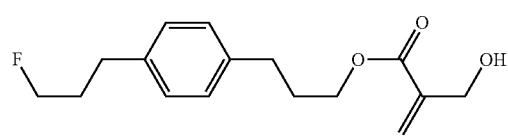 [SMILES: C=C(CO)C(=O)OCCCc1ccc(CCCF)cc1] |
| 1-3-34 | 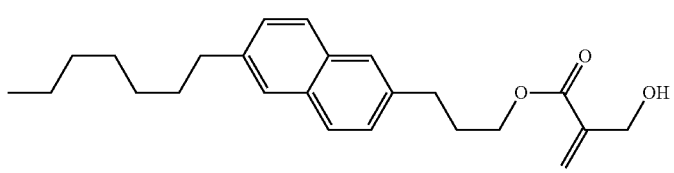 [SMILES: C=C(CO)C(=O)OCCCc1ccc2cc(CCCCCCC)ccc2c1] |
| 1-3-35 | 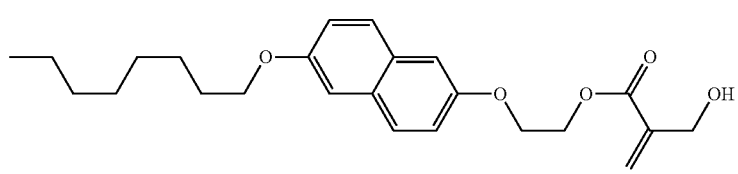 [SMILES: C=C(CO)C(=O)OCCOc1ccc2cc(OCCCCCCCC)ccc2c1] |
| 1-3-36 | 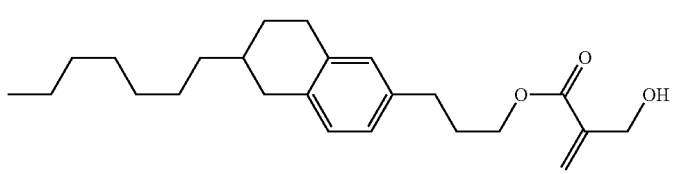 [SMILES: C=C(CO)C(=O)OCCCc1ccc2c(c1)CCC(CCCCCCC)C2] |
| 1-3-37 | 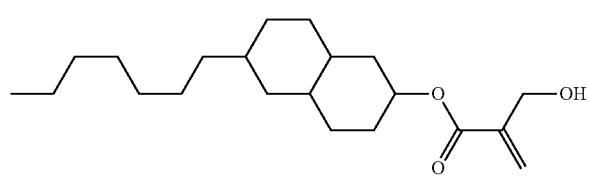 [SMILES: C=C(CO)C(=O)OC1CCC2CC(CCCCCCC)CCC2C1] |

| No. | |
|---|---|
| 1-3-38 | 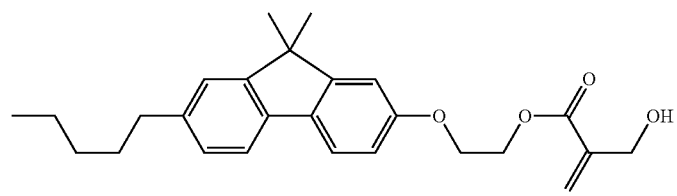 [SMILES: C=C(CO)C(=O)OCCOc1ccc2c(c1)C(C)(C)c1cc(CCCCC)ccc1-2] |
| 1-3-39 | 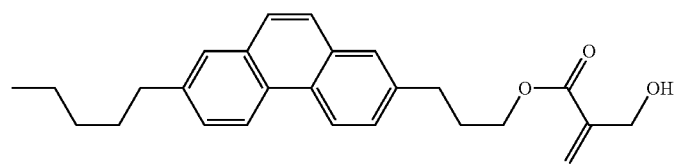 [SMILES: C=C(CO)C(=O)OCCCc1ccc2c(ccc3cc(CCCCC)ccc32)c1] |
| 1-3-40 | 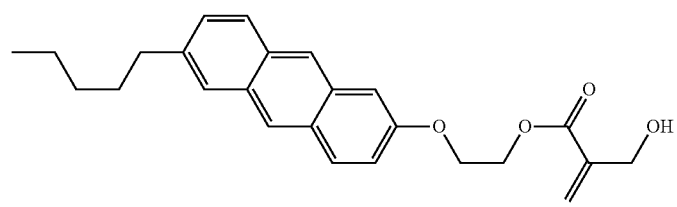 [SMILES: C=C(CO)C(=O)OCCOc1ccc2cc3cc(CCCCC)ccc3cc2c1] |
| 1-4-1 | 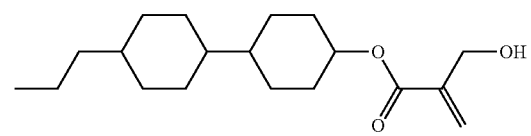 [SMILES: C=C(CO)C(=O)OC1CCC(C2CCC(CCC)CC2)CC1] |
| 1-4-2 | 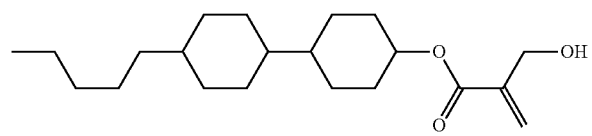 |
| 1-4-3 | 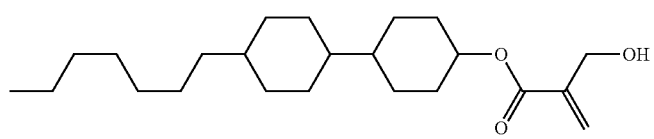 |
| 1-4-4 | 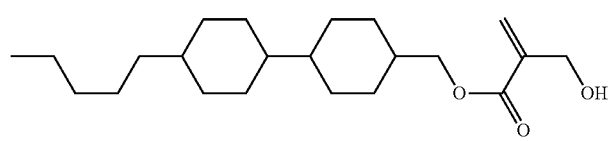 [SMILES: C=C(CO)C(=O)OCC1CCC(C2CCC(CCCCC)CC2)CC1] |
| 1-4-5 | 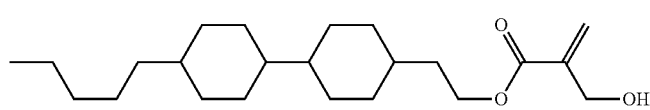 |
| 1-4-6 | 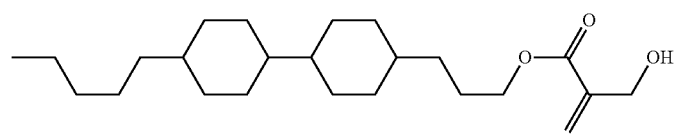 [SMILES: C=C(CO)C(=O)OCCCC1CCC(C2CCC(CCCCC)CC2)CC1] |
| 1-4-7 | 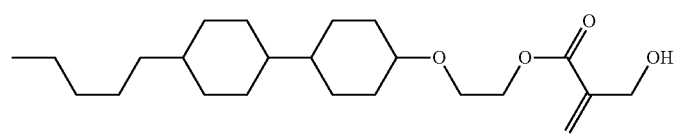 [SMILES: C=C(CO)C(=O)OCCOC1CCC(C2CCC(CCCCC)CC2)CC1] |

| No. | |
|---|---|
| 1-4-8 | 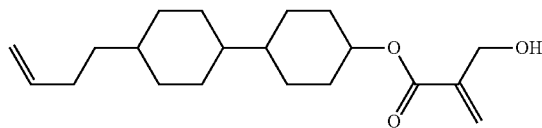 |
| 1-4-9 | 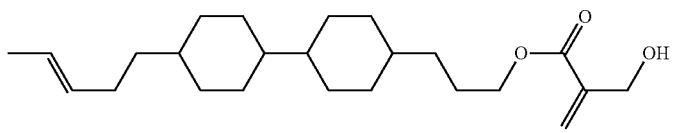 |
| 1-4-10 | 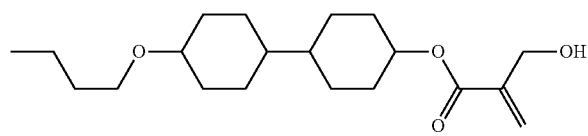 |
| 1-4-11 | 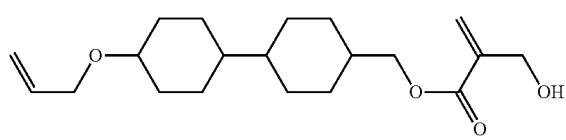 |
| 1-4-12 | 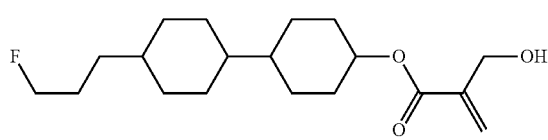 |
| 1-4-13 | 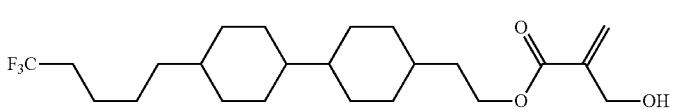 [SMILES: C=C(CO)C(=O)OCCC1CCC(C2CCC(CCCCC(F)(F)F)CC2)CC1] |
| 1-4-14 | 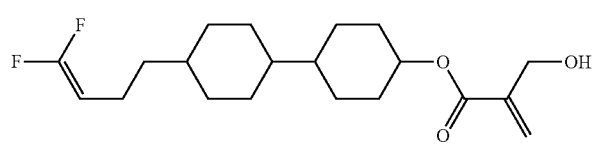 [SMILES: C=C(CO)C(=O)OC1CCC(C2CCC(CCC=C(F)F)CC2)CC1] |
| 1-4-15 | 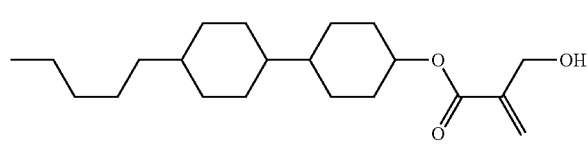 [SMILES: C=C(CO)C(=O)OC1CCC(C2CCC(CCCCC)CC2)CC1] |
| 1-4-16 | 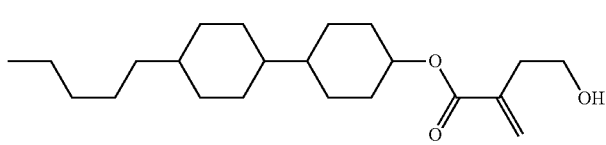 [SMILES: C=C(CCO)C(=O)OC1CCC(C2CCC(CCCCC)CC2)CC1] |
| 1-4-17 | 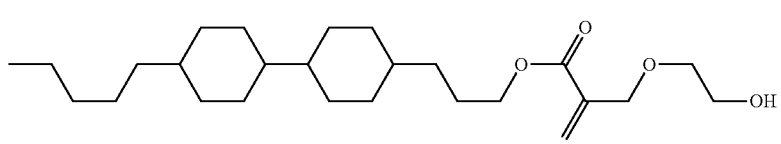 [SMILES: C=C(COCCO)C(=O)OCCCC1CCC(C2CCC(CCCCC)CC2)CC1] |
| 1-4-18 | 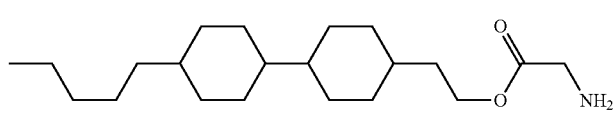 |

-continued
| No. | |
|---|---|
| 1-4-19 | 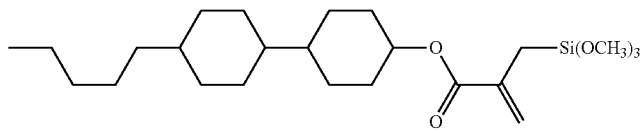 |
| 1-4-20 | 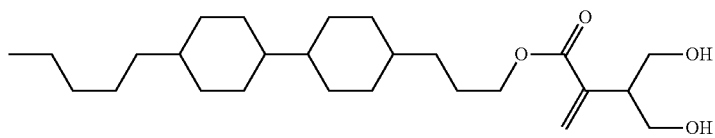 [SMILES: C=C(C(=O)OCCCC1CCC(C2CCC(CCCCC)CC2)CC1)C(CO)CO] |
| 1-4-21 | 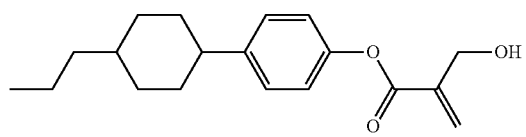 [SMILES: C=C(CO)C(=O)Oc1ccc(C2CCC(CCC)CC2)cc1] |
| 1-4-22 | 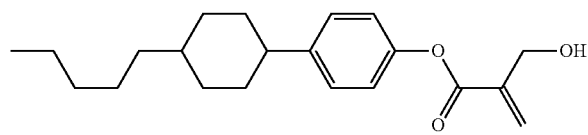 [SMILES: C=C(CO)C(=O)Oc1ccc(C2CCC(CCCCC)CC2)cc1] |
| 1-4-23 | 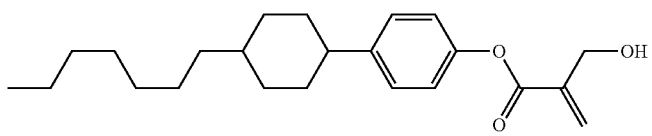 [SMILES: C=C(CO)C(=O)Oc1ccc(C2CCC(CCCCCCC)CC2)cc1] |
| 1-4-24 | 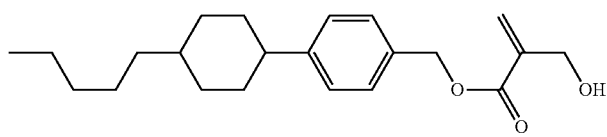 |
| 1-4-25 | 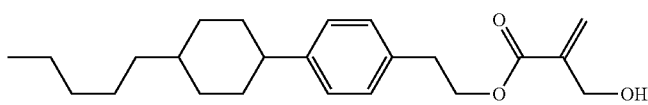 |
| 1-4-26 | 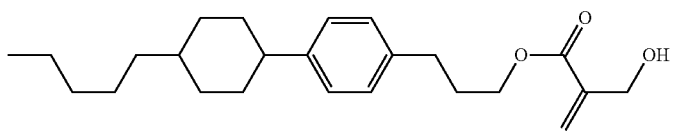 [SMILES: C=C(CO)C(=O)OCCCc1ccc(C2CCC(CCCCC)CC2)cc1] |
| 1-4-27 | 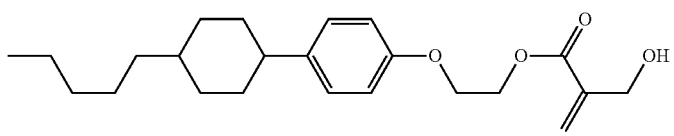 |
| 1-4-28 | 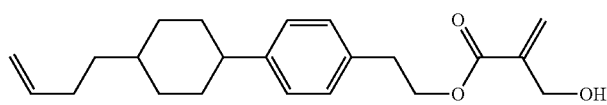 |
| 1-4-29 | 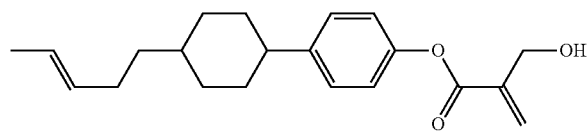 |

-continued
| No. | |
|---|---|
| 1-4-30 | 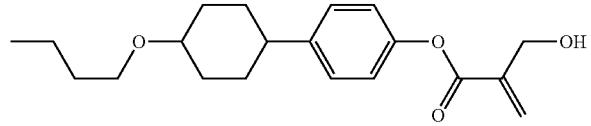 |
| 1-4-31 | 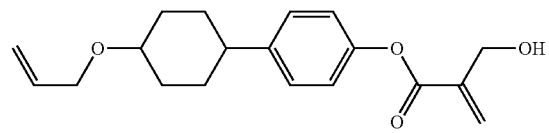 [SMILES: C=CCOC1CCC(c2ccc(OC(=O)C(=C)CO)cc2)CC1] |
| 1-4-32 | 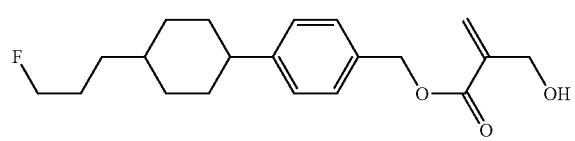 |
| 1-4-33 | 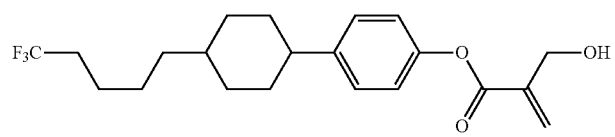 |
| 1-4-34 | 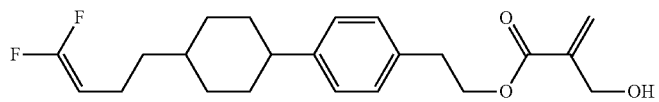 [SMILES: C=C(CO)C(=O)OCCc1ccc(C2CCC(CCC=C(F)F)CC2)cc1] |
| 1-4-35 | 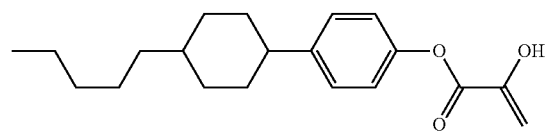 [SMILES: C=C(O)C(=O)Oc1ccc(C2CCC(CCCCC)CC2)cc1] |
| 1-4-36 | 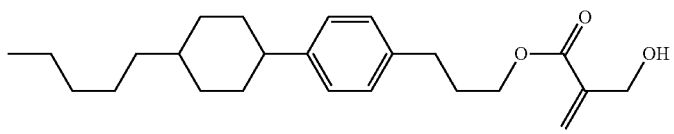 |
| 1-4-37 | 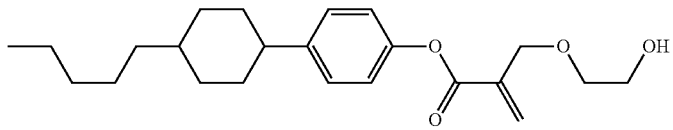 [SMILES: C=C(COCCO)C(=O)Oc1ccc(C2CCC(CCCCC)CC2)cc1] |
| 1-4-38 | 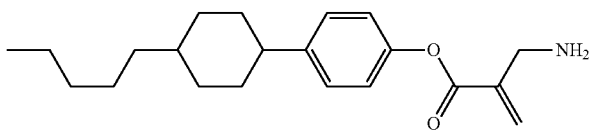 [SMILES: C=C(CN)C(=O)Oc1ccc(C2CCC(CCCCC)CC2)cc1] |
| 1-4-39 | 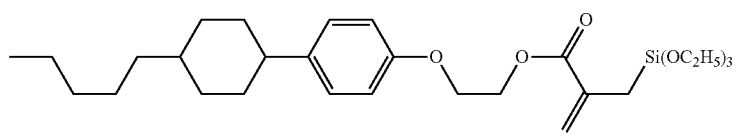 |
| 1-4-40 | 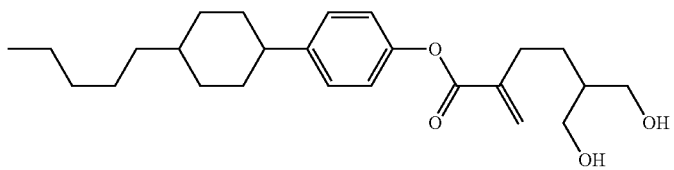 [SMILES: C=C(CCC(CO)CO)C(=O)Oc1ccc(C2CCC(CCCCC)CC2)cc1] |

-continued
| No. | |
|---|---|
| 1-4-41 | 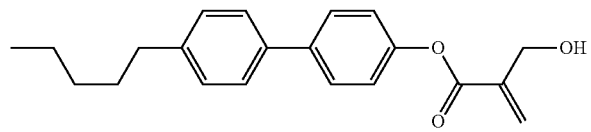 |
| 1-4-42 | 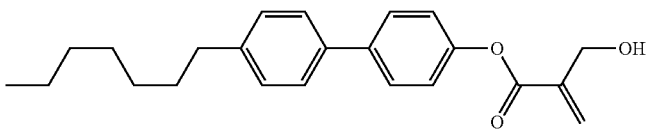 |
| 1-4-43 | 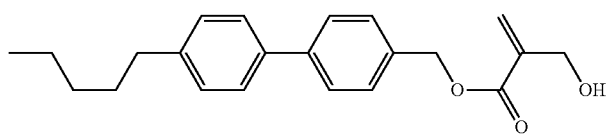 |
| 1-4-44 | 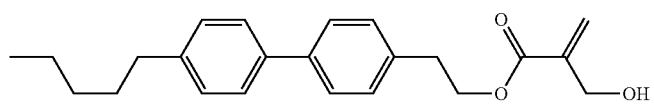 |
| 1-4-45 | 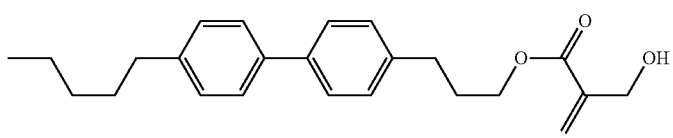 [SMILES: C=C(CO)C(=O)OCCCc1ccc(-c2ccc(CCCCC)cc2)cc1] |
| 1-4-46 | 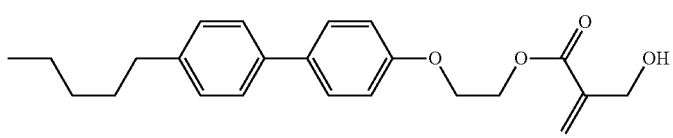 [SMILES: C=C(CO)C(=O)OCCOc1ccc(-c2ccc(CCCCC)cc2)cc1] |
| 1-4-47 | 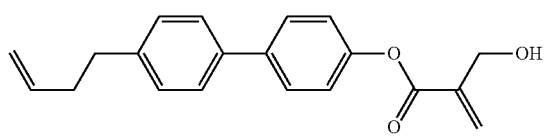 [SMILES: C=CCCc1ccc(-c2ccc(OC(=O)C(=C)CO)cc2)cc1] |
| 1-4-48 | 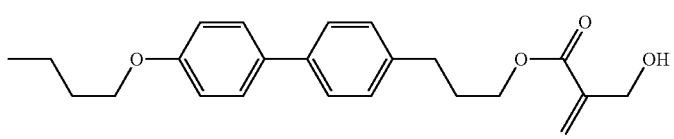 |
| 1-4-49 | 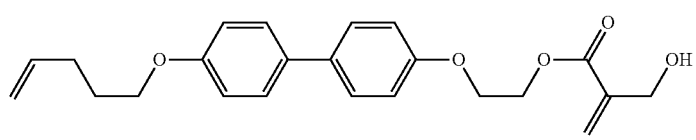 |
| 1-4-50 | 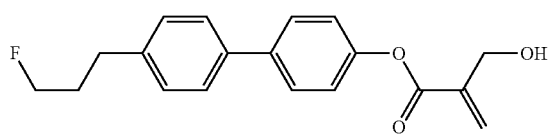 [SMILES: C=C(CO)C(=O)Oc1ccc(-c2ccc(CCCF)cc2)cc1] |
| 1-4-51 | 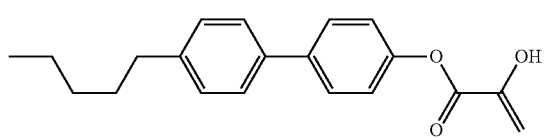 [SMILES: C=C(O)C(=O)Oc1ccc(-c2ccc(CCCCC)cc2)cc1] |

| No. | |
|---|---|
| 1-4-52 | 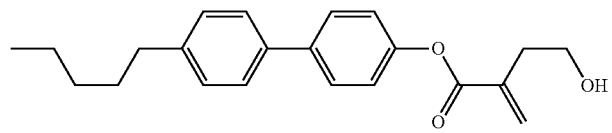 |
| 1-4-53 | 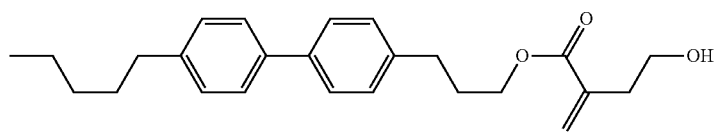 |
| 1-4-54 | 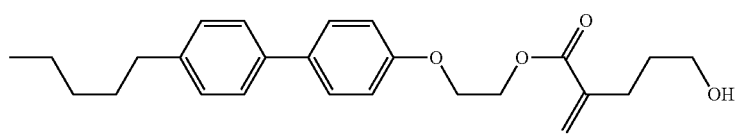 [SMILES: C=C(CCCO)C(=O)OCCOc1ccc(-c2ccc(CCCCC)cc2)cc1] |
| 1-4-55 | 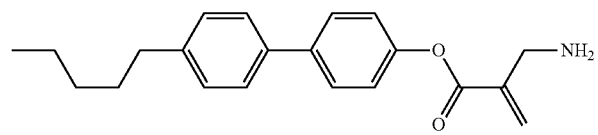 [SMILES: C=C(CN)C(=O)Oc1ccc(-c2ccc(CCCCC)cc2)cc1] |
| 1-4-56 | 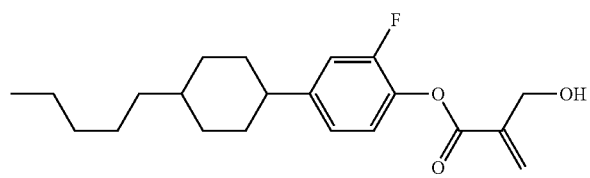 [SMILES: C=C(CO)C(=O)Oc1ccc(C2CCC(CCCCC)CC2)cc1F] |
| 1-4-57 | 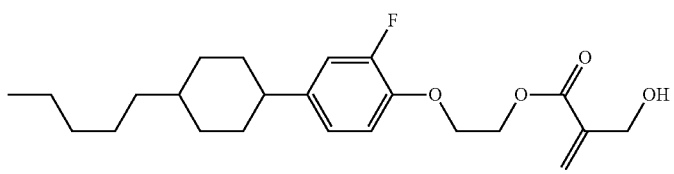 [SMILES: C=C(CO)C(=O)OCCOc1ccc(C2CCC(CCCCC)CC2)cc1F] |
| 1-4-58 | 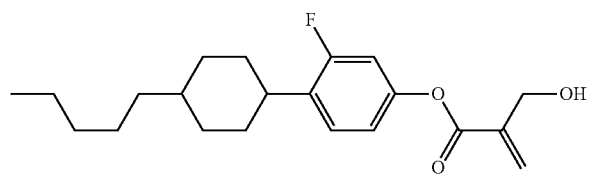 [SMILES: C=C(CO)C(=O)Oc1ccc(C2CCC(CCCCC)CC2)c(F)c1] |
| 1-4-59 | 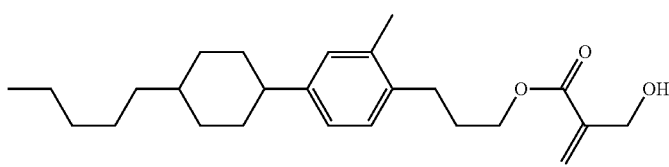 [SMILES: C=C(CO)C(=O)OCCCc1ccc(C2CCC(CCCCC)CC2)cc1C] |
| 1-4-60 | 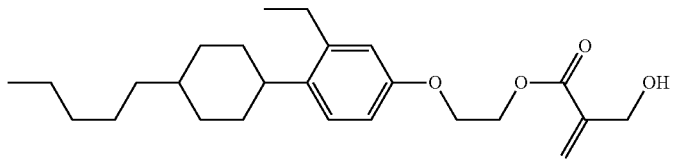 [SMILES: C=C(CO)C(=O)OCCOc1ccc(C2CCC(CCCCC)CC2)c(CC)c1] |

-continued
| No. | |
|---|---|
| 1-4-61 | 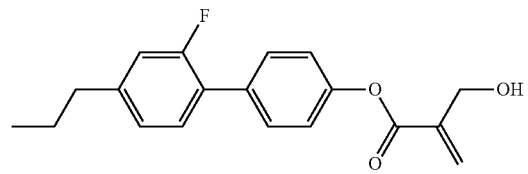 [SMILES: C=C(CO)C(=O)Oc1ccc(-c2ccc(CCC)cc2F)cc1] |
| 1-4-62 | 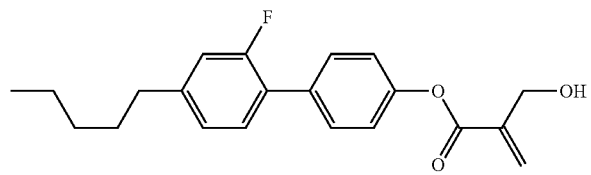 [SMILES: C=C(CO)C(=O)Oc1ccc(-c2ccc(CCCCC)cc2F)cc1] |
| 1-4-63 | 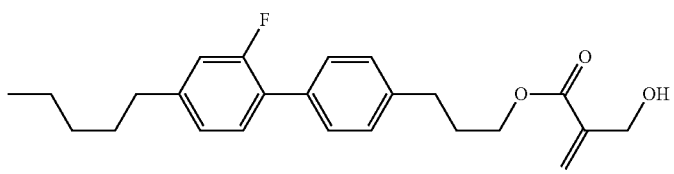 [SMILES: C=C(CO)C(=O)OCCCc1ccc(-c2ccc(CCCCC)cc2F)cc1] |
| 1-4-64 | 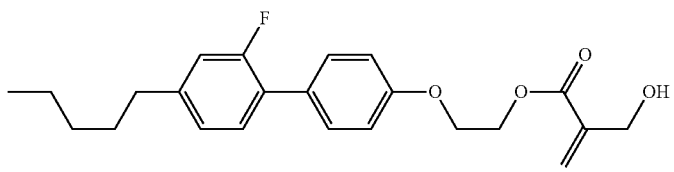 [SMILES: C=C(CO)C(=O)OCCOc1ccc(-c2ccc(CCCCC)cc2F)cc1] |
| 1-4-65 | 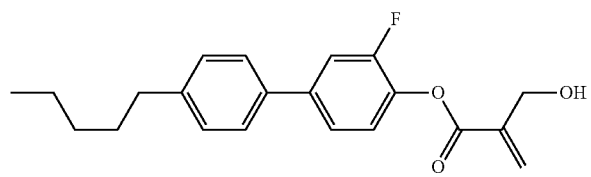 [SMILES: C=C(CO)C(=O)Oc1ccc(-c2ccc(CCCCC)cc2)cc1F] |
| 1-4-66 | 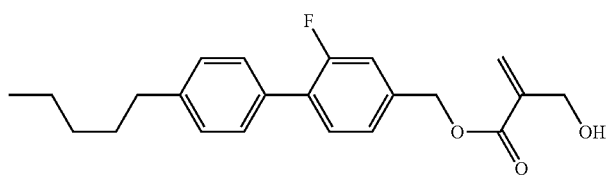 [SMILES: C=C(CO)C(=O)OCc1ccc(-c2ccc(CCCCC)cc2)c(F)c1] |
| 1-4-67 | 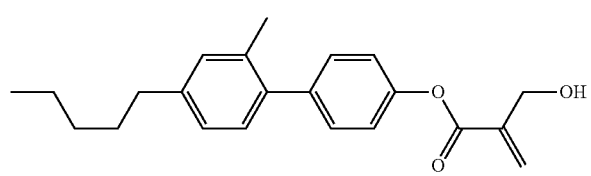 [SMILES: C=C(CO)C(=O)Oc1ccc(-c2ccc(CCCCC)cc2C)cc1] |
| 1-4-68 | 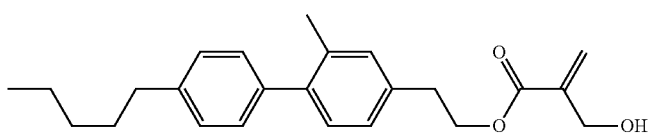 [SMILES: C=C(CO)C(=O)OCCc1ccc(-c2ccc(CCCCC)cc2)c(C)c1] |
| 1-4-69 | 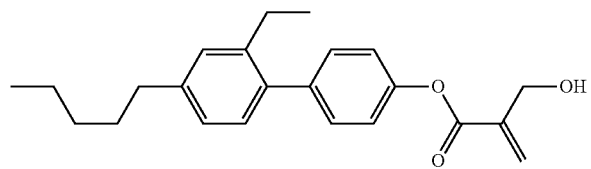 [SMILES: C=C(CO)C(=O)Oc1ccc(-c2ccc(CCCCC)cc2CC)cc1] |

-continued
| No. | |
|---|---|
| 1-4-70 | 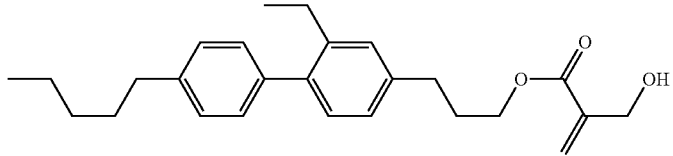 [SMILES: C=C(CO)C(=O)OCCCc1ccc(-c2ccc(CCCCC)cc2)c(CC)c1] |
| 1-4-71 | 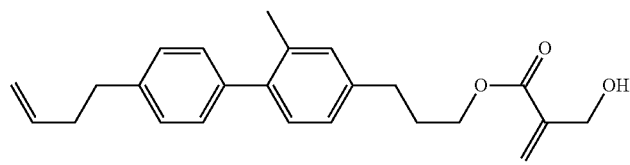 [SMILES: C=CCCc1ccc(-c2ccc(CCCOC(=O)C(=C)CO)cc2C)cc1] |
| 1-4-72 | 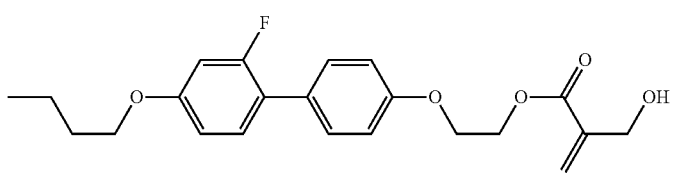 [SMILES: C=C(CO)C(=O)OCCOc1ccc(-c2ccc(OCCCC)cc2F)cc1] |
| 1-4-73 | 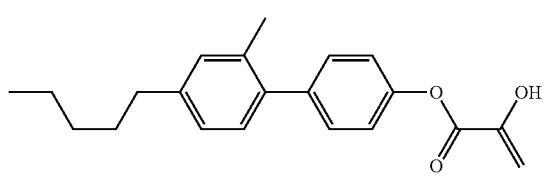 [SMILES: C=C(O)C(=O)Oc1ccc(-c2ccc(CCCCC)cc2C)cc1] |
| 1-4-74 | 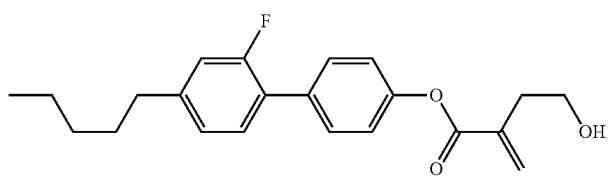 [SMILES: C=C(CCO)C(=O)Oc1ccc(-c2ccc(CCCCC)cc2F)cc1] |
| 1-4-75 | 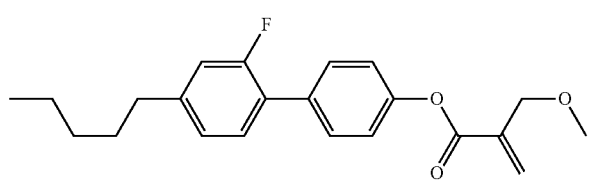 [SMILES: C=C(COC)C(=O)Oc1ccc(-c2ccc(CCCCC)cc2F)cc1] |
| 1-4-76 | 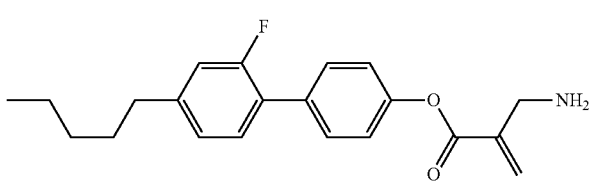 [SMILES: C=C(CN)C(=O)Oc1ccc(-c2ccc(CCCCC)cc2F)cc1] |
| 1-4-77 | 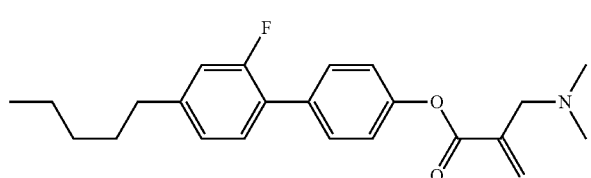 |
| 1-4-78 | 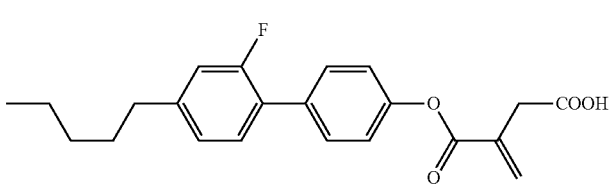 [SMILES: C=C(CC(=O)O)C(=O)Oc1ccc(-c2ccc(CCCCC)cc2F)cc1] |

| No. | |
|---|---|
| 1-4-79 | 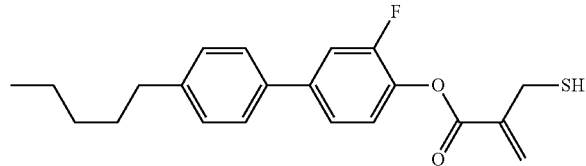 |
| 1-4-80 | 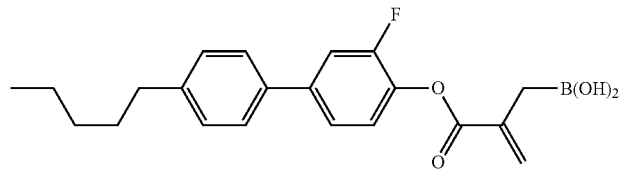 [SMILES: C=C(CB(O)O)C(=O)Oc1ccc(-c2ccc(CCCCC)cc2)cc1F] |
| 1-4-81 | 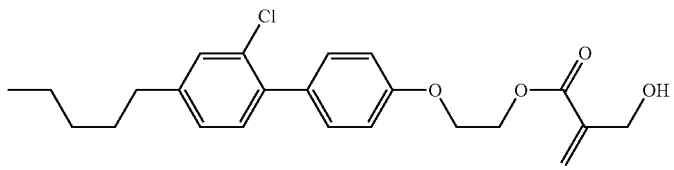 |
| 1-4-82 | 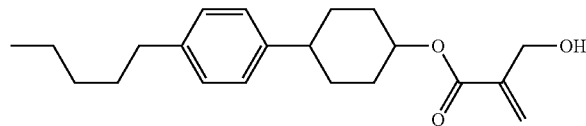 [SMILES: C=C(CO)C(=O)OC1CCC(c2ccc(CCCCC)cc2)CC1] |
| 1-4-83 | 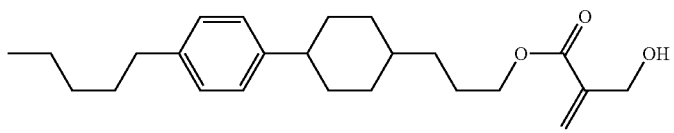 [SMILES: C=C(CO)C(=O)OCCCC1CCC(c2ccc(CCCCC)cc2)CC1] |
| 1-4-84 | 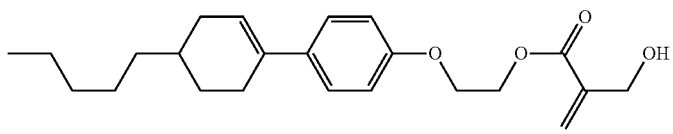 [SMILES: C=C(CO)C(=O)OCCOc1ccc(C2=CCC(CCCCC)CC2)cc1] |
| 1-4-85 | 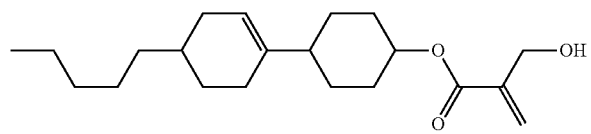 |
| 1-4-86 | 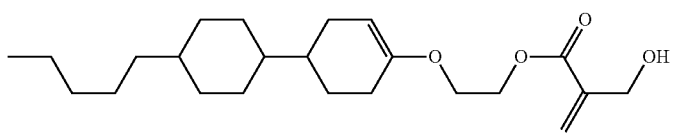 |
| 1-4-87 | 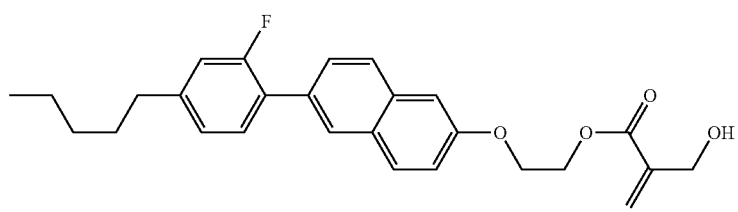 [SMILES: C=C(CO)C(=O)OCCOc1ccc2cc(-c3ccc(CCCCC)cc3F)ccc2c1] |

-continued
| No. | |
|---|---|
| 1-4-88 | 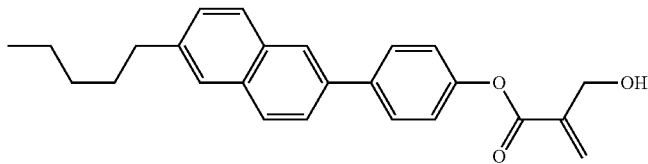 |
| 1-4-89 | 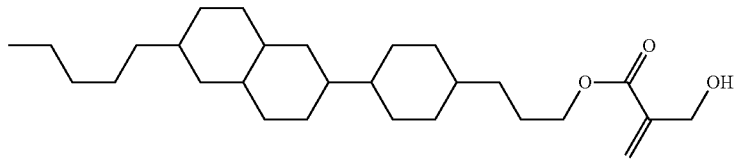 [SMILES: C=C(CO)C(=O)OCCCC1CCC(C2CCC3CC(CCCCC)CCC3C2)CC1] |
| 1-4-90 | 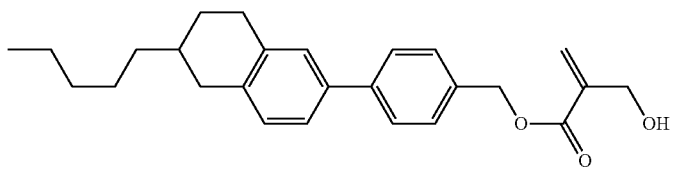 [SMILES: C=C(CO)C(=O)OCc1ccc(-c2ccc3c(c2)CCC(CCCCC)C3)cc1] |
| 1-4-91 | 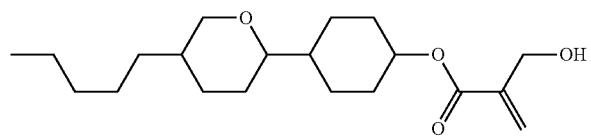 [SMILES: C=C(CO)C(=O)OC1CCC(C2CCC(CCCCC)CO2)CC1] |
| 1-4-92 | 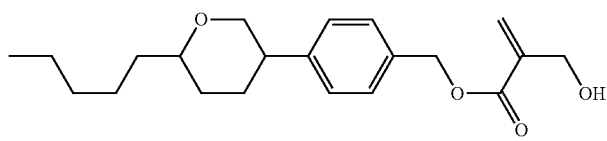 [SMILES: C=C(CO)C(=O)OCc1ccc(C2CCC(CCCCC)OC2)cc1] |
| 1-4-93 | 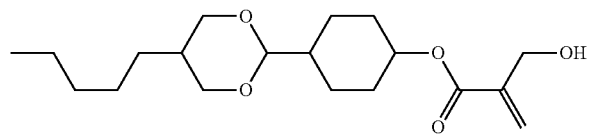 |
| 1-4-94 | 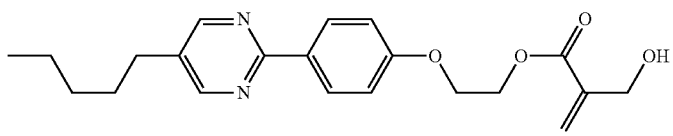 |
| 1-4-95 | 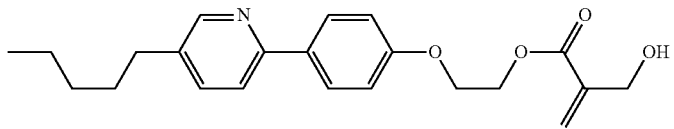 |
| 1-4-96 | 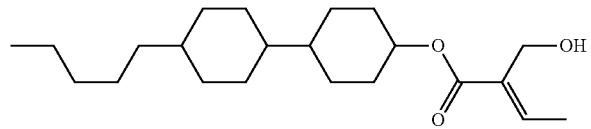 |
| 1-4-97 | 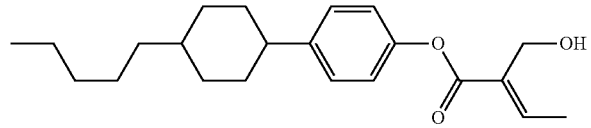 [SMILES: C/C=C(\CO)C(=O)Oc1ccc(C2CCC(CCCCC)CC2)cc1] |

-continued
| No. | |
|---|---|
| 1-4-98 | 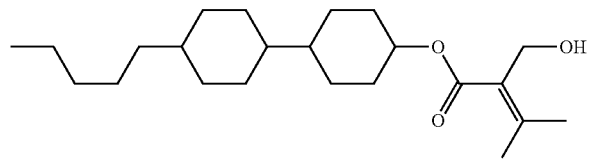 [SMILES: CCCCCC1CCC(C2CCC(OC(=O)C(CO)=C(C)C)CC2)CC1] |
| 1-4-99 | 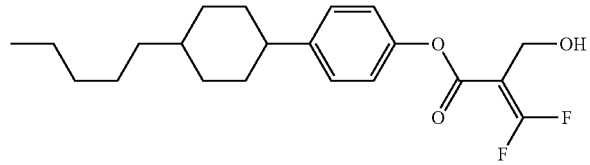 [SMILES: CCCCCC1CCC(c2ccc(OC(=O)C(CO)=C(F)F)cc2)CC1] |
| 1-4-100 | 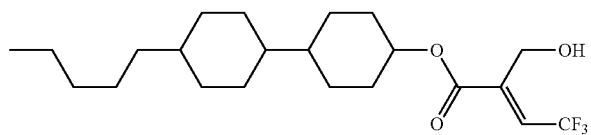 |
| 1-4-101 | 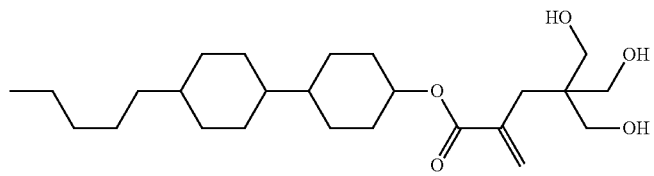 [SMILES: C=C(CC(CO)(CO)CO)C(=O)OC1CCC(C2CCC(CCCCC)CC2)CC1] |
| 1-4-102 | 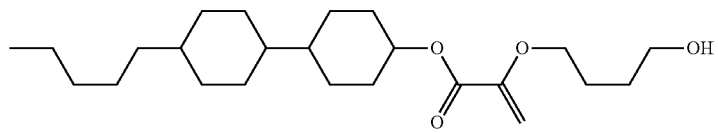 [SMILES: C=C(OCCCCO)C(=O)OC1CCC(C2CCC(CCCCC)CC2)CC1] |
| 1-4-103 | 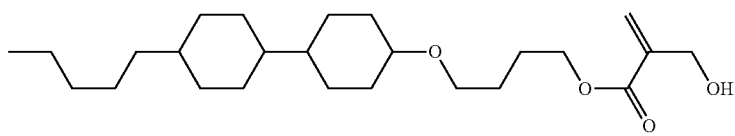 |
| 1-4-104 | 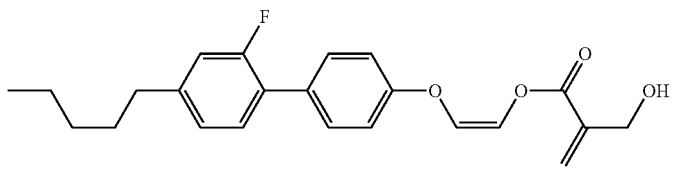 [SMILES: C=C(CO)C(=O)O/C=C\Oc1ccc(-c2ccc(CCCCC)cc2F)cc1] |
| 1-4-105 | 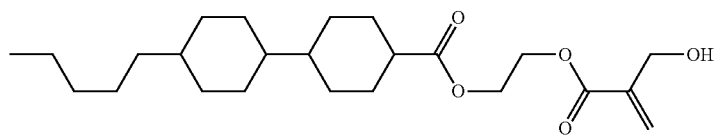 |
| 1-4-106 | 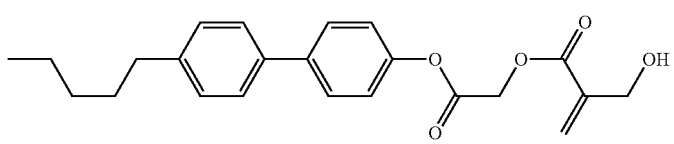 [SMILES: C=C(CO)C(=O)OCC(=O)Oc1ccc(-c2ccc(CCCCC)cc2)cc1] |
| 1-4-107 | 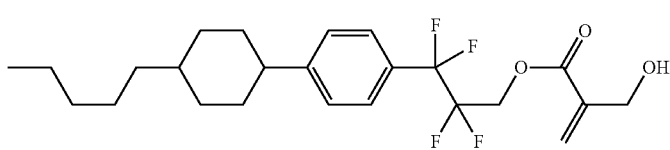 [SMILES: C=C(CO)C(=O)OCC(F)(F)C(F)(F)c1ccc(C2CCC(CCCCC)CC2)cc1] |

| No. | |
|---|---|
| 1-4-108 | 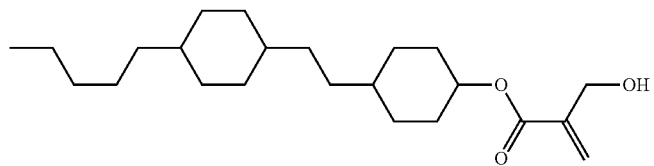 |
| 1-4-109 | 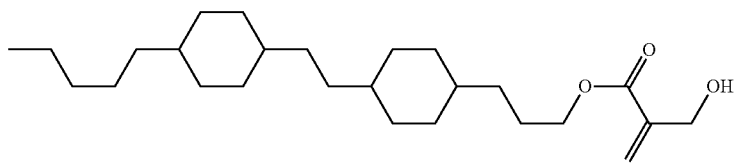 [SMILES: C=C(CO)C(=O)OCCCC1CCC(CCC2CCC(CCCCC)CC2)CC1] |
| 1-4-110 | 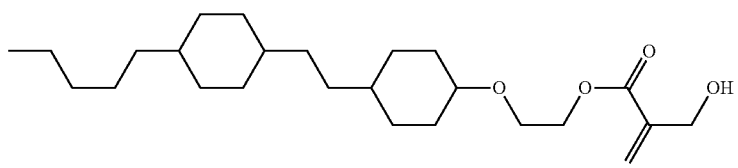 [SMILES: C=C(CO)C(=O)OCCOC1CCC(CCC2CCC(CCCCC)CC2)CC1] |
| 1-4-111 | 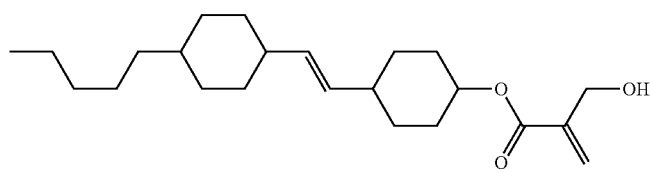 [SMILES: C=C(CO)C(=O)OC1CCC(/C=C/C2CCC(CCCCC)CC2)CC1] |
| 1-4-112 | 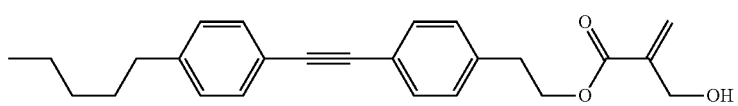 [SMILES: C=C(CO)C(=O)OCCc1ccc(C#Cc2ccc(CCCCC)cc2)cc1] |
| 1-4-113 | 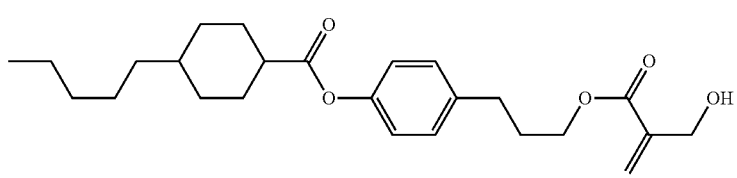 [SMILES: C=C(CO)C(=O)OCCCc1ccc(OC(=O)C2CCC(CCCCC)CC2)cc1] |
| 1-4-114 | 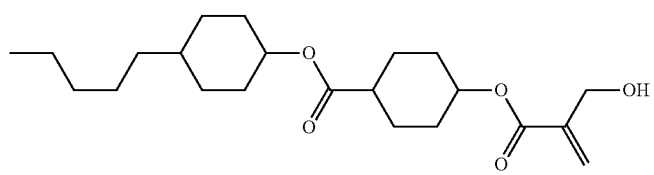 [SMILES: C=C(CO)C(=O)OC1CCC(C(=O)OC2CCC(CCCCC)CC2)CC1] |
| 1-4-115 | 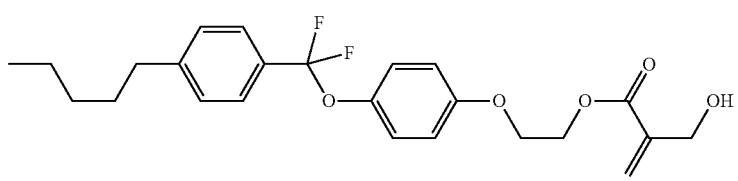 [SMILES: C=C(CO)C(=O)OCCOc1ccc(OC(F)(F)c2ccc(CCCCC)cc2)cc1] |
| 1-4-116 | 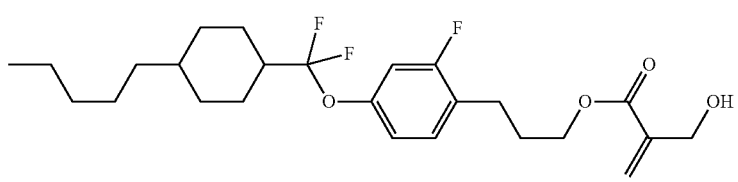 [SMILES: C=C(CO)C(=O)OCCCc1ccc(OC(F)(F)C2CCC(CCCCC)CC2)cc1F] |

-continued
| No. | |
|---|---|
| 1-4-117 | 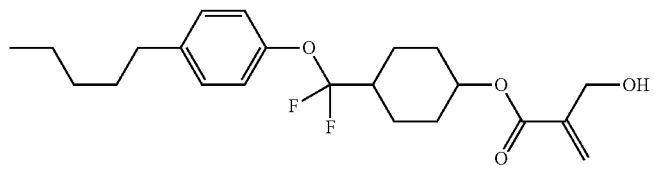 |
| 1-4-118 | 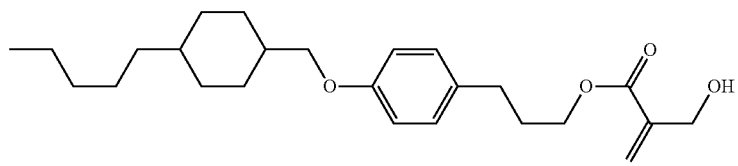 [SMILES: C=C(CO)C(=O)OCCCc1ccc(OCC2CCC(CCCCC)CC2)cc1] |
| 1-4-119 | 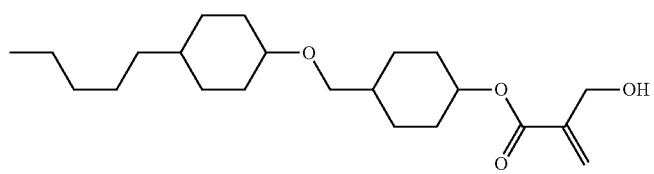 [SMILES: C=C(CO)C(=O)OC1CCC(COC2CCC(CCCCC)CC2)CC1] |
| 1-4-120 | 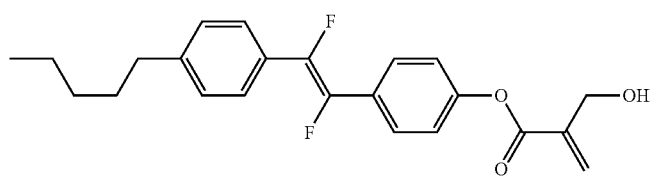 [SMILES: C=C(CO)C(=O)Oc1ccc(/C(F)=C(\F)c2ccc(CCCCC)cc2)cc1] |
| 1-5-1 | 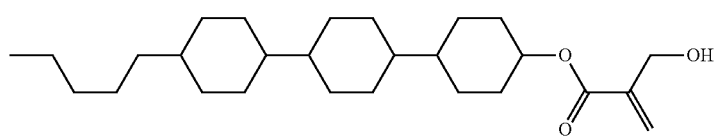 |
| 1-5-2 | 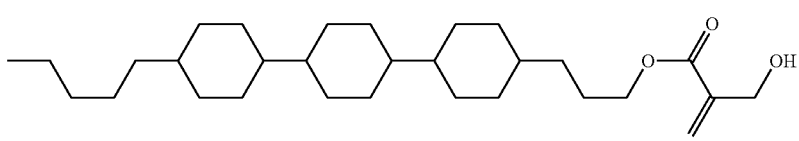 [SMILES: C=C(CO)C(=O)OCCCC1CCC(C2CCC(C3CCC(CCCCC)CC3)CC2)CC1] |
| 1-5-3 | 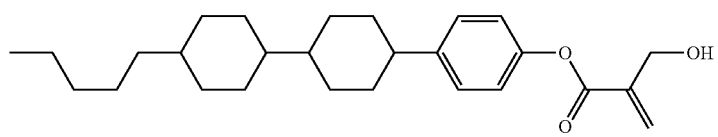 [SMILES: C=C(CO)C(=O)Oc1ccc(C2CCC(C3CCC(CCCCC)CC3)CC2)cc1] |
| 1-5-4 | 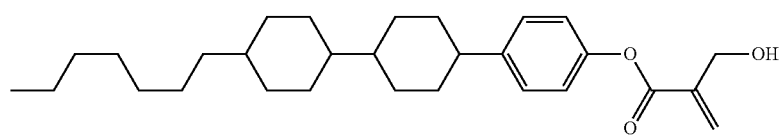 [SMILES: C=C(CO)C(=O)Oc1ccc(C2CCC(C3CCC(CCCCCCC)CC3)CC2)cc1] |
| 1-5-5 | 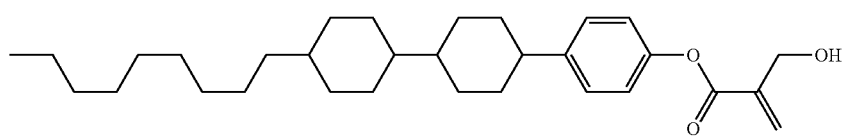 [SMILES: C=C(CO)C(=O)Oc1ccc(C2CCC(C3CCC(CCCCCCCCC)CC3)CC2)cc1] |
| 1-5-6 | 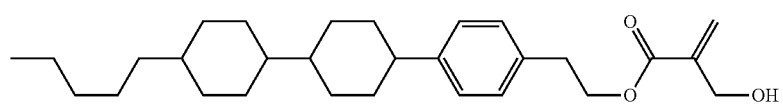 [SMILES: C=C(CO)C(=O)OCCc1ccc(C2CCC(C3CCC(CCCCC)CC3)CC2)cc1] |

-continued
| No. | |
|---|---|
| 1-5-7 | 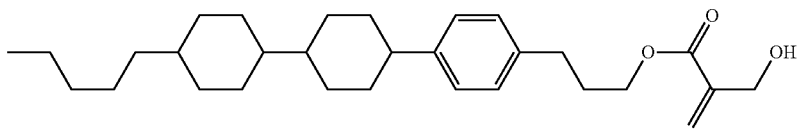 |
| 1-5-8 | 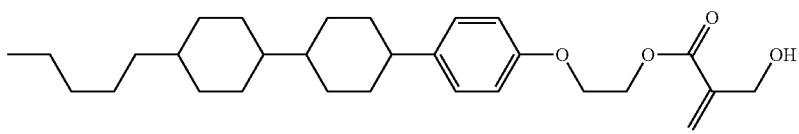 |
| 1-5-9 | 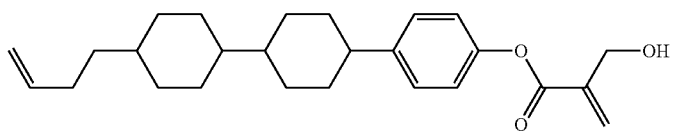 [SMILES: C=CCCC1CCC(C2CCC(c3ccc(OC(=O)C(=C)CO)cc3)CC2)CC1] |
| 1-5-10 | 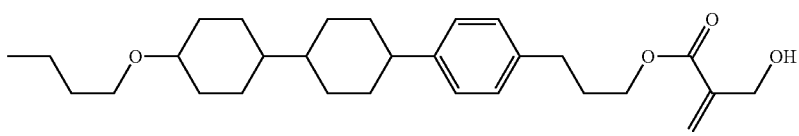 |
| 1-5-11 | 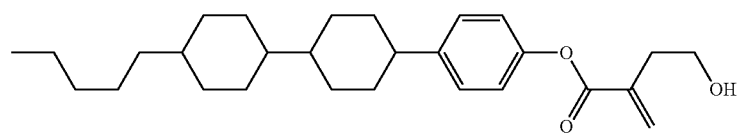 [SMILES: C=C(CCO)C(=O)Oc1ccc(C2CCC(C3CCC(CCCCC)CC3)CC2)cc1] |
| 1-5-12 | 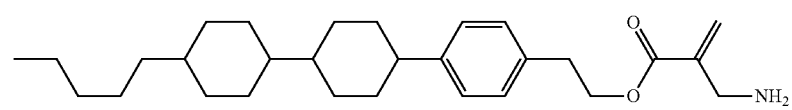 |
| 1-5-13 | 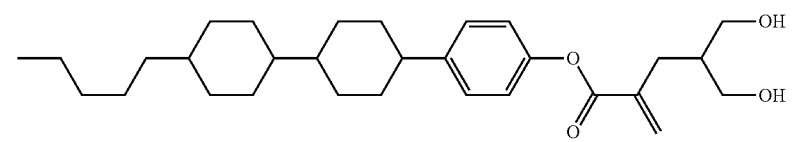 [SMILES: C=C(CC(CO)CO)C(=O)Oc1ccc(C2CCC(C3CCC(CCCCC)CC3)CC2)cc1] |
| 1-5-14 | 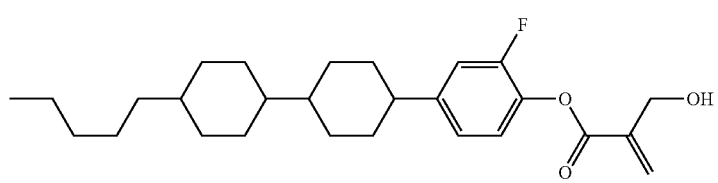 [SMILES: C=C(CO)C(=O)Oc1ccc(C2CCC(C3CCC(CCCCC)CC3)CC2)cc1F] |
| 1-5-15 | 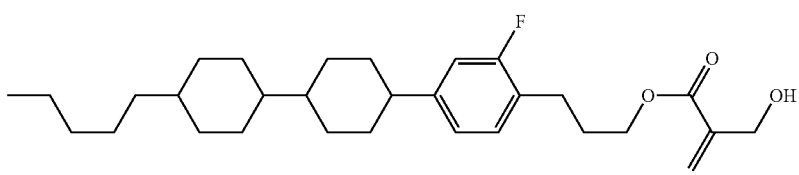 [SMILES: C=C(CO)C(=O)OCCCc1ccc(C2CCC(C3CCC(CCCCC)CC3)CC2)cc1F] |
| 1-5-16 | 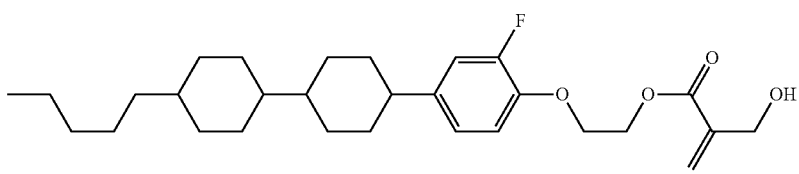 [SMILES: C=C(CO)C(=O)OCCOc1ccc(C2CCC(C3CCC(CCCCC)CC3)CC2)cc1F] |

-continued
| No. | |
|---|---|
| 1-5-17 | 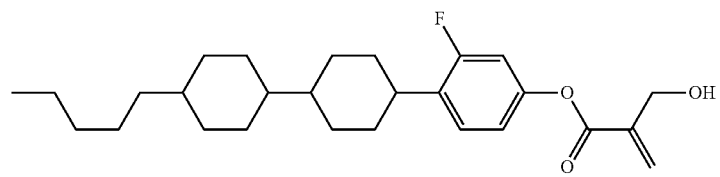 |
| 1-5-18 | 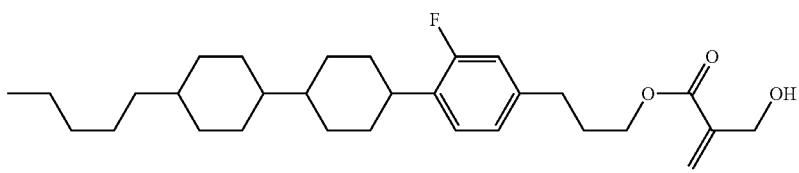 [SMILES: C=C(CO)C(=O)OCCCc1ccc(C2CCC(C3CCC(CCCCC)CC3)CC2)c(F)c1] |
| 1-5-19 | 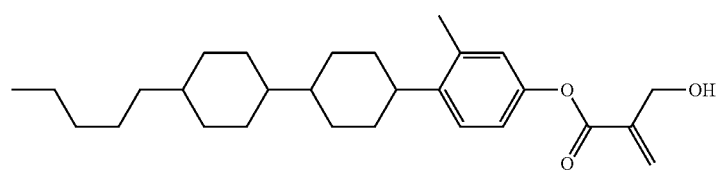 |
| 1-5-20 | 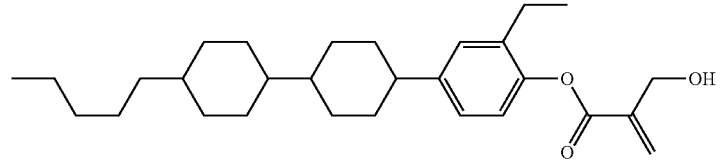 |
| 1-5-21 | 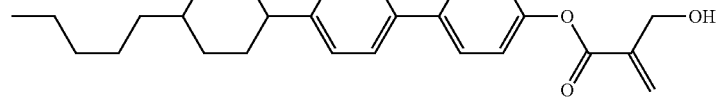 |
| 1-5-22 | 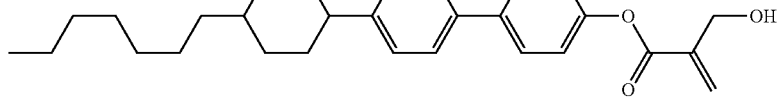 |
| 1-5-23 | 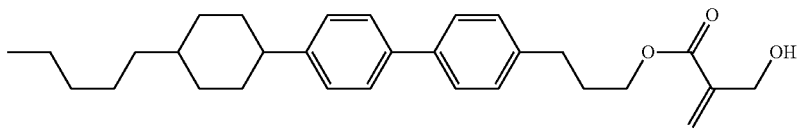 [SMILES: C=C(CO)C(=O)OCCCc1ccc(-c2ccc(C3CCC(CCCCC)CC3)cc2)cc1] |
| 1-5-24 | 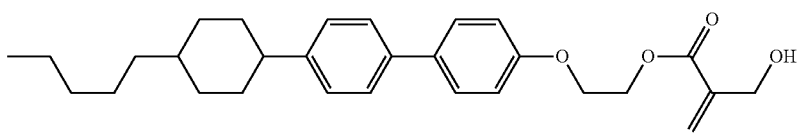 |
| 1-5-25 | 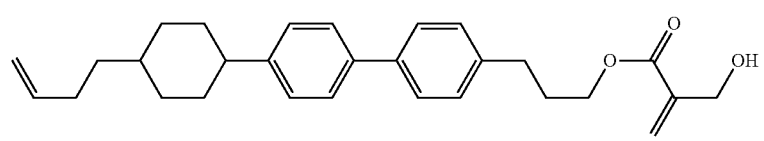 [SMILES: C=CCCC1CCC(c2ccc(-c3ccc(CCCOC(=O)C(=C)CO)cc3)cc2)CC1] |
| 1-5-26 | 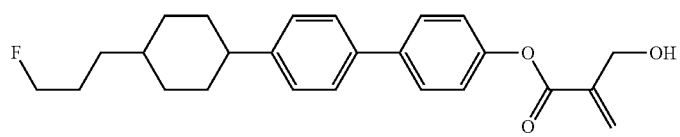 |

| No. | |
|---|---|
| 1-5-27 | 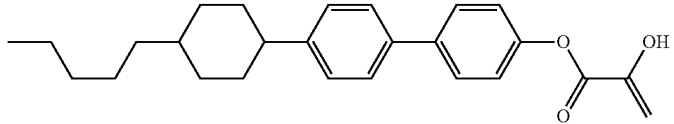 [SMILES: C=C(O)C(=O)Oc1ccc(-c2ccc(C3CCC(CCCCC)CC3)cc2)cc1] |
| 1-5-28 | 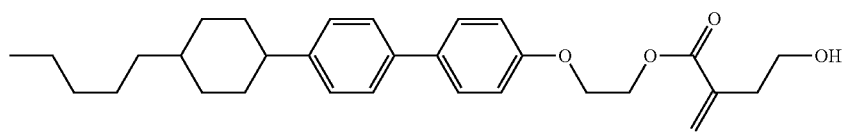 [SMILES: C=C(CCO)C(=O)OCCOc1ccc(-c2ccc(C3CCC(CCCCC)CC3)cc2)cc1] |
| 1-5-29 | 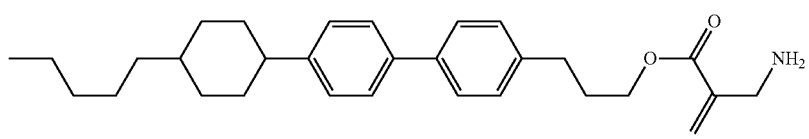 [SMILES: C=C(CN)C(=O)OCCCc1ccc(-c2ccc(C3CCC(CCCCC)CC3)cc2)cc1] |
| 1-5-30 | 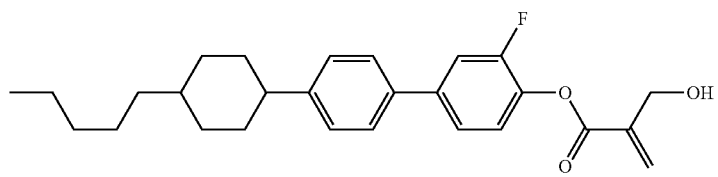 [SMILES: C=C(CO)C(=O)Oc1ccc(-c2ccc(C3CCC(CCCCC)CC3)cc2)cc1F] |
| 1-5-31 | 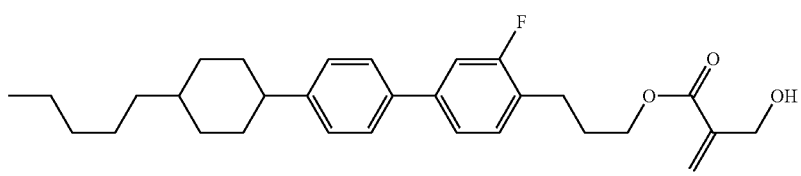 [SMILES: C=C(CO)C(=O)OCCCc1ccc(-c2ccc(C3CCC(CCCCC)CC3)cc2)cc1F] |
| 1-5-32 | 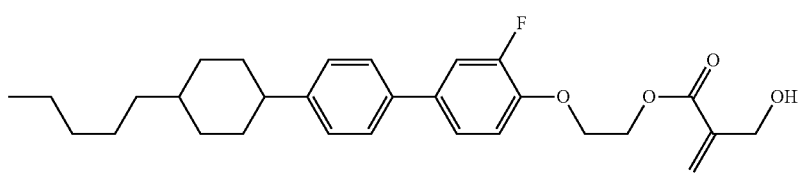 [SMILES: C=C(CO)C(=O)OCCOc1ccc(-c2ccc(C3CCC(CCCCC)CC3)cc2)cc1F] |
| 1-5-33 | 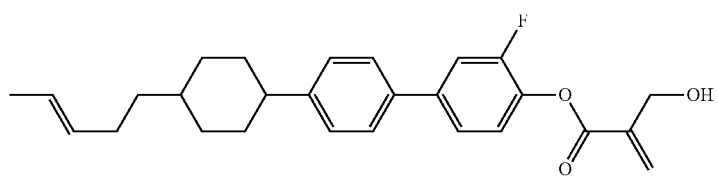 [SMILES: C=C(CO)C(=O)Oc1ccc(-c2ccc(C3CCC(CC/C=C/C)CC3)cc2)cc1F] |
| 1-5-34 | 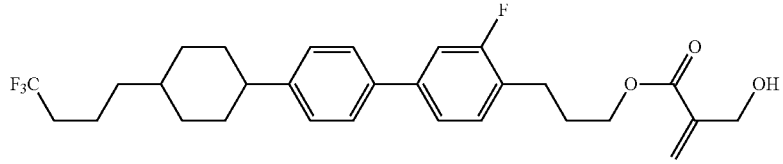 [SMILES: C=C(CO)C(=O)OCCCc1ccc(-c2ccc(C3CCC(CCCC(F)(F)F)CC3)cc2)cc1F] |
| 1-5-35 | 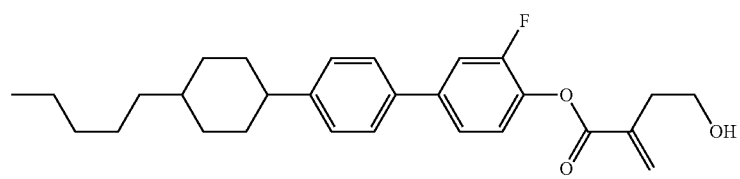 [SMILES: C=C(CCO)C(=O)Oc1ccc(-c2ccc(C3CCC(CCCCC)CC3)cc2)cc1F] |

-continued
| No. |
| --- |
| 1-5-36 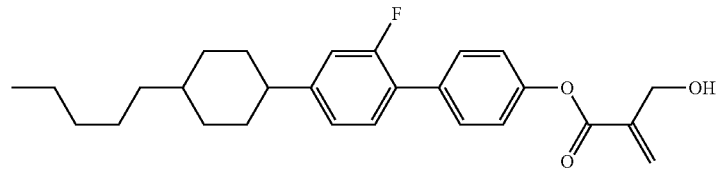 [SMILES: C=C(CO)C(=O)Oc1ccc(-c2ccc(C3CCC(CCCCC)CC3)cc2F)cc1] |
| 1-5-37 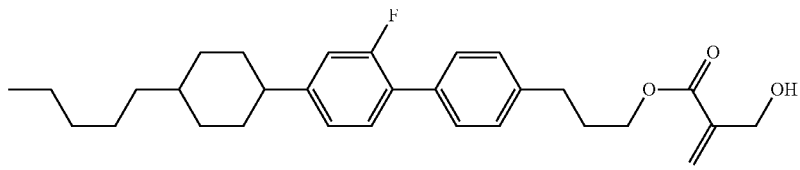 |
| 1-5-38 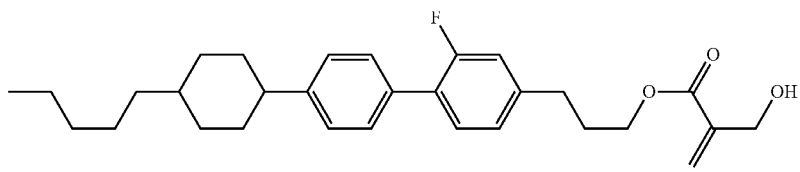 |
| 1-5-39 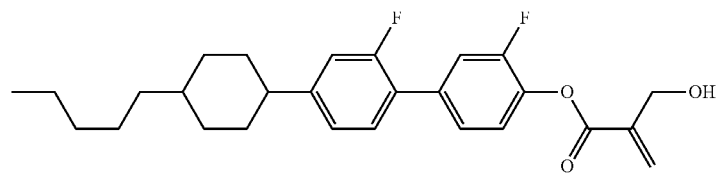 [SMILES: C=C(CO)C(=O)Oc1ccc(-c2ccc(C3CCC(CCCCC)CC3)cc2F)cc1F] |
| 1-5-40 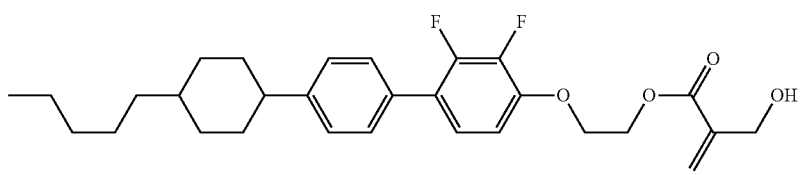 [SMILES: C=C(CO)C(=O)OCCOc1ccc(-c2ccc(C3CCC(CCCCC)CC3)cc2)c(F)c1F] |
| 1-5-41 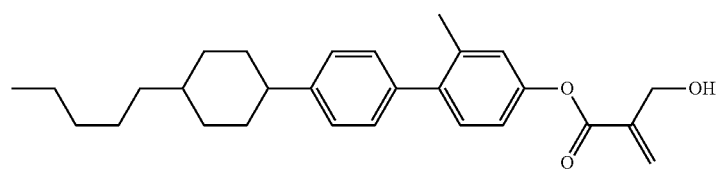 |
| 1-5-42 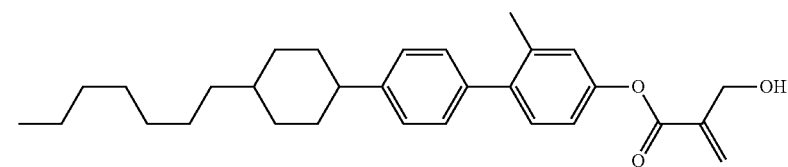 |
| 1-5-43 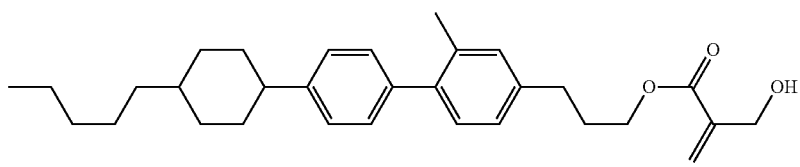 [SMILES: C=C(CO)C(=O)OCCCc1ccc(-c2ccc(C3CCC(CCCCC)CC3)cc2)c(C)c1] |
| 1-5-44 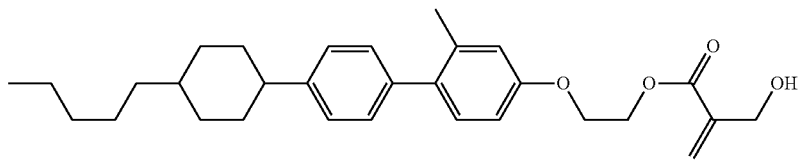 [SMILES: C=C(CO)C(=O)OCCOc1ccc(-c2ccc(C3CCC(CCCCC)CC3)cc2)c(C)c1] |

-continued
| No. | |
|---|---|
| 1-5-45 | 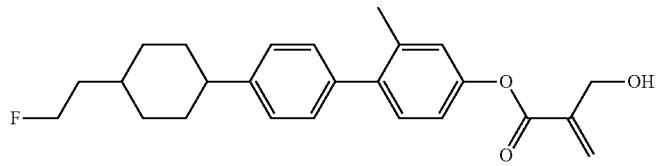 [SMILES: C=C(CO)C(=O)Oc1ccc(-c2ccc(C3CCC(CCF)CC3)cc2)c(C)c1] |
| 1-5-46 | 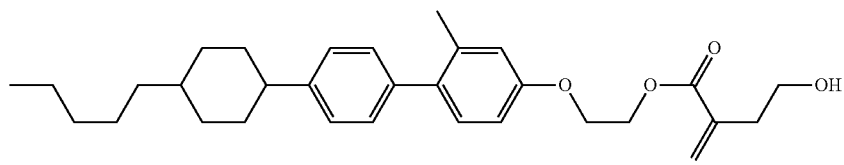 [SMILES: C=C(CCO)C(=O)OCCOc1ccc(-c2ccc(C3CCC(CCCCC)CC3)cc2)c(C)c1] |
| 1-5-47 | 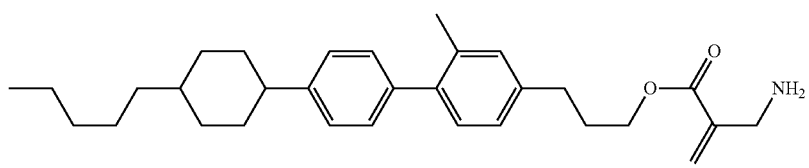 [SMILES: C=C(CN)C(=O)OCCCc1ccc(-c2ccc(C3CCC(CCCCC)CC3)cc2)c(C)c1] |
| 1-5-48 | 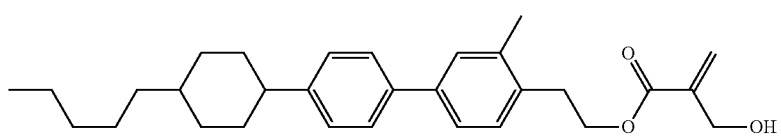 [SMILES: C=C(CO)C(=O)OCCc1ccc(-c2ccc(C3CCC(CCCCC)CC3)cc2)cc1C] |
| 1-5-49 | 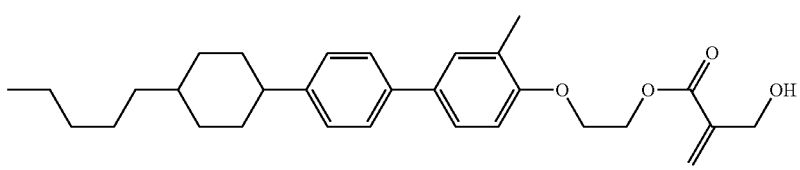 [SMILES: C=C(CO)C(=O)OCCOc1ccc(-c2ccc(C3CCC(CCCCC)CC3)cc2)cc1C] |
| 1-5-50 | 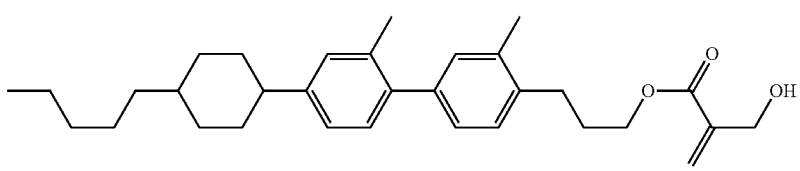 [SMILES: C=C(CO)C(=O)OCCCc1ccc(-c2ccc(C3CCC(CCCCC)CC3)cc2C)cc1C] |
| 1-5-51 | 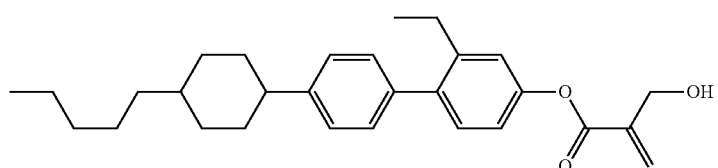 |
| 1-5-52 | 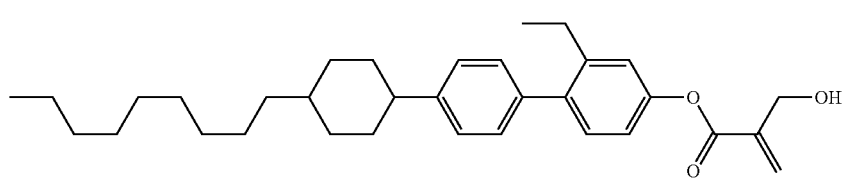 [SMILES: C=C(CO)C(=O)Oc1ccc(-c2ccc(C3CCC(CCCCCCCCC)CC3)cc2)c(CC)c1] |
| 1-5-53 | 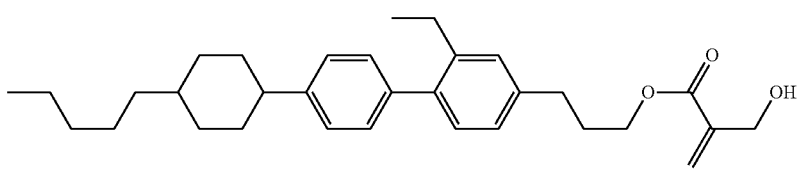 |

-continued
| No. | |
|---|---|
| 1-5-54 | 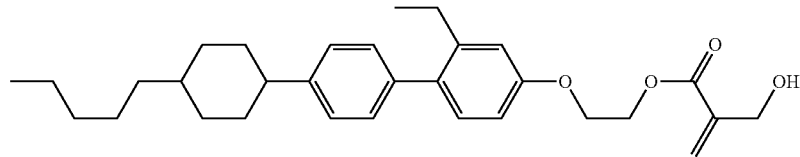 |
| 1-5-55 | 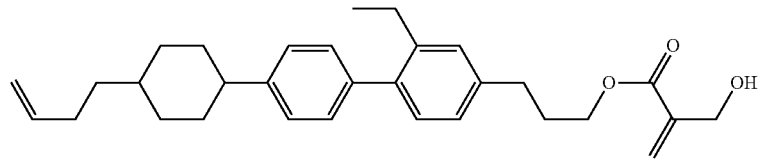 [SMILES: C=CCCC1CCC(c2ccc(-c3ccc(CCCOC(=O)C(=C)CO)cc3CC)cc2)CC1] |
| 1-5-56 | 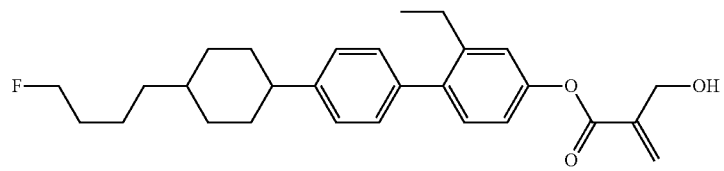 |
| 1-5-57 | 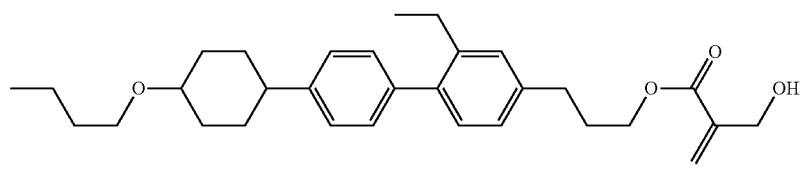 |
| 1-5-58 | 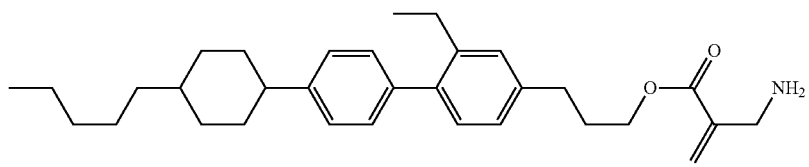 [SMILES: C=C(CN)C(=O)OCCCc1ccc(-c2ccc(C3CCC(CCCCC)CC3)cc2)c(CC)c1] |
| 1-5-59 | 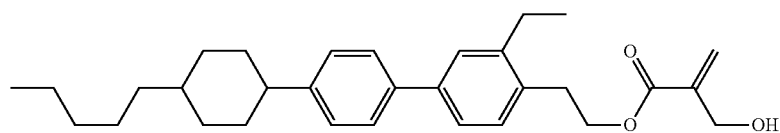 [SMILES: C=C(CO)C(=O)OCCc1ccc(-c2ccc(C3CCC(CCCCC)CC3)cc2)cc1CC] |
| 1-5-60 | 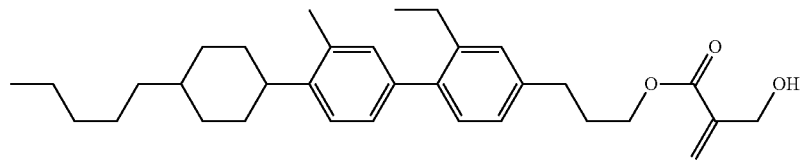 |
| 1-5-61 | 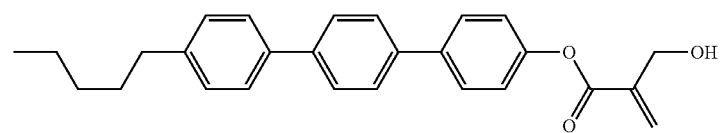 [SMILES: C=C(CO)C(=O)Oc1ccc(-c2ccc(-c3ccc(CCCCC)cc3)cc2)cc1] |
| 1-5-62 | 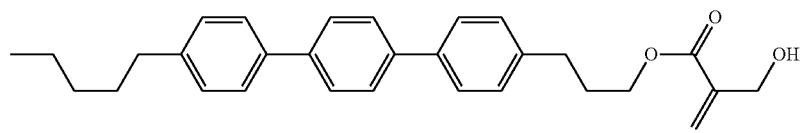 [SMILES: C=C(CO)C(=O)OCCCc1ccc(-c2ccc(-c3ccc(CCCCC)cc3)cc2)cc1] |

-continued
| No. |
|---|
| 1-5-63 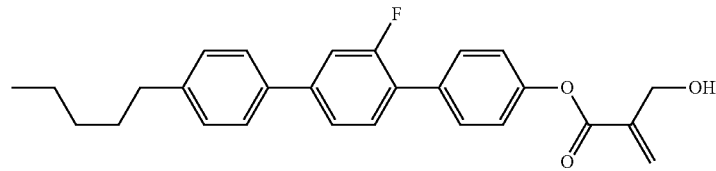 [SMILES: C=C(CO)C(=O)Oc1ccc(-c2ccc(-c3ccc(CCCCC)cc3)cc2F)cc1] |
| 1-5-64 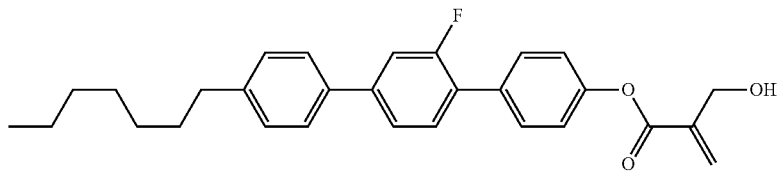 [SMILES: C=C(CO)C(=O)Oc1ccc(-c2ccc(-c3ccc(CCCCCCC)cc3)cc2F)cc1] |
| 1-5-65 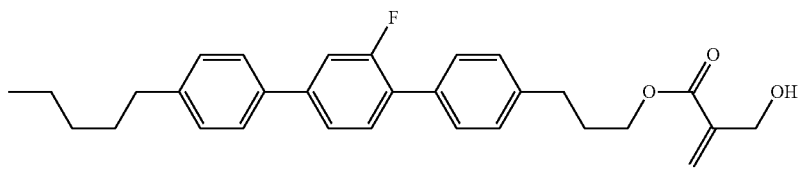 [SMILES: C=C(CO)C(=O)OCCCc1ccc(-c2ccc(-c3ccc(CCCCC)cc3)cc2F)cc1] |
| 1-5-66 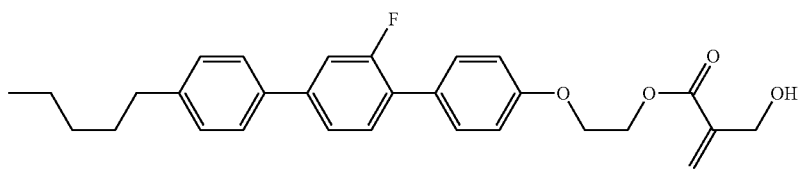 [SMILES: C=C(CO)C(=O)OCCOc1ccc(-c2ccc(-c3ccc(CCCCC)cc3)cc2F)cc1] |
| 1-5-67 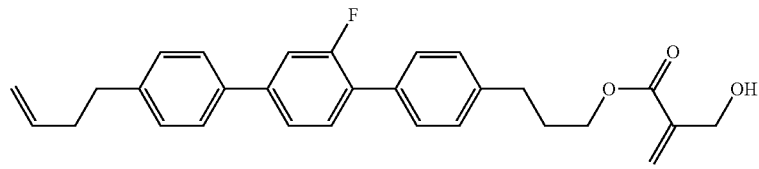 [SMILES: C=CCCc1ccc(-c2ccc(-c3ccc(CCCOC(=O)C(=C)CO)cc3)c(F)c2)cc1] |
| 1-5-68 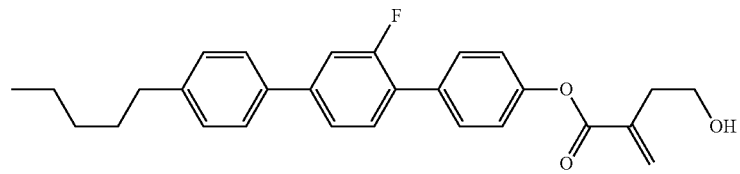 [SMILES: C=C(CCO)C(=O)Oc1ccc(-c2ccc(-c3ccc(CCCCC)cc3)cc2F)cc1] |
| 1-5-69 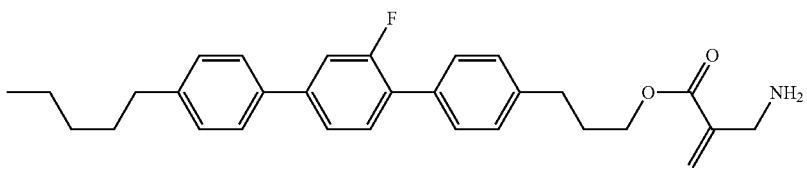 [SMILES: C=C(CN)C(=O)OCCCc1ccc(-c2ccc(-c3ccc(CCCCC)cc3)cc2F)cc1] |
| 1-5-70 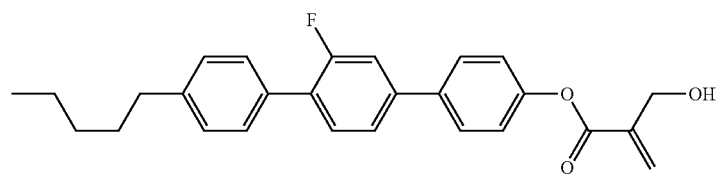 [SMILES: C=C(CO)C(=O)Oc1ccc(-c2ccc(-c3ccc(CCCCC)cc3)c(F)c2)cc1] |
| 1-5-71 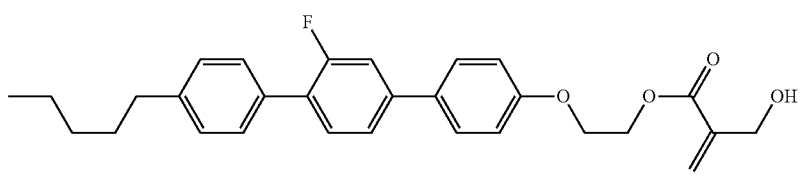 [SMILES: C=C(CO)C(=O)OCCOc1ccc(-c2ccc(-c3ccc(CCCCC)cc3)c(F)c2)cc1] |

| No. | |
|---|---|
| 1-5-72 | 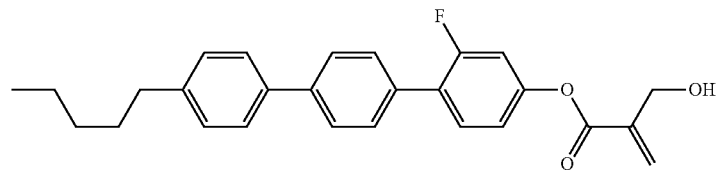 [SMILES: C=C(CO)C(=O)Oc1ccc(-c2ccc(-c3ccc(CCCCC)cc3)cc2)c(F)c1] |
| 1-5-73 | 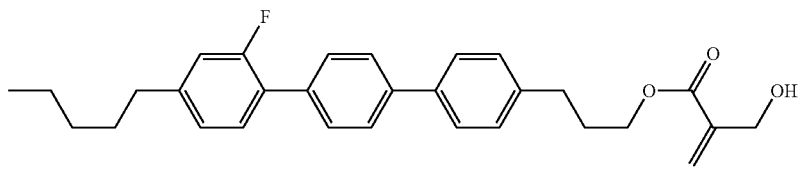 [SMILES: C=C(CO)C(=O)OCCCc1ccc(-c2ccc(-c3ccc(CCCCC)cc3F)cc2)cc1] |
| 1-5-74 | 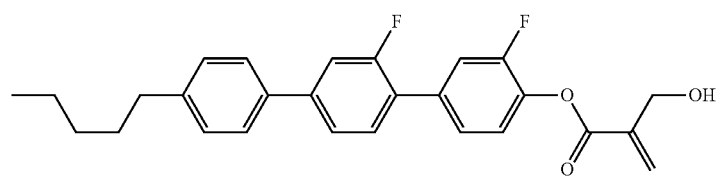 [SMILES: C=C(CO)C(=O)Oc1ccc(-c2ccc(-c3ccc(CCCCC)cc3)cc2F)cc1F] |
| 1-5-75 | 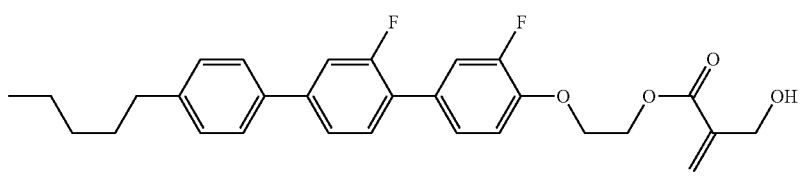 [SMILES: C=C(CO)C(=O)OCCOc1ccc(-c2ccc(-c3ccc(CCCCC)cc3)cc2F)cc1F] |
| 1-5-76 | 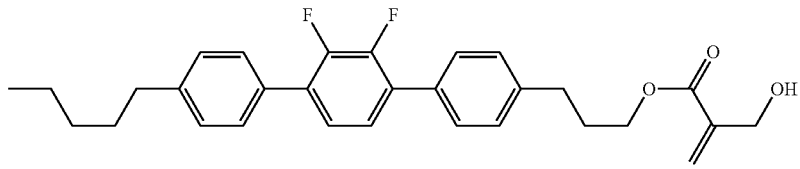 [SMILES: C=C(CO)C(=O)OCCCc1ccc(-c2ccc(-c3ccc(CCCCC)cc3)c(F)c2F)cc1] |
| 1-5-77 | 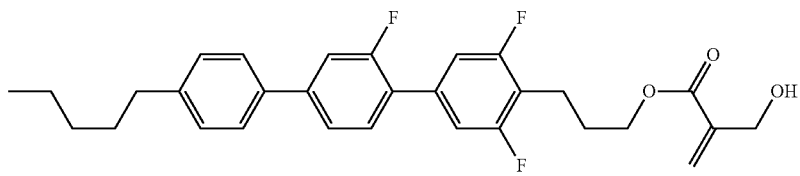 |
| 1-5-78 | 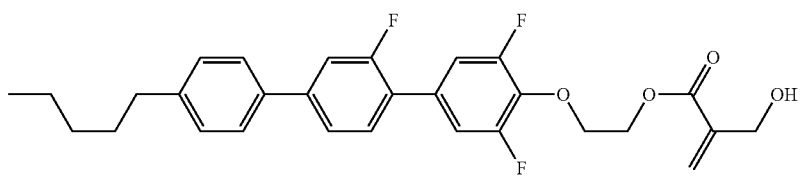 [SMILES: C=C(CO)C(=O)OCCOc1c(F)cc(-c2ccc(-c3ccc(CCCCC)cc3)cc2F)cc1F] |
| 1-5-79 | 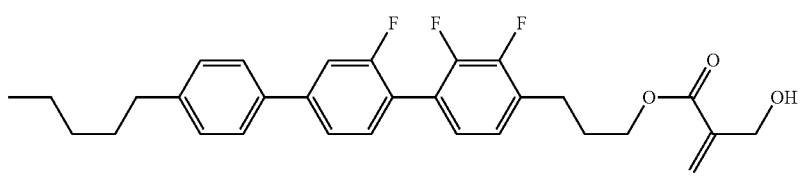 [SMILES: C=C(CO)C(=O)OCCCc1ccc(-c2ccc(-c3ccc(CCCCC)cc3)cc2F)c(F)c1F] |
| 1-5-80 | 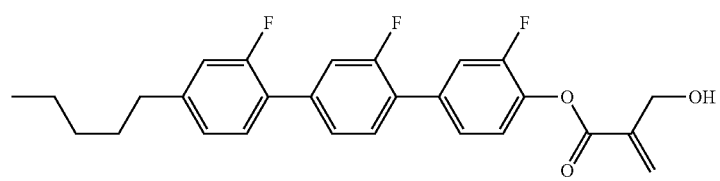 [SMILES: C=C(CO)C(=O)Oc1ccc(-c2ccc(-c3ccc(CCCCC)cc3F)cc2F)cc1F] |

| No. |  |
|---|---|
| 1-5-81 | 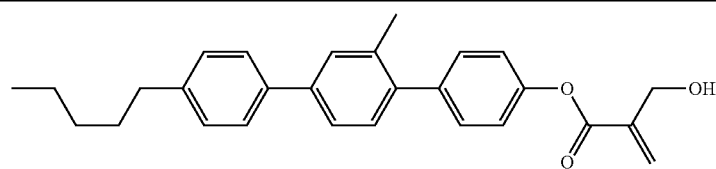 |
| 1-5-82 | 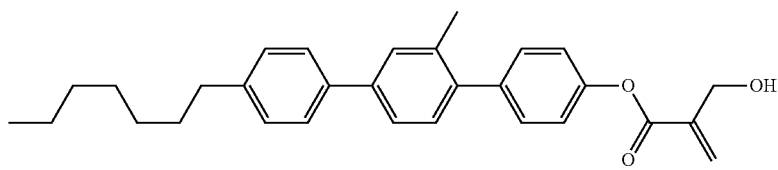 [SMILES: C=C(CO)C(=O)Oc1ccc(-c2ccc(-c3ccc(CCCCCCC)cc3)cc2C)cc1] |
| 1-5-83 | 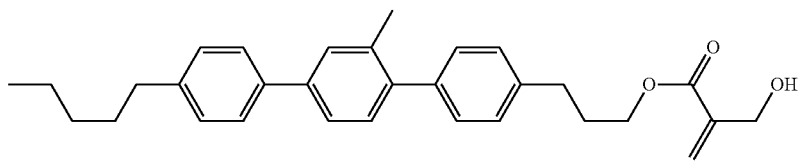 |
| 1-5-84 | 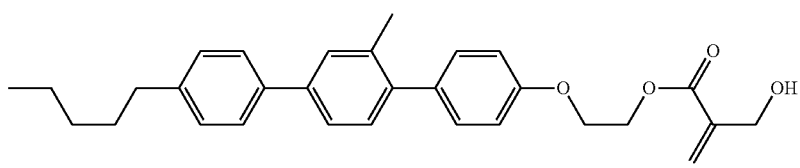 [SMILES: C=C(CO)C(=O)OCCOc1ccc(-c2ccc(-c3ccc(CCCCC)cc3)cc2C)cc1] |
| 1-5-85 | 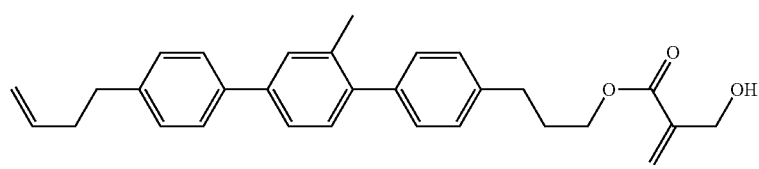 [SMILES: C=CCCc1ccc(-c2ccc(-c3ccc(CCCOC(=O)C(=C)CO)cc3)c(C)c2)cc1] |
| 1-5-86 | 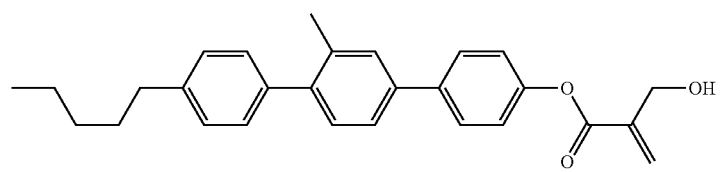 [SMILES: C=C(CO)C(=O)Oc1ccc(-c2ccc(-c3ccc(CCCCC)cc3)c(C)c2)cc1] |
| 1-5-87 | 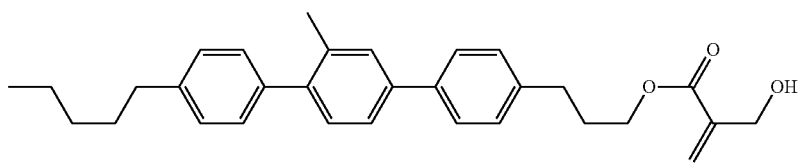 |
| 1-5-88 | 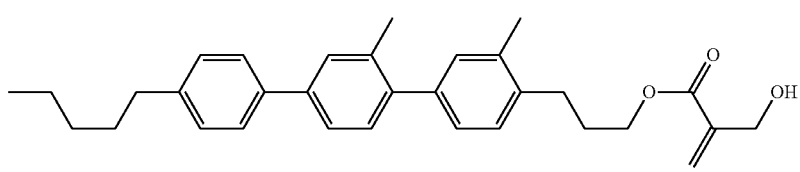 [SMILES: C=C(CO)C(=O)OCCCc1ccc(-c2ccc(-c3ccc(CCCCC)cc3)cc2C)cc1C] |
| 1-5-89 | 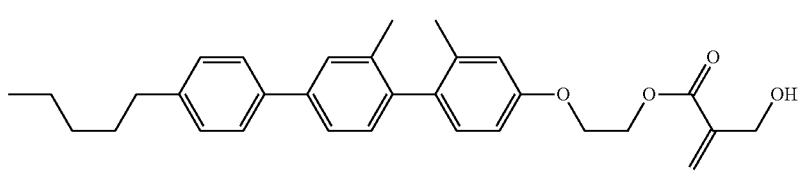 [SMILES: C=C(CO)C(=O)OCCOc1ccc(-c2ccc(-c3ccc(CCCCC)cc3)cc2C)c(C)c1] |

-continued
| No. |  |
|---|---|
| 1-5-90 | 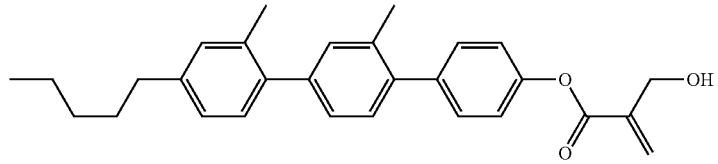 [SMILES: C=C(CO)C(=O)Oc1ccc(-c2ccc(-c3ccc(CCCCC)cc3C)cc2C)cc1] |
| 1-5-91 | 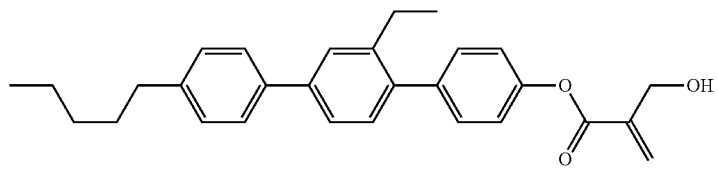 |
| 1-5-92 | 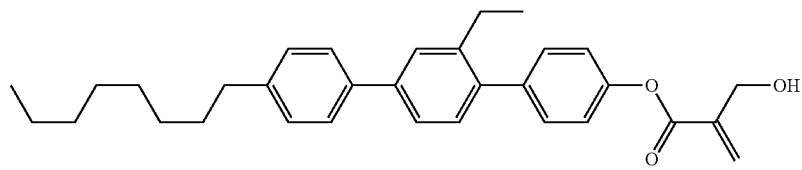 [SMILES: C=C(CO)C(=O)Oc1ccc(-c2ccc(-c3ccc(CCCCCCCC)cc3)cc2CC)cc1] |
| 1-5-93 | 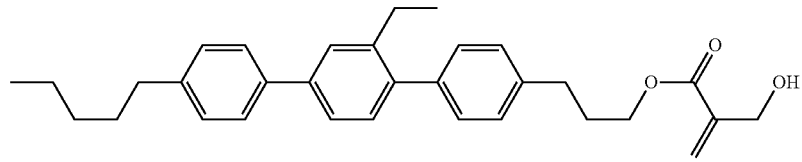 |
| 1-5-94 | 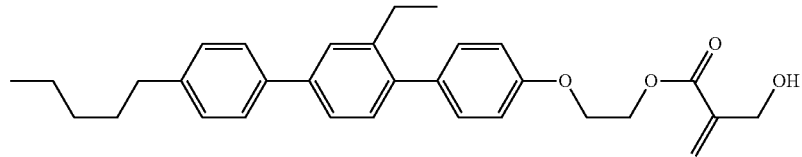 |
| 1-5-95 | 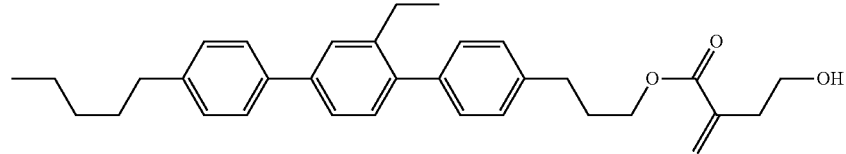 [SMILES: C=C(CCO)C(=O)OCCCc1ccc(-c2ccc(-c3ccc(CCCCC)cc3)cc2CC)cc1] |
| 1-5-96 | 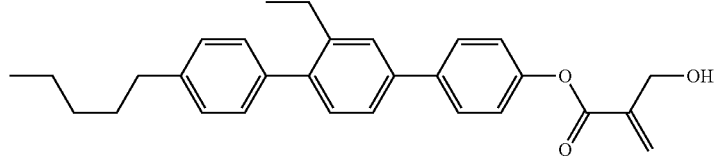 [SMILES: C=C(CO)C(=O)Oc1ccc(-c2ccc(-c3ccc(CCCCC)cc3)c(CC)c2)cc1] |
| 1-5-97 | 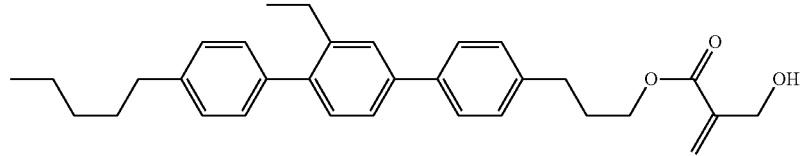 |
| 1-5-98 | 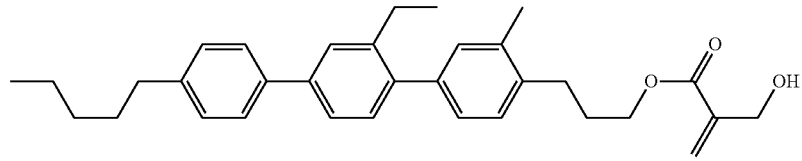 |

-continued
| No. | |
|---|---|
| 1-5-99 | 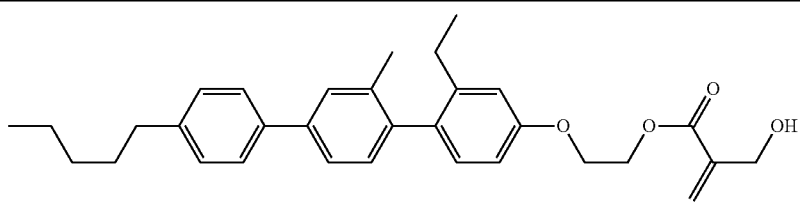 |
| 1-5-100 | 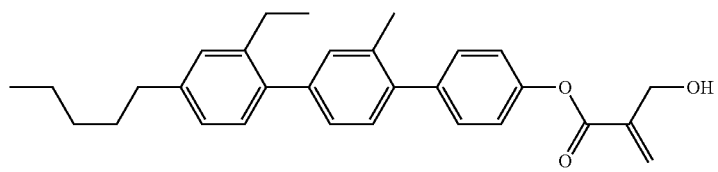 [SMILES: C=C(CO)C(=O)Oc1ccc(-c2ccc(-c3ccc(CCCCC)cc3CC)cc2C)cc1] |
| 1-5-101 | 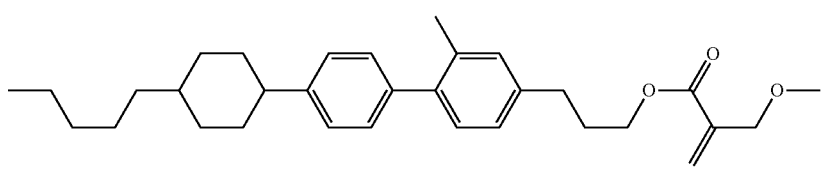 [SMILES: C=C(COC)C(=O)OCCCc1ccc(-c2ccc(C3CCC(CCCCC)CC3)cc2)c(C)c1] |
| 1-5-102 | 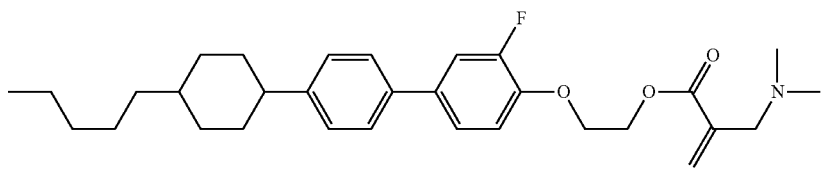 [SMILES: C=C(CN(C)C)C(=O)OCCOc1ccc(-c2ccc(C3CCC(CCCCC)CC3)cc2)cc1F] |
| 1-5-103 | 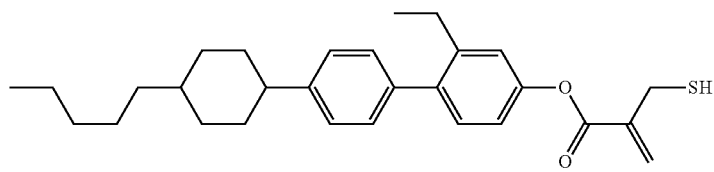 [SMILES: C=C(CS)C(=O)Oc1ccc(-c2ccc(C3CCC(CCCCC)CC3)cc2)c(CC)c1] |
| 1-5-104 | 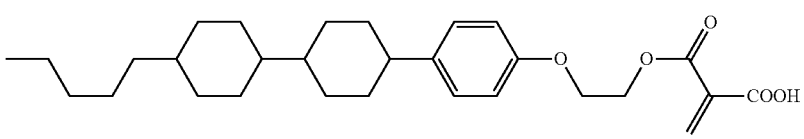 |
| 1-5-105 | 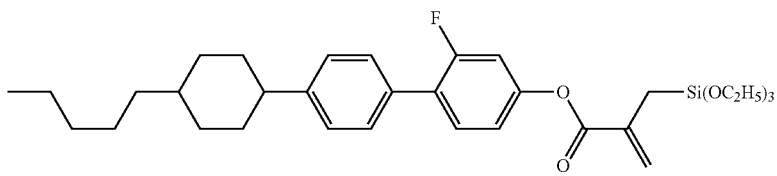 |
| 1-5-106 | 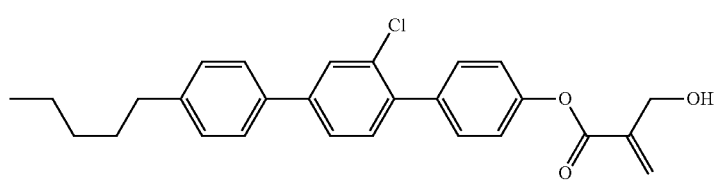 [SMILES: C=C(CO)C(=O)Oc1ccc(-c2ccc(-c3ccc(CCCCC)cc3)cc2Cl)cc1] |
| 1-5-107 | 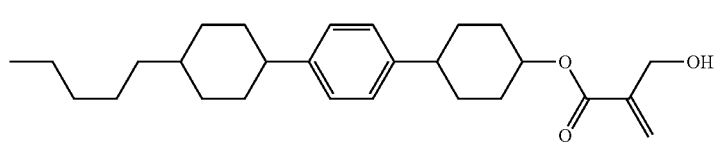 |

| No. | |
|---|---|
| 1-5-108 | 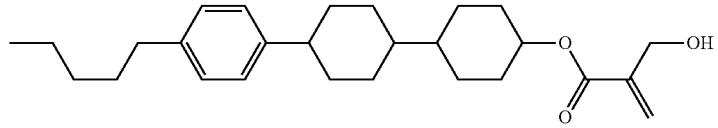 [SMILES: C=C(CO)C(=O)OC1CCC(C2CCC(c3ccc(CCCCC)cc3)CC2)CC1] |
| 1-5-109 | 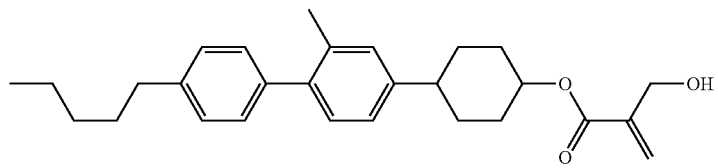 [SMILES: C=C(CO)C(=O)OC1CCC(c2ccc(-c3ccc(CCCCC)cc3)c(C)c2)CC1] |
| 1-5-110 | 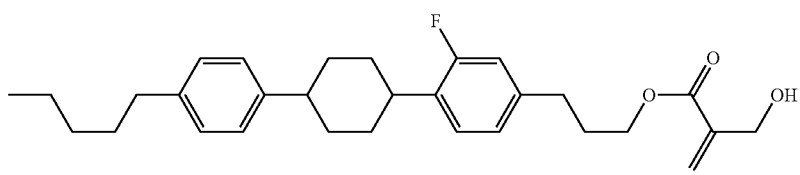 [SMILES: C=C(CO)C(=O)OCCCc1ccc(C2CCC(c3ccc(CCCCC)cc3)CC2)c(F)c1] |
| 1-5-111 | 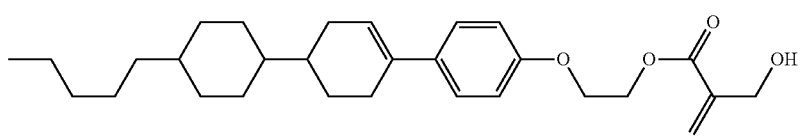 |
| 1-5-112 | 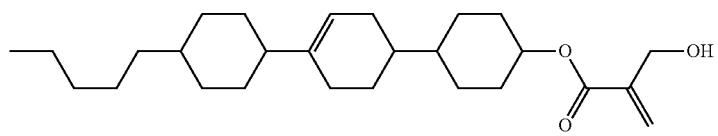 |
| 1-5-113 | 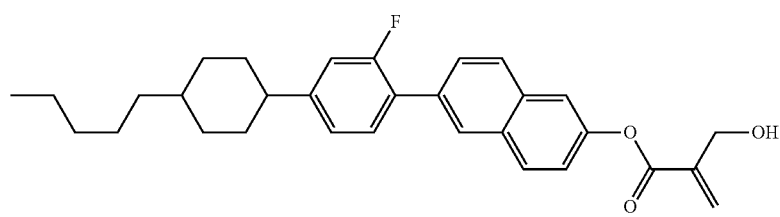 [SMILES: C=C(CO)C(=O)Oc1ccc2cc(-c3ccc(C4CCC(CCCCC)CC4)cc3F)ccc2c1] |
| 1-5-114 | 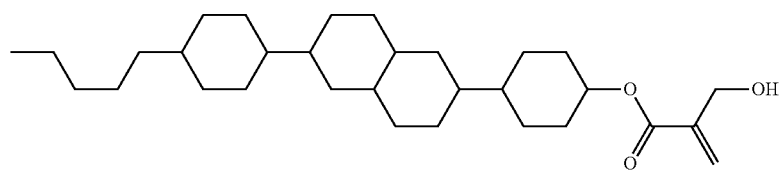 |
| 1-5-115 | 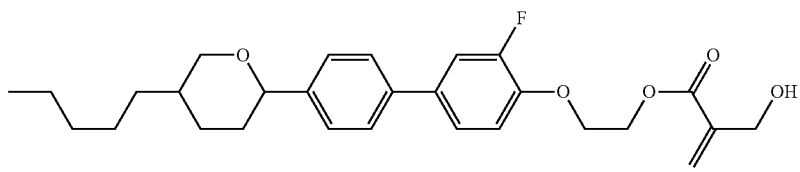 [SMILES: C=C(CO)C(=O)OCCOc1ccc(-c2ccc(C3CCC(CCCCC)CO3)cc2)cc1F] |
| 1-5-116 | 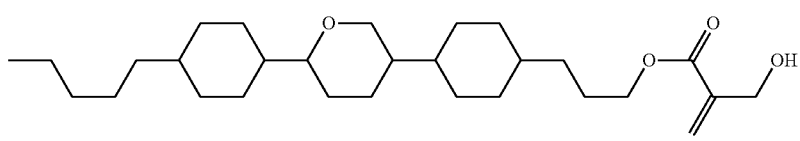 |

| No. | |
|---|---|
| 1-5-117 | 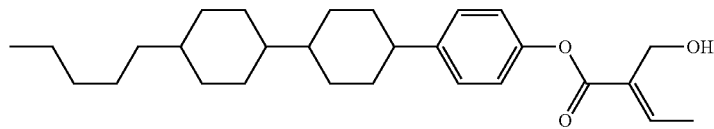 |
| 1-5-118 | 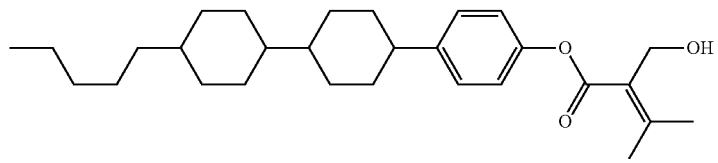 [SMILES: CCCCCC1CCC(C2CCC(c3ccc(OC(=O)C(CO)=C(C)C)cc3)CC2)CC1] |
| 1-5-119 | 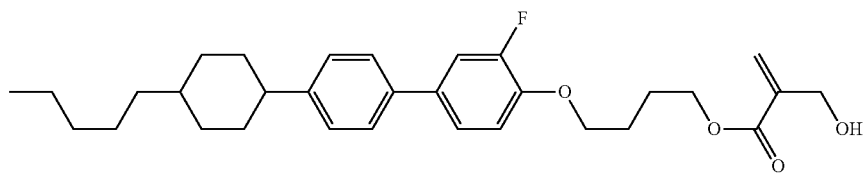 [SMILES: C=C(CO)C(=O)OCCCCOc1ccc(-c2ccc(C3CCC(CCCCC)CC3)cc2)cc1F] |
| 1-5-120 | 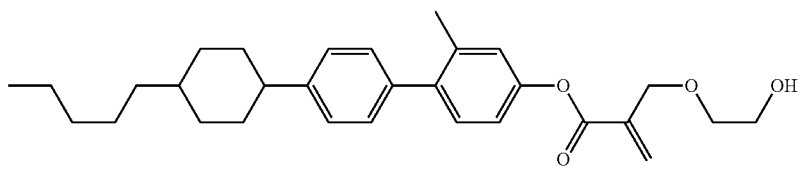 [SMILES: C=C(COCCO)C(=O)Oc1ccc(-c2ccc(C3CCC(CCCCC)CC3)cc2)c(C)c1] |
| 1-5-121 | 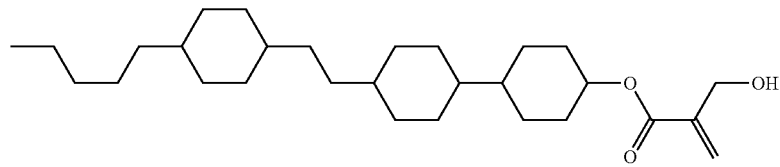 |
| 1-5-122 | 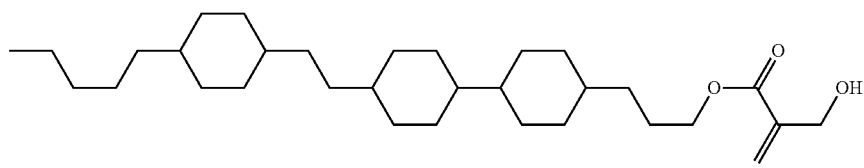 [SMILES: C=C(CO)C(=O)OCCCC1CCC(C2CCC(CCC3CCC(CCCCC)CC3)CC2)CC1] |
| 1-5-123 | 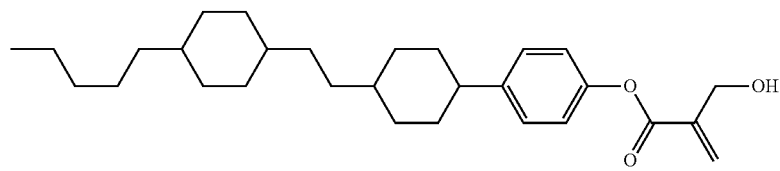 [SMILES: C=C(CO)C(=O)Oc1ccc(C2CCC(CCC3CCC(CCCCC)CC3)CC2)cc1] |
| 1-5-124 | 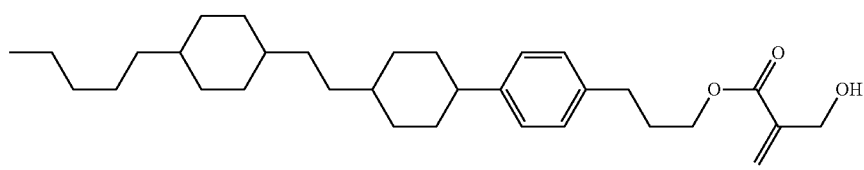 [SMILES: C=C(CO)C(=O)OCCCc1ccc(C2CCC(CCC3CCC(CCCCC)CC3)CC2)cc1] |
| 1-5-125 | 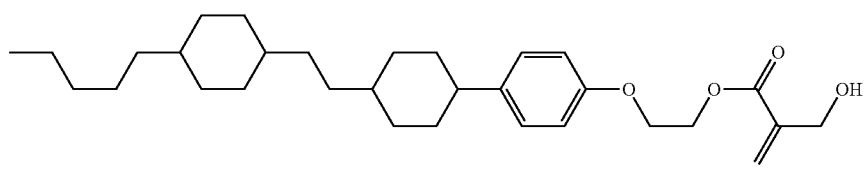 |

-continued
| No. | |
|---|---|
| 1-5-126 | 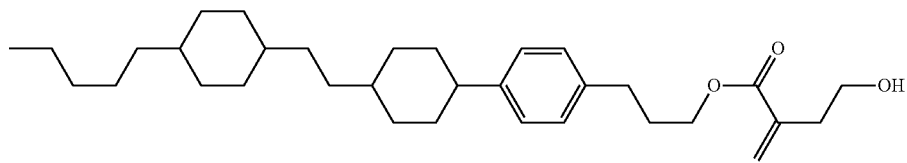 [SMILES: C=C(CCO)C(=O)OCCCc1ccc(C2CCC(CCC3CCC(CCCCC)CC3)CC2)cc1] |
| 1-5-127 | 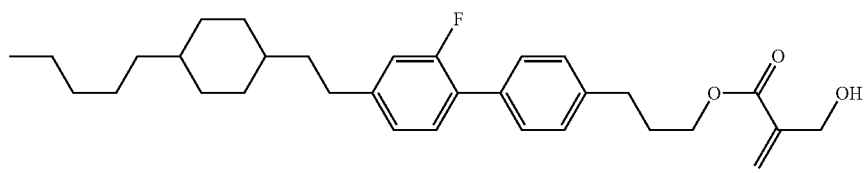 [SMILES: C=C(CO)C(=O)OCCCc1ccc(-c2ccc(CCC3CCC(CCCCC)CC3)cc2F)cc1] |
| 1-5-128 | 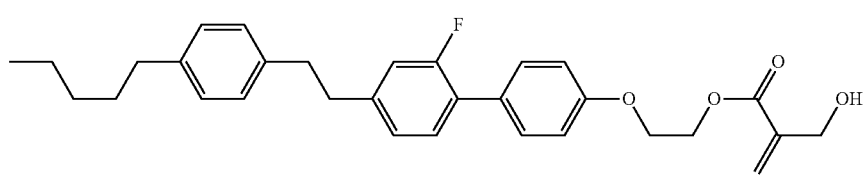 |
| 1-5-129 | 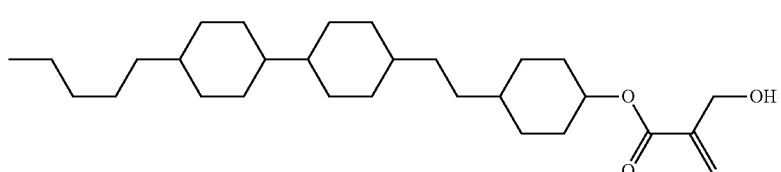 |
| 1-5-130 | 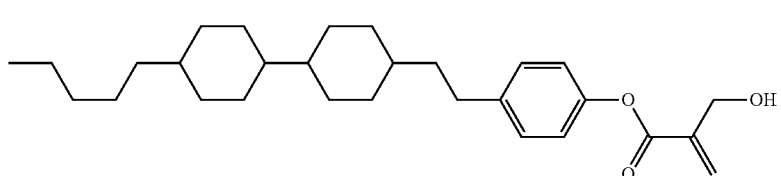 |
| 1-5-131 | 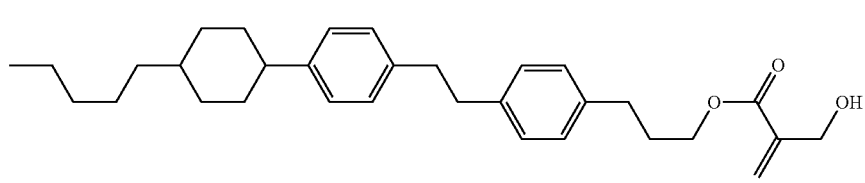 [SMILES: C=C(CO)C(=O)OCCCc1ccc(CCc2ccc(C3CCC(CCCCC)CC3)cc2)cc1] |
| 1-5-132 | 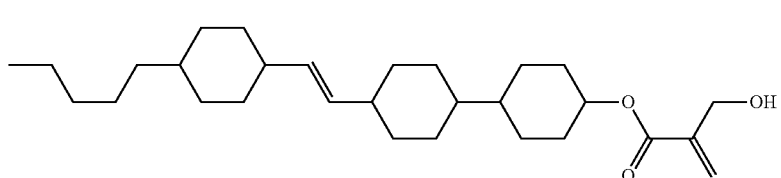 |
| 1-5-133 | 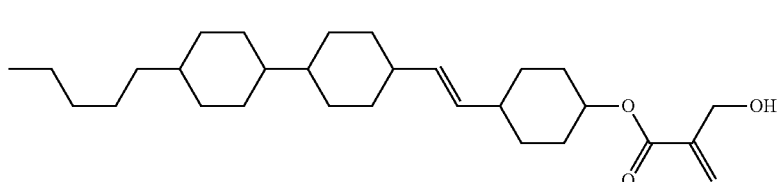 |
| 1-5-134 | 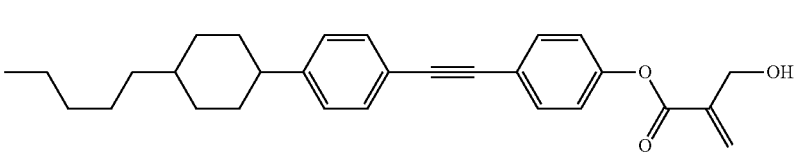 [SMILES: C=C(CO)C(=O)Oc1ccc(C#Cc2ccc(C3CCC(CCCCC)CC3)cc2)cc1] |

-continued
| No. | |
|---|---|
| 1-5-135 | 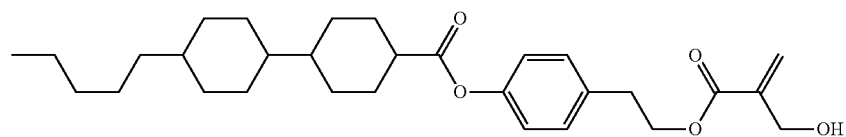 [SMILES: C=C(CO)C(=O)OCCc1ccc(OC(=O)C2CCC(C3CCC(CCCCC)CC3)CC2)cc1] |
| 1-5-136 | 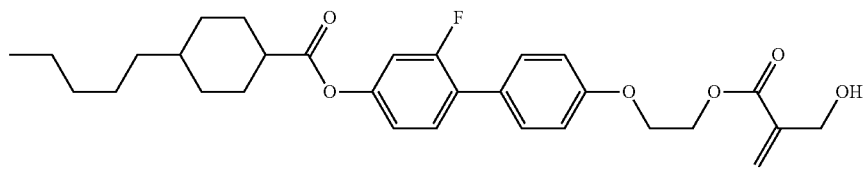 [SMILES: C=C(CO)C(=O)OCCOc1ccc(-c2ccc(OC(=O)C3CCC(CCCCC)CC3)cc2F)cc1] |
| 1-5-137 | 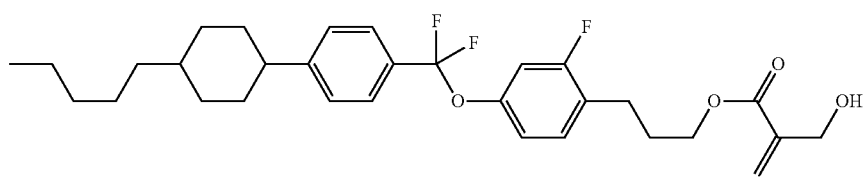 [SMILES: C=C(CO)C(=O)OCCCc1ccc(OC(F)(F)c2ccc(C3CCC(CCCCC)CC3)cc2)cc1F] |
| 1-5-138 | 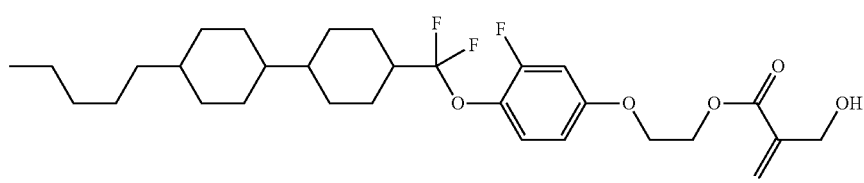 [SMILES: C=C(CO)C(=O)OCCOc1ccc(OC(F)(F)C2CCC(C3CCC(CCCCC)CC3)CC2)c(F)c1] |
| 1-5-139 | 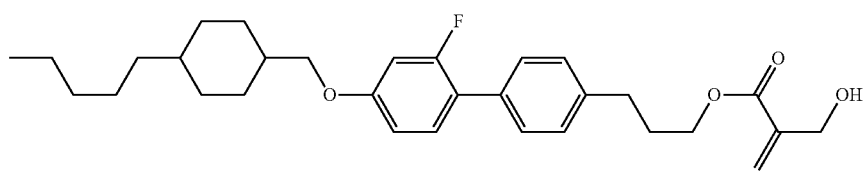 [SMILES: C=C(CO)C(=O)OCCCc1ccc(-c2ccc(OCC3CCC(CCCCC)CC3)cc2F)cc1] |
| 1-5-140 | 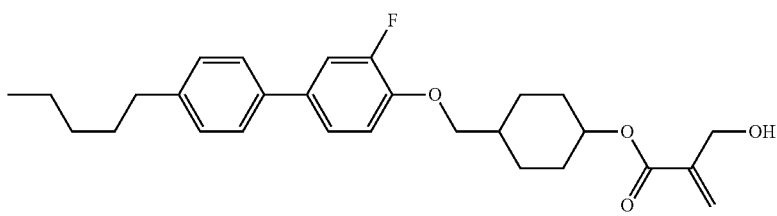 [SMILES: C=C(CO)C(=O)OC1CCC(COc2ccc(-c3ccc(CCCCC)cc3)cc2F)CC1] |
| 1-6-1 | 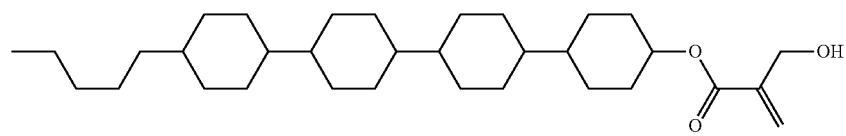 |
| 1-6-2 | 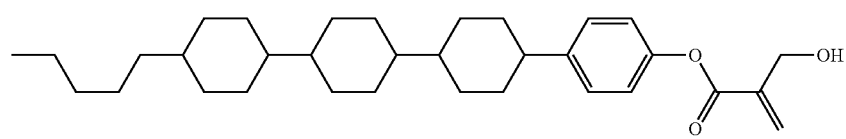 |
| 1-6-3 | 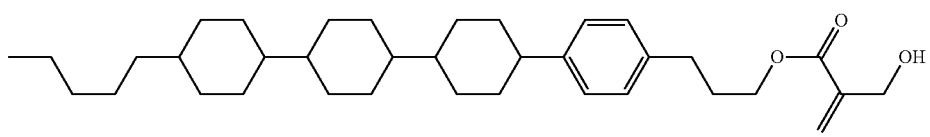 |

-continued
| No. |
|---|
| 1-6-4 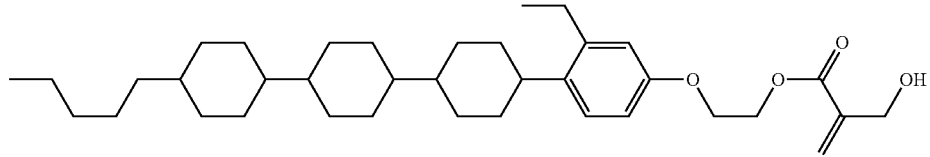 [SMILES: C=C(CO)C(=O)OCCOc1ccc(C2CCC(C3CCC(C4CCC(CCCCC)CC4)CC3)CC2)c(CC)c1] |
| 1-6-5 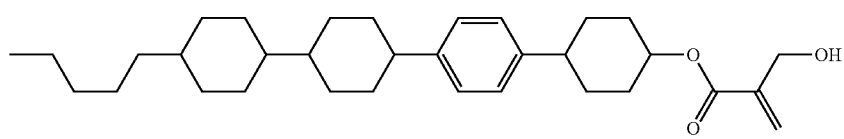 |
| 1-6-6 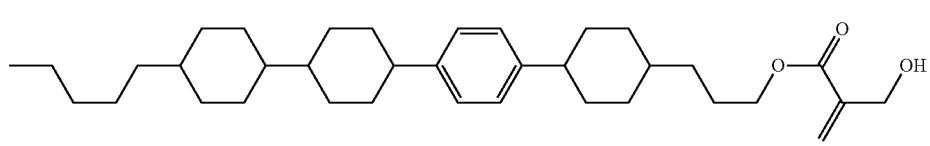 [SMILES: C=C(CO)C(=O)OCCCC1CCC(c2ccc(C3CCC(C4CCC(CCCCC)CC4)CC3)cc2)CC1] |
| 1-6-7 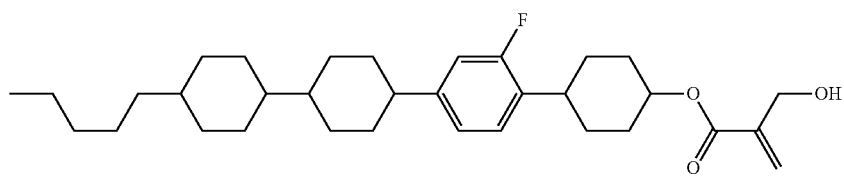 |
| 1-6-8 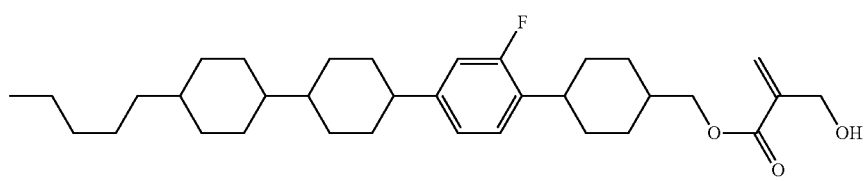 [SMILES: C=C(CO)C(=O)OCC1CCC(c2ccc(C3CCC(C4CCC(CCCCC)CC4)CC3)cc2F)CC1] |
| 1-6-9 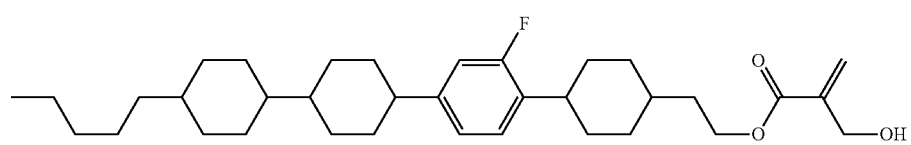 [SMILES: C=C(CO)C(=O)OCCC1CCC(c2ccc(C3CCC(C4CCC(CCCCC)CC4)CC3)cc2F)CC1] |
| 1-6-10 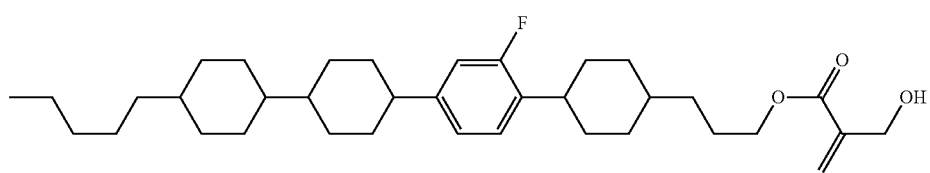 [SMILES: C=C(CO)C(=O)OCCCC1CCC(c2ccc(C3CCC(C4CCC(CCCCC)CC4)CC3)cc2F)CC1] |
| 1-6-11 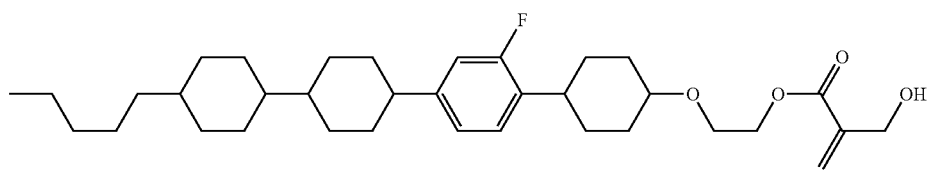 [SMILES: C=C(CO)C(=O)OCCOC1CCC(c2ccc(C3CCC(C4CCC(CCCCC)CC4)CC3)cc2F)CC1] |
| 1-6-12 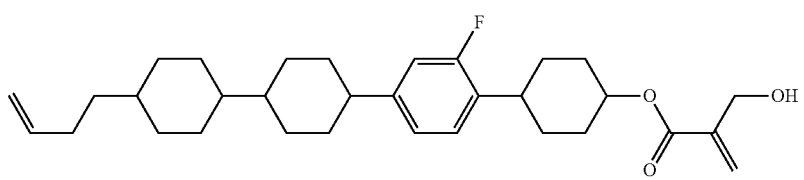 [SMILES: C=CCCC1CCC(C2CCC(c3ccc(C4CCC(OC(=O)C(=C)CO)CC4)c(F)c3)CC2)CC1] |

|No.|
|---|
| 1-6-13 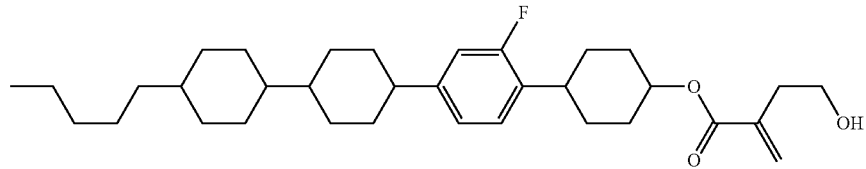 [SMILES: C=C(CCO)C(=O)OC1CCC(c2ccc(C3CCC(C4CCC(CCCCC)CC4)CC3)cc2F)CC1] |
| 1-6-14 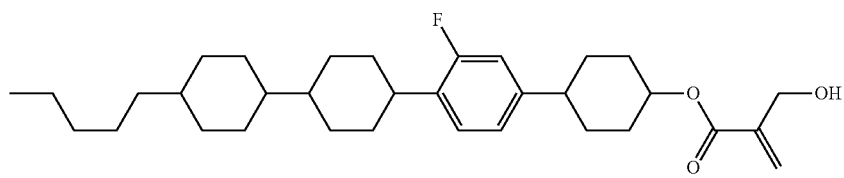 [SMILES: C=C(CO)C(=O)OC1CCC(c2ccc(C3CCC(C4CCC(CCCCC)CC4)CC3)c(F)c2)CC1] |
| 1-6-15 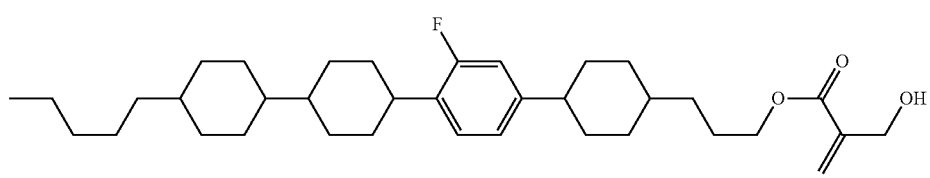 [SMILES: C=C(CO)C(=O)OCCCC1CCC(c2ccc(C3CCC(C4CCC(CCCCC)CC4)CC3)c(F)c2)CC1] |
| 1-6-16 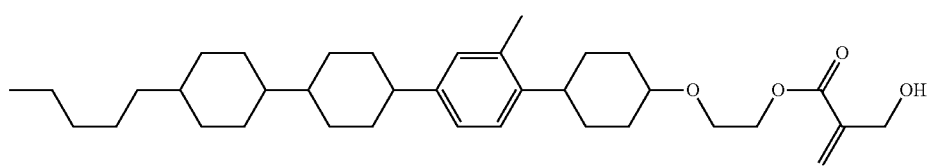 [SMILES: C=C(CO)C(=O)OCCOC1CCC(c2ccc(C3CCC(C4CCC(CCCCC)CC4)CC3)cc2C)CC1] |
| 1-6-17 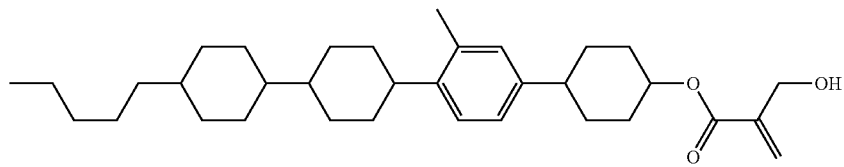 [SMILES: C=C(CO)C(=O)OC1CCC(c2ccc(C3CCC(C4CCC(CCCCC)CC4)CC3)c(C)c2)CC1] |
| 1-6-18 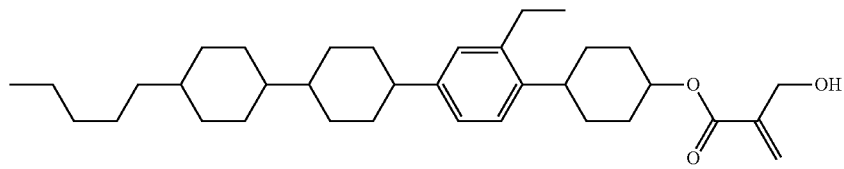 |
| 1-6-19 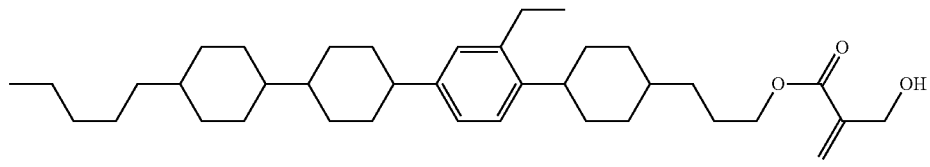 |
| 1-6-20 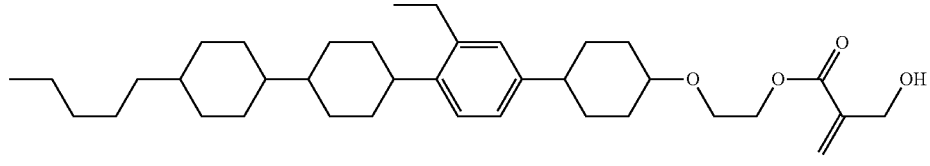 |
| 1-6-21 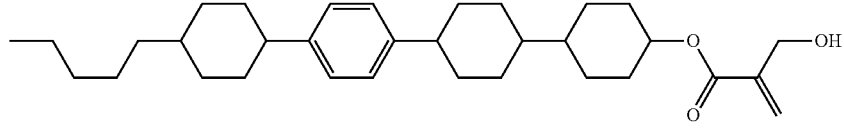 [SMILES: C=C(CO)C(=O)OC1CCC(C2CCC(c3ccc(C4CCC(CCCCC)CC4)cc3)CC2)CC1] |

-continued
| No. | |
|---|---|
| 1-6-22 | 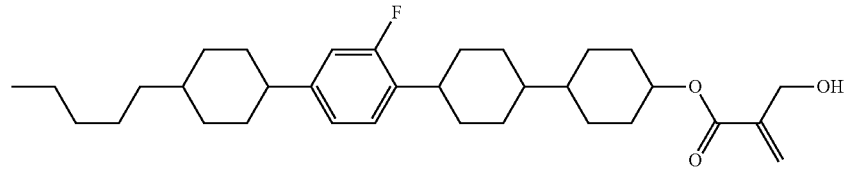 [SMILES: C=C(CO)C(=O)OC1CCC(C2CCC(c3ccc(C4CCC(CCCCC)CC4)cc3F)CC2)CC1] |
| 1-6-23 | 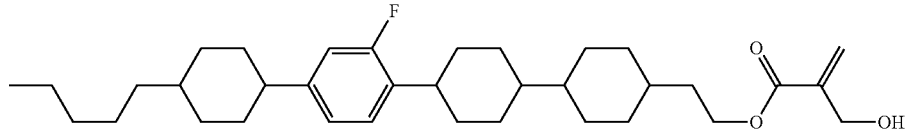 [SMILES: C=C(CO)C(=O)OCCC1CCC(C2CCC(c3ccc(C4CCC(CCCCC)CC4)cc3F)CC2)CC1] |
| 1-6-24 | 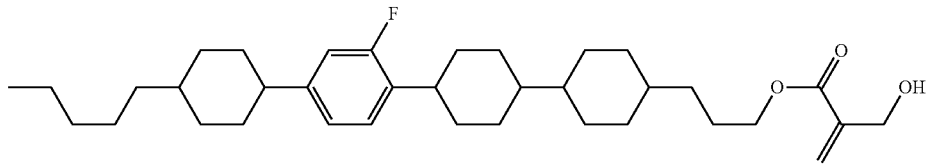 [SMILES: C=C(CO)C(=O)OCCCC1CCC(C2CCC(c3ccc(C4CCC(CCCCC)CC4)cc3F)CC2)CC1] |
| 1-6-25 | 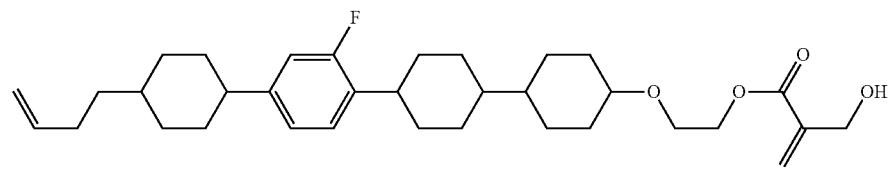 [SMILES: C=CCCC1CCC(c2ccc(C3CCC(C4CCC(OCCOC(=O)C(=C)CO)CC4)CC3)c(F)c2)CC1] |
| 1-6-26 | 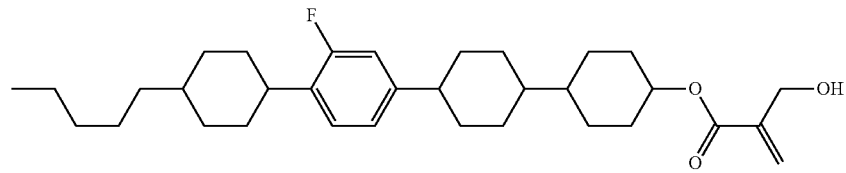 [SMILES: C=C(CO)C(=O)OC1CCC(C2CCC(c3ccc(C4CCC(CCCCC)CC4)c(F)c3)CC2)CC1] |
| 1-6-27 | 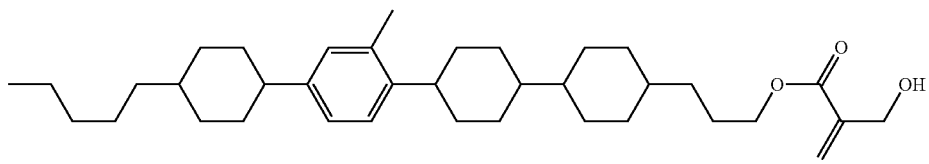 [SMILES: C=C(CO)C(=O)OCCCC1CCC(C2CCC(c3ccc(C4CCC(CCCCC)CC4)cc3C)CC2)CC1] |
| 1-6-28 | 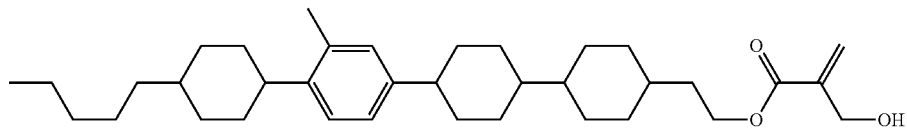 [SMILES: C=C(CO)C(=O)OCCC1CCC(C2CCC(c3ccc(C4CCC(CCCCC)CC4)c(C)c3)CC2)CC1] |
| 1-6-29 | 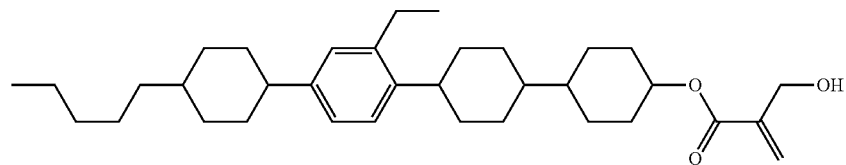 [SMILES: C=C(CO)C(=O)OC1CCC(C2CCC(c3ccc(C4CCC(CCCCC)CC4)cc3CC)CC2)CC1] |
| 1-6-30 | 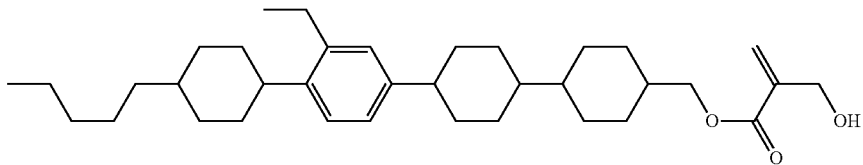 [SMILES: C=C(CO)C(=O)OCC1CCC(C2CCC(c3ccc(C4CCC(CCCCC)CC4)c(CC)c3)CC2)CC1] |

-continued
| No. | |
|---|---|
| 1-6-31 | 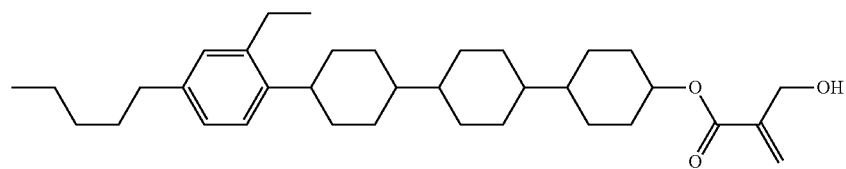 [SMILES: C=C(CO)C(=O)OC1CCC(C2CCC(C3CCC(c4ccc(CCCCC)cc4CC)CC3)CC2)CC1] |
| 1-6-32 | 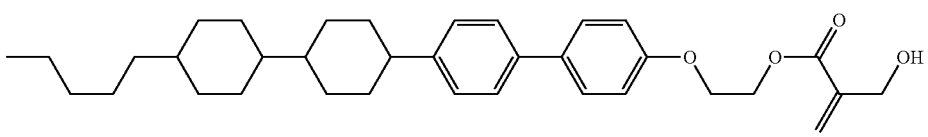 |
| 1-6-33 | 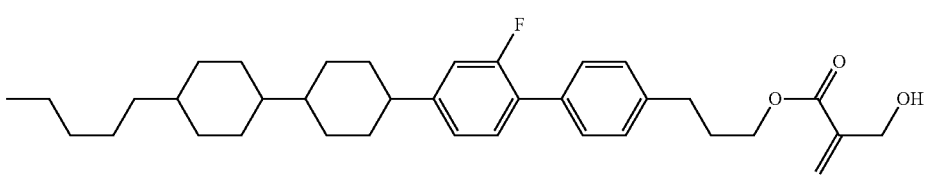 |
| 1-6-34 | 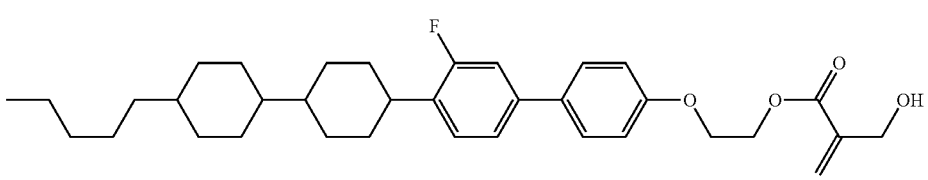 [SMILES: C=C(CO)C(=O)OCCOc1ccc(-c2ccc(C3CCC(C4CCC(CCCCC)CC4)CC3)c(F)c2)cc1] |
| 1-6-35 | 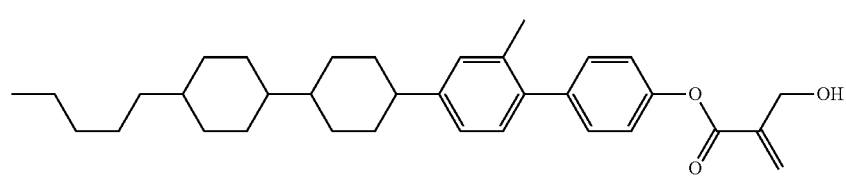 [SMILES: C=C(CO)C(=O)Oc1ccc(-c2ccc(C3CCC(C4CCC(CCCCC)CC4)CC3)cc2C)cc1] |
| 1-6-36 | 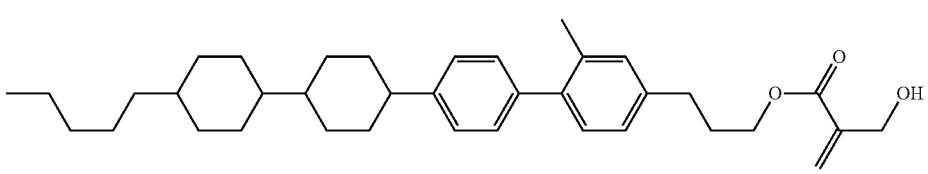 [SMILES: C=C(CO)C(=O)OCCCc1ccc(-c2ccc(C3CCC(C4CCC(CCCCC)CC4)CC3)cc2)c(C)c1] |
| 1-6-37 | 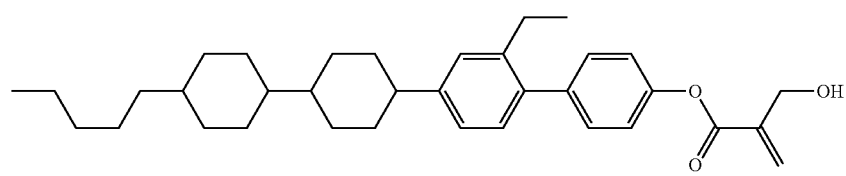 [SMILES: C=C(CO)C(=O)Oc1ccc(-c2ccc(C3CCC(C4CCC(CCCCC)CC4)CC3)cc2CC)cc1] |
| 1-6-38 | 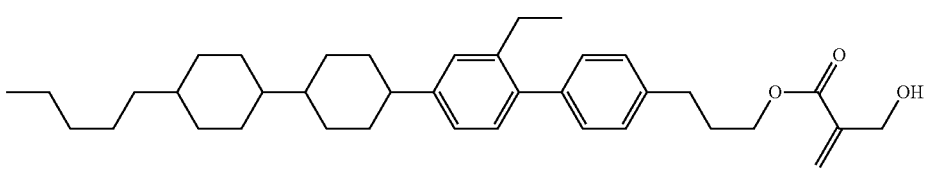 |
| 1-6-39 | 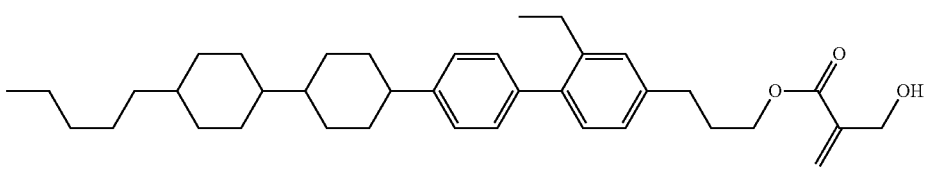 [SMILES: C=C(CO)C(=O)OCCCc1ccc(-c2ccc(C3CCC(C4CCC(CCCCC)CC4)CC3)cc2)c(CC)c1] |

-continued
| No. | |
|---|---|
| 1-6-40 | 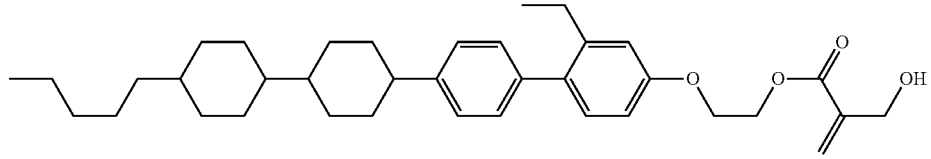 [SMILES: C=C(CO)C(=O)OCCOc1ccc(-c2ccc(C3CCC(C4CCC(CCCCC)CC4)CC3)cc2)c(CC)c1] |
| 1-6-41 | 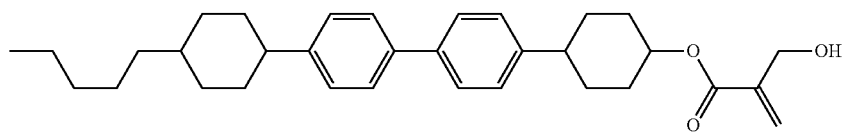 [SMILES: C=C(CO)C(=O)OC1CCC(c2ccc(-c3ccc(C4CCC(CCCCC)CC4)cc3)cc2)CC1] |
| 1-6-42 | 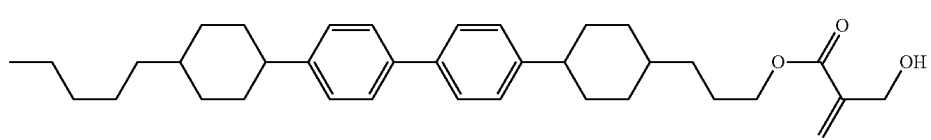 [SMILES: C=C(CO)C(=O)OCCCC1CCC(c2ccc(-c3ccc(C4CCC(CCCCC)CC4)cc3)cc2)CC1] |
| 1-6-43 | 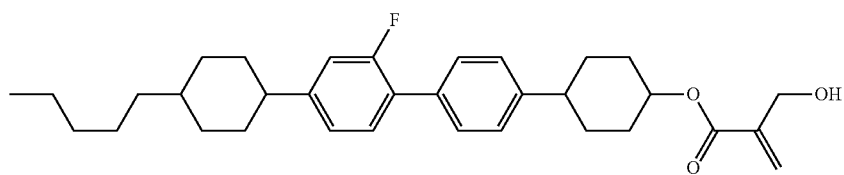 [SMILES: C=C(CO)C(=O)OC1CCC(c2ccc(-c3ccc(C4CCC(CCCCC)CC4)cc3F)cc2)CC1] |
| 1-6-44 | 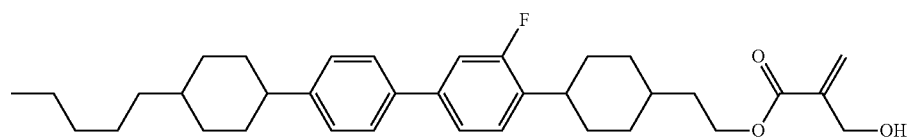 [SMILES: C=C(CO)C(=O)OCCC1CCC(c2ccc(-c3ccc(C4CCC(CCCCC)CC4)cc3)cc2F)CC1] |
| 1-6-45 | 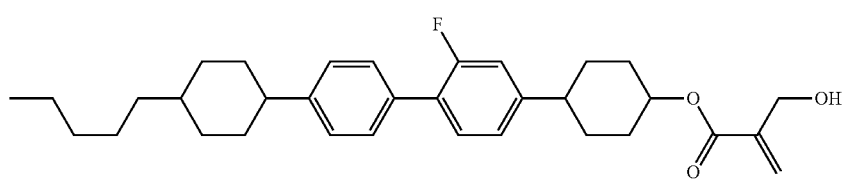 [SMILES: C=C(CO)C(=O)OC1CCC(c2ccc(-c3ccc(C4CCC(CCCCC)CC4)cc3)c(F)c2)CC1] |
| 1-6-46 | 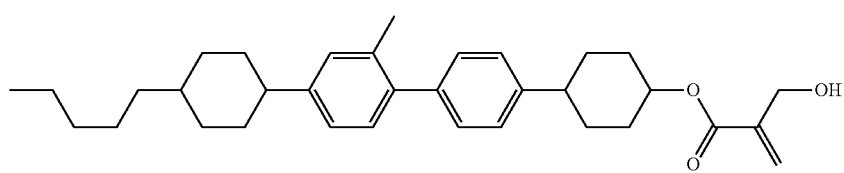 [SMILES: C=C(CO)C(=O)OC1CCC(c2ccc(-c3ccc(C4CCC(CCCCC)CC4)cc3C)cc2)CC1] |
| 1-6-47 | 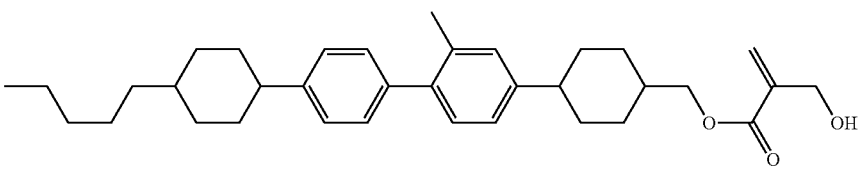 [SMILES: C=C(CO)C(=O)OCC1CCC(c2ccc(-c3ccc(C4CCC(CCCCC)CC4)cc3)c(C)c2)CC1] |
| 1-6-48 | 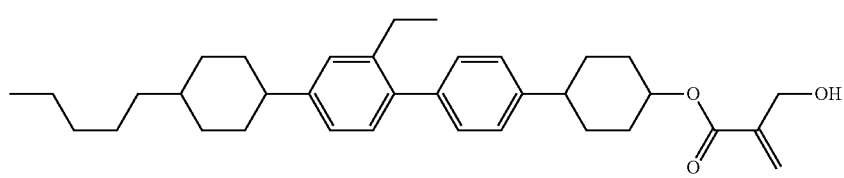 |

-continued
| No. | |
|---|---|
| 1-6-49 | 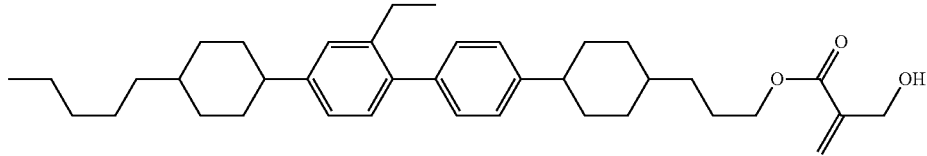 |
| 1-6-50 | 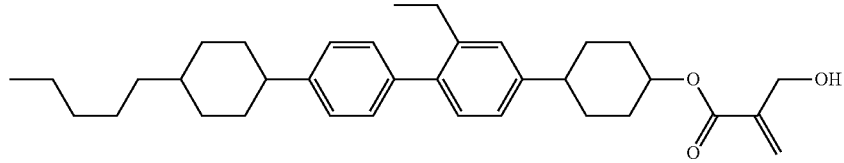 [SMILES: C=C(CO)C(=O)OC1CCC(c2ccc(-c3ccc(C4CCC(CCCCC)CC4)cc3)c(CC)c2)CC1] |
| 1-6-51 | 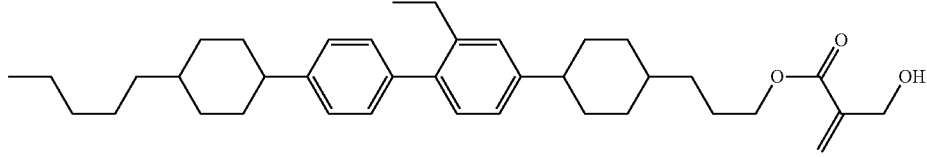 |
| 1-6-52 | 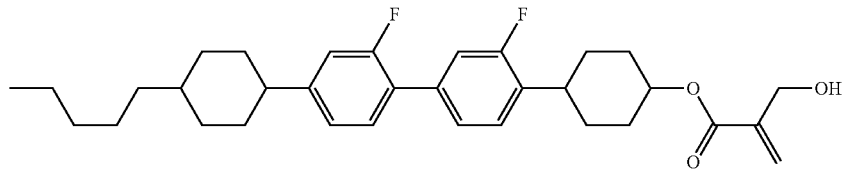 |
| 1-6-53 | 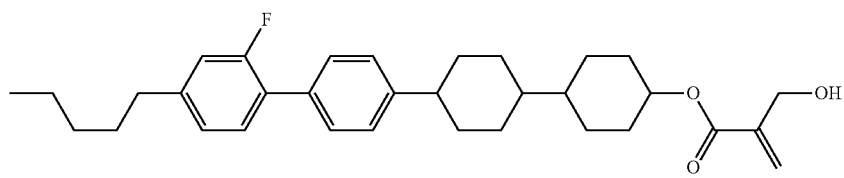 |
| 1-6-54 | 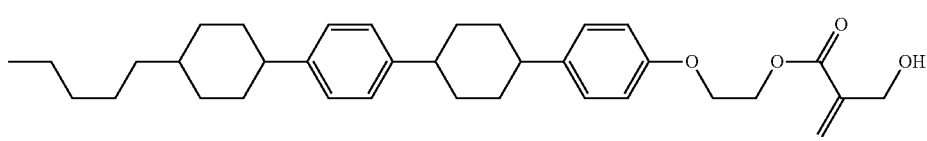 |
| 1-6-55 | 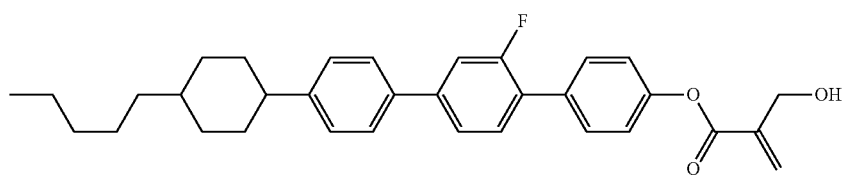 [SMILES: C=C(CO)C(=O)Oc1ccc(-c2ccc(-c3ccc(C4CCC(CCCCC)CC4)cc3)cc2F)cc1] |
| 1-6-56 | 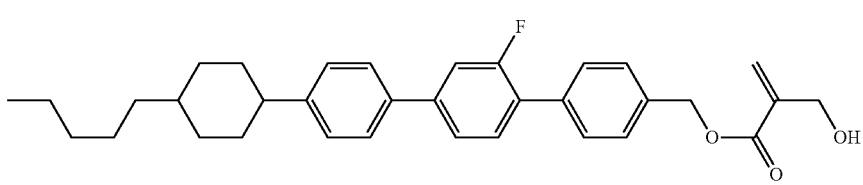 |
| 1-6-57 | 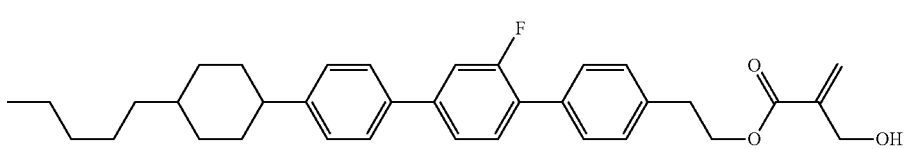 [SMILES: C=C(CO)C(=O)OCCc1ccc(-c2ccc(-c3ccc(C4CCC(CCCCC)CC4)cc3)cc2F)cc1] |

| No. | |
|---|---|
| 1-6-58 | 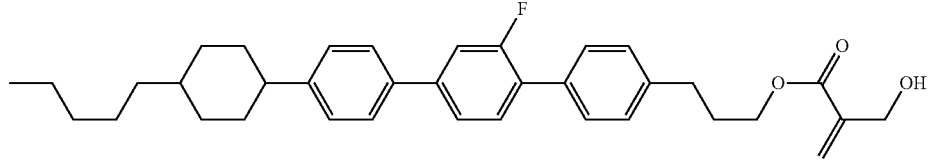 |
| 1-6-59 | 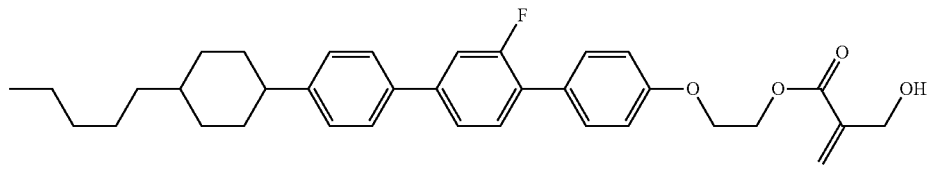 |
| 1-6-60 | 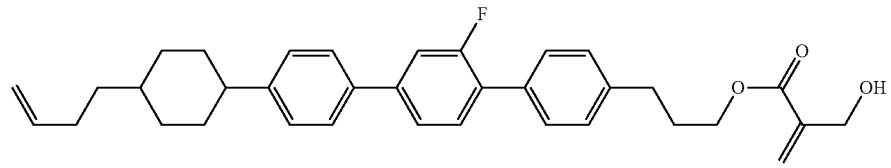 [SMILES: C=CCCC1CCC(c2ccc(-c3ccc(-c4ccc(CCCOC(=O)C(=C)CO)cc4)c(F)c3)cc2)CC1] |
| 1-6-61 | 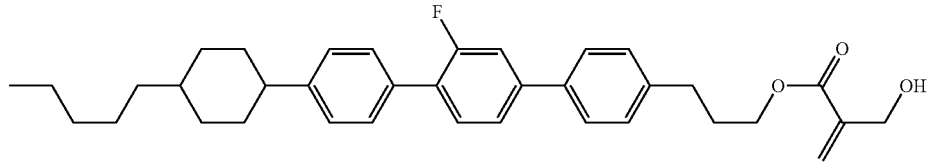 |
| 1-6-62 | 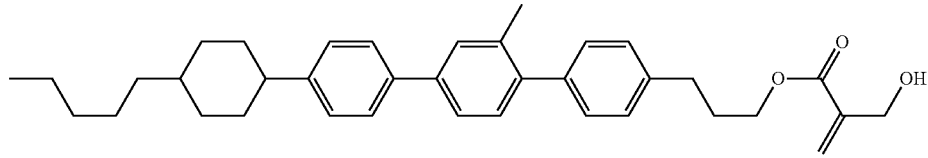 |
| 1-6-63 | 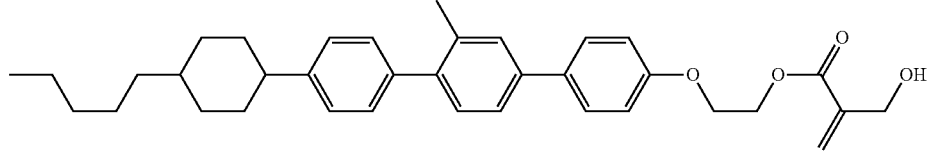 |
| 1-6-64 | 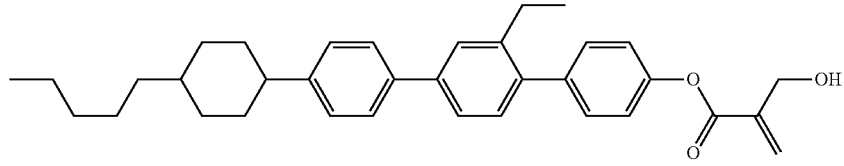 |
| 1-6-65 | 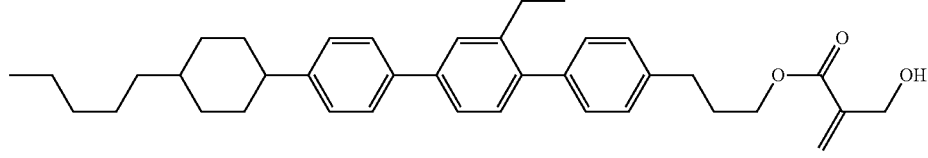 [SMILES: C=C(CO)C(=O)OCCCc1ccc(-c2ccc(-c3ccc(C4CCC(CCCCC)CC4)cc3)cc2CC)cc1] |
| 1-6-66 | 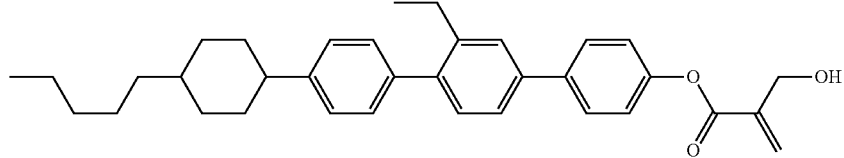 |

-continued
| No. | |
|---|---|
| 1-6-67 | 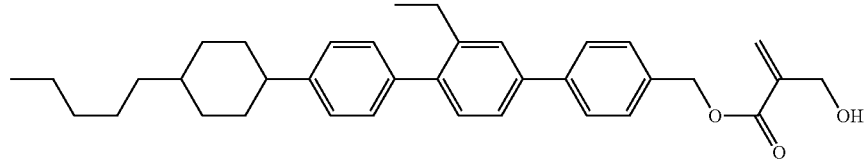 [SMILES: C=C(CO)C(=O)OCc1ccc(-c2ccc(-c3ccc(C4CCC(CCCCC)CC4)cc3)c(CC)c2)cc1] |
| 1-6-68 | 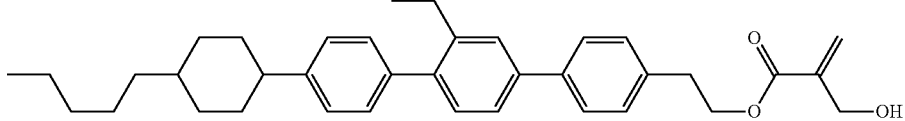 |
| 1-6-69 | 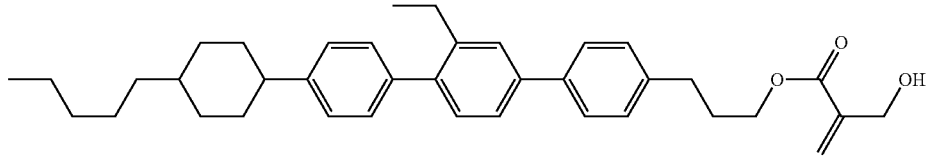 [SMILES: C=C(CO)C(=O)OCCCc1ccc(-c2ccc(-c3ccc(C4CCC(CCCCC)CC4)cc3)c(CC)c2)cc1] |
| 1-6-70 | 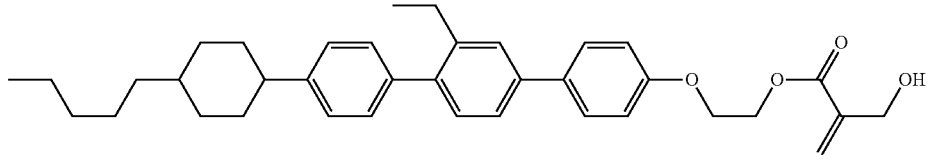 |
| 1-6-71 | 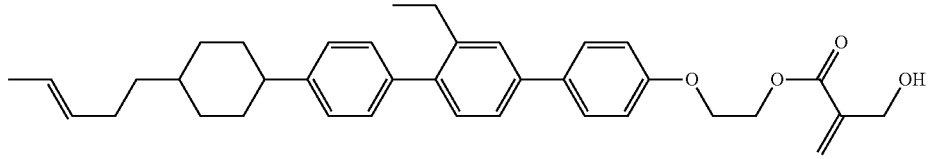 |
| 1-6-72 | 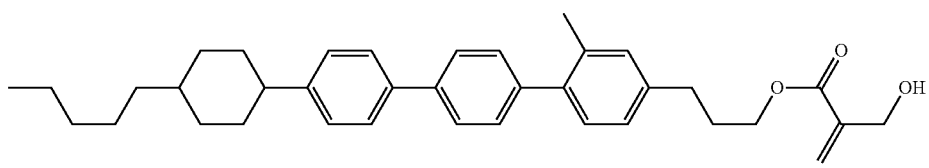 |
| 1-6-73 | 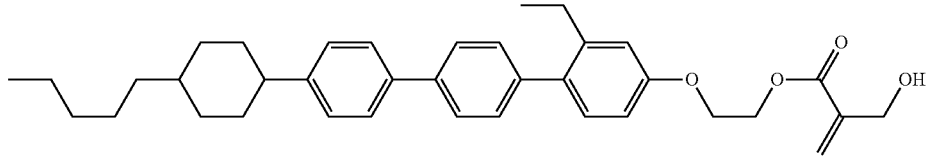 |
| 1-6-74 | 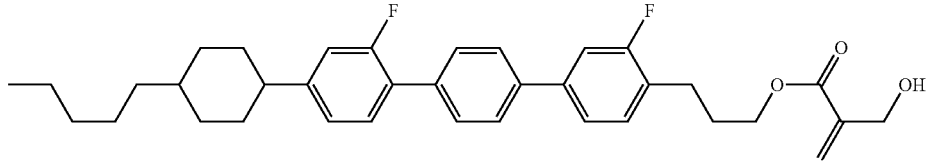 |
| 1-6-75 | 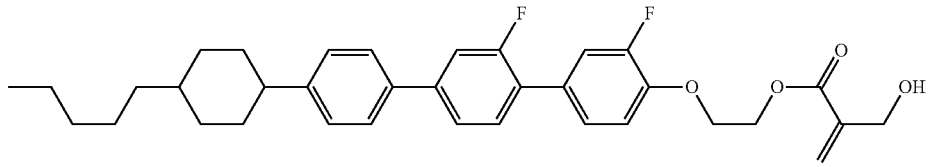 |

-continued
| No. |
|---|
| 1-6-76 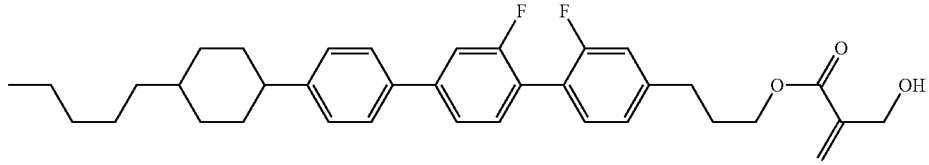 |
| 1-6-77 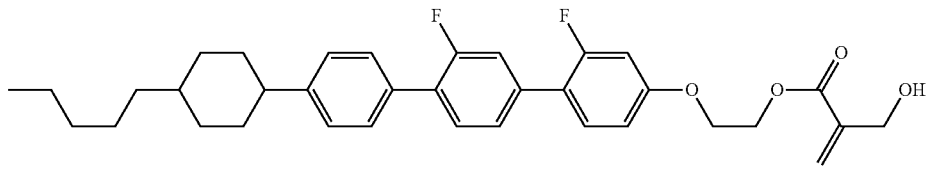 |
| 1-6-78 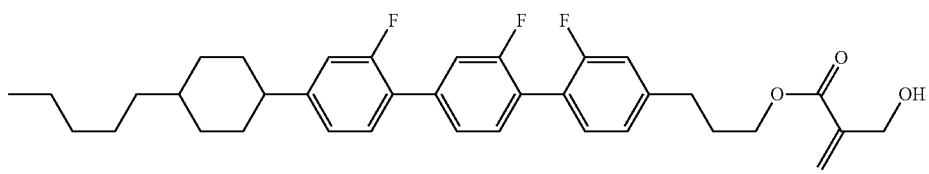 |
| 1-6-79 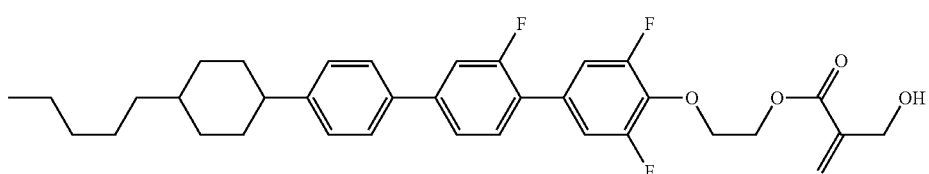 [SMILES: C=C(CO)C(=O)OCCOc1ccc(-c2ccc(-c3ccc(C4CCC(CCCCC)CC4)cc3)cc2F)cc1F] |
| 1-6-80 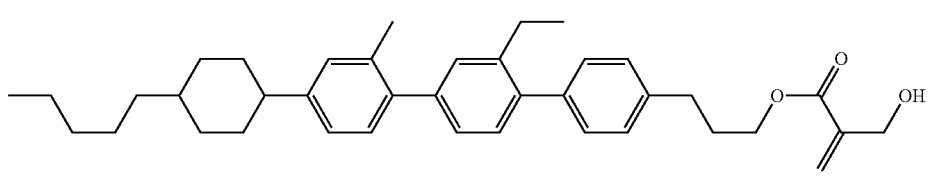 [SMILES: C=C(CO)C(=O)OCCCc1ccc(-c2ccc(-c3ccc(C4CCC(CCCCC)CC4)cc3C)cc2CC)cc1] |
| 1-6-81 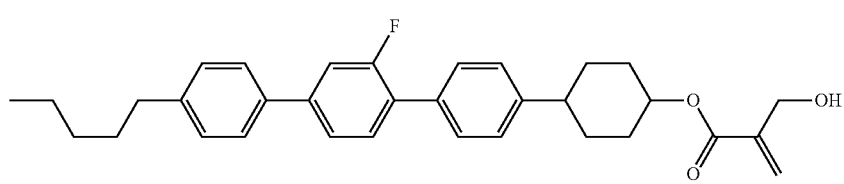 [SMILES: C=C(CO)C(=O)OC1CCC(c2ccc(-c3ccc(-c4ccc(CCCCC)cc4)cc3F)cc2)CC1] |
| 1-6-82 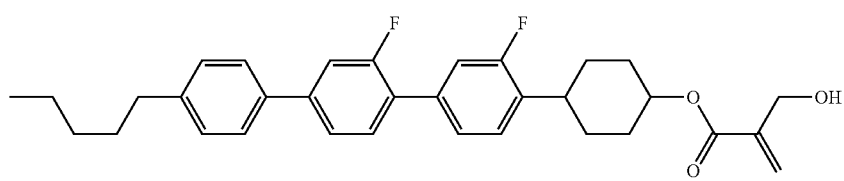 [SMILES: C=C(CO)C(=O)OC1CCC(c2ccc(-c3ccc(-c4ccc(CCCCC)cc4)cc3F)cc2F)CC1] |
| 1-6-83 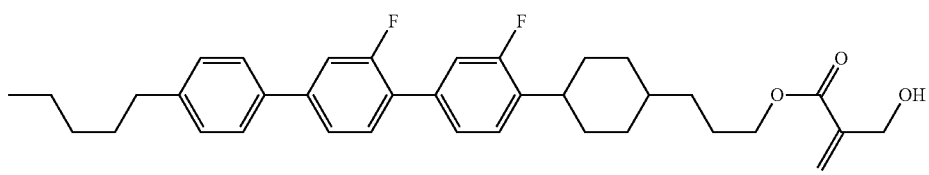 [SMILES: C=C(CO)C(=O)OCCCC1CCC(c2ccc(-c3ccc(-c4ccc(CCCCC)cc4)cc3F)cc2F)CC1] |

-continued
| No. | |
|---|---|
| 1-6-84 | 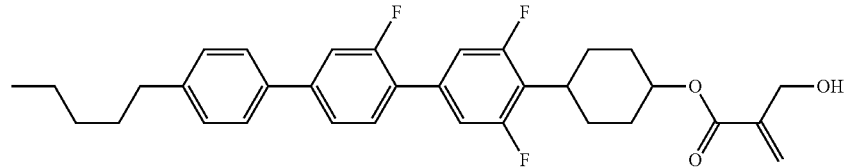 |
| 1-6-85 | 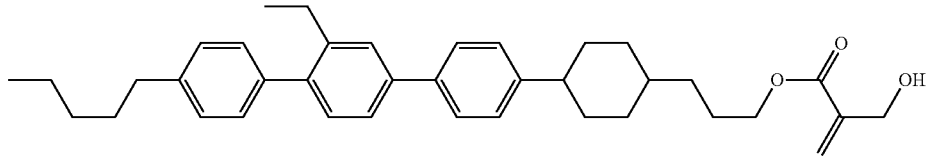 [SMILES: C=C(CO)C(=O)OCCCC1CCC(c2ccc(-c3ccc(-c4ccc(CCCCC)cc4)c(CC)c3)cc2)CC1] |
| 1-6-86 | 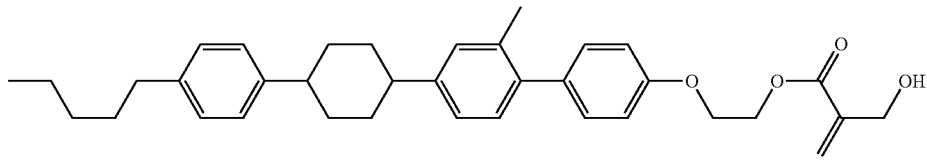 [SMILES: C=C(CO)C(=O)OCCOc1ccc(-c2ccc(C3CCC(c4ccc(CCCCC)cc4)CC3)cc2C)cc1] |
| 1-6-87 | 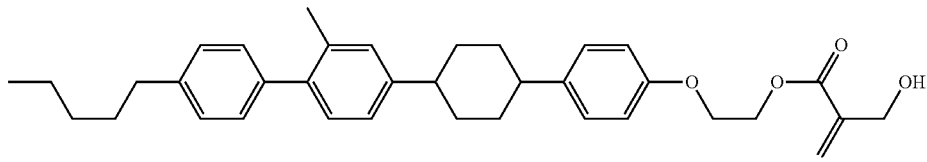 [SMILES: C=C(CO)C(=O)OCCOc1ccc(C2CCC(c3ccc(-c4ccc(CCCCC)cc4)c(C)c3)CC2)cc1] |
| 1-6-88 | 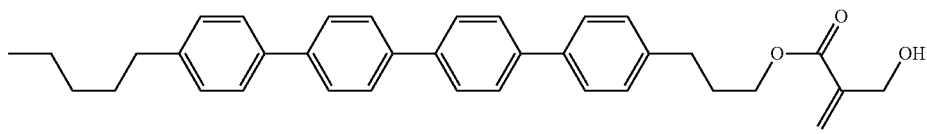 [SMILES: C=C(CO)C(=O)OCCCc1ccc(-c2ccc(-c3ccc(-c4ccc(CCCCC)cc4)cc3)cc2)cc1] |
| 1-6-89 | 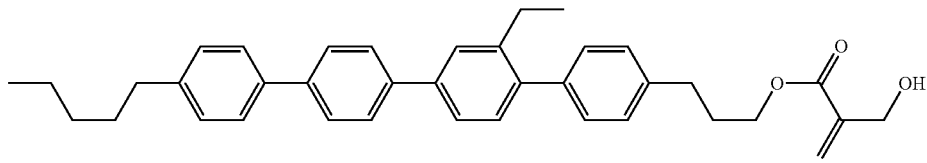 [SMILES: C=C(CO)C(=O)OCCCc1ccc(-c2ccc(-c3ccc(-c4ccc(CCCCC)cc4)cc3)cc2CC)cc1] |
| 1-6-90 | 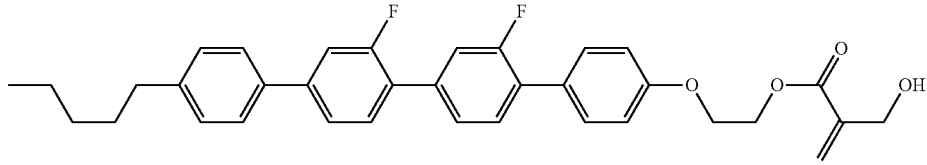 |
| 1-6-91 | 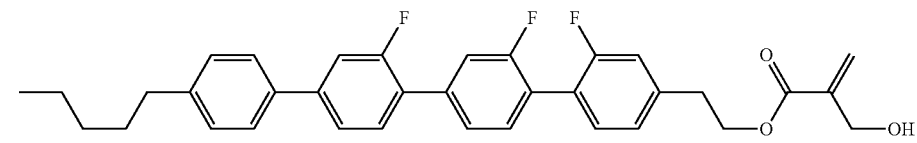 [SMILES: C=C(CO)C(=O)OCCc1ccc(-c2ccc(-c3ccc(-c4ccc(CCCCC)cc4)cc3F)cc2F)c(F)c1] |
| 1-6-92 | 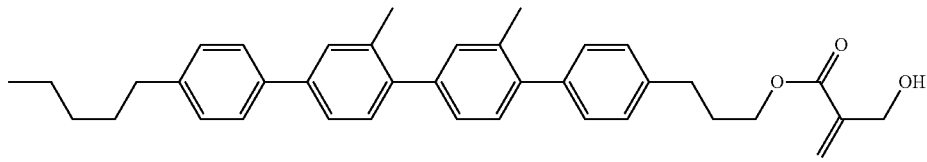 [SMILES: C=C(CO)C(=O)OCCCc1ccc(-c2ccc(-c3ccc(-c4ccc(CCCCC)cc4)cc3C)cc2C)cc1] |

-continued
| No. |
|---|
| 1-6-93 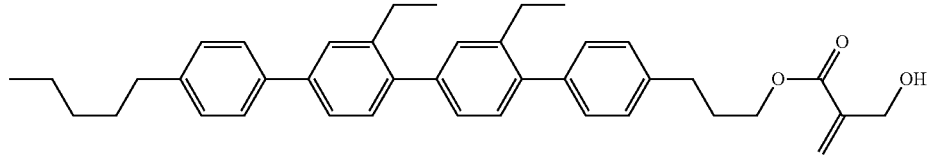 [SMILES: C=C(CO)C(=O)OCCCc1ccc(-c2ccc(-c3ccc(-c4ccc(CCCCC)cc4)cc3CC)cc2CC)cc1] |
| 1-6-94 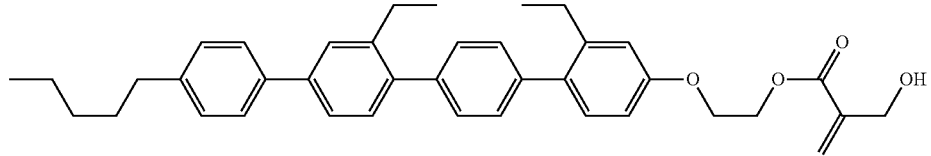 [SMILES: C=C(CO)C(=O)OCCOc1ccc(-c2ccc(-c3ccc(-c4ccc(CCCCC)cc4)cc3CC)cc2)c(CC)c1] |
| 1-6-95 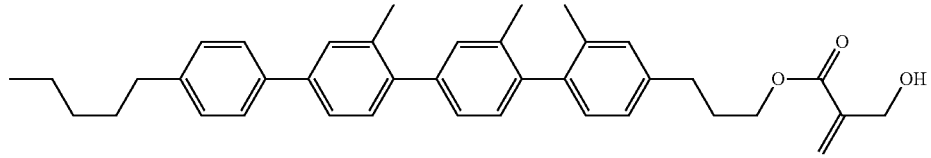 |
| 1-6-96 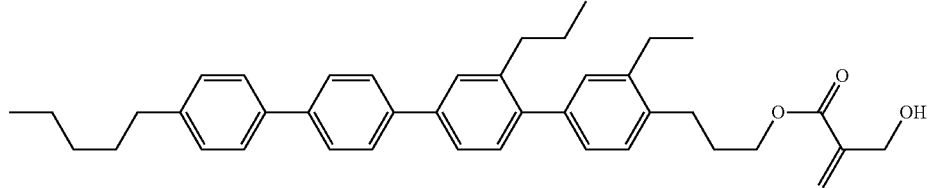 [SMILES: C=C(CO)C(=O)OCCCc1ccc(-c2ccc(-c3ccc(-c4ccc(CCCCC)cc4)cc3)cc2CCC)cc1CC] |
| 1-6-97 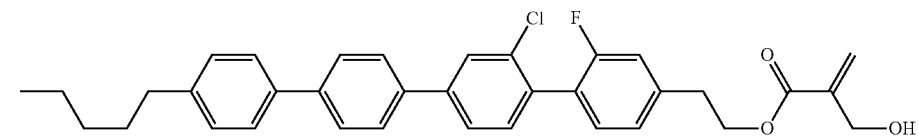 |
| 1-6-98 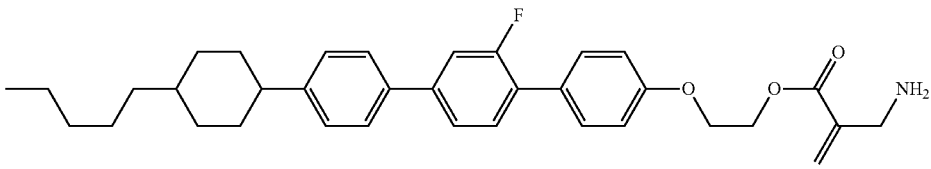 [SMILES: C=C(CN)C(=O)OCCOc1ccc(-c2ccc(-c3ccc(C4CCC(CCCCC)CC4)cc3)cc2F)cc1] |
| 1-6-99 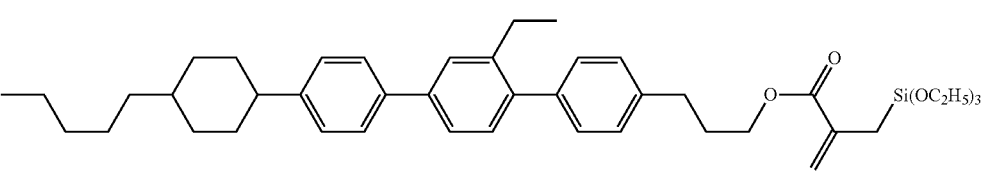 |
| 1-6-100 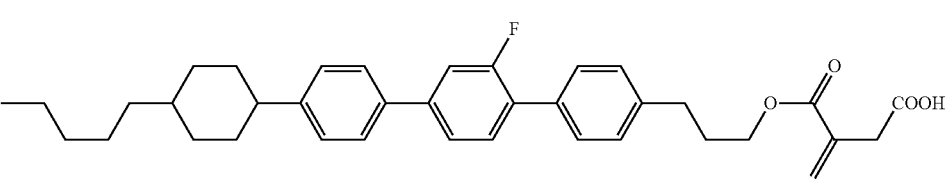 [SMILES: C=C(CC(=O)O)C(=O)OCCCc1ccc(-c2ccc(-c3ccc(C4CCC(CCCCC)CC4)cc3)cc2F)cc1] |
| 1-6-101 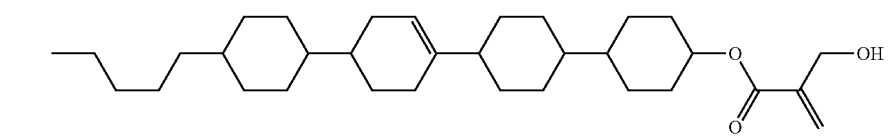 |

-continued
| No. | |
|---|---|
| 1-6-102 | 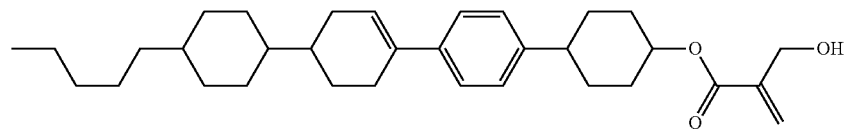 |
| 1-6-103 | 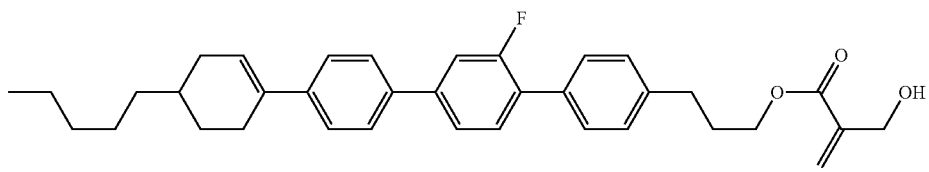 [SMILES: C=C(CO)C(=O)OCCCc1ccc(-c2ccc(-c3ccc(C4=CCC(CCCCC)CC4)cc3)cc2F)cc1] |
| 1-6-104 | 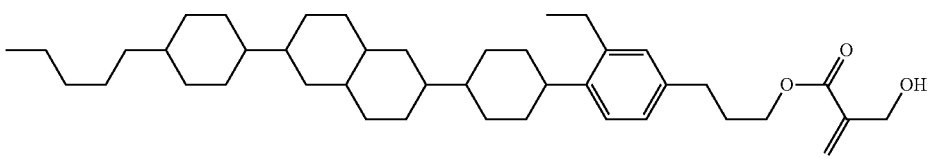 [SMILES: C=C(CO)C(=O)OCCCc1ccc(C2CCC(C3CCC4CC(C5CCC(CCCCC)CC5)CCC4C3)CC2)c(CC)c1] |
| 1-6-105 | 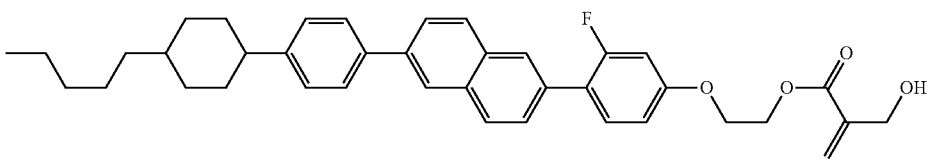 [SMILES: C=C(CO)C(=O)OCCOc1ccc(-c2ccc3cc(-c4ccc(C5CCC(CCCCC)CC5)cc4)ccc3c2)c(F)c1] |
| 1-6-106 | 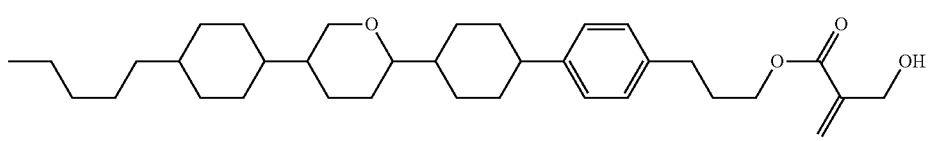 [SMILES: C=C(CO)C(=O)OCCCc1ccc(C2CCC(C3CCC(C4CCC(CCCCC)CC4)CO3)CC2)cc1] |
| 1-6-107 | 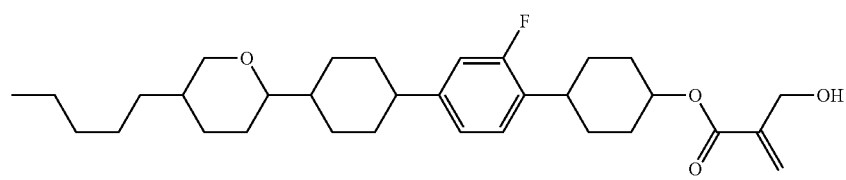 [SMILES: C=C(CO)C(=O)OC1CCC(c2ccc(C3CCC(C4CCC(CCCCC)CO4)CC3)cc2F)CC1] |
| 1-6-108 | 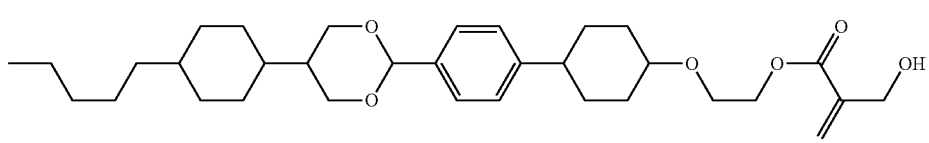 [SMILES: C=C(CO)C(=O)OCCOC1CCC(c2ccc(C3OCC(C4CCC(CCCCC)CC4)CO3)cc2)CC1] |
| 1-6-109 | 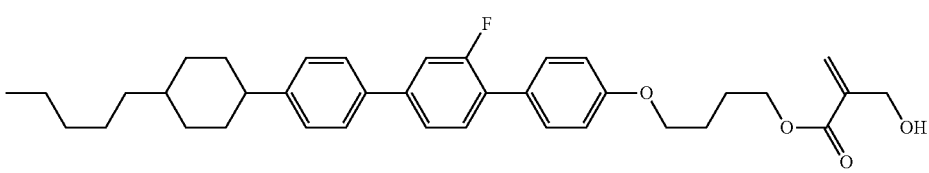 [SMILES: C=C(CO)C(=O)OCCCCOc1ccc(-c2ccc(-c3ccc(C4CCC(CCCCC)CC4)cc3)cc2F)cc1] |
| 1-6-110 | 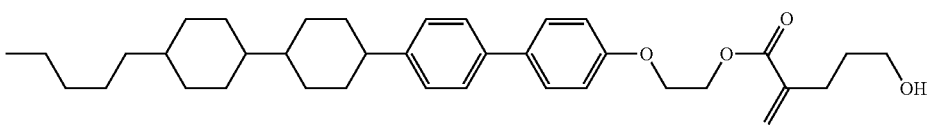 |
| 1-6-111 | 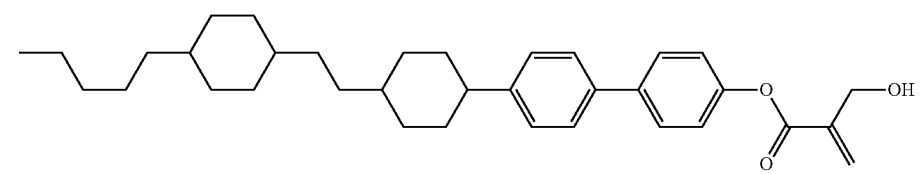 [SMILES: C=C(CO)C(=O)Oc1ccc(-c2ccc(C3CCC(CCC4CCC(CCCCC)CC4)CC3)cc2)cc1] |

-continued
| No. | |
|---|---|
| 1-6-112 | 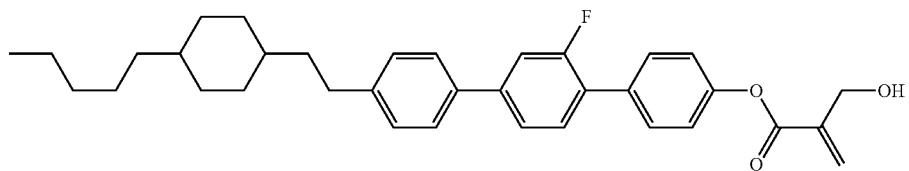 [SMILES: C=C(CO)C(=O)Oc1ccc(-c2ccc(-c3ccc(CCC4CCC(CCCCC)CC4)cc3)cc2F)cc1] |
| 1-6-113 | 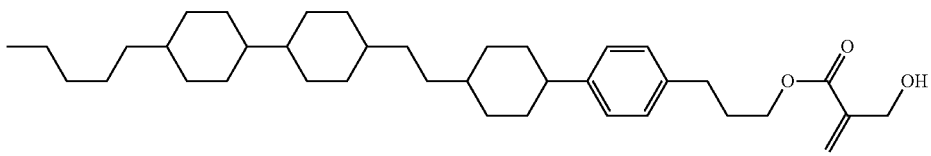 [SMILES: C=C(CO)C(=O)OCCCc1ccc(C2CCC(CCC3CCC(C4CCC(CCCCC)CC4)CC3)CC2)cc1] |
| 1-6-114 | 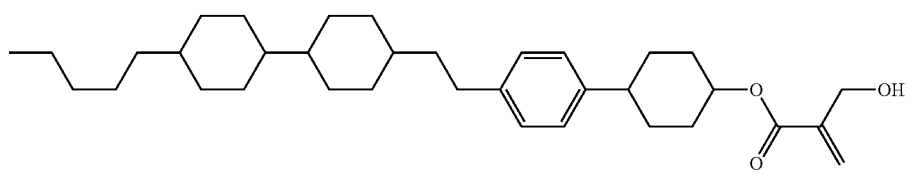 [SMILES: C=C(CO)C(=O)OC1CCC(c2ccc(CCC3CCC(C4CCC(CCCCC)CC4)CC3)cc2)CC1] |
| 1-6-115 | 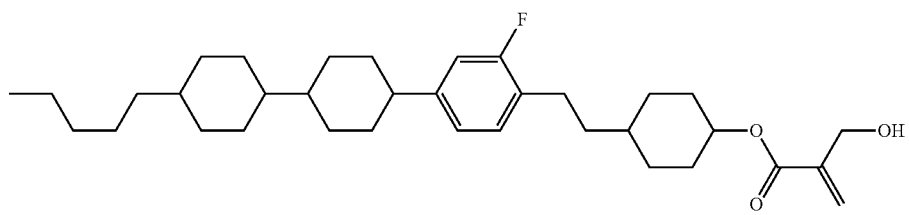 |
| 1-6-116 | 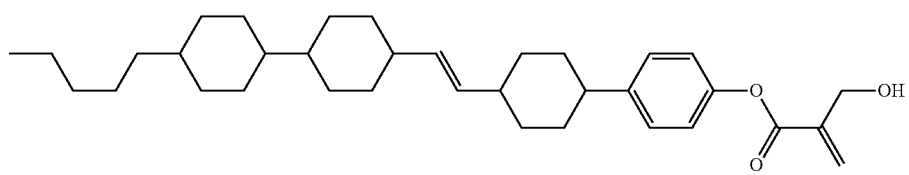 [SMILES: C=C(CO)C(=O)Oc1ccc(C2CCC(/C=C/C3CCC(C4CCC(CCCCC)CC4)CC3)CC2)cc1] |
| 1-6-117 | 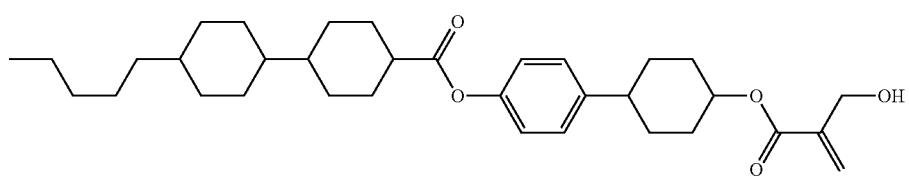 [SMILES: C=C(CO)C(=O)OC1CCC(c2ccc(OC(=O)C3CCC(C4CCC(CCCCC)CC4)CC3)cc2)CC1] |
| 1-6-118 | 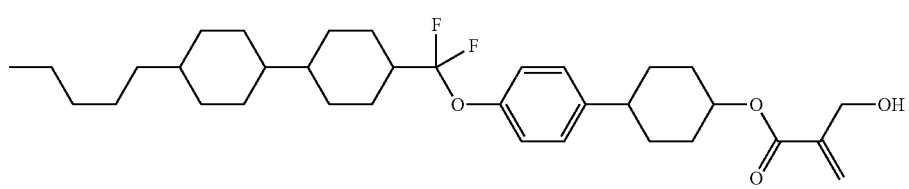 [SMILES: C=C(CO)C(=O)OC1CCC(c2ccc(OC(F)(F)C3CCC(C4CCC(CCCCC)CC4)CC3)cc2)CC1] |
| 1-6-119 | 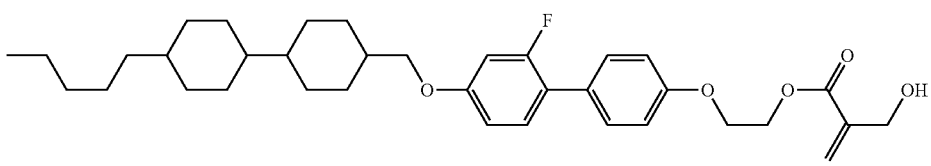 [SMILES: C=C(CO)C(=O)OCCOc1ccc(-c2ccc(OCC3CCC(C4CCC(CCCCC)CC4)CC3)cc2F)cc1] |

| No. | |
|---|---|
| 1-6-120 | 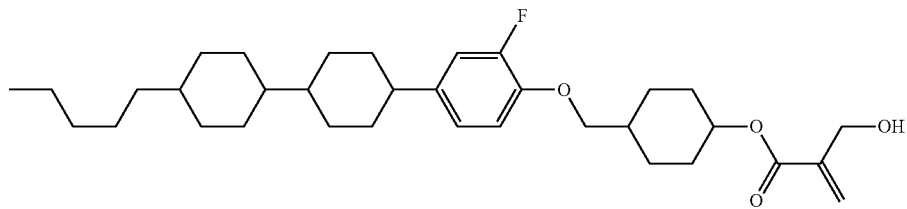 [SMILES: C=C(CO)C(=O)OC1CCC(COc2ccc(C3CCC(C4CCC(CCCCC)CC4)CC3)cc2F)CC1] |
| 1-6-121 | 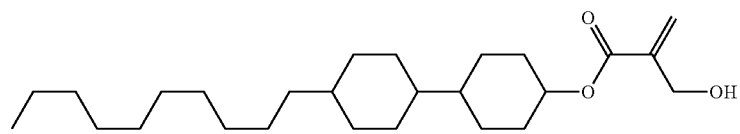 [SMILES: C=C(CO)C(=O)OC1CCC(C2CCC(CCCCCCCCCC)CC2)CC1] |
| 1-6-122 | 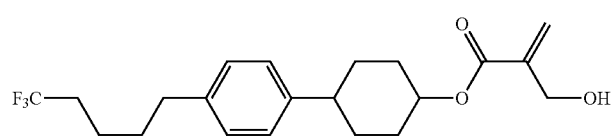 [SMILES: C=C(CO)C(=O)OC1CCC(c2ccc(CCCCC(F)(F)F)cc2)CC1] |
| 1-6-123 | 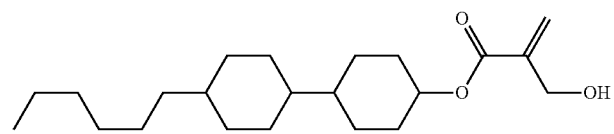 |
| 1-6-124 | 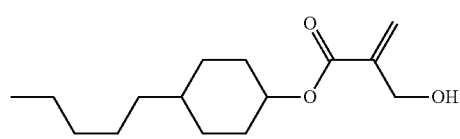 [SMILES: C=C(CO)C(=O)OC1CCC(CCCCC)CC1] |
| 1-6-125 | 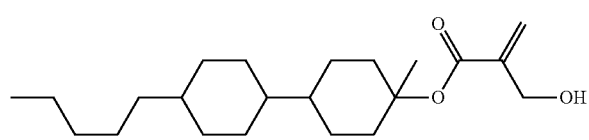 [SMILES: C=C(CO)C(=O)OC1(C)CCC(C2CCC(CCCCC)CC2)CC1] |
| 1-6-126 | 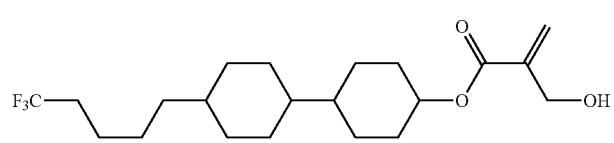 [SMILES: C=C(CO)C(=O)OC1CCC(C2CCC(CCCCC(F)(F)F)CC2)CC1] |
| 1-6-127 | 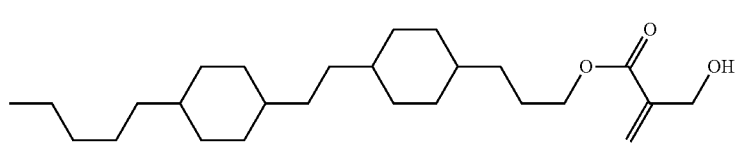 |
| 1-6-128 | 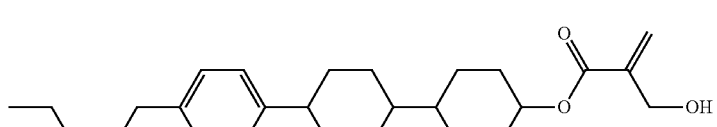 |
| 1-6-129 | 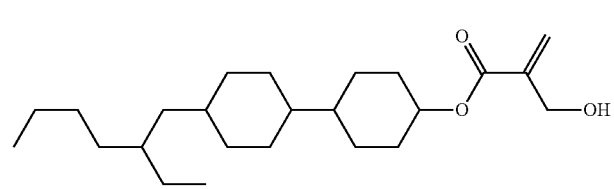 [SMILES: C=C(CO)C(=O)OC1CCC(C2CCC(CC(CC)CCCC)CC2)CC1] |

-continued
| No. | |
|---|---|
| 1-6-130 | 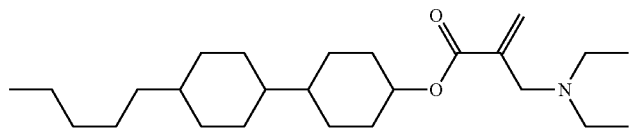 |
| 1-6-131 | 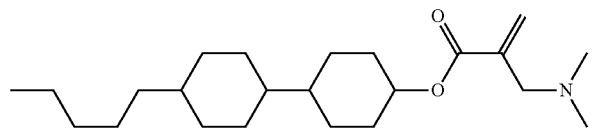 [SMILES: C=C(CN(C)C)C(=O)OC1CCC(C2CCC(CCCCC)CC2)CC1] |
| 1-6-132 | 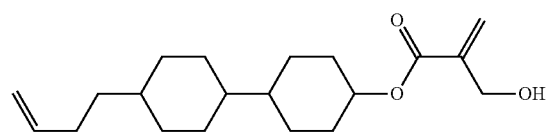 [SMILES: C=CCCC1CCC(C2CCC(OC(=O)C(=C)CO)CC2)CC1] |
| 1-6-133 | 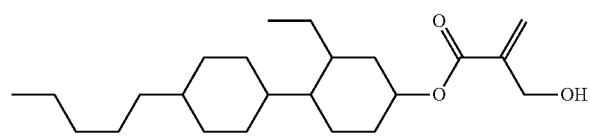 [SMILES: C=C(CO)C(=O)OC1CCC(C2CCC(CCCCC)CC2)C(CC)C1] |
| 1-6-134 | 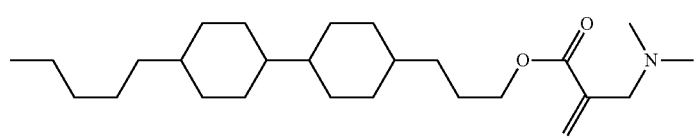 |
| 1-6-135 | 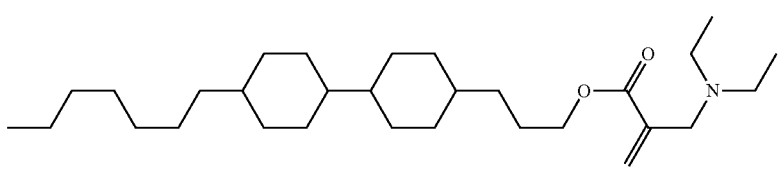 [SMILES: C=C(CN(CC)CC)C(=O)OCCCC1CCC(C2CCC(CCCCCCC)CC2)CC1] |
| 1-6-136 | 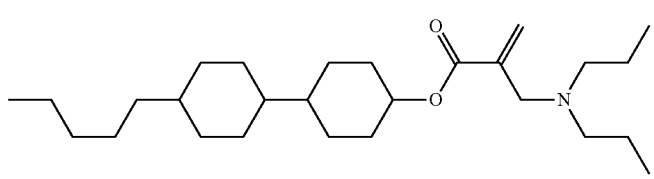 |
| 1-6-137 | 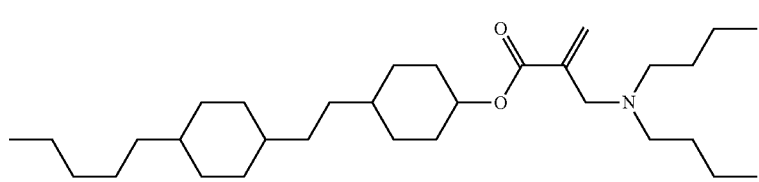 [SMILES: C=C(CN(CCCC)CCCC)C(=O)OC1CCC(CCC2CCC(CCCCC)CC2)CC1] |
| 1-6-138 | 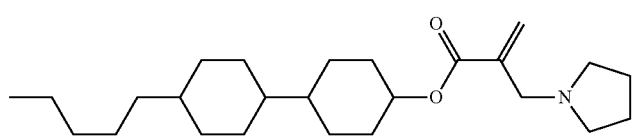 [SMILES: C=C(CN1CCCC1)C(=O)OC1CCC(C2CCC(CCCCC)CC2)CC1] |
| 1-6-139 | 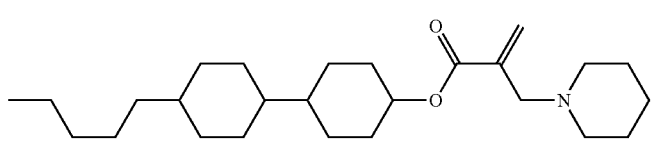 |

-continued
| No. | |
|---|---|
| 1-6-140 | 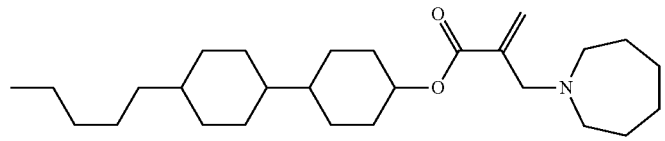 [SMILES: C=C(CN1CCCCCC1)C(=O)OC1CCC(C2CCC(CCCCC)CC2)CC1] |
| 1-6-141 | 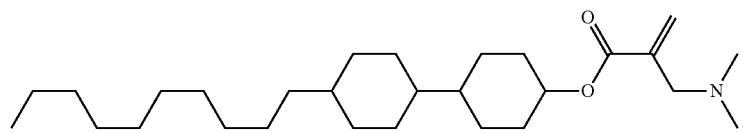 [SMILES: C=C(CN(C)C)C(=O)OC1CCC(C2CCC(CCCCCCCCCC)CC2)CC1] |
| 1-6-142 | 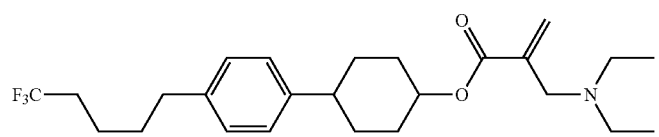 |
| 1-6-143 | 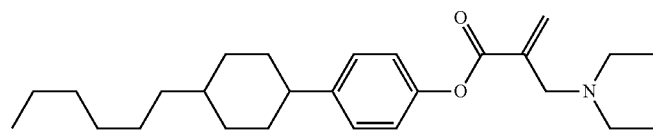 [SMILES: C=C(CN(CC)CC)C(=O)Oc1ccc(C2CCC(CCCCCC)CC2)cc1] |
| 1-6-144 | 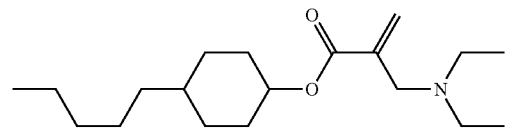 [SMILES: C=C(CN(CC)CC)C(=O)OC1CCC(CCCCC)CC1] |
| 1-6-145 | 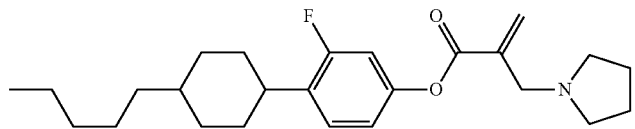 |
| 1-6-146 | 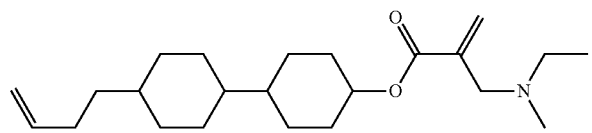 [SMILES: C=CCCC1CCC(C2CCC(OC(=O)C(=C)CN(C)CC)CC2)CC1] |
| 1-6-147 | 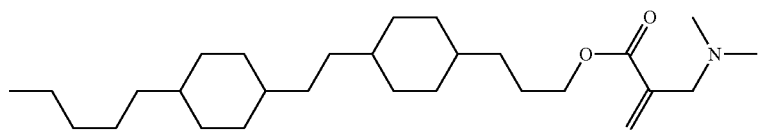 |
| 1-6-148 | 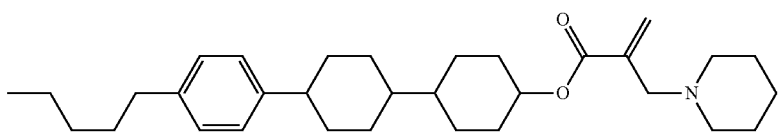 [SMILES: C=C(CN1CCCCC1)C(=O)OC1CCC(C2CCC(c3ccc(CCCCC)cc3)CC2)CC1] |
| 1-6-149 | 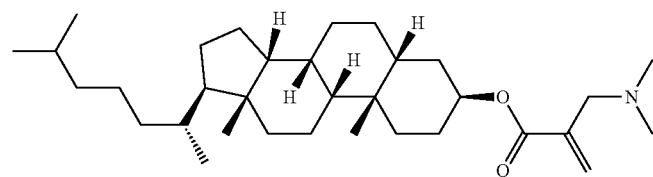 |

| No. | |
|---|---|
| 1-6-150 | 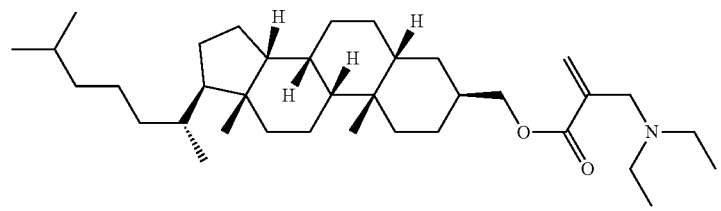 |
| 1-6-151 | 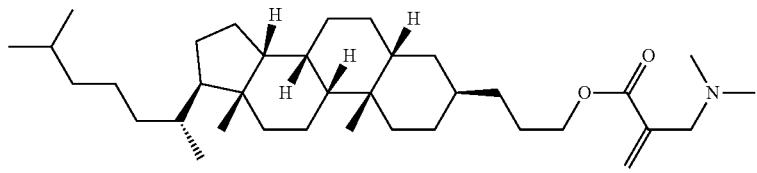 |
| 1-6-152 | 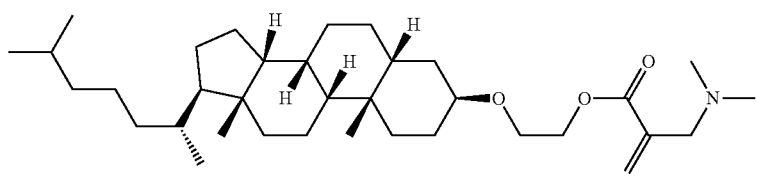 |
| 1-6-153 | 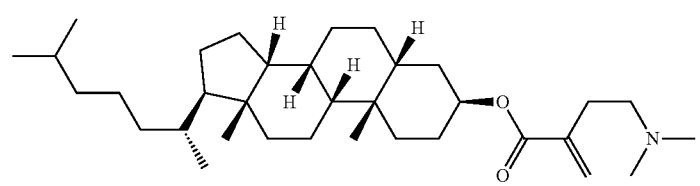 |
| 1-6-154 | 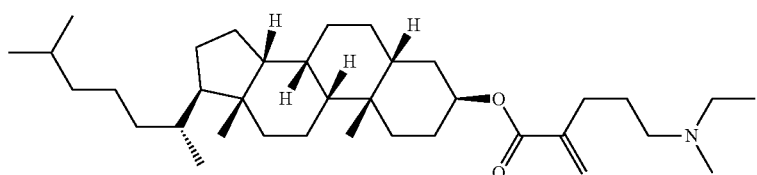 |
| 1-6-155 | 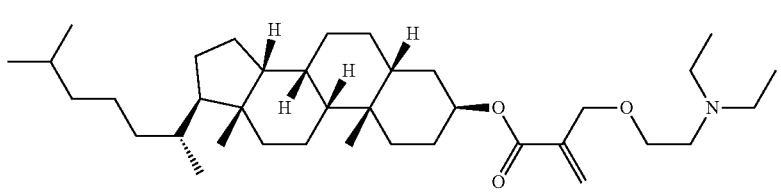 |
| 1-6-156 | 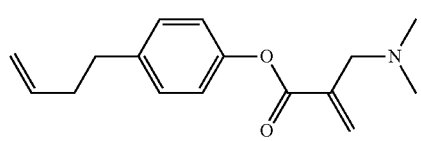 [SMILES: C=CCCc1ccc(OC(=O)C(=C)CN(C)C)cc1] |
| 1-6-157 | 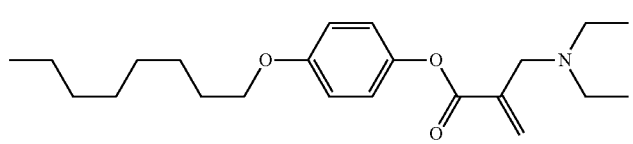 [SMILES: C=C(CN(CC)CC)C(=O)Oc1ccc(OCCCCCCCC)cc1] |
| 1-6-158 | 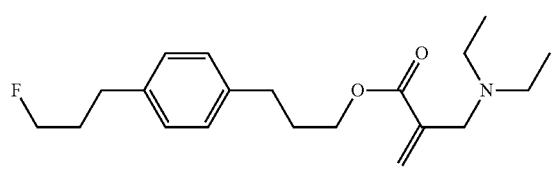 [SMILES: C=C(CN(CC)CC)C(=O)OCCCc1ccc(CCCF)cc1] |

-continued
| No. | |
|---|---|
| 1-6-159 | 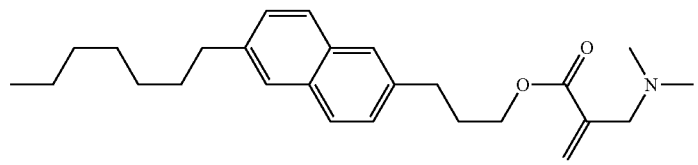 |
| 1-6-160 | 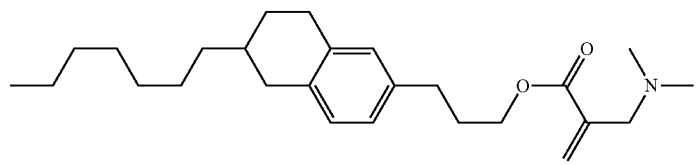 [SMILES: C=C(CN(C)C)C(=O)OCCCc1ccc2c(c1)CCC(CCCCCCC)C2] |
| 1-6-161 | 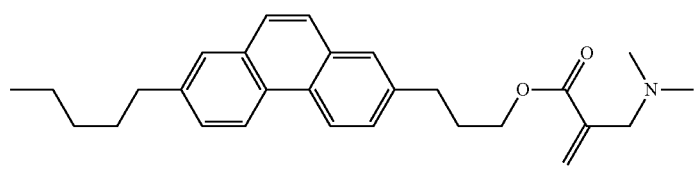 |
| 1-6-162 | 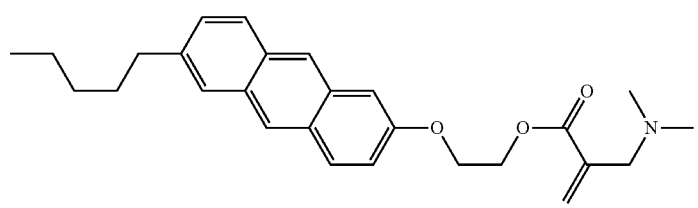 [SMILES: C=C(CN(C)C)C(=O)OCCOc1ccc2cc3cc(CCCCC)ccc3cc2c1] |
| 1-6-163 | 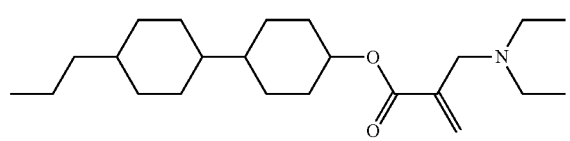 [SMILES: C=C(CN(CC)CC)C(=O)OC1CCC(C2CCC(CCC)CC2)CC1] |
| 1-6-164 | 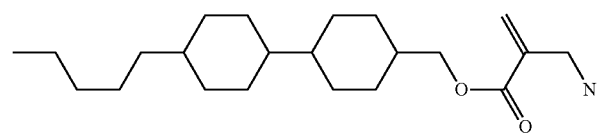 [SMILES: C=C(CN)C(=O)OCC1CCC(C2CCC(CCCCC)CC2)CC1] |
| 1-6-165 | 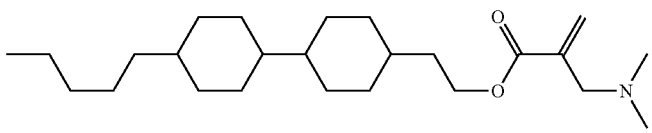 |
| 1-6-166 | 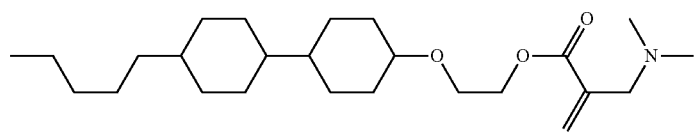 |
| 1-6-167 | 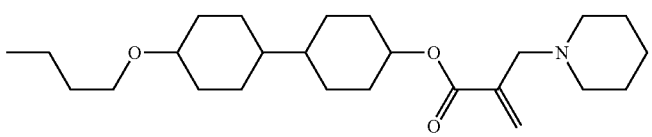 |
| 1-6-168 | 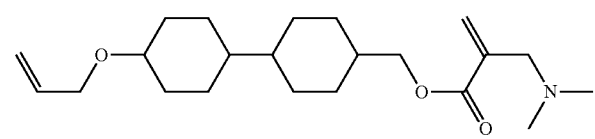 [SMILES: C=CCOC1CCC(C2CCC(COC(=O)C(=C)CN(C)C)CC2)CC1] |

-continued
| No. | |
|---|---|
| 1-6-169 | 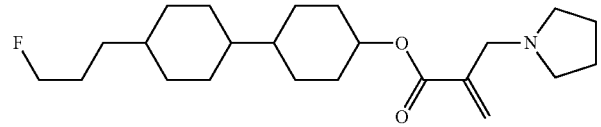 [SMILES: C=C(CN1CCCC1)C(=O)OC1CCC(C2CCC(CCCF)CC2)CC1] |
| 1-6-170 | 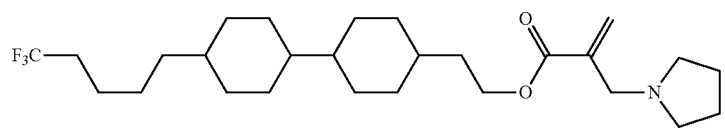 [SMILES: C=C(CN1CCCC1)C(=O)OCCC1CCC(C2CCC(CCCCC(F)(F)F)CC2)CC1] |
| 1-6-171 | 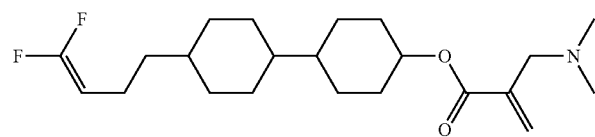 |
| 1-6-172 | 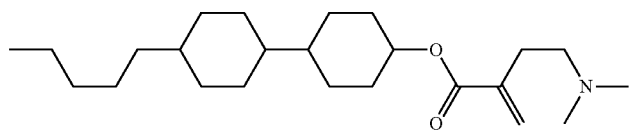 |
| 1-6-173 | 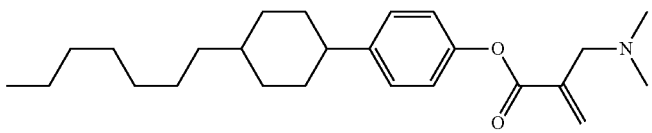 [SMILES: C=C(CN(C)C)C(=O)Oc1ccc(C2CCC(CCCCCCC)CC2)cc1] |
| 1-6-174 | 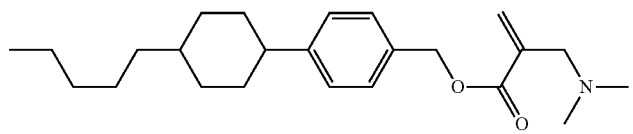 [SMILES: C=C(CN(C)C)C(=O)OCc1ccc(C2CCC(CCCCC)CC2)cc1] |
| 1-6-175 | 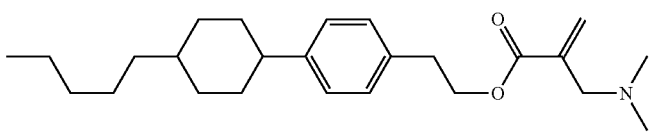 [SMILES: C=C(CN(C)C)C(=O)OCCc1ccc(C2CCC(CCCCC)CC2)cc1] |
| 1-6-176 | 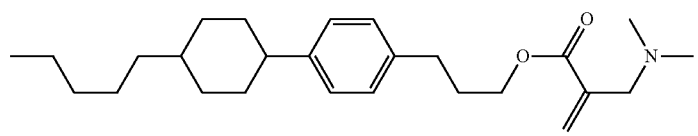 [SMILES: C=C(CN(C)C)C(=O)OCCCc1ccc(C2CCC(CCCCC)CC2)cc1] |
| 1-6-177 | 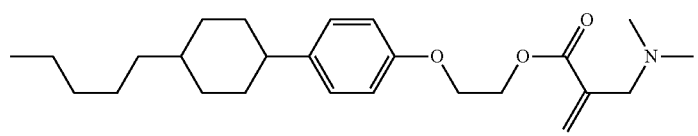 [SMILES: C=C(CN(C)C)C(=O)OCCOc1ccc(C2CCC(CCCCC)CC2)cc1] |
| 1-6-178 | 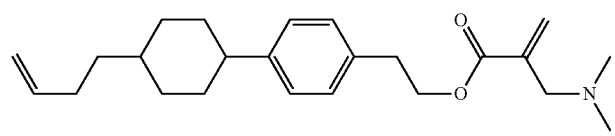 |
| 1-6-179 | 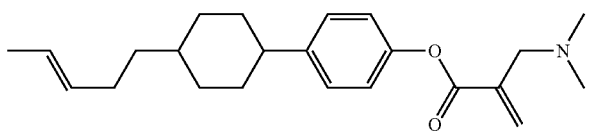 [SMILES: C=C(CN(C)C)C(=O)Oc1ccc(C2CCC(CC/C=C/C)CC2)cc1] |

-continued
| No. | |
|---|---|
| 1-6-180 | 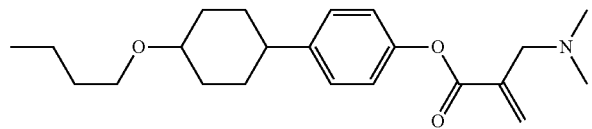 [SMILES: C=C(CN(C)C)C(=O)Oc1ccc(C2CCC(OCCCC)CC2)cc1] |
| 1-6-181 | 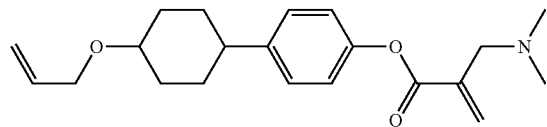 |
| 1-6-182 | 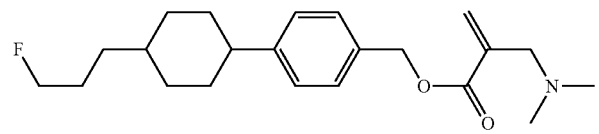 |
| 1-6-183 | 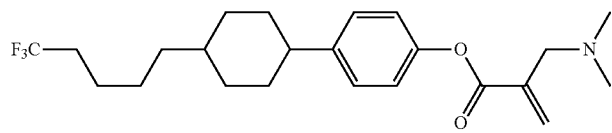 [SMILES: C=C(CN(C)C)C(=O)Oc1ccc(C2CCC(CCCCC(F)(F)F)CC2)cc1] |
| 1-6-184 | 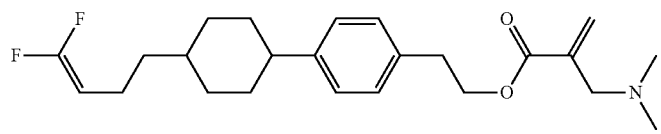 [SMILES: C=C(CN(C)C)C(=O)OCCc1ccc(C2CCC(CCC=C(F)F)CC2)cc1] |
| 1-6-185 | 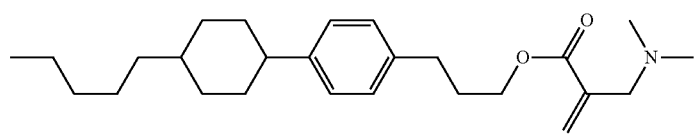 [SMILES: C=C(CN(C)C)C(=O)OCCCc1ccc(C2CCC(CCCCC)CC2)cc1] |
| 1-6-186 | 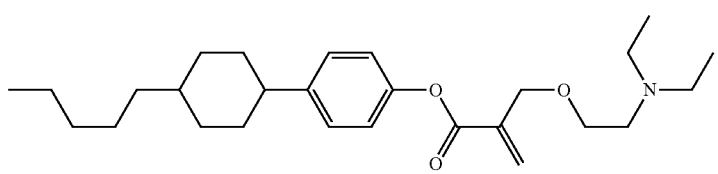 [SMILES: C=C(COCCN(CC)CC)C(=O)Oc1ccc(C2CCC(CCCCC)CC2)cc1] |
| 1-6-187 | 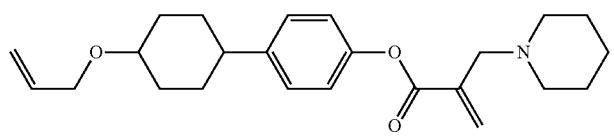 [SMILES: C=CCOC1CCC(c2ccc(OC(=O)C(=C)CN3CCCCC3)cc2)CC1] |
| 1-6-188 | 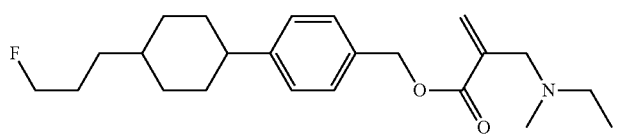 |
| 1-6-189 | 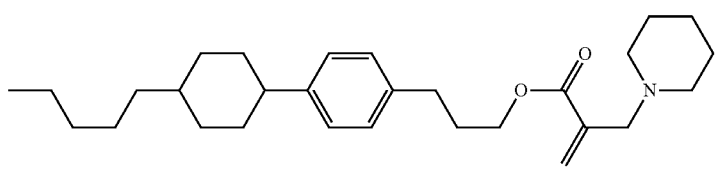 [SMILES: C=C(CN1CCCCC1)C(=O)OCCCc1ccc(C2CCC(CCCCC)CC2)cc1] |

| No. | |
|---|---|
| 1-6-190 | 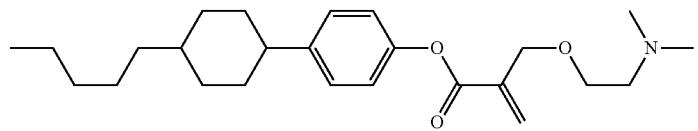 [SMILES: C=C(COCCN(C)C)C(=O)Oc1ccc(C2CCC(CCCCC)CC2)cc1] |
| 1-6-191 | 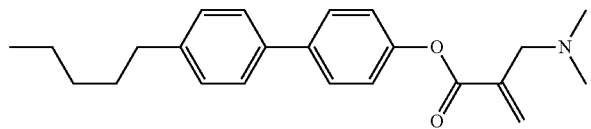 [SMILES: C=C(CN(C)C)C(=O)Oc1ccc(-c2ccc(CCCCC)cc2)cc1] |
| 1-6-192 | 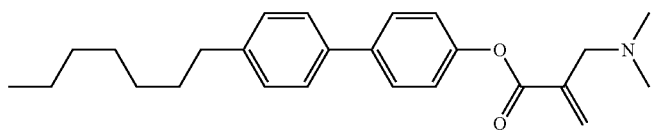 [SMILES: C=C(CN(C)C)C(=O)Oc1ccc(-c2ccc(CCCCCCC)cc2)cc1] |
| 1-6-193 | 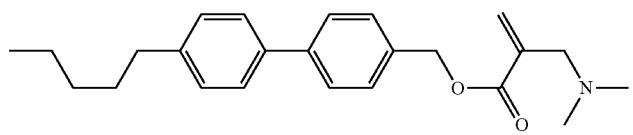 [SMILES: C=C(CN(C)C)C(=O)OCc1ccc(-c2ccc(CCCCC)cc2)cc1] |
| 1-6-194 | 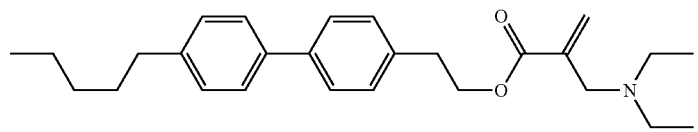 |
| 1-6-195 | 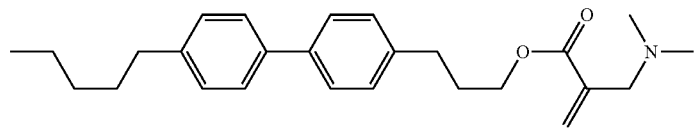 [SMILES: C=C(CN(C)C)C(=O)OCCCc1ccc(-c2ccc(CCCCC)cc2)cc1] |
| 1-6-196 | 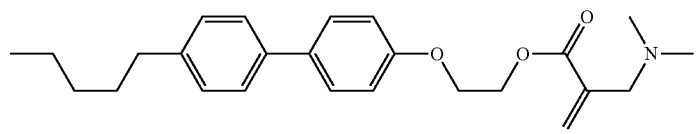 |
| 1-6-197 | 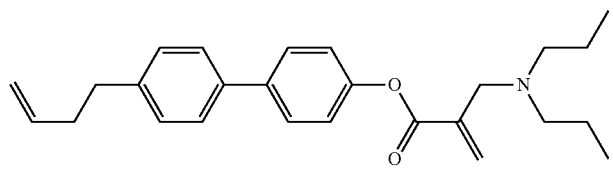 [SMILES: C=CCCc1ccc(-c2ccc(OC(=O)C(=C)CN(CCC)CCC)cc2)cc1] |
| 1-6-198 | 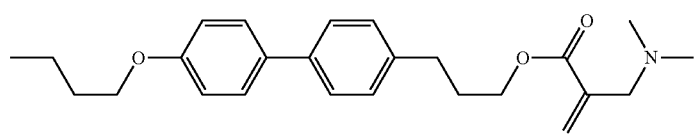 |
| 1-6-199 | 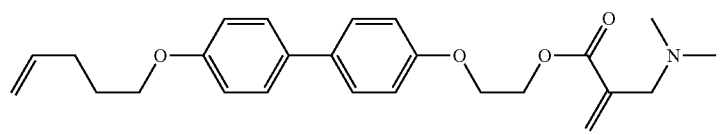 [SMILES: C=CCCCOc1ccc(-c2ccc(OCCOC(=O)C(=C)CN(C)C)cc2)cc1] |
| 1-6-200 | 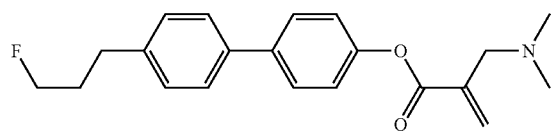 [SMILES: C=C(CN(C)C)C(=O)Oc1ccc(-c2ccc(CCCF)cc2)cc1] |

| No. | |
|---|---|
| 1-6-201 | 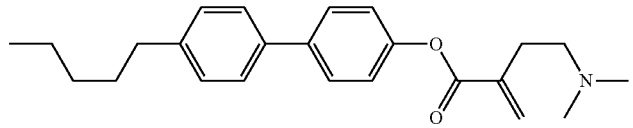 [SMILES: C=C(CCN(C)C)C(=O)Oc1ccc(-c2ccc(CCCCC)cc2)cc1] |
| 1-6-202 | 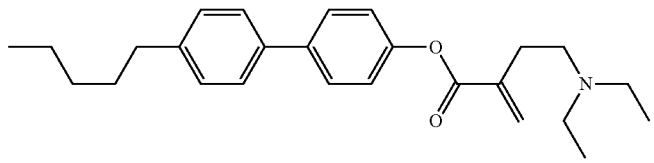 [SMILES: C=C(CCN(CC)CC)C(=O)Oc1ccc(-c2ccc(CCCCC)cc2)cc1] |
| 1-6-203 | 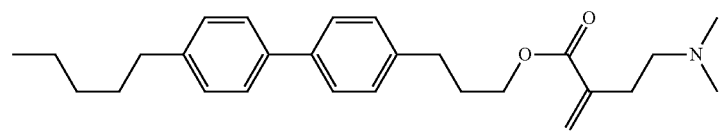 [SMILES: C=C(CCN(C)C)C(=O)OCCCc1ccc(-c2ccc(CCCCC)cc2)cc1] |
| 1-6-204 | 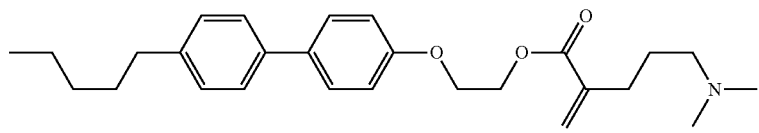 |
| 1-6-205 | 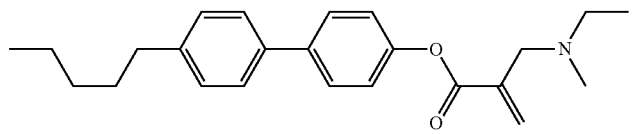 [SMILES: C=C(CN(C)CC)C(=O)Oc1ccc(-c2ccc(CCCCC)cc2)cc1] |
| 1-6-206 | 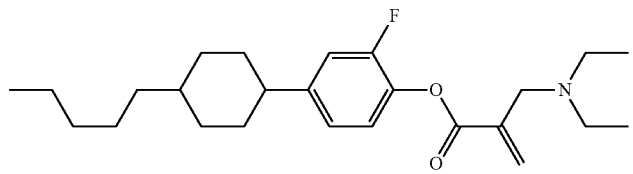 |
| 1-6-207 | 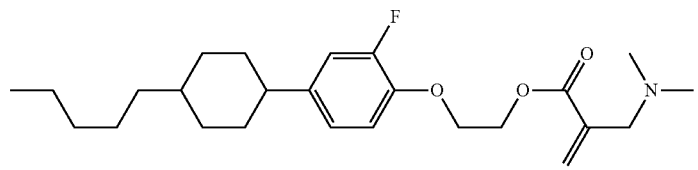 [SMILES: C=C(CN(C)C)C(=O)OCCOc1ccc(C2CCC(CCCCC)CC2)cc1F] |
| 1-6-208 | 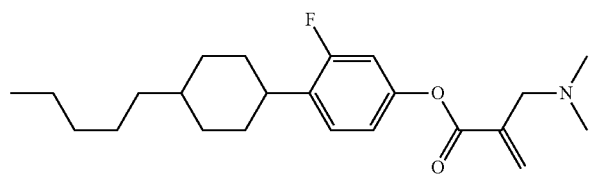 [SMILES: C=C(CN(C)C)C(=O)Oc1ccc(C2CCC(CCCCC)CC2)c(F)c1] |
| 1-6-209 | 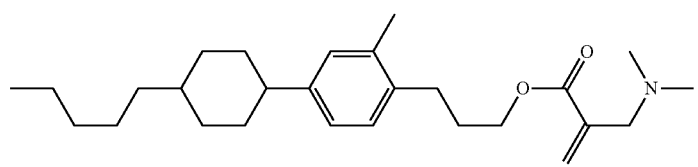 [SMILES: C=C(CN(C)C)C(=O)OCCCc1ccc(C2CCC(CCCCC)CC2)cc1C] |

| No. |
|---|
| 1-6-210 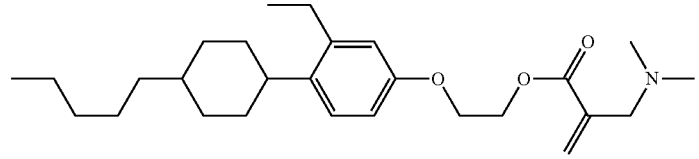 [SMILES: C=C(CN(C)C)C(=O)OCCOc1ccc(C2CCC(CCCCC)CC2)c(CC)c1] |
| 1-6-211 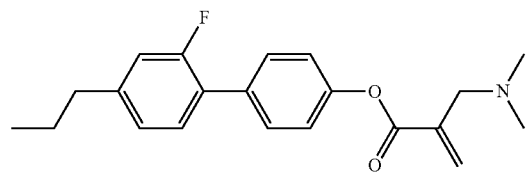 [SMILES: C=C(CN(C)C)C(=O)Oc1ccc(-c2ccc(CCC)cc2F)cc1] |
| 1-6-212 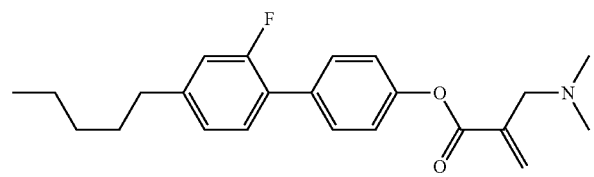 |
| 1-6-213 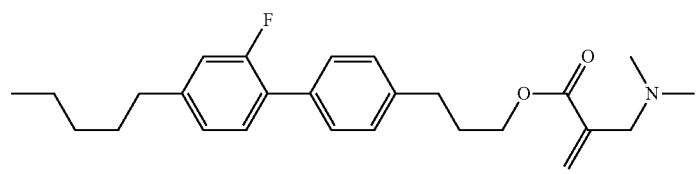 [SMILES: C=C(CN(C)C)C(=O)OCCCc1ccc(-c2ccc(CCCCC)cc2F)cc1] |
| 1-6-214 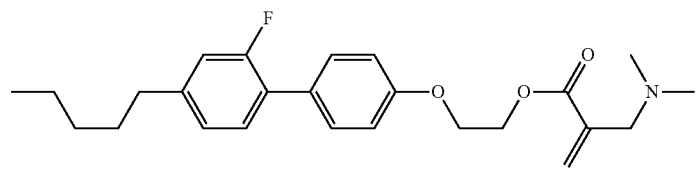 |
| 1-6-215 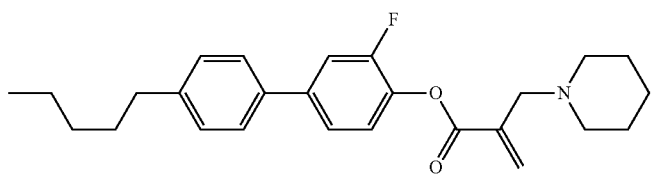 [SMILES: C=C(CN1CCCCC1)C(=O)Oc1ccc(-c2ccc(CCCCC)cc2)cc1F] |
| 1-6-216 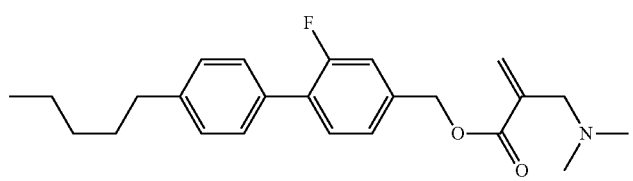 [SMILES: C=C(CN(C)C)C(=O)OCc1ccc(-c2ccc(CCCCC)cc2)c(F)c1] |
| 1-6-217 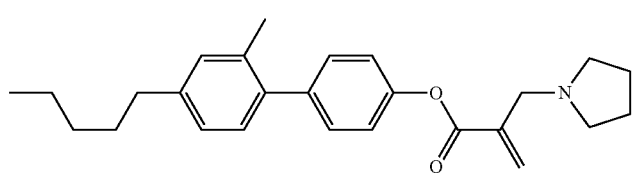 [SMILES: C=C(CN1CCCC1)C(=O)Oc1ccc(-c2ccc(CCCCC)cc2C)cc1] |
| 1-6-218 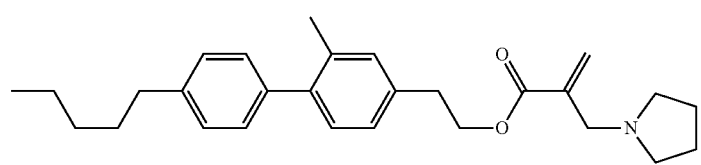 [SMILES: C=C(CN1CCCC1)C(=O)OCCc1ccc(-c2ccc(CCCCC)cc2)c(C)c1] |

| No. | |
|---|---|
| 1-6-219 | 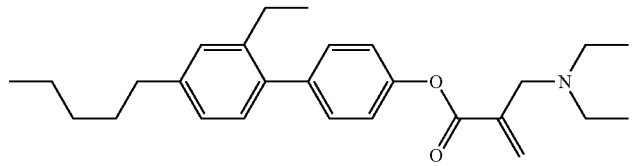 [SMILES: C=C(CN(CC)CC)C(=O)Oc1ccc(-c2ccc(CCCCC)cc2CC)cc1] |
| 1-6-220 | 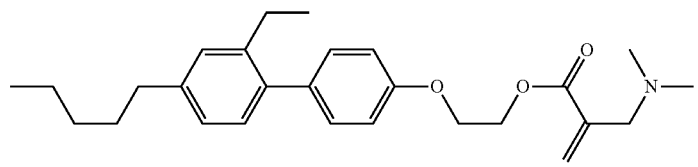 [SMILES: C=C(CN(C)C)C(=O)OCCOc1ccc(-c2ccc(CCCCC)cc2CC)cc1] |
| 1-6-221 | 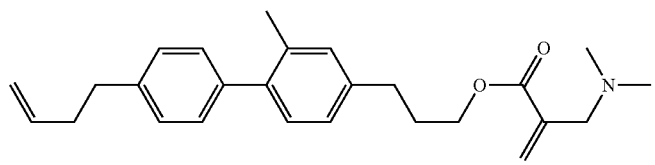 [SMILES: C=CCCc1ccc(-c2ccc(CCCOC(=O)C(=C)CN(C)C)cc2C)cc1] |
| 1-6-222 | 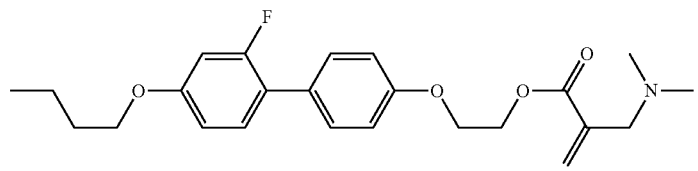 [SMILES: C=C(CN(C)C)C(=O)OCCOc1ccc(-c2ccc(OCCCC)cc2F)cc1] |
| 1-6-223 | 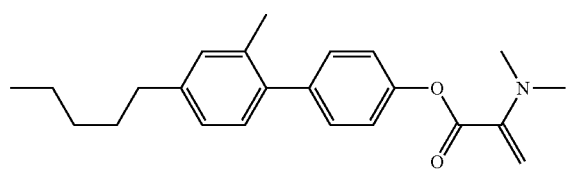 [SMILES: C=C(C(=O)Oc1ccc(-c2ccc(CCCCC)cc2C)cc1)N(C)C] |
| 1-6-224 | 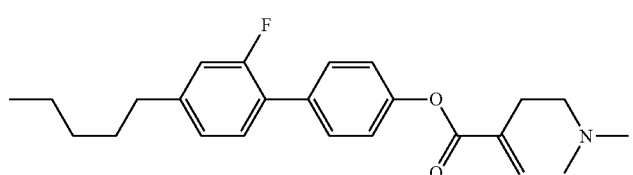 |
| 1-6-225 | 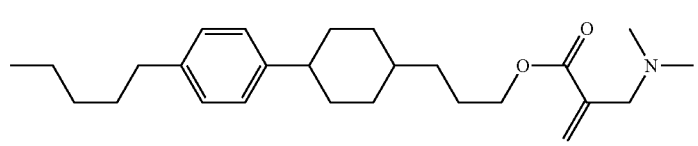 [SMILES: C=C(CN(C)C)C(=O)OCCCC1CCC(c2ccc(CCCCC)cc2)CC1] |
| 1-6-226 | 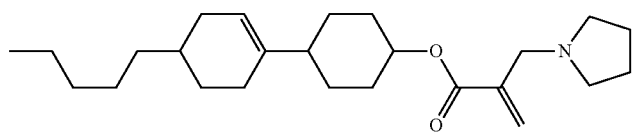 [SMILES: C=C(CN1CCCC1)C(=O)OC1CCC(C2=CCC(CCCCC)CC2)CC1] |
| 1-6-227 | 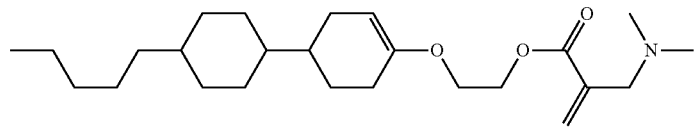 [SMILES: C=C(CN(C)C)C(=O)OCCOC1=CCC(C2CCC(CCCCC)CC2)CC1] |

-continued
| No. | |
|---|---|
| 1-6-228 | 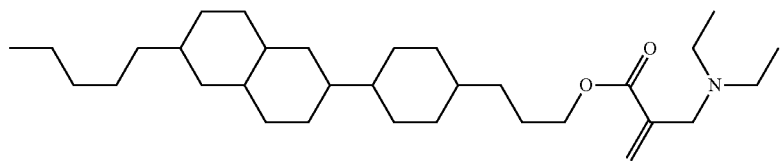 [SMILES: C=C(CN(CC)CC)C(=O)OCCCC1CCC(C2CCC3CC(CCCCC)CCC3C2)CC1] |
| 1-6-229 | 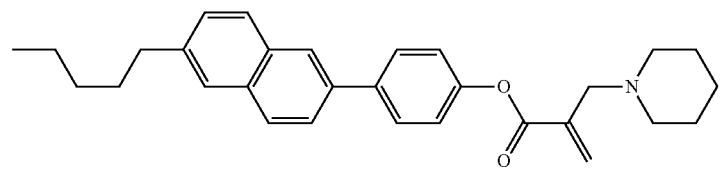 |
| 1-6-230 | 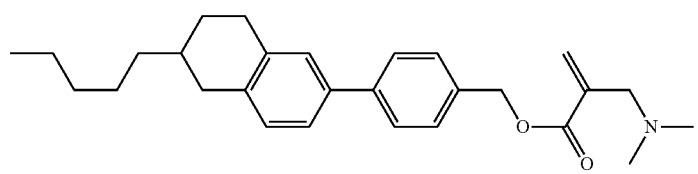 [SMILES: C=C(CN(C)C)C(=O)OCc1ccc(-c2ccc3c(c2)CCC(CCCCC)C3)cc1] |
| 1-6-231 | 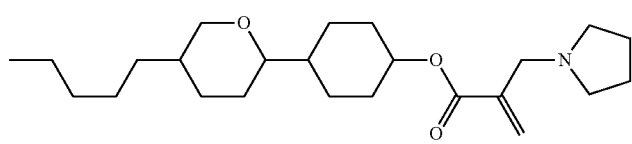 |
| 1-6-232 | 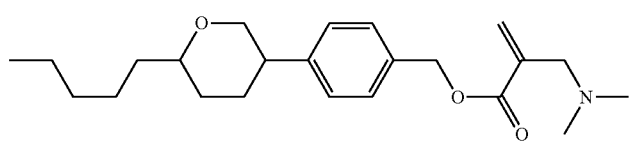 [SMILES: C=C(CN(C)C)C(=O)OCc1ccc(C2CCC(CCCCC)OC2)cc1] |
| 1-6-233 | 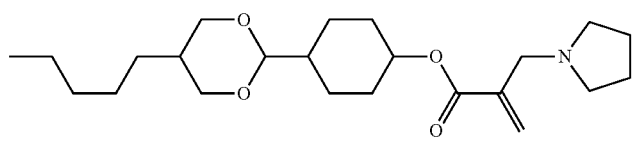 [SMILES: C=C(CN1CCCC1)C(=O)OC1CCC(C2OCC(CCCCC)CO2)CC1] |
| 1-6-234 | 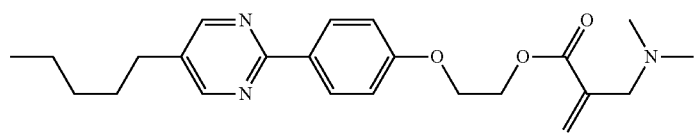 [SMILES: C=C(CN(C)C)C(=O)OCCOc1ccc(-c2ncc(CCCCC)cn2)cc1] |
| 1-6-235 | 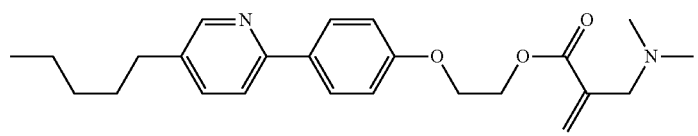 [SMILES: C=C(CN(C)C)C(=O)OCCOc1ccc(-c2ccc(CCCCC)cn2)cc1] |
| 1-6-236 | 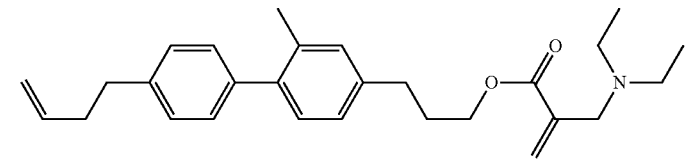 [SMILES: C=CCCc1ccc(-c2ccc(CCCOC(=O)C(=C)CN(CC)CC)cc2C)cc1] |
| 1-6-237 | 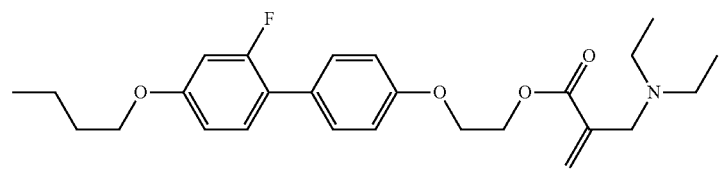 [SMILES: C=C(CN(CC)CC)C(=O)OCCOc1ccc(-c2ccc(OCCCC)cc2F)cc1] |

US 10,392,339 B2
249 250
-continued
| No. |
|---|
| 1-6-238 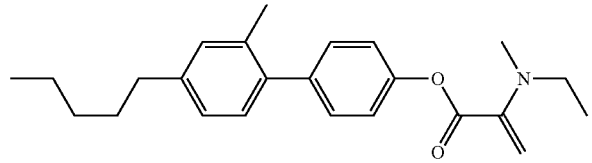 |
| 1-6-239 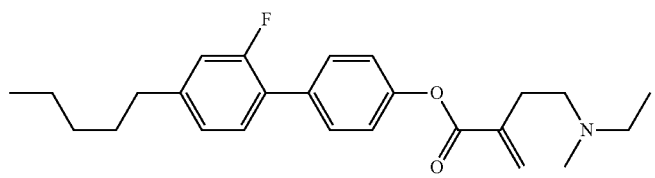 [SMILES: C=C(CCN(C)CC)C(=O)Oc1ccc(-c2ccc(CCCCC)cc2F)cc1] |
| 1-6-240 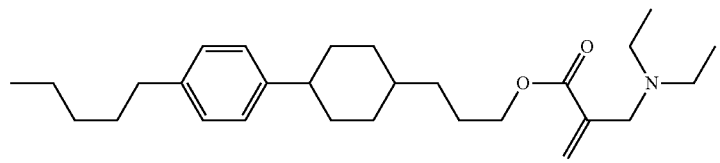 [SMILES: C=C(CN(CC)CC)C(=O)OCCCC1CCC(c2ccc(CCCCC)cc2)CC1] |
| 1-4-241 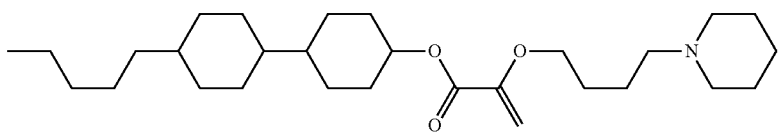 [SMILES: C=C(OCCCCN1CCCCC1)C(=O)OC1CCC(C2CCC(CCCCC)CC2)CC1] |
| 1-4-242 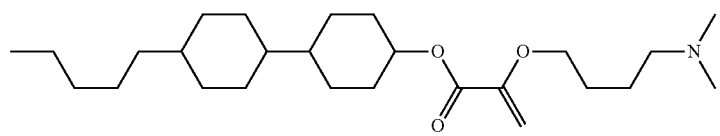 [SMILES: C=C(OCCCCN(C)C)C(=O)OC1CCC(C2CCC(CCCCC)CC2)CC1] |
| 1-4-243 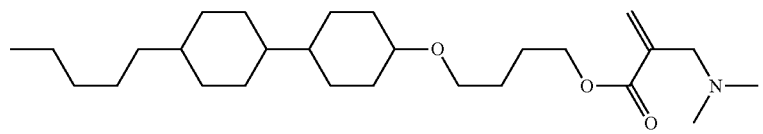 [SMILES: C=C(CN(C)C)C(=O)OCCCCOC1CCC(C2CCC(CCCCC)CC2)CC1] |
| 1-4-244 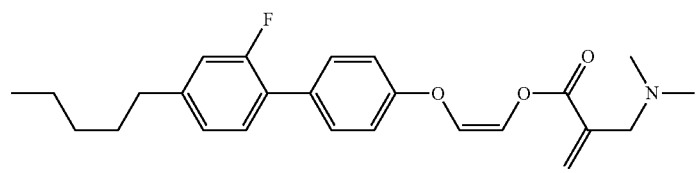 [SMILES: C=C(CN(C)C)C(=O)O/C=C\Oc1ccc(-c2ccc(CCCCC)cc2F)cc1] |
| 1-4-245 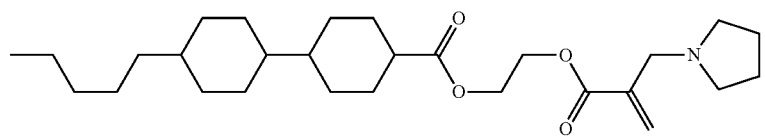 [SMILES: C=C(CN1CCCC1)C(=O)OCCOC(=O)C1CCC(C2CCC(CCCCC)CC2)CC1] |
| 1-4-246 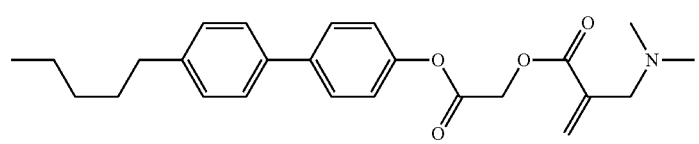 |
| 1-4-247 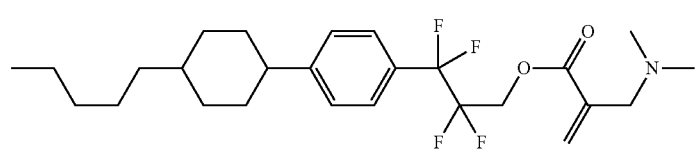 [SMILES: C=C(CN(C)C)C(=O)OCC(F)(F)C(F)(F)c1ccc(C2CCC(CCCCC)CC2)cc1] |

-continued
| No. | |
|---|---|
| 1-4-248 | 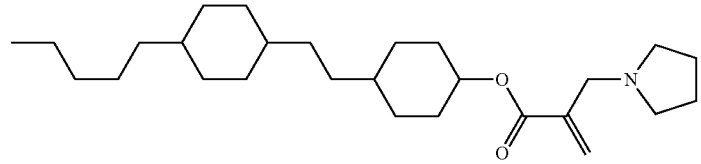 [SMILES: C=C(CN1CCCC1)C(=O)OC1CCC(CCC2CCC(CCCCC)CC2)CC1] |
| 1-4-249 | 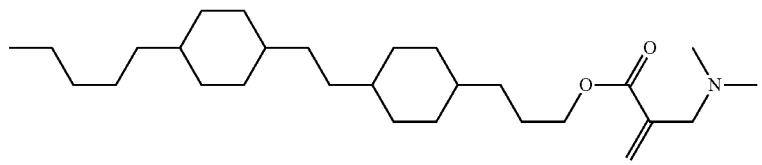 |
| 1-4-250 | 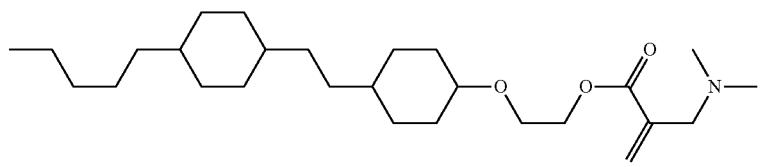 |
| 1-4-251 | 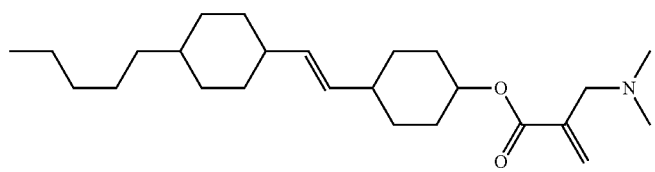 [SMILES: C=C(CN(C)C)C(=O)OC1CCC(/C=C/C2CCC(CCCCC)CC2)CC1] |
| 1-4-252 | 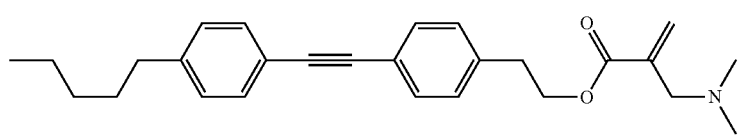 |
| 1-4-253 | 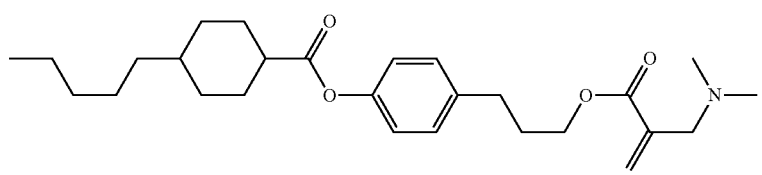 [SMILES: C=C(CN(C)C)C(=O)OCCCc1ccc(OC(=O)C2CCC(CCCCC)CC2)cc1] |
| 1-4-254 | 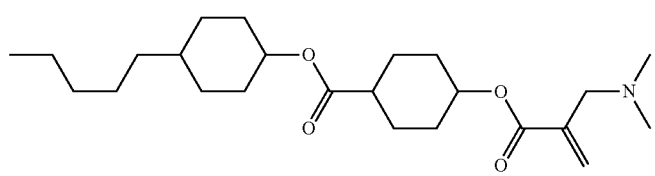 |
| 1-4-255 | 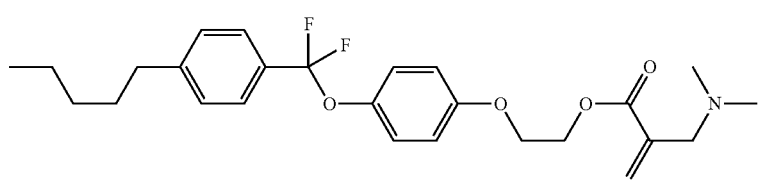 [SMILES: C=C(CN(C)C)C(=O)OCCOc1ccc(OC(F)(F)c2ccc(CCCCC)cc2)cc1] |
| 1-4-256 | 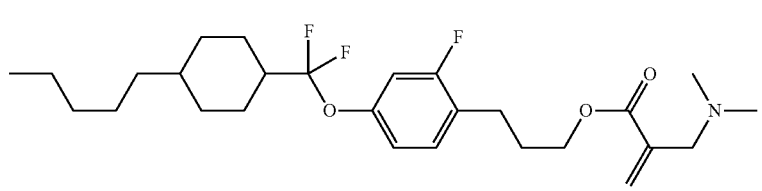 [SMILES: C=C(CN(C)C)C(=O)OCCCc1ccc(OC(F)(F)C2CCC(CCCCC)CC2)cc1F] |

-continued

| No. | |
|---|---|
| 1-4-257 | 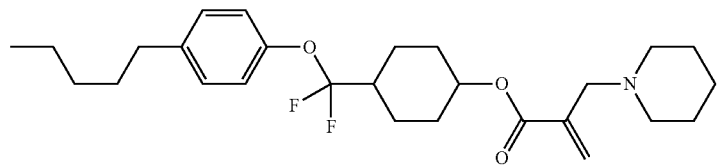 [SMILES: C=C(CN1CCCCC1)C(=O)OC1CCC(C(F)(F)Oc2ccc(CCCCC)cc2)CC1] |
| 1-4-258 | 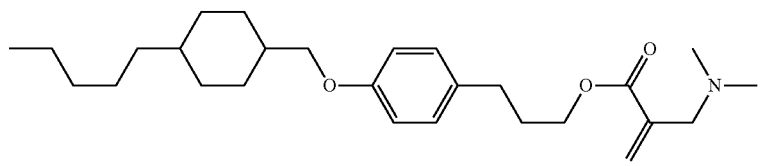 [SMILES: C=C(CN(C)C)C(=O)OCCCc1ccc(OCC2CCC(CCCCC)CC2)cc1] |
| 1-4-259 | 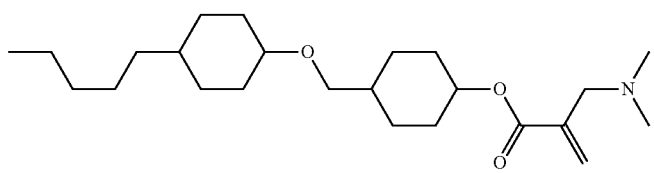 [SMILES: C=C(CN(C)C)C(=O)OC1CCC(COC2CCC(CCCCC)CC2)CC1] |
| 1-4-260 | 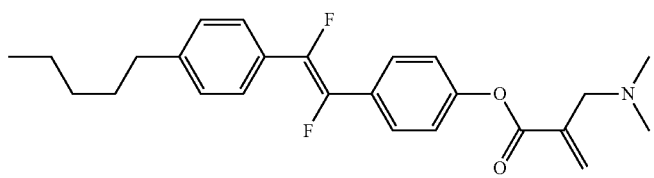 [SMILES: C=C(CN(C)C)C(=O)Oc1ccc(/C(F)=C(\F)c2ccc(CCCCC)cc2)cc1] |

2. Example of Composition

The compounds in Examples were represented using symbols according to definitions in Table 3 described below. In Table 3, the configuration of 1,4-cyclohexylene is trans. A parenthesized number next to a symbolized compound corresponds to the number of the compound. A symbol (-) means any other liquid crystal compound. A proportion (percentage) of the liquid crystal compound is expressed in terms of weight percent (% by weight) based on the weight of the liquid crystal composition. Values of the characteristics of the liquid crystal composition were summarized in the last part. The characteristics were measured according to the methods described above, and measured values are directly described (without extrapolation).

TABLE 3

Table 3. Method for Description of Compounds using Symbols
R—(A$_1$)—Z$_1$— . . . —Z$_n$—(A$_n$)—R'

| 1) Left-terminal Group R— | Symbol |
|---|---|
| C$_n$H$_{2n+1}$— | n- |
| C$_n$H$_{2n+1}$O— | nO— |
| C$_m$H$_{2m+1}$OC$_n$H$_{2n}$— | mOn— |
| CH$_2$=CH— | V— |
| C$_n$H$_{2n+1}$—CH=CH— | nV— |
| CH$_2$=CH—C$_n$H$_{2n}$— | Vn— |
| C$_m$H$_{2m+1}$—CH=CH—C$_n$H$_{2n}$— | mVn— |
| CF$_2$=CH— | VFF— |
| CF$_2$=CH—C$_n$H$_{2n}$— | VFFn— |

| 2) Right-terminal Group —R' | Symbol |
|---|---|
| —C$_n$H$_{2n+1}$ | -n |
| —OC$_n$H$_{2n+1}$ | —On |

TABLE 3-continued

Table 3. Method for Description of Compounds using Symbols
R—(A$_1$)—Z$_1$— . . . —Z$_n$—(A$_n$)—R'

| | |
|---|---|
| —COOCH$_3$ | —EMe |
| —CH=CH$_2$ | —V |
| —CH=CH—C$_n$H$_{2n+1}$ | —Vn |
| —C$_n$H$_{2n}$—CH=CH$_2$ | —nV |
| —C$_m$H$_{2m}$—CH=CH—C$_n$H$_{2n+1}$ | —mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —OCH=CH—CF$_3$ | —OVCF3 |
| —C≡N | —C |

| 3) Bonding Group —Z$_n$— | Symbol |
|---|---|
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C≡C— | T |

| 4) Ring Structure —A$_n$— | Symbol |
|---|---|
| (cyclohexane) | H |
| (benzene) | B |

TABLE 3-continued

Table 3. Method for Description of Compounds using Symbols
R—(A₁)—Z₁— ... —Zₙ—(Aₙ)—R'

| | |
|---|---|
| 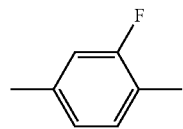 | B(F) |
| 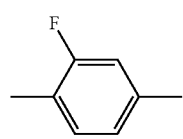 | B(2F) |
| 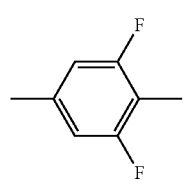 | B(F,F) |
| 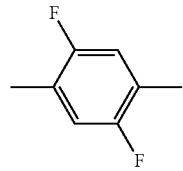 | B(2F,5F) |
| 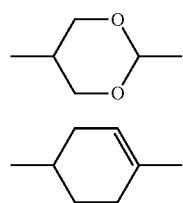 | B(2F,3F) |
| 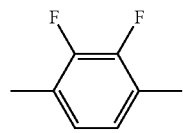 | Py |
| 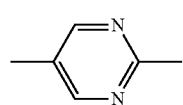 | G |
|  | ch |

5) Examples of Description

Example 1 3-HB—CL

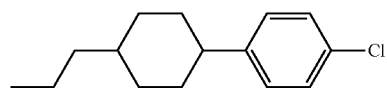

Example 2 5-HHBB(F,F)—F

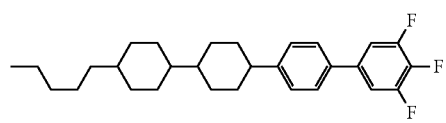 [SMILES: CCCCCC1CCC(C2CCC(c3ccc(-c4cc(F)c(F)c(F)c4)cc3)CC2)CC1]

Example 3 3-HB—O2

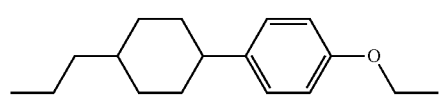

Example 4 3-HBB(F,F)—F

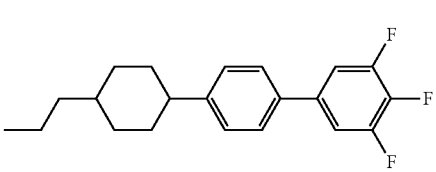 [SMILES: CCCC1CCC(c2ccc(-c3cc(F)c(F)c(F)c3)cc2)CC1]

Use Example 1

| | | |
|---|---|---|
| 2-HB-C | (8-1) | 5% |
| 3-HB-C | (8-1) | 12% |
| 3-HB-O2 | (2-5) | 15% |
| 2-BTB-1 | (2-10) | 3% |
| 3-HHB-F | (6-1) | 4% |
| 3-HHB-1 | (3-1) | 8% |
| 3-HHB-O1 | (3-1) | 5% |
| 3-HHB-3 | (3-1) | 14% |
| 3-HHEB-F | (6-10) | 5% |
| 5-HHEB-F | (6-10) | 3% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

Compound (1-4-2) described below was added to the composition described above in a proportion of 5% by weight.

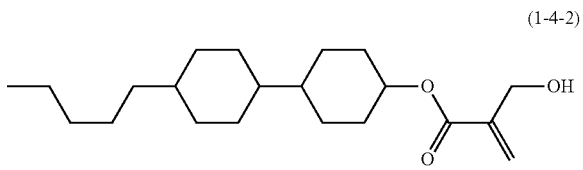 [SMILES: C=C(CO)C(=O)OC1CCC(C2CCC(CCCCC)CC2)CC1]

(1-4-2)

NI=100.5° C.; η=17.6 mPa·s; Δn=0.100; Δε=4.7.

Use Example 2

| | | |
|---|---|---|
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 11% |
| 4-PyBB-F | (6-80) | 9% |
| 5-PyBB-F | (6-80) | 11% |
| 5-HBB(F)B-2 | (4-5) | 9% |
| 5-HBB(F)B-3 | (4-5) | 10% |

Compound (1-4-22) described below was added to the composition described above in a proportion of 5% by weight.

(1-4-22)

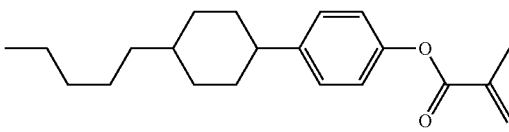

NI=98.5° C.; η=39.5 mPa·s; Δn=0.190; Δε=8.1.

Use Example 3

| 5-HB-CL | (5-2) | 16% |
|---|---|---|
| 3-HH-4 | (2-1) | 11% |
| 3-HH-5 | (2-1) | 4% |
| 3-HHB-F | (6-1) | 3% |
| 3-HHB-CL | (6-1) | 3% |
| 4-HHB-CL | (6-1) | 4% |
| 3-HHB(F)-F | (6-2) | 10% |
| 4-HHB(F)-F | (6-2) | 9% |
| 5-HHB(F)-F | (6-2) | 9% |
| 7-HHB(F)-F | (6-2) | 9% |
| 5-HBB(F)-F | (6-23) | 3% |
| 1O1-HBBH-5 | (4-1) | 3% |
| 3-HHBB(F,F)-F | (7-6) | 3% |
| 4-HHBB(F,F)-F | (7-6) | 3% |
| 5-HHBB(F,F)-F | (7-6) | 3% |

-continued

| 3-HH2BB(F,F)-F | (7-15) | 4% |
|---|---|---|
| 4-HH2BB(F,F)-F | (7-15) | 3% |

Compound (1-4-27) described below was added to the composition described above in a proportion of 5% by weight.

(1-4-27)

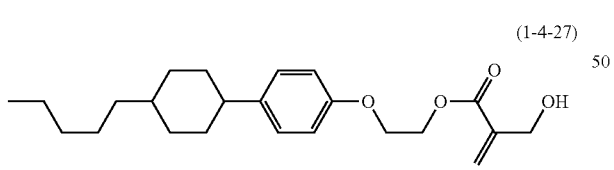

Compound (M-1-1) described below was further added thereto in a proportion of 0.3% by weight.

(M-1-1)

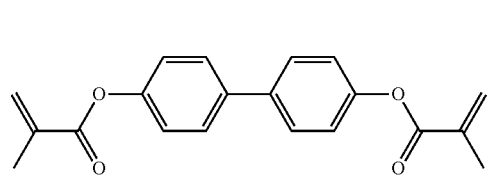

NI=115.9° C.; η=20.2 mPa·s; Δn=0.092; Δε=4.0.

Use Example 4

| 5-HB-CL | (5-2) | 16% |
|---|---|---|
| 7-HB(F,F)-F | (5-4) | 5% |
| 3-HH-4 | (2-1) | 10% |
| 3-HH-5 | (2-1) | 5% |
| 3-HB-O2 | (2-5) | 14% |
| 3-HHB-1 | (3-1) | 8% |
| 3-HHB-O1 | (3-1) | 6% |
| 2-HHB(F)-F | (6-2) | 6% |
| 3-HHB(F)-F | (6-2) | 7% |
| 5-HHB(F)-F | (6-2) | 7% |
| 3-HHB(F,F)-F | (6-3) | 6% |
| 3-H2HB(F,F)-F | (6-15) | 5% |
| 4-H2HB(F,F)-F | (6-15) | 5% |

Compound (1-5-31) described below was added to the composition described above in a proportion of 3% by weight.

(1-5-31)

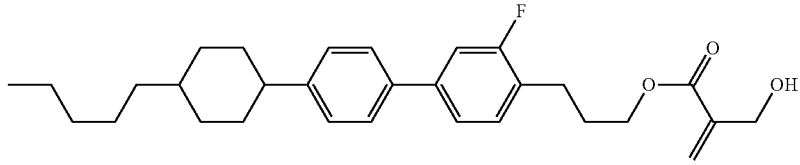

NI=70.5° C.; η=13.9 mPa·s; Δn=0.073; Δε=2.8.

Use Example 5

| 3-HHB(F,F)-F | (6-3) | 10% |
|---|---|---|
| 3-H2HB(F,F)-F | (6-15) | 9% |
| 4-H2HB(F,F)-F | (6-15) | 8% |
| 5-H2HB(F,F)-F | (6-15) | 7% |
| 3-HBB(F,F)-F | (6-24) | 20% |
| 5-HBB(F,F)-F | (6-24) | 18% |
| 3-H2BB(F,F)-F | (6-27) | 12% |
| 5-HHBB(F,F)-F | (7-6) | 3% |
| 5-HHEBB-F | (7-17) | 2% |
| 3-HH2BB(F,F)-F | (7-15) | 3% |
| 1O1-HBBH-4 | (4-1) | 5% |
| 1O1-HBBH-5 | (4-1) | 3% |

Compound (1-3-1) described below was added to the composition described above in a proportion of 1% by weight.

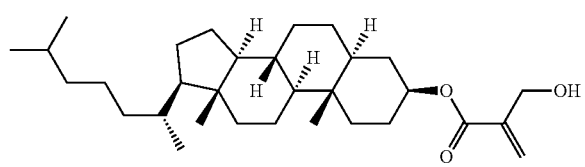

(1-3-1)

NI=97.5° C.; η=34.8 mPa·s; Δn=0.115; Δε=9.0.

Use Example 6

| | | |
|---|---|---|
| 5-HB-CL | (5-2) | 9% |
| 3-HH-4 | (2-1) | 9% |
| 3-HHB-1 | (3-1) | 4% |
| 3-HHB(F,F)-F | (6-3) | 8% |
| 3-HBB(F,F)-F | (6-24) | 19% |
| 5-HBB(F,F)-F | (6-24) | 13% |
| 3-HHEB(F,F)-F | (6-12) | 9% |
| 4-HHEB(F,F)-F | (6-12) | 5% |
| 5-HHEB(F,F)-F | (6-12) | 4% |
| 2-HBEB(F,F)-F | (6-39) | 5% |
| 3-HBEB(F,F)-F | (6-39) | 5% |
| 5-HBEB(F,F)-F | (6-39) | 4% |
| 3-HHBB(F,F)-F | (7-6) | 6% |

Compound (1-5-53) described below was added to the composition described above in a proportion of 2% by weight.

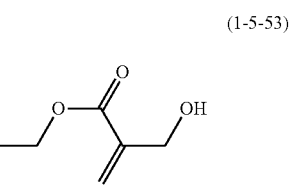

(1-5-53)

NI=81.4° C.; η=23.6 mPa·s; Δn=0.102; Δε=9.2.

Use Example 7

| | | |
|---|---|---|
| 5-HB-F | (5-2) | 12% |
| 6-HB-F | (5-2) | 9% |
| 7-HB-F | (5-2) | 7% |
| 2-HHB-OCF3 | (6-1) | 5% |
| 3-HHB-OCF3 | (6-1) | 7% |
| 4-HHB-OCF3 | (6-1) | 7% |
| 5-HHB-OCF3 | (6-1) | 5% |
| 3-HH2B-OCF3 | (6-4) | 7% |
| 5-HH2B-OCF3 | (6-4) | 4% |
| 3-HHB(F,F)-OCF2H | (6-3) | 5% |
| 3-HHB(F,F)-OCF3 | (6-3) | 4% |
| 3-HH2B(F)-F | (6-5) | 3% |
| 3-HBB(F)-F | (6-23) | 11% |
| 5-HBB(F)-F | (6-23) | 8% |
| 5-HBBH-3 | (4-1) | 3% |
| 3-HB(F)BH-3 | (4-2) | 3% |

Compound (1-4-70) described below was added to the composition described above in a proportion of 5% by weight.

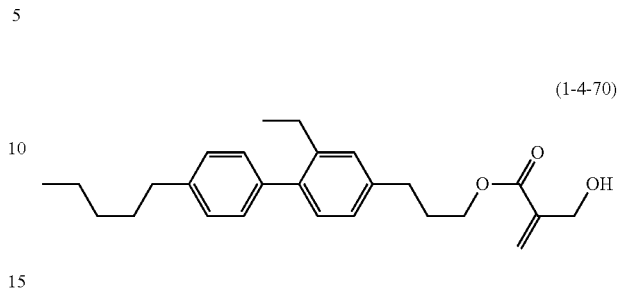

(1-4-70)

Compound (M-1-2) described below was further added thereto in a proportion of 0.3% by weight.

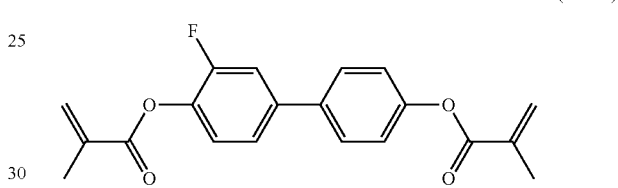

(M-1-2)

NI=86.0° C.; η=14.7 mPa·s; Δn=0.092; Δε=4.4.

Use Example 8

| | | |
|---|---|---|
| 1V2-BEB(F,F)-C | (8-15) | 7% |
| 3-HB-C | (8-1) | 18% |
| 2-BTB-1 | (2-10) | 10% |
| 5-HH-VFF | (2-1) | 30% |
| 3-HHB-1 | (3-1) | 6% |
| VFF-HHB-1 | (3-1) | 5% |
| VFF2-HHB-1 | (3-1) | 11% |
| 3-H2BTB-2 | (3-17) | 4% |
| 3-H2BTB-3 | (3-17) | 5% |
| 3-H2BTB-4 | (3-17) | 4% |

Compound (1-6-69) described below was added to the composition described above in a proportion of 0.5% by weight.

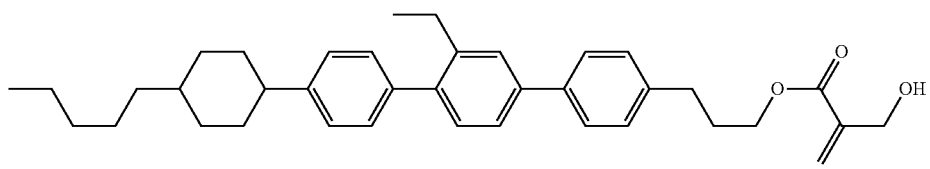
(1-6-69)

NI=80.5° C.; η=12.2 mPa·s; Δn=0.130; Δε=7.1.

Use Example 9

| 3-HB-CL | (5-2) | 7% |
| --- | --- | --- |
| 5-HB-CL | (5-2) | 3% |
| 3-HHB-OCF3 | (6-1) | 5% |
| 3-H2HB-OCF3 | (6-13) | 5% |
| 5-H4HB-OCF3 | (6-19) | 15% |
| V-HHB(F)-F | (6-2) | 5% |
| 3-HHB(F)-F | (6-2) | 6% |
| 5-HHB(F)-F | (6-2) | 4% |
| 3-H4HB(F,F)-CF3 | (6-21) | 8% |
| 5-H4HB(F,F)-CF3 | (6-21) | 10% |
| 5-H2HB(F,F)-F | (6-15) | 5% |
| 5-H4HB(F,F)-F | (6-21) | 7% |
| 2-H2BB(F)-F | (6-26) | 5% |
| 3-H2BB(F)-F | (6-26) | 10% |
| 3-HBEB(F,F)-F | (6-39) | 5% |

Compound (1-4-6) described below was added to the composition described above in a proportion of 4% by weight.

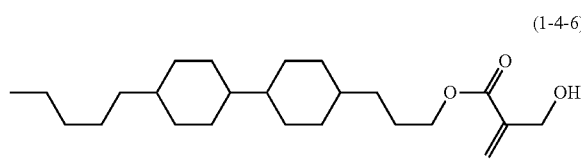 [SMILES: C=C(CO)C(=O)OCCCC1CCC(C2CCC(CCCCC)CC2)CC1]
(1-4-6)

NI=69.6° C.; η=25.3 mPa·s; Δn=0.097; Δε=8.3.

Use Example 10

| 5-HB-CL | (5-2) | 3% |
| --- | --- | --- |
| 7-HB(F)-F | (5-3) | 7% |
| 3-HH-4 | (2-1) | 9% |
| 3-HH-EMe | (2-2) | 21% |
| 3-HHEB-F | (6-10) | 9% |
| 5-HHEB-F | (6-10) | 7% |
| 3-HHEB(F,F)-F | (6-12) | 10% |
| 4-HHEB(F,F)-F | (6-12) | 6% |
| 4-HGB(F,F)-F | (6-103) | 6% |
| 5-HGB(F,F)-F | (6-103) | 6% |
| 2-H2GB(F,F)-F | (6-106) | 4% |
| 3-H2GB(F,F)-F | (6-106) | 6% |
| 5-GHB(F,F)-F | (6-109) | 6% |

Compound (1-3-16) described below was added to the composition described above in a proportion of 2% by weight.

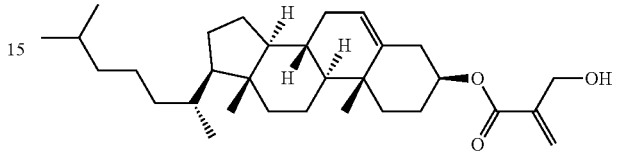
(1-3-16)

NI=79.5° C.; η=20.2 mPa·s; Δn=0.064; Δε=5.8.

Use Example 11

| 7-HB(F,F)-F | (5-4) | 3% |
| --- | --- | --- |
| 3-HB-O2 | (2-5) | 7% |
| 2-HHB(F)-F | (6-2) | 9% |
| 3-HHB(F)-F | (6-2) | 11% |
| 5-HHB(F)-F | (6-2) | 9% |
| 2-HBB(F)-F | (6-23) | 9% |
| 3-HBB(F)-F | (6-23) | 10% |
| 5-HBB(F)-F | (6-23) | 15% |
| 2-HBB-F | (6-22) | 4% |
| 3-HBB-F | (6-22) | 5% |
| 5-HBB-F | (6-22) | 3% |
| 3-HBB(F,F)-F | (6-24) | 5% |
| 5-HBB(F,F)-F | (6-24) | 10% |

Compound (1-4-16) described below was added to the composition described above in a proportion of 5% by weight.

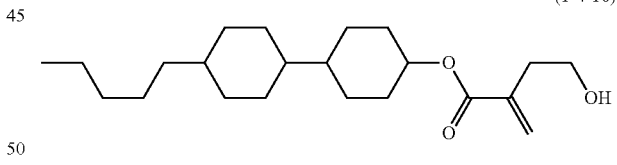
(1-4-16)

NI=85.6° C.; η=24.9 mPa·s; Δn=0.116; Δε=5.8.

Use Example 12

| 3-HB-O2 | (2-5) | 9% |
| --- | --- | --- |
| 5-HB-CL | (5-2) | 12% |
| 3-HBB(F,F)-F | (6-24) | 8% |
| 3-PyB(F)-F | (5-15) | 10% |
| 5-PyB(F)-F | (5-15) | 10% |
| 3-PyBB-F | (6-80) | 11% |
| 4-PyBB-F | (6-80) | 10% |
| 5-PyBB-F | (6-80) | 11% |
| 5-HBB(F)B-2 | (4-5) | 9% |
| 5-HBB(F)B-3 | (4-5) | 10% |

Compound (1-4-82) described below was added to the composition described above in a proportion of 4% by weight.

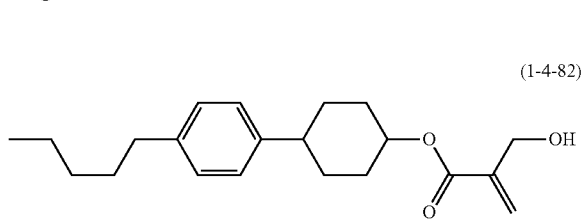
(1-4-82)

NI=100.2° C.; η=40.5 mPa·s; Δn=0.193; Δε=8.3.

Use Example 13

| 5-HB-CL | (5-2) | 9% |
| 3-HH-4 | (2-1) | 9% |
| 3-HHB-1 | (3-1) | 4% |
| 3-HHB(F,F)-F | (6-3) | 8% |
| 3-HBB(F,F)-F | (6-24) | 20% |
| 5-HBB(F,F)-F | (6-24) | 14% |
| 3-HHEB(F,F)-F | (6-12) | 9% |
| 4-HHEB(F,F)-F | (6-12) | 3% |
| 5-HHEB(F,F)-F | (6-12) | 4% |
| 2-HBEB(F,F)-F | (6-39) | 4% |
| 3-HBEB(F,F)-F | (6-39) | 5% |
| 5-HBEB(F,F)-F | (6-39) | 5% |
| 3-HHBB(F,F)-F | (7-6) | 6% |

Compound (1-4-41) described below was added to the composition described above in a proportion of 3% by weight.

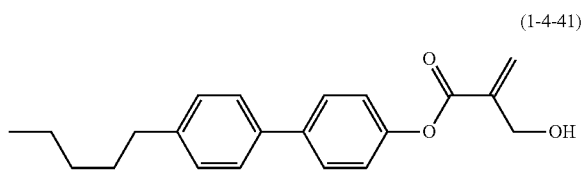 [SMILES: C=C(CO)C(=O)Oc1ccc(-c2ccc(CCCCC)cc2)cc1]
(1-4-41)

NI=80.9° C.; η=23.5 mPa·s; Δn=0.103; Δε=9.1.

Use Example 14

| 5-HB-CL | (5-2) | 16% |
| 7-HB(F,F)-F | (5-4) | 4% |
| 3-HH-4 | (2-1) | 10% |
| 3-HH-5 | (2-1) | 6% |
| 3-HB-O2 | (2-5) | 14% |
| 3-HHB-1 | (3-1) | 8% |
| 3-HHB-O1 | (3-1) | 6% |
| 2-HHB(F)-F | (6-2) | 6% |
| 3-HHB(F)-F | (6-2) | 6% |
| 5-HHB(F)-F | (6-2) | 6% |
| 3-HHB(F,F)-F | (6-3) | 5% |
| 3-H2HB(F,F)-F | (6-15) | 7% |
| 4-H2HB(F,F)-F | (6-15) | 6% |

Compound (1-6-124) described below was added to the composition described above in a proportion of 3% by weight.

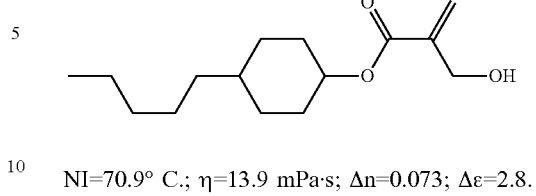
(1-6-124)

NI=70.9° C.; η=13.9 mPa·s; Δn=0.073; Δε=2.8.

Use Example 15

| 7-HB(F,F)-F | (5-4) | 4% |
| 3-HB-O2 | (2-5) | 7% |
| 2-HHB(F)-F | (6-2) | 9% |
| 3-HHB(F)-F | (6-2) | 12% |
| 5-HHB(F)-F | (6-2) | 9% |
| 2-HBB(F)-F | (6-23) | 9% |
| 3-HBB(F)-F | (6-23) | 10% |
| 5-HBB(F)-F | (6-23) | 15% |
| 2-HBB-F | (6-22) | 4% |
| 3-HBB-F | (6-22) | 5% |
| 5-HBB-F | (6-22) | 3% |
| 3-HBB(F,F)-F | (6-24) | 5% |
| 5-HBB(F,F)-F | (6-24) | 8% |

Compound (1-4-5) described below was added to the composition described above in a proportion of 5% by weight.

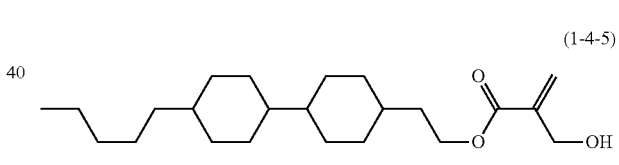
(1-4-5)

NI=84.8° C.; η=24.5 mPa·s; Δn=0.114; Δε=5.6.

Use Example 16

| 2-HB-C | (8-1) | 5% |
| 3-HB-C | (8-1) | 12% |
| 3-HB-O2 | (2-5) | 15% |
| 2-BTB-1 | (2-10) | 3% |
| 3-HHB-F | (6-1) | 3% |
| 3-HHB-1 | (3-1) | 7% |
| 3-HHB-O1 | (3-1) | 4% |
| 3-HHB-3 | (3-1) | 15% |
| 3-HHEB-F | (6-10) | 5% |
| 5-HHEB-F | (6-10) | 3% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 7% |

Compound (1-4-4) described below was added to the composition described above in a proportion of 0.5% by weight.

(1-4-4)

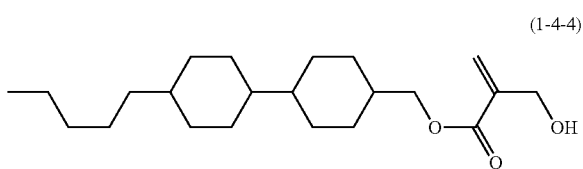 [SMILES: C=C(CO)C(=O)OCC1CCC(C2CCC(CCCCC)CC2)CC1]

NI=98.6° C.; η=17.6 mPa·s; Δn=0.099; Δε=4.8.

Use Example 17

| | | |
|---|---|---|
| 1V2-BEB(F,F)-C | (8-15) | 8% |
| 3-HB-C | (8-1) | 18% |
| 2-BTB-1 | (2-10) | 10% |
| 5-HH-VFF | (2-1) | 28% |
| 3-HHB-1 | (3-1) | 6% |
| VFF-HHB-1 | (3-1) | 6% |
| VFF2-HHB-1 | (3-1) | 11% |
| 3-H2BTB-2 | (3-17) | 4% |
| 3-H2BTB-3 | (3-17) | 4% |
| 3-H2BTB-4 | (3-17) | 5% |

Compound (1-4-108) described below was added to the composition described above in a proportion of 4% by weight.

(1-4-108)

Compound (M-1-1) described below was further added thereto in a proportion of 0.3% by weight.

(M-1-1)

NI=80.9° C.; η=13.2 mPa·s; Δn=0.132; Δε=7.8.

Use Example 18

| | | |
|---|---|---|
| 5-HB-CL | (5-2) | 17% |
| 3-HH-4 | (2-1) | 11% |
| 3-HH-5 | (2-1) | 4% |
| 3-HHB-F | (6-1) | 3% |
| 3-HHB-CL | (6-1) | 3% |
| 4-HHB-CL | (6-1) | 4% |
| 3-HHB(F)-F | (6-2) | 10% |
| 4-HHB(F)-F | (6-2) | 10% |
| 5-HHB(F)-F | (6-2) | 10% |
| 7-HHB(F)-F | (6-2) | 7% |
| 5-HBB(F)-F | (6-23) | 3% |
| 1O1-HBBH-5 | (4-1) | 3% |
| 3-HHBB(F,F)-F | (7-6) | 2% |
| 4-HHBB(F,F)-F | (7-6) | 3% |
| 5-HHBB(F,F)-F | (7-6) | 2% |

-continued

| | | |
|---|---|---|
| 3-HH2BB(F,F)-F | (7-15) | 4% |
| 4-HH2BB(F,F)-F | (7-15) | 4% |

Compound (1-4-26) described below was added to the composition described above in a proportion of 2% by weight.

(1-4-26)

NI=113.9° C.; η=19.1 mPa·s; Δn=0.091; Δε=3.9.

Use Example 19

| | | |
|---|---|---|
| 3-HHB(F,F)-F | (6-3) | 10% |
| 3-H2HB(F,F)-F | (6-15) | 9% |
| 4-H2HB(F,F)-F | (6-15) | 8% |
| 5-H2HB(F,F)-F | (6-15) | 7% |
| 3-HBB(F,F)-F | (6-24) | 20% |
| 5-HBB(F,F)-F | (6-24) | 21% |
| 3-H2BB(F,F)-F | (6-27) | 11% |
| 5-HHBB(F,F)-F | (7-6) | 3% |
| 5-HHBBB-F | (7-17) | 2% |
| 3-HH2BB(F,F)-F | (7-15) | 3% |
| 1O1-HBBH-4 | (4-1) | 3% |
| 1O1-HBBH-5 | (4-1) | 3% |

Compound (1-6-127) described below was added to the composition described above in a proportion of 3% by weight.

(1-6-127)

NI=93.9° C.; η=34.5 mPa·s; Δn=0.114; Δε=9.2.

Use Example 20

| | | |
|---|---|---|
| 5-HB-CL | (5-2) | 3% |
| 7-HB(F)-F | (5-3) | 5% |
| 3-HH-4 | (2-1) | 9% |
| 3-HH-EMe | (2-2) | 20% |
| 3-HHEB-F | (6-10) | 10% |
| 5-HHEB-F | (6-10) | 10% |
| 3-HHEB(F,F)-F | (6-12) | 10% |
| 4-HHEB(F,F)-F | (6-12) | 6% |
| 4-HGB(F,F)-F | (6-103) | 7% |
| 5-HGB(F,F)-F | (6-103) | 6% |
| 2-H2GB(F,F)-F | (6-106) | 4% |
| 3-H2GB(F,F)-F | (6-106) | 4% |
| 5-GHB(F,F)-F | (6-109) | 6% |

Compound (1-6-122) described below was added to the composition described above in a proportion of 5% by weight.

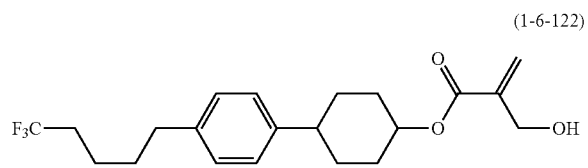 [SMILES: C=C(CO)C(=O)OC1CCC(c2ccc(CCCCC(F)(F)F)cc2)CC1]
(1-6-122)

NI=85.6° C.; η=21.1 mPa·s; Δn=0.066; Δε=5.8.

Use Example 21

| 5-HB-F | (5-2) | 12% |
| 6-HB-F | (5-2) | 9% |
| 7-HB-F | (5-2) | 7% |
| 2-HHB-OCF3 | (6-1) | 6% |
| 3-HHB-OCF3 | (6-1) | 6% |
| 4-HHB-OCF3 | (6-1) | 7% |
| 5-HHB-OCF3 | (6-1) | 5% |
| 3-HH2B-OCF3 | (6-4) | 6% |
| 5-HH2B-OCF3 | (6-4) | 4% |
| 3-HHB(F,F)-OCF2H | (6-3) | 5% |
| 3-HHB(F,F)-OCF3 | (6-3) | 5% |
| 3-HH2B(F)-F | (6-5) | 3% |
| 3-HHB(F)-F | (6-2) | 11% |
| 5-HBB(F)-F | (6-23) | 8% |
| 5-HBBH-3 | (4-1) | 3% |
| 3-HB(F)BH-3 | (4-2) | 3% |

Compound (1-6-121) described below was added to the composition described above in a proportion of 3% by weight.

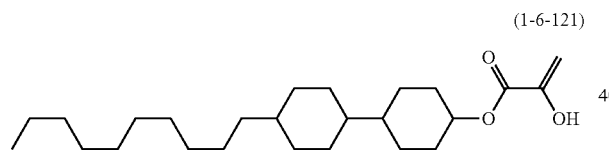
(1-6-121)

NI=85.4° C.; η=15.0 mPa·s; Δn=0.092; Δε=4.5.

Use Example 22

| 3-HB-CL | (5-2) | 6% |
| 5-HB-CL | (5-2) | 3% |
| 3-HHB-OCF3 | (6-1) | 4% |
| 3-H2HB-OCF3 | (6-4) | 5% |
| 5-H4HB-OCF3 | (6-7) | 15% |
| V-HHB(F)-F | (6-2) | 7% |
| 3-HHB(F)-F | (6-2) | 5% |
| 5-HHB(F)-F | (6-2) | 5% |
| 3-H4HB(F,F)-CF3 | (6-21) | 8% |
| 5-H4HB(F,F)-CF3 | (6-21) | 10% |
| 5-H2HB(F,F)-F | (6-15) | 5% |
| 5-H4HB(F,F)-F | (6-21) | 7% |
| 2-H2BB(F)-F | (6-5) | 5% |
| 3-H2BB(F)-F | (6-5) | 10% |
| 3-HBEB(F,F)-F | (6-39) | 5% |

Compound (1-6-123) described below was added to the composition described above in a proportion of 5% by weight.

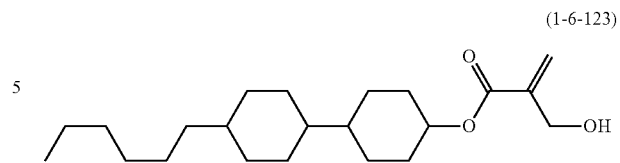
(1-6-123)

NI=70.5° C.; η=25.6 mPa·s; Δn=0.097; Δε=8.3.

Use Example 23

| 5-HB-CL | (5-2) | 9% |
| 3-HH-4 | (2-1) | 9% |
| 3-HHB-1 | (3-1) | 5% |
| 3-HHB(F,F)-F | (6-3) | 8% |
| 3-HBB(F,F)-F | (6-24) | 14% |
| 5-HBB(F,F)-F | (6-24) | 16% |
| 3-HHEB(F,F)-F | (6-12) | 9% |
| 4-HHEB(F,F)-F | (6-12) | 5% |
| 5-HHEB(F,F)-F | (6-12) | 5% |
| 2-HBEB(F,F)-F | (6-39) | 5% |
| 3-HBEB(F,F)-F | (6-39) | 5% |
| 5-HBEB(F,F)-F | (6-39) | 4% |
| 3-HHBB(F,F)-F | (7-6) | 6% |

Compound (1-4-3) described below was added to the composition described above in a proportion of 2.5% by weight.

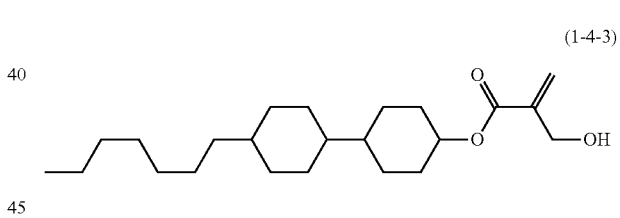
(1-4-3)

NI=83.3° C.; η=23.6 mPa·s; Δn=0.101; Δε=9.1.

Use Example 24

| 7-HB(F,F)-F | (5-4) | 3% |
| 3-HB-O2 | (2-5) | 5% |
| 2-HHB(F)-F | (6-2) | 9% |
| 3-HHB(F)-F | (6-2) | 13% |
| 5-HHB(F)-F | (6-2) | 9% |
| 2-HBB(F)-F | (6-23) | 9% |
| 3-HBB(F)-F | (6-23) | 9% |
| 5-HBB(F)-F | (6-23) | 15% |
| 2-HBB-F | (6-22) | 4% |
| 3-HBB-F | (6-22) | 5% |
| 5-HBB-F | (6-22) | 5% |
| 3-HBB(F,F)-F | (6-24) | 5% |
| 5-HBB(F,F)-F | (6-24) | 9% |

Compound (1-6-126) described below was added to the composition described above in a proportion of 5% by weight.

(1-6-126)

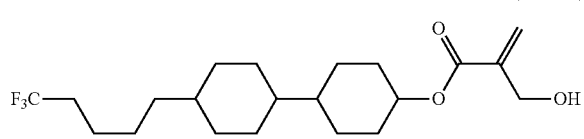

NI=88.3° C.; η=25.5 mPa·s; Δn=0.117; Δε=5.8.

Use Example 25

| | | |
|---|---|---|
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 12% |
| 4-PyBB-F | (6-80) | 8% |
| 5-PyBB-F | (6-80) | 13% |
| 5-HBB(F) B-2 | (4-5) | 7% |
| 5-HBB(F) B-3 | (4-5) | 10% |

Compound (1-6-129) described below was added to the composition described above in a proportion of 5% by weight.

(1-6-129)

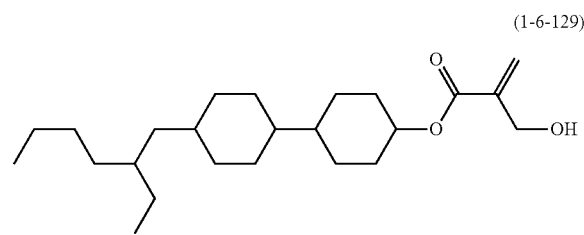 [SMILES: C=C(CO)C(=O)OC1CCC(C2CCC(CC(CC)CCCC)CC2)CC1]

Compound (M-1-2) described below was further added thereto in a proportion of 0.3% by weight.

(M-1-2)

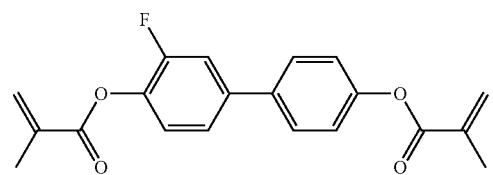

NI=96.8° C.; η=39.3 mPa·s; Δn=0.190; Δε=8.4.

Use Example 26

| | | |
|---|---|---|
| 1V2-BEB(F,F)-C | (8-15) | 7% |
| 3-HB-C | (8-1) | 20% |
| 2-BTB-1 | (2-10) | 10% |
| 5-HH-VFF | (2-1) | 30% |
| 3-HHB-1 | (3-1) | 6% |
| VFF-HHB-1 | (3-1) | 5% |
| VFF2-HHB-1 | (3-1) | 9% |
| 3-H2BTB-2 | (3-17) | 3% |
| 3-H2BTB-3 | (3-17) | 7% |
| 3-H2BTB-4 | (3-17) | 3% |

Compound (1-6-128) described below was added to the composition described above in a proportion of 3% by weight.

(1-6-128)

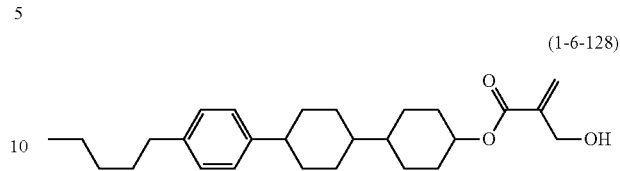

NI=78.6° C.; η=12.3 mPa·s; Δn=0.130; Δε=7.3.

Use Example 28

| | | |
|---|---|---|
| 3-HB-CL | (5-2) | 8% |
| 5-HB-CL | (5-2) | 3% |
| 3-HHB-OCF3 | (6-1) | 5% |
| 3-H2HB-OCF3 | (6-4) | 5% |
| 5-H4HB-OCF3 | (6-7) | 15% |
| V-HHB(F)-F | (6-2) | 5% |
| 3-HHB(F)-F | (6-2) | 4% |
| 5-HHB(F)-F | (6-2) | 7% |
| 3-H4HB(F,F)-CF3 | (6-21) | 8% |
| 5-H4HB(F,F)-CF3 | (6-21) | 10% |
| 5-H2HB(F,F)-F | (6-15) | 5% |
| 5-H4HB(F,F)-F | (6-21) | 7% |
| 2-H2BB(F)-F | (6-26) | 5% |
| 3-H2BB(F)-F | (6-26) | 8% |
| 3-HBEB(F,F)-F | (6-39) | 5% |

Compound (1-6-125) described below was added to the composition described above in a proportion of 5% by weight.

(1-6-125)

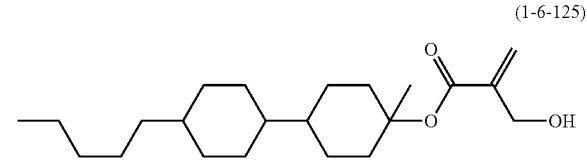 [SMILES: C=C(CO)C(=O)OC1(C)CCC(C2CCC(CCCCC)CC2)CC1]

NI=69.1° C.; η=24.7 mPa·s; Δn=0.096; Δε=8.2.

Use Example 29

| | | |
|---|---|---|
| 5-HB-F | (5-2) | 12% |
| 6-HB-F | (5-2) | 9% |
| 7-HB-F | (5-2) | 7% |
| 2-HHB-OCF3 | (6-1) | 5% |
| 3-HHB-OCF3 | (6-1) | 6% |
| 4-HHB-OCF3 | (6-1) | 7% |
| 5-HHB-OCF3 | (6-1) | 5% |
| 3-HH2B-OCF3 | (6-4) | 5% |
| 5-HH2B-OCF3 | (6-4) | 4% |
| 3-HHB(F,F)-OCF2H | (6-3) | 5% |
| 3-HHB(F,F)-OCF3 | (6-3) | 5% |
| 3-HH2B(F)-F | (6-5) | 3% |
| 3-HBB(F)-F | (6-23) | 11% |
| 5-HBB(F)-F | (6-23) | 10% |
| 5-HBBH-3 | (4-1) | 3% |
| 3-HB(F)BH-3 | (4-2) | 3% |

Compound (1-6-132) described below was added to the composition described above in a proportion of 5% by weight.

(1-6-132)

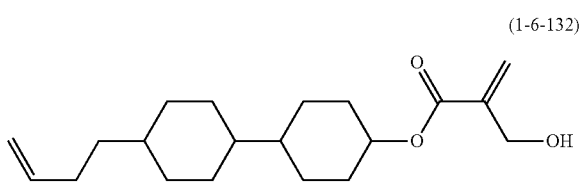 [SMILES: C=CCCC1CCC(C2CCC(OC(=O)C(=C)CO)CC2)CC1]

NI=85.1° C.; η=15.3 mPa·s; Δn=0.093; Δε=4.5.

Use Example 30

| | | |
|---|---|---|
| 5-HB-CL | (5-2) | 16% |
| 3-HH-4 | (2-1) | 13% |
| 3-HH-5 | (2-1) | 4% |
| 3-HHB-F | (6-1) | 3% |
| 3-HHB-CL | (6-1) | 3% |
| 4-HHB-CL | (6-1) | 4% |
| 3-HHB(F)-F | (6-2) | 10% |
| 4-HHB(F)-F | (6-2) | 10% |
| 5-HHB(F)-F | (6-2) | 8% |
| 7-HHB(F)-F | (6-2) | 8% |
| 5-HBB(F)-F | (6-23) | 3% |
| 1O1-HBBH-5 | (4-1) | 3% |
| 3-HHBB(F,F)-F | (7-6) | 3% |
| 4-HHBB(F,F)-F | (7-6) | 3% |
| 5-HHBB(F,F)-F | (7-6) | 3% |
| 3-HH2BB(F,F)-F | (7-15) | 3% |
| 4-HH2BB(F,F)-F | (7-15) | 3% |

Compound (1-6-133) described below was added to the composition described above in a proportion of 3% by weight.

(1-6-133)

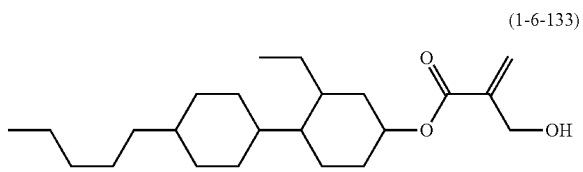 [SMILES: C=C(CO)C(=O)OC1CCC(C2CCC(CCCCC)CC2)C(CC)C1]

NI=114.2° C.; η=18.9 mPa·s; Δn=0.090; Δε=3.8.

Use Example 31

| | | |
|---|---|---|
| 5-HB-CL | (5-2) | 3% |
| 7-HB(F)-F | (5-3) | 7% |
| 3-HH-4 | (2-1) | 9% |
| 3-HH-EMe | (2-2) | 21% |
| 3-HHEB-F | (6-10) | 9% |
| 5-HHEB-F | (6-10) | 8% |
| 3-HHEB(F,F)-F | (6-12) | 9% |
| 4-HHEB(F,F)-F | (6-12) | 7% |
| 4-HGB(F,F)-F | (6-103) | 6% |
| 5-HGB(F,F)-F | (6-103) | 6% |
| 2-H2GB(F,F)-F | (6-106) | 4% |
| 3-H2GB(F,F)-F | (6-106) | 6% |
| 5-GHB(F,F)-F | (6-109) | 5% |

Compound (1-6-131) described below was added to the composition described above in a proportion of 5% by weight.

(1-6-131)

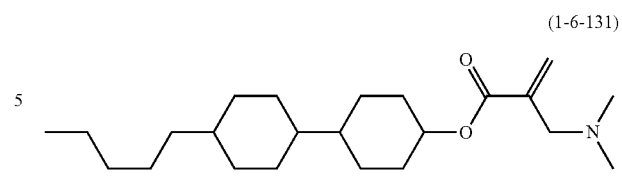

NI=80.6° C.; η=19.8 mPa·s; Δn=0.065; Δε=5.6.

INDUSTRIAL APPLICABILITY

Compound (1) has high chemical stability, high capability of aligning liquid crystal molecules, high solubility in a liquid crystal composition, and a large voltage holding ratio when used in a liquid crystal display device. A liquid crystal composition containing compound (1) satisfies at least one of characteristics such as high maximum temperature, low minimum temperature, small viscosity, suitable optical anisotropy, large positive or negative dielectric anisotropy, large specific resistance, high stability to ultraviolet light, high stability to heat and a large elastic constant. A liquid crystal display device including the composition has characteristics such as a wide temperature range in which the device can be used, a short response time, a large voltage holding ratio, low threshold voltage, a large contrast ratio and a long service life, and therefore can be used in a liquid crystal projector, a liquid crystal television and so forth.

What is claimed is:
1. A compound, represented by formula (1):

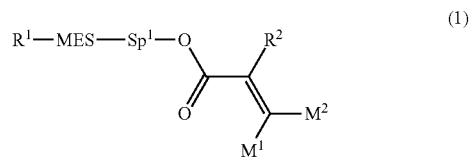

wherein, in formula (1),
R$^1$ is alkyl having 1 to 15 carbons, and in the alkyl, at least one —CH$_2$— may be replaced by —O— or —S—, and at least one piece of —(CH$_2$)$_2$— may be replaced by —CH=CH— or —C≡C—, and in the groups, at least one hydrogen may be replaced by halogen;
MES is a mesogen group having at least one ring;
Sp$^1$ is a single bond or alkylene having 1 to 10 carbons, and in the alkylene, at least one —CH$_2$— may be replaced by —O—, —CO—, —COO—, —OCO— or —OCOO—, and at least one (CH$_2$)$_2$— may be replaced by —CH=CH— or —C≡C—, and in the groups, at least one hydrogen may be replaced by halogen;
M$^1$ and M$^2$ are independently hydrogen, halogen, alkyl having 1 to 5 carbons, or alkyl having 1 to 5 carbons in which at least one hydrogen is replaced by halogen; and
R$^2$ is a group represented by formula (1a), formula (1b) or formula (1c):

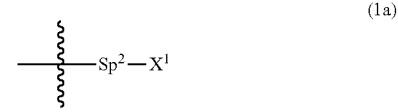

-continued

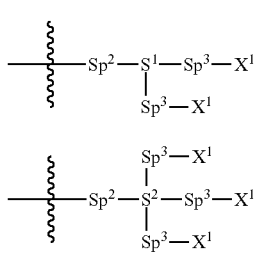

wherein, in formula (1a), formula (1b) and formula (1c),
Sp² and Sp³ are independently a single bond or alkylene having 1 to 10 carbons, and in the alkylene, at least one —CH₂— may be replaced by —O—, —NH—, —CO—, —COO—, —OCO— or —OCOO—, and at least one —(CH₂)₂— may be replaced by —CH=CH— or —C≡C— and in the groups, at least one hydrogen may be replaced by halogen;
S¹ is >CH— or >N—;
S² is >C< or >Si<; and
X¹ is a group represented by —OH, —NH₂, —OR³, —N(R³)₂, formula (x1), —COOH, —SH, —B(OH)₂ or —Si(R³)₃, in which R³ is hydrogen or alkyl having 1 to 10 carbons, and in the alkyl, at least one CH₂— may be replaced by —O—, and at least one —(CH₂)₂— may be replaced by —CH=CH—, and in the groups, at least one hydrogen may be replaced by halogen, and w in formula (x1) is 1, 2, 3 or 4:

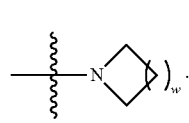

2. The compound according to claim 1, represented by formula (1-1):

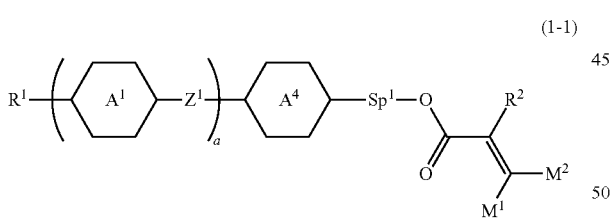

wherein, in formula (1-1),
R¹ is alkyl having 1 to 15 carbons, and in the alkyl, at least one —CH₂— may be replaced by —O— or —S—, and at least one —(CH₂)₂— may be replaced by —CH=CH— or —C≡C, and in the groups, at least one hydrogen may be replaced by halogen;
ring A¹ and ring A⁴ are independently 1,4-cyclohexylene, 1,4-cyclohexenylene, 1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, fluorene-2,7-diyl, phenanthrene-2,7-diyl, anthracene-2,6-diyl, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one hydrogen may be replaced by fluorine or chlorine;
Z¹ is a single bond or alkylene having 1 to 10 carbons, and in the alkylene, at least one —CH₂— may be replaced by —O—, —CO—, —COO—, —OCO— or —OCOO—, and at least one —(CH₂)₂— may be replaced by —CH=CH— or —C≡C—, and in the groups, at least one hydrogen may be replaced by halogen;
Sp¹ is a single bond or alkylene having 1 to 10 carbons, and in the alkylene, at least one —CH₂— may be replaced by —O—, —CO—, —COO—, —OCO— or —OCOO—, and at least one —(CH₂)₂— may be replaced by —CH=CH— or —C≡C— and in the groups, at least one hydrogen may be replaced by halogen;
M¹ and M² are independently hydrogen, halogen, alkyl having 1 to 5 carbons, or alkyl having 1 to 5 carbons in which at least one hydrogen is replaced by halogen;
a is 0, 1, 2, 3 or 4; and
R² is a group represented by formula (1a) or formula (1b):

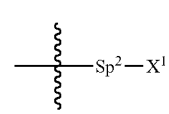

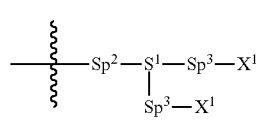

wherein, in formula (1a) and formula (1b),
Sp² and Sp³ are independently a single bond or alkylene having 1 to 10 carbons, and in the alkylene, at least one —CH₂— may be replaced by —O—, —NH—, —CO—, —COO—, —OCO— or —OCOO—, and at least one —(CH₂)₂— may be replaced by —CH=CH— or —C≡C— and in the groups, at least one hydrogen may be replaced by halogen;
S¹ is >CH— or >N—; and
X¹ is a group represented by —OH, —NH₂, —OR³, —N(R³)₂, formula (x1), —COOH, —SH, —B(OH)₂ or —Si(R³)₃, in which R³ is hydrogen or alkyl having 1 to 10 carbons, and in the alkyl, at least one CH₂— may be replaced by —O—, and at least one —(CH₂)₂— may be replaced by —CH=CH—, and in the groups, at least one hydrogen may be replaced by halogen, and w in formula (x1) is 1, 2, 3 or 4:

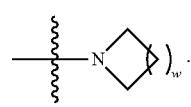

3. The compound according to claim 1, represented by formula (1-2):

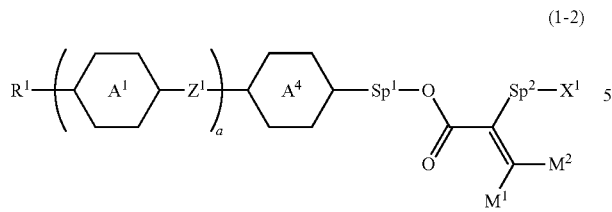

(1-2)

wherein, in formula (1-2),
R¹ is alkyl having 1 to 15 carbons, alkenyl having 2 to 15 carbons, alkoxy having 1 to 14 carbons or alkenyloxy having 2 to 14 carbons, and in the groups, at least one hydrogen may be replaced by fluorine or chlorine;

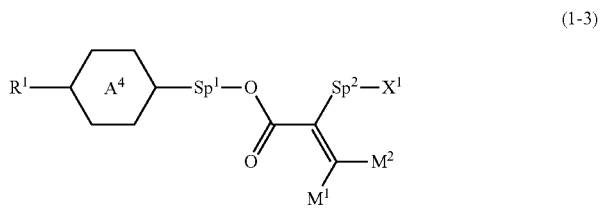

(1-3)

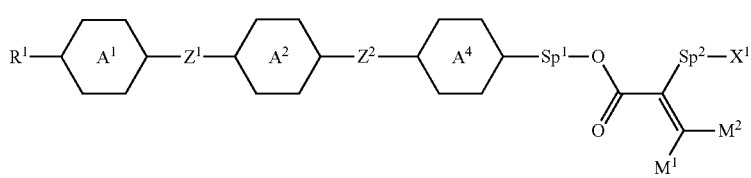

(1-5)

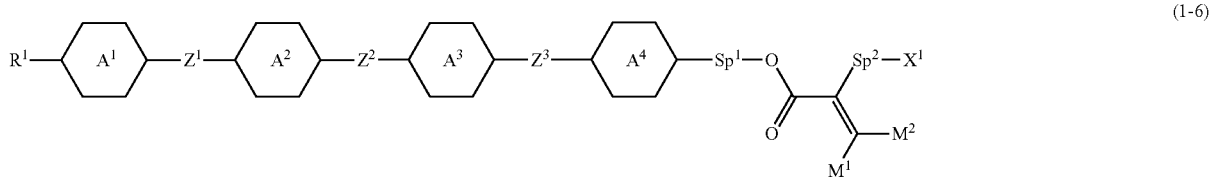

(1-6)

ring $A^1$ and ring $A^4$ are independently 1,4-cyclohexylene, 1,4-cyclohexenylene, 1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one hydrogen may be replaced by fluorine or chlorine;
$Z^1$ is a single bond, —(CH$_2$)$_2$—, —CH=CH—, —COO—, —OCO—, —CF$_2$O—, —OCF$_2$—, —CH$_2$O—, —OCH$_2$— or —CF=CF—;
Sp¹ and Sp² are independently a single bond or alkylene having 1 to 10 carbons, and in the alkylene, at least one —CH$_2$— may be replaced by —O—, —COO— or —OCO—, and at least one —(CH$_2$)$_2$— may be replaced by —CH=CH—, and in the groups, at least one hydrogen may be replaced by fluorine or chlorine;
$M^1$ and $M^2$ are independently hydrogen, fluorine, alkyl having 1 to 5 carbons, or alkyl having 1 to 5 carbons in which at least one hydrogen is replaced by fluorine;
$X^1$ is a group represented by —OH, —NH$_2$, —OR³, —N(R³)$_2$, formula (x1), —COOH, —SH, —B(OH)$_2$ or —Si(R³)$_3$, in which R³ is hydrogen or alkyl having 1 to 10 carbons, and in the alkyl, at least one —CH$_2$— may be replaced by —O—, and at least one —(CH$_2$)$_2$— may be replaced by —CH=CH—, and in the groups, at least one hydrogen may be replaced by fluorine or chlorine, and w in formula (x1) is 1, 2, 3 or 4; and

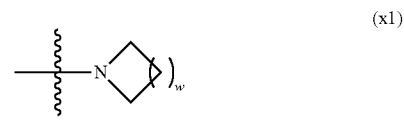

(x1)

wherein, a is 0, 1, 2, 3 or 4.

4. The compound according to claim 1, represented by any one of formula (1-3) to formula (1-6):

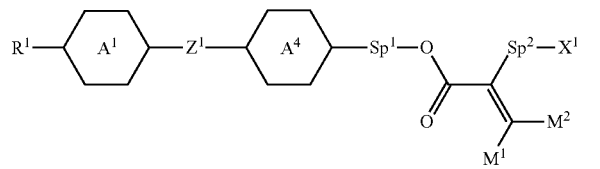

(1-4)

wherein, in formula (1-3) to formula (1-6),
R¹ is alkyl having 1 to 15 carbons, alkenyl having 2 to 15 carbons, alkoxy having 1 to 14 carbons or alkenyloxy having 2 to 14 carbons, and in the groups, at least one hydrogen may be replaced by fluorine;
ring $A^1$, ring $A^2$, ring $A^3$ and ring $A^4$ are independently 1,4-cyclohexylene, 1,4-cyclohexenylene, 1,4-phenylene, naphthalene-2,6-diyl, decahydronaphthalene-2,6-diyl, tetrahydropyran-2,5-diyl, 1,3-dioxane-2,5-diyl, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be replaced by fluorine, chlorine, alkyl having 1 to 7 carbons, alkenyl having 2 to 7 carbons or alkoxy having 1 to 6 carbons;
$Z^1$, $Z^2$ and $Z^3$ are independently a single bond, —(CH$_2$)$_2$—, —CH=CH—, —COO—, —OCO—, —CF$_2$O—, —OCF$_2$—, —CH$_2$O—, —OCH$_2$— or —CF=CF—;
Sp¹ and Sp² are independently a single bond or alkylene having 1 to 7 carbons, and in the alkylene, at least one —CH$_2$— may be replaced by —O—, —COO— or —OCO—, and at least one —(CH$_2$)$_2$— may be replaced by —CH=CH—, and in the groups, at least one hydrogen may be replaced by fluorine;
$M^1$ and $M^2$ are independently hydrogen, fluorine, methyl, ethyl or trifluoromethyl; and
$X^1$ is a group represented by —OH, —NH$_2$, —OR³, —N(R³)$_2$, formula (x1) or —Si(R³)$_3$, in which R³ is hydrogen or alkyl having 1 to 5 carbons, and in the alkyl, at least one —CH$_2$— may be replaced by —O—, and at least one —(CH$_2$)$_2$— may be replaced by —CH=CH—, and in the groups, at least one hydrogen may be replaced by fluorine, and w in formula (x1) is 1, 2, 3 or 4:

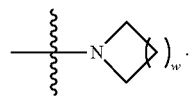
(x1)

5. The compound according to claim 1, represented by any one of formula (1-7) to formula (1-10):

perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be replaced by fluorine, chlorine, alkyl having 1 to 5 carbons, alkenyl having 2 to 5 carbons or alkoxy having 1 to 4 carbons;

$Z^1$, $Z^2$ and $Z^3$ are independently a single bond, —(CH$_2$)$_2$— or —CH=CH—;

Sp$^1$ is a single bond or alkylene having 1 to 7 carbons, and in the alkylene, at least one —CH$_2$— may be replaced by —O—, and at least one —(CH$_2$)$_2$— may be replaced by —CH=CH—;

Sp$^2$ is alkylene having 1 to 7 carbons, and in the alkylene, at least one —CH$_2$— may be replaced by —O—; and

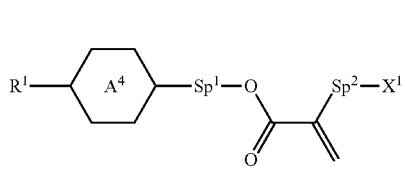
(1-7)

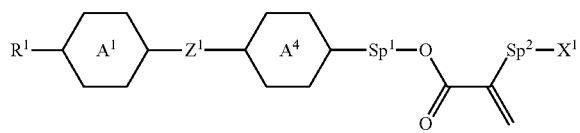
(1-8)

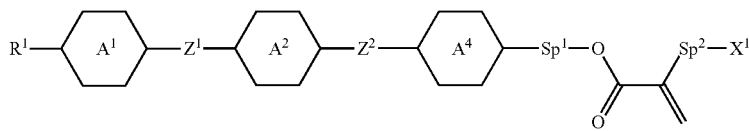
(1-9)

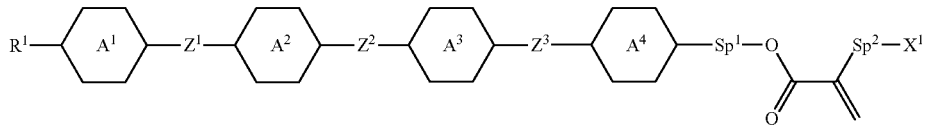
(1-10)

wherein, in formula (1-7) to formula (1-10),

R$^1$ is alkyl having 1 to 10 carbons, alkenyl having 2 to 10 carbons or alkoxy having 1 to 9 carbons, and in the groups, at least one hydrogen may be replaced by fluorine;

ring A$^1$, ring A$^2$, ring A$^3$ and ring A$^4$ are independently 1,4-cyclohexylene, 1,4-cyclohexenylene, 1,4-phenylene, tetrahydropyran-2,5-diyl, 1,3-dioxane-2,5-diyl, X$^1$ is —OH, —NH$_2$ or —N(R$^3$)$_2$, in which R$^3$ is hydrogen or alkyl having 1 to 5 carbons, and in the alkyl, at least one —CH$_2$— may be replaced by —O—, and at least one —(CH$_2$)$_2$— may be replaced by —CH=CH—, and in the groups, at least one hydrogen may be replaced by fluorine.

6. The compound according to claim 1, represented by any one of formula (1-11) to formula (1-14):

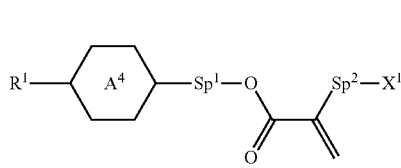
(1-11)

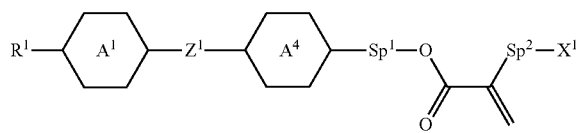
(1-12)

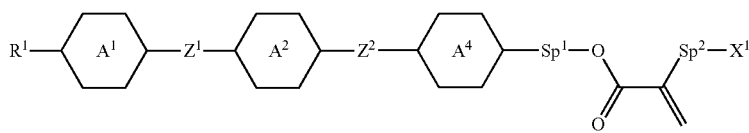
(1-13)

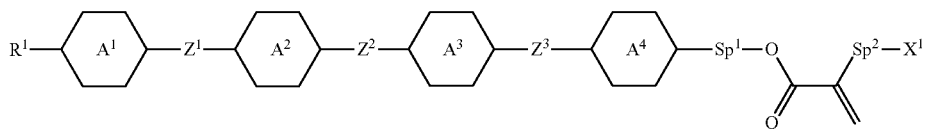
(1-14)

wherein, in formula (1-11) to formula (1-14),

R¹ is alkyl having 1 to 10 carbons, alkenyl having 2 to 10 carbons or alkoxy having 1 to 9 carbons, and in the groups, at least one hydrogen may be replaced by fluorine;

ring $A^1$, ring $A^2$, ring $A^3$ and ring $A^4$ are independently 1,4-cyclohexylene, 1,4-phenylene, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be replaced by fluorine or alkyl having 1 to 5 carbons;

$Z^1$, $Z^2$ and $Z^3$ are independently a single bond or —(CH$_2$)$_2$—;

$Sp^1$ is a single bond or alkylene having 1 to 5 carbons, and in the alkylene, at least one —CH$_2$— may be replaced by —O—;

$Sp^2$ is alkylene having 1 to 5 carbons, and in the alkylene, at least one —CH$_2$— may be replaced by —O—; and $X^1$ is —OH, —NH$_2$ or —N(R$^3$)$_2$, in which R$^3$ is hydrogen or alkyl having 1 to 5 carbons, and in the alkyl, at least one —CH$_2$— may be replaced by —O—, and at least one —(CH$_2$)$_2$— may be replaced by —CH═CH—, and in the groups, at least one hydrogen may be replaced by fluorine.

7. The compound according to claim 1, represented by any one of formula (1-15) to formula (1-31):

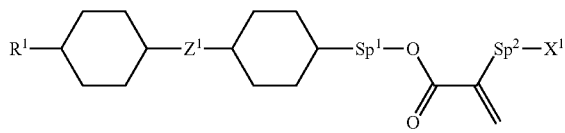
(1-15)

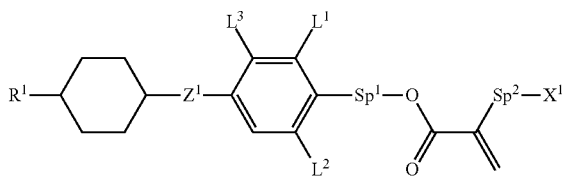
(1-16)

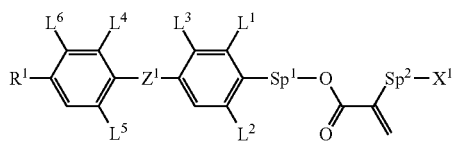
(1-18)

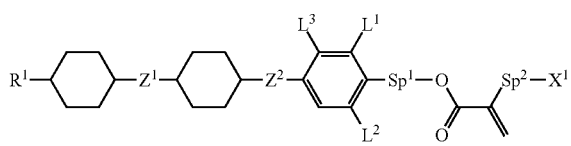
(1-17)

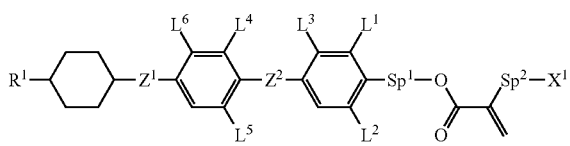
(1-19)

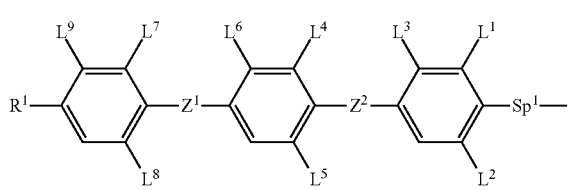
(1-20)

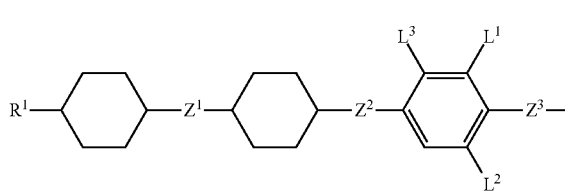
(1-21)

(1-22)

(1-23)

(1-24)

-continued

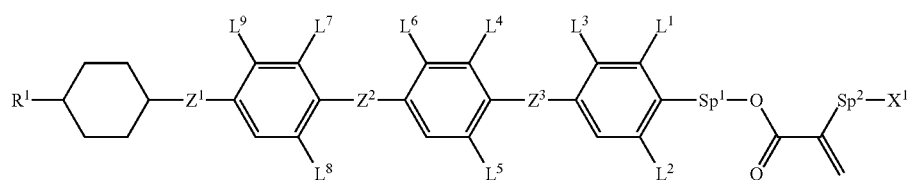
(1-25)

(1-26)

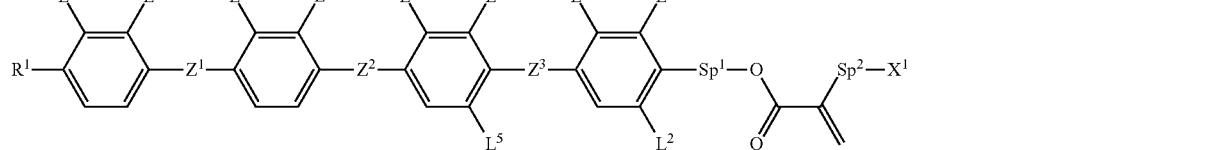

(1-27) (1-28)

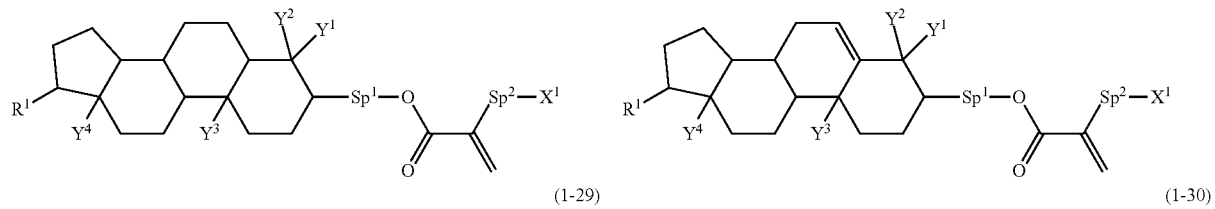

(1-29) (1-30)

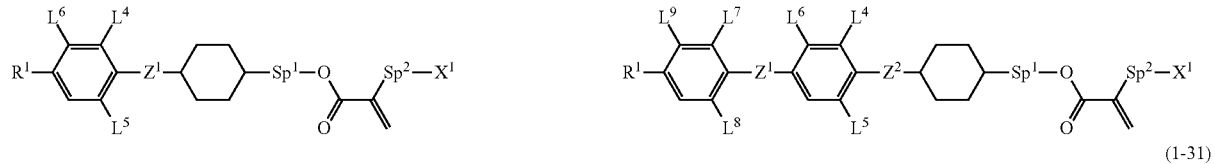

(1-31)

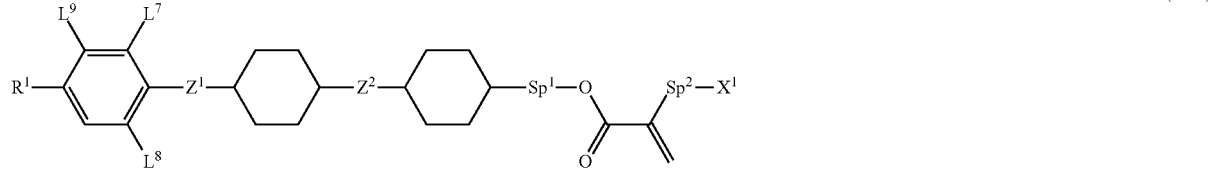

wherein, in formula (1-15) to formula (1-31),
$R^1$ is alkyl having 1 to 10 carbons, alkenyl having 2 to 10 carbons or alkoxy having 1 to 9 carbons, and in the groups, at least one hydrogen may be replaced by fluorine;
$Z^1$, $Z^2$ and $Z^3$ are independently a single bond or —(CH$_2$)$_2$—;
$Sp^1$ is a single bond or alkylene having 1 to 5 carbons, and in the alkylene, at least one —CH$_2$— may be replaced by —O—;
$Sp^2$ is alkylene having 1 to 5 carbons, and in the alkylene, at least one —CH$_2$— may be replaced by —O—;

$L^1$, $L^2$, $L^3$, $L^4$, $L^5$, $L^6$, $L^7$, $L^8$, $L^9$ and $L^{10}$ are independently hydrogen, fluorine, methyl or ethyl;
$Y^1$, $Y^2$, $Y^3$ and $Y^4$ are independently hydrogen or methyl; and
$X^1$ is —OH, —NH$_2$ or —N(R$^3$)$_2$, in which R$^3$ is hydrogen or alkyl having 1 to 4 carbons, and in the alkyl, at least one —CH$_2$— may be replaced by —O—, and in the groups, at least one hydrogen may be replaced by fluorine.

8. The compound according to claim 1, represented by any one of formula (1-32) to formula (1-43):

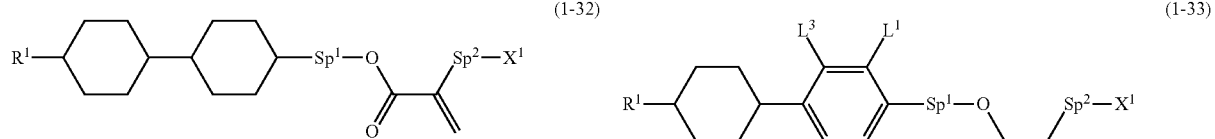

(1-32) (1-33)

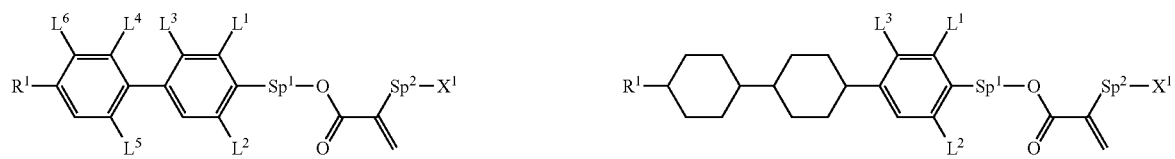

(1-34) (1-35)

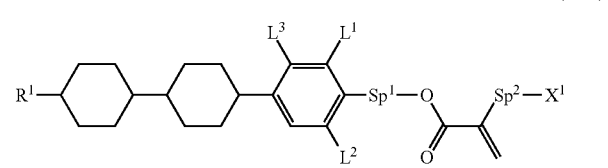

-continued (1-36)
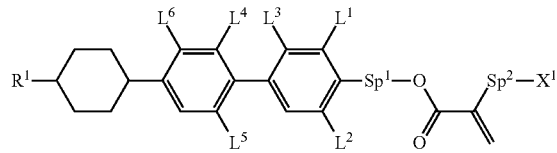

(1-37)
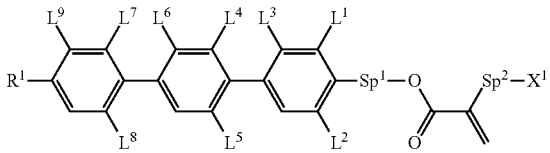

(1-38)
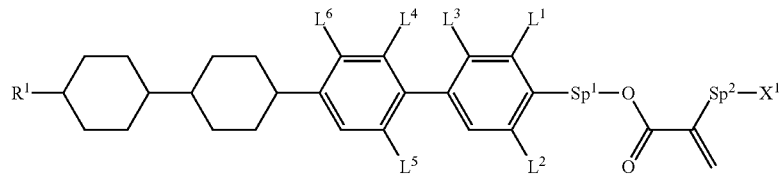

(1-39)
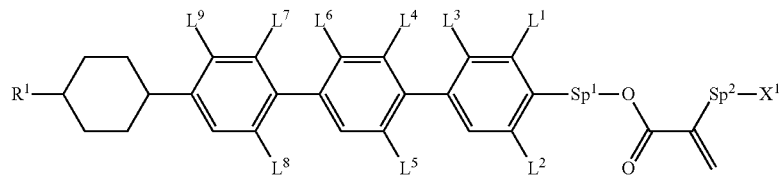

(1-40)
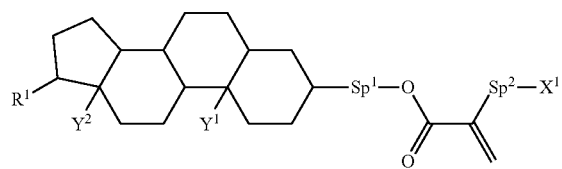

(1-41)
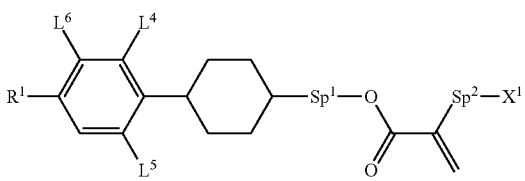

(1-42)
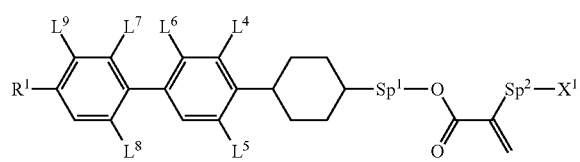

wherein, in formula (1-32) to formula (1-43),
  $R^1$ is alkyl having 1 to 10 carbons;
  $Sp^1$ is a single bond or alkylene having 1 to 5 carbons, and in the alkylene, at least one —$CH_2$— may be replaced by —O—, and in the groups, at least one hydrogen may be replaced by fluorine;
  $Sp^2$ is alkylene having 1 to 5 carbons, and in the alkylene, at least one —$CH_2$— may be replaced by —O—;
  $L^1$, $L^2$, $L^3$, $L^4$, $L^5$, $L^6$, $L^7$, $L^8$ and $L^9$ are independently hydrogen, fluorine, methyl or ethyl;
  $Y^1$ and $Y^2$ are independently hydrogen or methyl; and
  $X^1$ is —OH, —$NH_2$ or —$N(R^3)_2$, in which $R^3$ is hydrogen or alkyl having 1 to 4 carbons, and in the alkyl, at least one —$CH_2$— may be replaced by —O—.

9. The compound according to claim 1, represented by any one of formula (1-44) to formula (1-63):

(1-44)
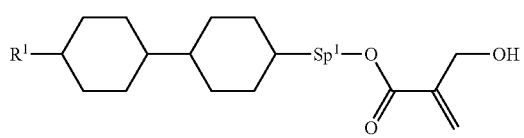

-continued (1-45)
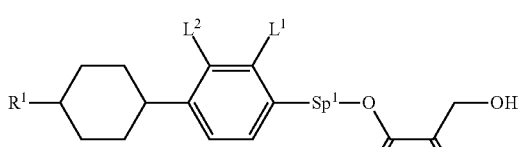

(1-46)
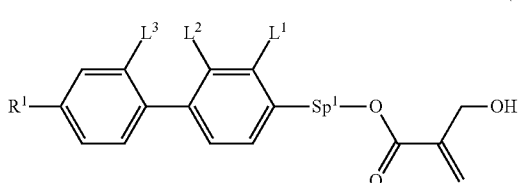

(1-47)
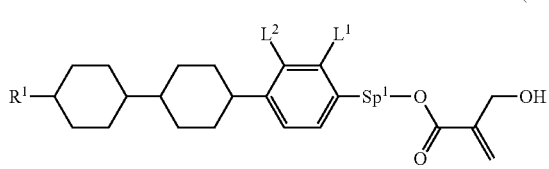

(1-48) 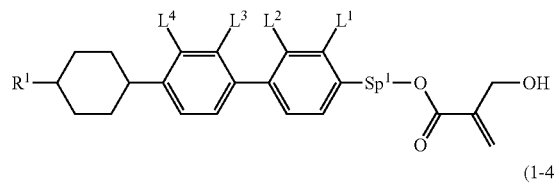
(1-49) 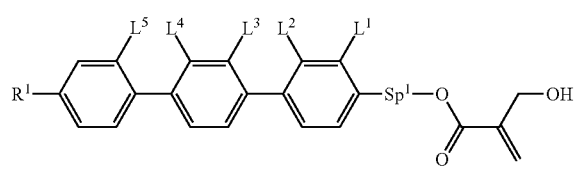
(1-50) 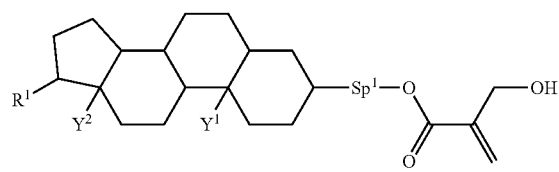
(1-51) 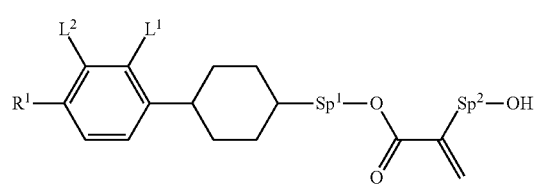
(1-52) 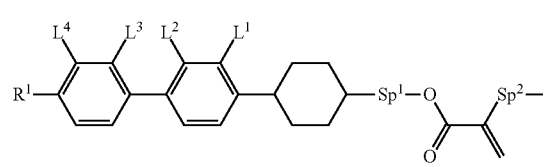
(1-53) 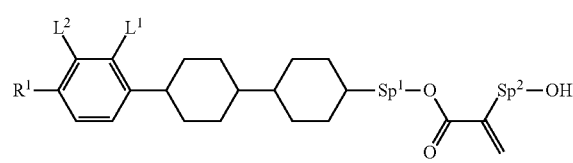
(1-54) 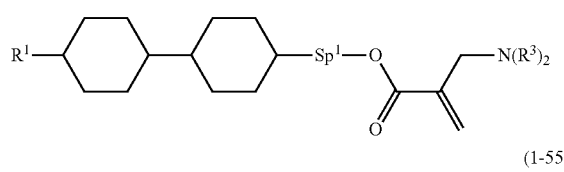
(1-55) 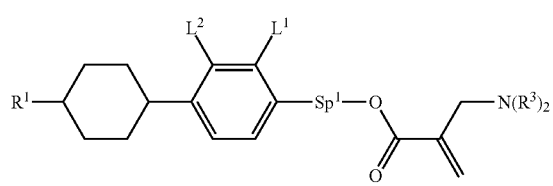
(1-56) 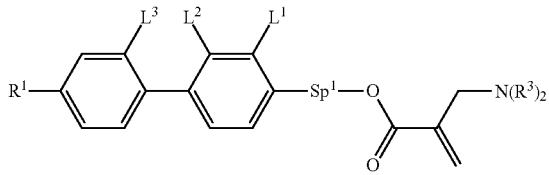
(1-57) 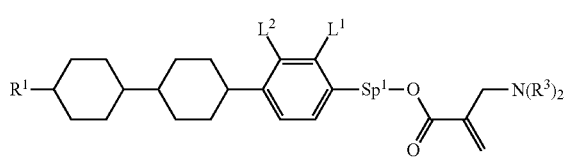
(1-58) 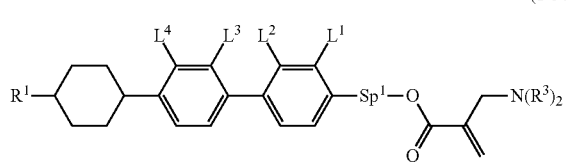
(1-59) 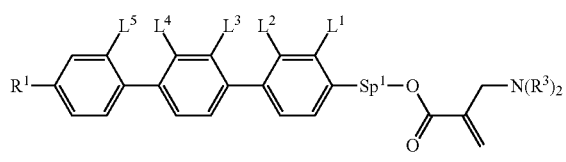
(1-60) 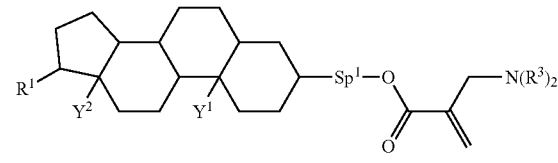
(1-61) 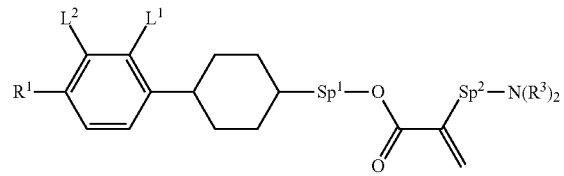
(1-62) 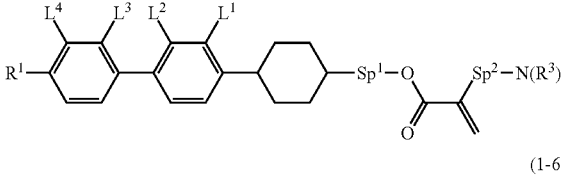
(1-63) 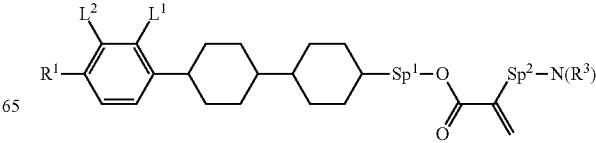

wherein, in formula (1-44) to formula (1-63),
R$^1$ is alkyl having 1 to 10 carbons;
Sp$^1$ is a single bond or alkylene having 1 to 3 carbons, and in the alkylene, at least one —CH$_2$— may be replaced by —O—, and in the groups, at least one hydrogen may be replaced by fluorine;
Sp$^2$ is alkylene having 1 to 5 carbons, and in the alkylene, at least one —CH$_2$— may be replaced by —O—;
L$^1$, L$^2$, L$^3$, L$^4$ and L$^5$ are independently hydrogen, fluorine, methyl or ethyl;
Y$^1$ and Y$^2$ are independently hydrogen or methyl; and
R$^3$ is hydrogen, methyl or ethyl.

10. A liquid crystal composition, comprising at least one compound according to claim 1.

11. The liquid crystal composition according to claim 10, further comprising at least one compound selected from the group consisting of a compound represented by formula (2), a compound represented by formula (3) and a compound represented by formula (4):

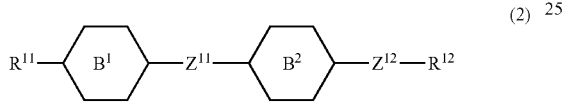  (2)

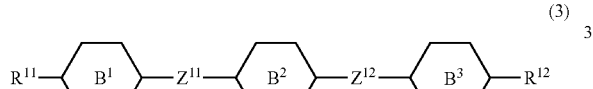  (3)

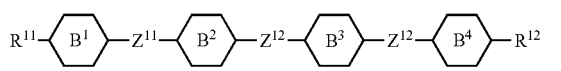  (4)

wherein, in formula (2), formula (3) and formula (4),
R$^{11}$ and R$^{12}$ are independently alkyl having 1 to 10 carbons or alkenyl having 2 to 10 carbons, and in the alkyl and the alkenyl, at least one —CH$_2$— may be replaced by —O—, and at least one hydrogen may be replaced by fluorine;
ring B$^1$, ring B$^2$, ring B$^3$ and ring B$^4$ are independently 1,4-cyclohexylene, 1,4-phenylene, 2-fluoro-1,4-phenylene, 2,5-difluoro-1,4-phenylene or pyrimidine-2,5-diyl; and
Z$^{11}$, Z$^{12}$ and Z$^{13}$ are independently a single bond, —(CH$_2$)$_2$—, —CH=CH—, —C≡C— or —COO—.

12. The liquid crystal composition according to claim 10, further comprising at least one compound selected from the group consisting of a compound represented by formula (5), a compound represented by formula (6) and a compound represented by formula (7):

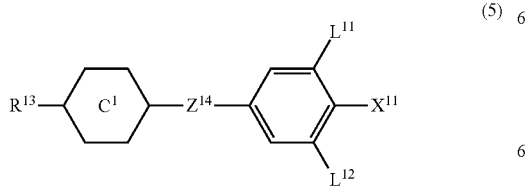  (5)

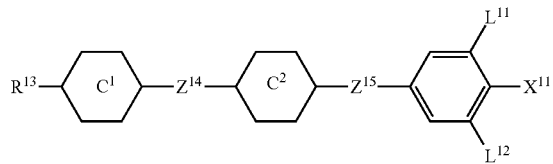  (6)

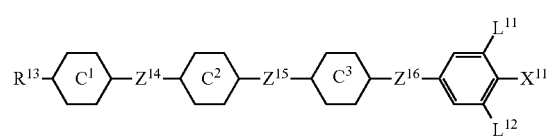  (7)

wherein, in formula (5), formula (6) and formula (7),
R$^{13}$ is alkyl having 1 to 10 carbons or alkenyl having 2 to 10 carbons, and in the alkyl and the alkenyl, at least one —CH$_2$— may be replaced by —O—, and at least one hydrogen may be replaced by fluorine;
X$^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
ring C$^1$, ring C$^2$ and ring C$^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
Z$^{14}$, Z$^{15}$ and Z$^{16}$ are independently a single bond, —(CH$_2$)$_2$—, —CH=CH—, —C≡C—, —COO—, —CF$_2$O—, —OCF$_2$—, —CH$_2$O— or —(CH$_2$)$_4$—; and
L$^{11}$ and L$^{12}$ are independently hydrogen or fluorine.

13. The liquid crystal composition according to claim 10, further comprising at least one compound represented by formula (8):

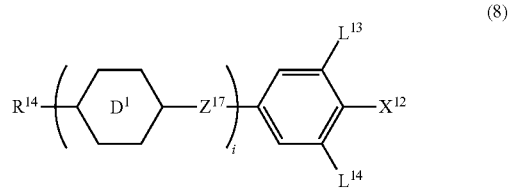  (8)

wherein, in formula (8),
R$^{14}$ is alkyl having 1 to 10 carbons or alkenyl having 2 to 10 carbons, and in the alkyl and the alkenyl, at least one —CH$_2$— may be replaced by —O—, and at least one hydrogen may be replaced by fluorine;
X$^{12}$ is —C≡N or —C≡C—C≡N;
ring D$^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
Z$^{17}$ is a single bond, —(CH$_2$)$_2$—, —C≡C—, —COO—, —CF$_2$O—, —OCF$_2$— or —CH$_2$O—;
L$^{13}$ and L$^{14}$ are independently hydrogen or fluorine; and
i is 1, 2, 3 or 4.

14. The liquid crystal composition according to claim 10, further comprising at least one compound selected from the group consisting of a compound represented by formula (9), a compound represented by formula (10), a compound represented by formula (11), a compound represented by formula (12), a compound represented by formula (13), a compound represented by formula (14) and a compound represented by formula (15):

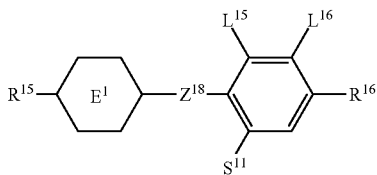

(9)

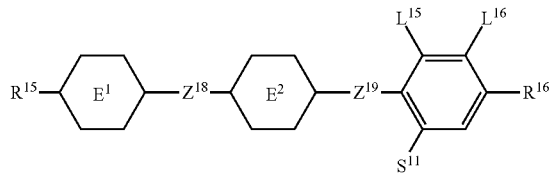

(10)

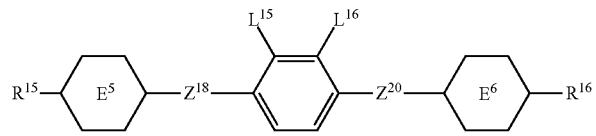

(11)

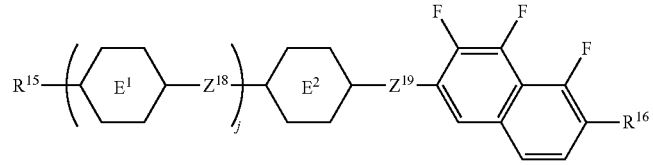

(12)

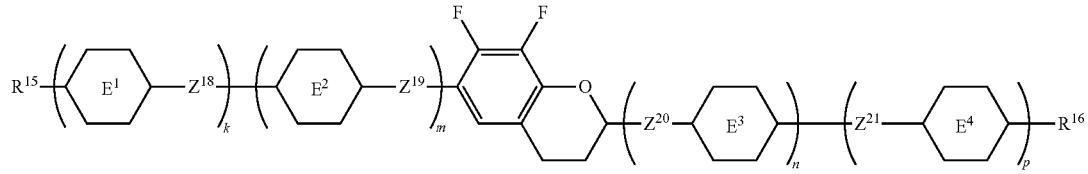

(13)

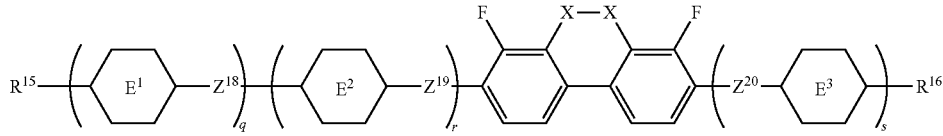

(14)

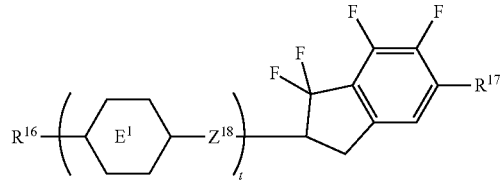

(15)

wherein, in formula (9), formula (10), formula (11), formula (12), formula (13), formula (14) and formula (15),

- $R^{15}$ and $R^{16}$ are independently alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
- $R^{17}$ is hydrogen, fluorine, alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
- ring $E^1$, ring $E^2$, ring $E^3$ and ring $E^4$ are independently 1,4-cyclohexylene, 1,4-cyclohexenylene, 1,4-phenylene in which at least one hydrogen may be replaced by fluorine, tetrahydropyran-2,5-diyl or decahydronaphthalene-2,6-diyl;
- ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;
- $Z^{18}$, $Z^{19}$, $Z^{20}$ and $Z^{21}$ are independently a single bond, —$(CH_2)_2$—, —COO—, —$CH_2O$—, —$OCF_2$— or —$OCF_2CH_2CH_2$—;
- $L^{15}$ and $L^{16}$ are independently fluorine or chlorine;
- $S^{11}$ is hydrogen or methyl;
- X is —CHF— or —$CF_2$—; and
- j, k, m, n, p, q, r and s are independently 0 or 1, a sum of k, m, n and p is 1 or 2, a sum of q, r and s is 0, 1, 2 or 3, and t is 1, 2 or 3.

15. The liquid crystal composition according to claim 10, further comprising at least one polymerizable compound represented by formula (16):

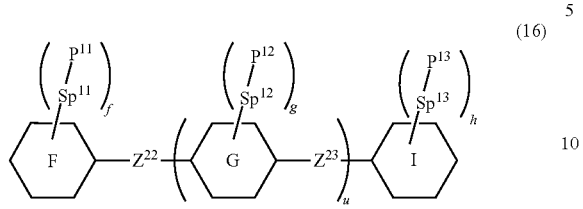
(16)

wherein, in formula (16),
ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one hydrogen may be replaced by halogen, alkyl having 1 to 12 carbons, or alkyl having 1 to 12 carbons in which at least one hydrogen is replaced by halogen;
ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be replaced by halogen, alkyl having 1 to 12 carbons, alkoxy having 1 to 12 carbons, or alkyl having 1 to 12 carbons in which at least one hydrogen is replaced by halogen;
$Z^{22}$ and $Z^{23}$ are independently a single bond or alkylene having 1 to 10 carbons, and in the alkylene, at least one —$CH_2$— may be replaced by —O—, —CO—, —COO— or —OCO—, and at least one —$(CH_2)_2$— may be replaced by —CH=CH—, —C($CH_3$)=CH—, —CH=C($CH_3$)— or —C($CH_3$)=C($CH_3$)—, and in the groups, at least one hydrogen may be replaced by fluorine or chlorine;
$P^{11}$, $P^{12}$ and $P^{13}$ are independently a polymerizable group;
$Sp^{11}$, $Sp^{12}$ and $Sp^{13}$ are independently a single bond or alkylene having 1 to 10 carbons, and in the alkylene, at least one —$CH_2$— may be replaced by —O—, —COO—, —OCO— or —OCOO—, and at least one —$(CH_2)_2$— may be replaced by —CH=CH— or —C≡C— and in the groups, at least one hydrogen may be replaced by fluorine or chlorine;
u is 0, 1 or 2; and
f, g and h are independently 0, 1, 2, 3 or 4, and a sum of f, g and h is 2 or more.

16. The liquid crystal composition according to claim 15, wherein, in formula (16), $P^{11}$, $P^{12}$ and $P^{13}$ are independently a polymerizable group selected from the group consisting of groups a group represented by formula (P-1), a group represented by formula (P-2), a group represented by formula (P-3), a group represented by formula (P-4) and a group represented by formula (P-5):

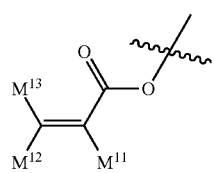
(P-1)

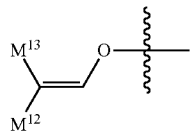
(P-2)

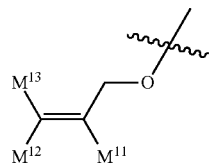
(P-3)

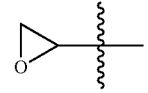
(P-4)

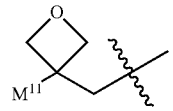
(P-5)

wherein, in formula (P-1), formula (P-2), formula (P-3), formula (P-4) and formula (P-5), $M^{11}$, $M^{12}$ and $M^{13}$ are independently hydrogen, fluorine, alkyl having 1 to 5 carbons, or alkyl having 1 to 5 carbons in which at least one hydrogen is replaced by halogen.

17. The liquid crystal composition according to claim 10, further comprising at least one polymerizable compound selected from the group consisting of a compound represented by formula (16-1), a compound represented by formula (16-2), a compound represented by formula (16-3), a compound represented by formula (16-4), a compound represented by formula (16-5), a compound represented by formula (16-6), a compound represented by formula (16-7), a compound represented by formula (16-8), a compound represented by formula (16-9), a compound represented by formula (16-10), a compound represented by formula (16-11), a compound represented by formula (16-12), a compound represented by formula (16-13), a compound represented by formula (16-14), a compound represented by formula (16-15), a compound represented by formula (16-16), a compound represented by formula (16-17), a compound represented by formula (16-18), a compound represented by formula (16-19), a compound represented by formula (16-20), a compound represented by formula (16-21), a compound represented by formula (16-22), a compound represented by formula (16-23), a compound represented by formula (16-24), a compound represented by formula (16-25), a compound represented by formula (16-26) and a compound represented by formula (16-27):

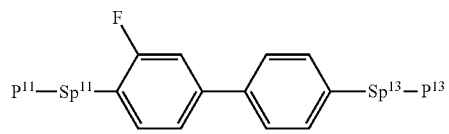
(16-1)

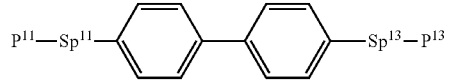
(16-2)

-continued
(16-3)
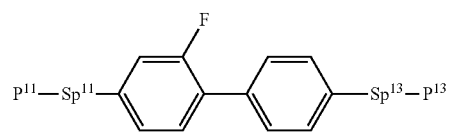
(16-4)
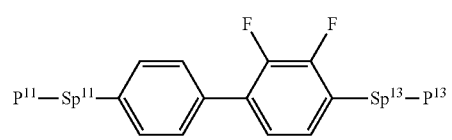
(16-5)
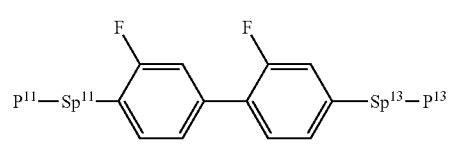
(16-6)
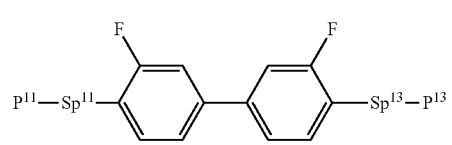
(16-7)
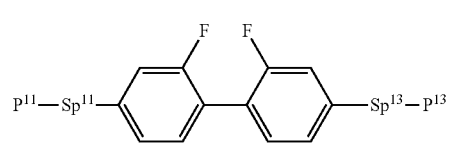
(16-8)
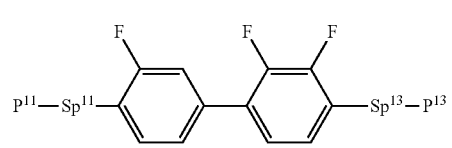
(16-9)
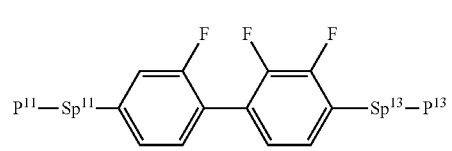
(16-10)
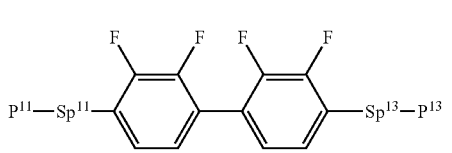
(16-11)
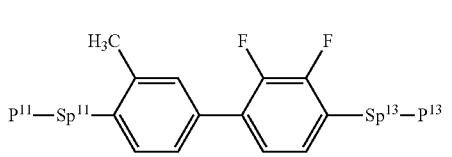
(16-12)
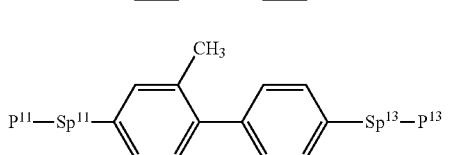
(16-13)
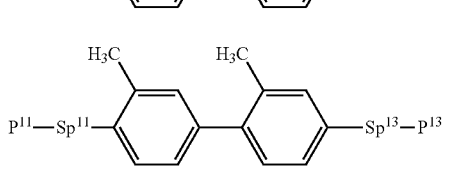
-continued
(16-14)
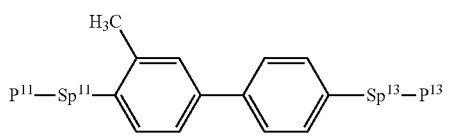
(16-15)
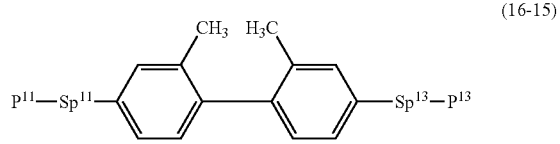
(16-16)
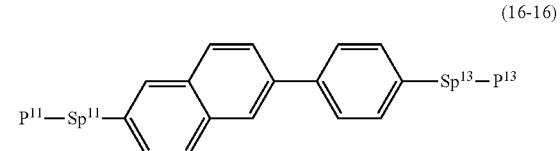
(16-17)
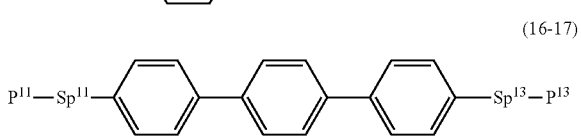
(16-18)
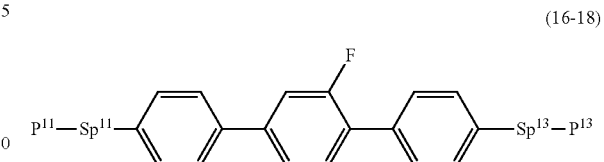
(16-19)
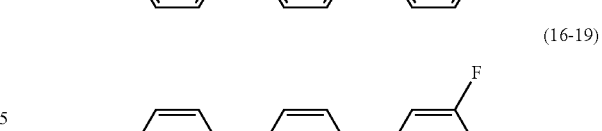
(16-20)
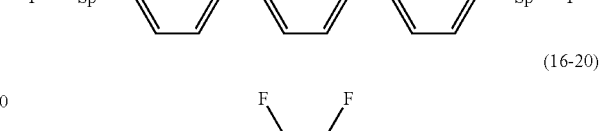
(16-21)
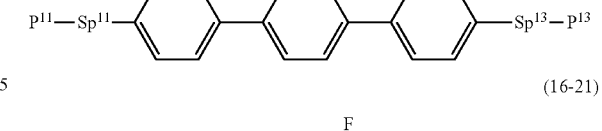
(16-22)
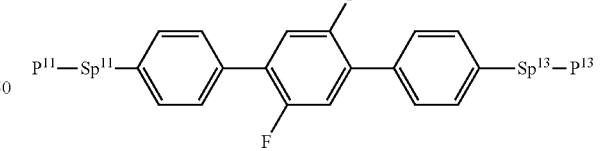
(16-23)
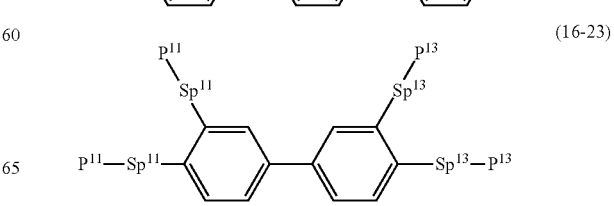

(16-24)

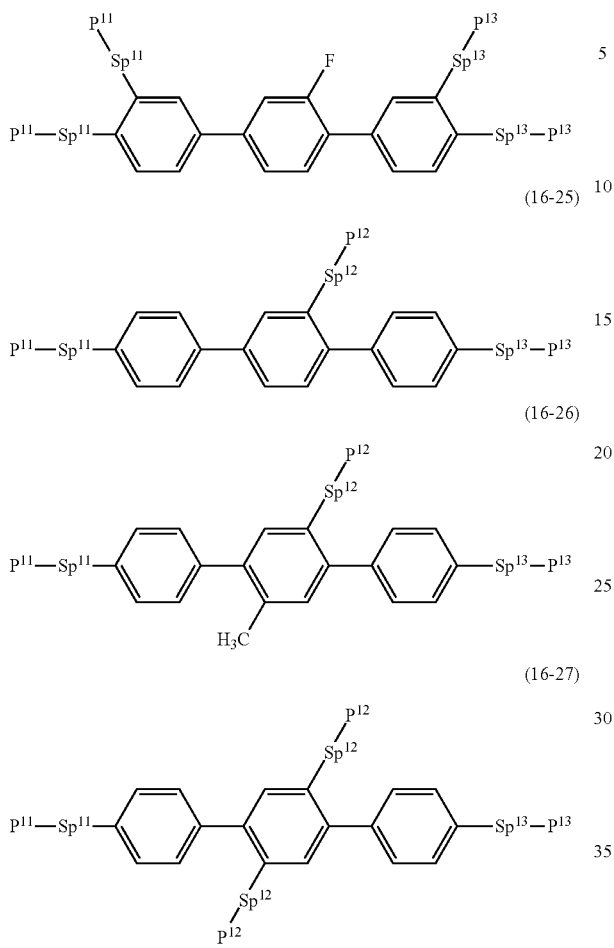

(16-25)

(16-26)

(16-27)

wherein, in formula (16-1), formula (16-2), formula (16-3), formula (16-4), formula (16-5), formula (16-6), formula (16-7), formula (16-8), formula (16-9), formula (16-10), formula (16-11), formula (16-12), formula (16-13), formula (16-14), formula (16-15), formula (16-16), formula (16-17), formula (16-18), formula (16-19), formula (16-20), formula (16-21), formula (16-22), formula (16-23), formula (16-24), formula (16-25), formula (16-26) and formula (16-27), $P^{11}$, $P^{12}$ and $P^{13}$ are independently a polymerizable group selected from the group consisting of groups a group represented by formula (P-1), a group represented by formula (P-2) and a group represented by formula (P-3), in which $M^{11}$, $M^{12}$ and $M^{13}$ are independently hydrogen, fluorine, alkyl having 1 to 5 carbons, or alkyl having 1 to 5 carbons in which at least one hydrogen is replaced by halogen:

(P-1)

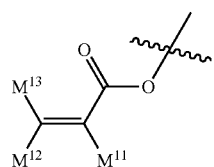

(P-2)

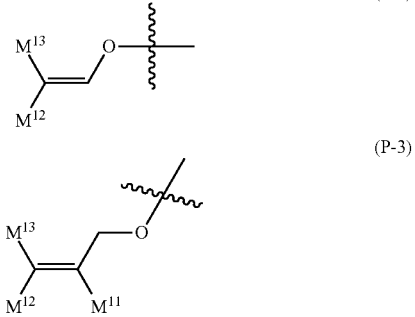

(P-3)

wherein, $Sp^{11}$, $Sp^{12}$ and $Sp^{13}$ are independently a single bond or alkylene having 1 to 10 carbons, and in the alkylene, at least one —$CH_2$— may be replaced by —O—, —COO—, —OCO— or —OCOO—, and at least one —$(CH_2)_2$— may be replaced by —CH=CH— or —C≡C— and in the groups, at least one hydrogen may be replaced by fluorine or chlorine.

18. The liquid crystal composition according to claim 10, further comprising at least one polymerizable compound, a polymerization initiator, a polymerization inhibitor, an optically active compound, an antioxidant, an ultraviolet light absorber, a light stabilizer, a heat stabilizer and an antifoaming agent, wherein the at least one polymerizable compound is not a compound represented by formula (1), (1)

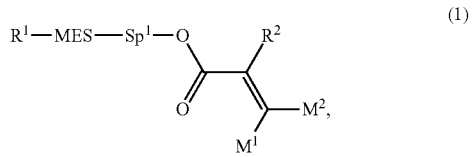

wherein, in formula (1),
$R^1$ is alkyl having 1 to 15 carbons, and in the alkyl, at least one —$CH_2$— may be replaced by —O— or —S—, and at least one —$(CH_2)_2$— may be replaced by —CH=CH— or —C≡C, and in the groups, at least one hydrogen may be replaced by halogen;
MES is a mesogen group having at least one ring;
$Sp^1$ is a single bond or alkylene having 1 to 10 carbons, and in the alkylene, at least one —$CH_2$— may be replaced with —O—, —CO—, —COO—, —OCO— or —OCOO—, and at least one —$(CH_2)_2$— may be replaced with —CH=CH— or —C≡C—, and in the groups, at least one hydrogen may be replaced by halogen;
$M^1$ and $M^2$ are independently hydrogen, halogen, alkyl having 1 to 5 carbons, or alkyl having 1 to 5 carbons in which at least one hydrogen is replaced by halogen; and
$R^2$ is a group represented by formula (1a), formula (1b) or formula (1c):

(1a)

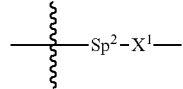

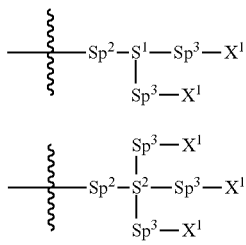

(1b)

(1c)

wherein, in formula (1a), formula (1b) and formula (1c), $Sp^2$ and $Sp^3$ are independently a single bond or alkylene having 1 to 10 carbons, and in the alkylene, at least one —$CH_2$— may be replaced by —O—, —NH—, —CO—, —COO—, —OCO— or —OCOO—, and at least one —$(CH_2)_2$— may be replaced by —CH=CH— or —C≡C— and in the groups, at least one hydrogen may be replaced by halogen;

$S^1$ is >CH— or >N—;

$S^2$ is >C< or >Si<, and $X^1$ is a group represented by —OH, —$NH$, —$OR^3$, —$N(R^3)_2$, formula (x1), —COOH, —SH, —$B(OH)_2$ or —$Si(R^3)_3$, in which $R^3$ is hydrogen or alkyl having 1 to 10 carbons, and in the alkyl, at least one —$CH_2$— may be replaced by —O—, and at least one —$(CH_2)_2$— may be replaced by —CH=CH—, and in the groups, at least one hydrogen may be replaced by halogen, and w in formula (x1) is 1, 2, 3 or 4:

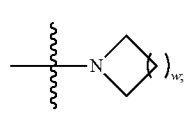

(x1)

and wherein the at least one polymerizable compound is not a compound represented by formula (16),

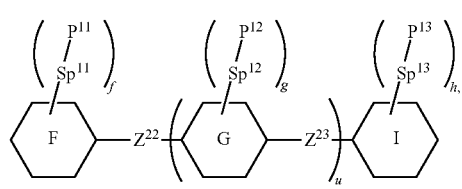

(16)

wherein, in formula (16), ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one hydrogen may be replaced by halogen, alkyl having 1 to 12 carbons, or alkyl having 1 to 12 carbons in which at least one hydrogen is replaced by halogen;

ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be replaced by halogen, alkyl having 1 to 12 carbons, alkoxy having 1 to 12 carbons, or alkyl having 1 to 12 carbons in which at least one hydrogen is replaced by halogen;

$Z^{22}$ and $Z^{23}$ are independently a single bond or alkylene having 1 to 10 carbons, and in the alkylene, at least one —$CH_2$— may be replaced by —O—, —CO—, —COO— or —OCO—, and at least one —$(CH_2)_2$— may be replaced by —CH=CH—, —C(CH)=CH—, —CH=C(CH)— or —C(CH)=C(CH)—, and in the groups, at least one hydrogen may be replaced by fluorine or chlorine;

$P^{11}$, $P^{12}$ and $P^{13}$ are independently a polymerizable group;

$Sp^{11}$, $Sp^{12}$ and $Sp^{13}$ are independently a single bond or alkylene having 1 to 10 carbons, and in the alkylene, at least one —$CH_2$— may be replaced by —O—, —COO—, —OCO— or —OCOO—, and at least one —$(CH_2)_2$— may be replaced by —CH=CH— or —C≡C— and in the groups, at least one hydrogen may be replaced by fluorine or chlorine;

u is 0, 1 or 2; and f, g and h are independently 0, 1, 2, 3 or 4, and a sum of f, g and h is 2 or more.

19. A liquid crystal display device, comprising at least one liquid crystal composition according to claim 10.

* * * * *